US012799458B2

(12) United States Patent
Takebe et al.

(10) Patent No.: US 12,799,458 B2
(45) Date of Patent: Nov. 17, 2026

(54) LIVER ORGANOID COMPOSITIONS AND METHODS OF MAKING AND USING SAME

(71) Applicants: Children's Hospital Medical Center, Cincinnati, OH (US); Japan Science and Technology Agency, Kawaguchi (JP)

(72) Inventors: Takanori Takebe, Cincinnati, OH (US); Tadahiro Shinozawa, Fujisawa (JP); Hiroyuki Koike, Tokyo (JP); Masaki Kimura, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 752 days.

(21) Appl. No.: 16/611,998

(22) PCT Filed: Feb. 19, 2018

(86) PCT No.: PCT/US2018/018585

§ 371 (c)(1),
(2) Date: Nov. 8, 2019

(87) PCT Pub. No.: WO2018/226267

PCT Pub. Date: Dec. 13, 2018

(65) Prior Publication Data

US 2020/0199537 A1 Jun. 25, 2020

Related U.S. Application Data

(60) Provisional application No. 62/517,414, filed on Jun. 9, 2017.

(51) Int. Cl.
*C12N 5/06* (2006.01)
*C12N 5/071* (2010.01)

(52) U.S. Cl.
CPC ...... *C12N 5/0671* (2013.01); *C12N 2501/119* (2013.01); *C12N 2501/12* (2013.01); *C12N 2501/155* (2013.01); *C12N 2501/16* (2013.01); *C12N 2501/237* (2013.01); *C12N 2501/385* (2013.01); *C12N 2501/39* (2013.01); *C12N 2503/02* (2013.01); *C12N 2506/45* (2013.01); *C12N 2533/90* (2013.01)

(58) Field of Classification Search
CPC .................................................... C12N 5/0671
See application file for complete search history.

(56) References Cited

U.S. PATENT DOCUMENTS

| | | | |
|---|---|---|---|
| 5,912,227 | A | 6/1999 | Croom, Jr. et al. |
| 5,942,435 | A | 8/1999 | Wheeler |
| 6,607,501 | B2 | 8/2003 | Gorsuch |
| 7,160,719 | B2 | 1/2007 | Nyberg |
| 7,291,626 | B1 | 11/2007 | Beachy et al. |
| 7,326,572 | B2 | 2/2008 | Fisk et al. |
| 7,510,876 | B2 | 3/2009 | D'Amour et al. |
| 7,514,185 | B2 | 4/2009 | Fukushima et al. |
| 7,541,185 | B2 | 6/2009 | D'Amour et al. |
| 7,625,753 | B2 | 12/2009 | Kelly et al. |
| 7,695,958 | B2 | 4/2010 | Funatsu et al. |
| 7,704,738 | B2 | 4/2010 | D'Amour et al. |
| 7,727,998 | B2 | 6/2010 | Moriya et al. |
| 7,776,592 | B2 | 8/2010 | Wandinger-Ness et al. |
| 7,927,869 | B2 | 4/2011 | Rosero |
| 7,985,585 | B2 | 7/2011 | D'Amour et al. |
| 7,993,916 | B2 | 8/2011 | Agulnick et al. |
| 8,187,878 | B2 | 5/2012 | Dalton et al. |
| 8,216,826 | B2 | 7/2012 | Lee et al. |
| 8,216,836 | B2 | 7/2012 | D'Amour et al. |
| 8,298,822 | B2 | 10/2012 | Kruse et al. |
| 8,318,492 | B2 | 11/2012 | Choo et al. |
| 8,501,476 | B2 | 8/2013 | Morgan et al. |
| 8,586,357 | B2 | 11/2013 | D'Amour et al. |
| 8,603,809 | B2 | 12/2013 | Kruse |
| 8,609,406 | B2 | 12/2013 | Subramanian et al. |
| 8,609,413 | B2 | 12/2013 | Suter et al. |
| 8,623,645 | B2 | 1/2014 | D'Amour et al. |
| 8,632,645 | B2 | 1/2014 | Daitou et al. |
| 8,633,024 | B2 | 1/2014 | D'Amour et al. |
| 8,642,339 | B2 | 2/2014 | Sato et al. |
| 8,647,873 | B2 | 2/2014 | D'Amour et al. |
| 8,658,151 | B2 | 2/2014 | Kelly et al. |

(Continued)

FOREIGN PATENT DOCUMENTS

| | | | |
|---|---|---|---|
| AU | 2019291955 | A1 | 2/2021 |
| CA | 2864702 | A1 | 8/2013 |

(Continued)

OTHER PUBLICATIONS

Sohail et al. (2021, Int. J. Mol. Sci., vol. 22, pp. 1-22). (Year: 2021).*
Ader M., et al., "Modeling Human Development in 3D Culture," Current Opinion in Cell Biology, Dec 2014, vol. 31, pp. 23-28.
Adorini L., et al., "Farnesoid X Receptor Targeting 1 Steatohepatitis," Drug Discovery Today, Sep. 2012, vol. 17 (17/18), pp. 988-997.
Agopian V.G., et al., "Intestinal Stem Cell Organoid Transplantation Generates Neomucosa in Dogs," Journal of Gastrointestinal Surgery, Jan. 23, 2009, vol. 13 (5), pp. 971-982.
Ahnfelt-Ronne J., et al., "An Improved Method for Three-Dimensional Reconstruction of Protein Expression Patterns in Intact Mouse and Chicken Embryos and Organs," Journal of Histochemistry and Cytochemistry, 2007, vol. 55 (9), pp. 925-930.

(Continued)

*Primary Examiner* — Anoop K Singh
*Assistant Examiner* — David A Montanari
(74) *Attorney, Agent, or Firm* — Norton Rose Fulbright US LLP

(57) ABSTRACT

Disclosed are methods of inducing formation of a liver organoid from precursor cells, such as iPSC cells. The disclosed liver organoids may be used for screening for a serious adverse event (SAE), such as liver failure and/or drug induced liver injury (DILI), and/or drug toxicity. The disclosed liver organoids may also be used to treat an individual having liver damage, or for identifying a preferred therapeutic agent.

21 Claims, 32 Drawing Sheets

(56) References Cited

U.S. PATENT DOCUMENTS 8,685,386 B2 4/2014 West et al.
8,685,730 B2 4/2014 Odorico et al.
8,758,323 B2 6/2014 Michaud et al.
9,127,254 B2 9/2015 Cohen et al.
9,133,439 B2 9/2015 Davis et al.
9,181,301 B2 11/2015 Carlson et al.
9,200,258 B2 12/2015 Mezghanni et al.
9,206,393 B2 12/2015 Kruse
9,234,170 B2 1/2016 Snoeck et al.
9,334,479 B2 5/2016 Herrera Sanchez et al.
9,375,514 B2 6/2016 Kruse et al.
9,381,181 B2 7/2016 Roberts et al.
9,394,522 B2 7/2016 Brolen et al.
9,446,076 B2 9/2016 Gaussin et al.
9,447,380 B2 9/2016 Subramanian et al.
9,476,030 B2 10/2016 Gadue et al.
9,499,795 B2 11/2016 D'Amour et al.
9,605,243 B2 3/2017 D'Amour et al.
9,616,039 B2 4/2017 Roberts et al.
9,618,500 B2 4/2017 Giselbrecht et al.
9,650,609 B2 5/2017 Nyberg
9,675,646 B2 6/2017 Bitar
9,677,085 B2 6/2017 Guye et al.
9,719,067 B2 8/2017 Snoeck et al.
9,719,068 B2 8/2017 Wells et al.
9,732,116 B2 8/2017 Steiner et al.
9,752,124 B2 9/2017 Sato et al.
9,763,964 B2 9/2017 Pellicciari et al.
9,765,301 B2 9/2017 Huch Ortega et al.
9,771,562 B2 9/2017 Shen et al.
9,790,470 B2 10/2017 Vallier et al.
9,828,583 B2 11/2017 Rajagopal et al.
9,849,104 B2 12/2017 Bisgaier et al.
9,850,461 B2 12/2017 Rizzi et al.
9,856,458 B2 1/2018 Rosowski et al.
9,878,005 B2 1/2018 Johns et al.
9,914,920 B2 3/2018 Goodwin et al.
9,926,532 B2 3/2018 Esteban et al.
9,938,499 B2 4/2018 Slukvin et al.
10,000,740 B2 6/2018 Vallier et al.
10,023,922 B2 7/2018 Stelzer et al.
10,045,977 B2 8/2018 Wu et al.
10,047,341 B2 8/2018 Yu et al.
10,052,337 B2 8/2018 Lancaster et al.
10,087,416 B2 10/2018 Chan et al.
10,087,417 B2 10/2018 Freed et al.
10,100,279 B2 10/2018 Nicholas et al.
10,130,748 B2 11/2018 Nyberg et al.
10,172,889 B2 1/2019 Sokal et al.
10,174,289 B2 1/2019 Wells et al.
10,179,176 B2 1/2019 Kay et al.
10,220,386 B2 3/2019 Williamson et al.
10,222,370 B2 3/2019 Keshavarzian et al.
10,260,039 B2 4/2019 Bhatia et al.
10,265,153 B2 4/2019 La Francesca et al.
10,265,453 B2 4/2019 Flieg et al.
10,301,303 B2 5/2019 Liu
10,350,147 B2 7/2019 Kyrkanides et al.
10,369,254 B2 8/2019 Yanagawa et al.
10,407,664 B2 9/2019 Knoblich et al.
10,426,757 B2 10/2019 Sabatini et al.
10,449,221 B2 10/2019 Kotton et al.
10,472,612 B2 11/2019 Ingber et al.
10,479,977 B2 11/2019 Wang et al.
10,487,314 B2 11/2019 Accili et al.
10,532,111 B2 1/2020 Kay et al.
10,538,741 B2 1/2020 Sokal et al.
10,545,133 B2 1/2020 Ewald et al.
10,555,929 B2 2/2020 Mantzoros
10,597,633 B2 3/2020 Huch Ortega et al.
10,668,108 B2 6/2020 Takebe et al.
10,781,425 B2 9/2020 Wells et al.
11,021,686 B2 6/2021 Vallier et al.
11,053,477 B2 7/2021 Wells et al.
11,066,650 B2 7/2021 Wells et al.
2003/0129751 A1 7/2003 Grikscheit et al.
2003/0228685 A1 12/2003 Nyberg
2005/0266554 A1 12/2005 D'Amour et al.
2006/0110369 A1 5/2006 Funatsu et al.
2006/0236415 A1 10/2006 Silversides et al.
2007/0238169 A1 10/2007 Abilez et al.
2007/0239083 A1 10/2007 Voss
2008/0193421 A1 8/2008 Kruse et al.
2008/0195224 A1 8/2008 Teitelbaum et al.
2008/0286366 A1 11/2008 Fischer et al.
2009/0011502 A1 1/2009 D'Amour et al.
2009/0042287 A1 2/2009 D'Amour et al.
2009/0220959 A1 9/2009 D'Amour et al.
2009/0253202 A1 10/2009 D'Amour et al.
2009/0263357 A1 10/2009 Sayre et al.
2009/0311765 A1 12/2009 Maguire et al.
2010/0016410 A1 1/2010 Wagner et al.
2010/0041150 A1 2/2010 Kelly et al.
2010/0048871 A1 2/2010 Cho et al.
2010/0075295 A1 3/2010 Dryden et al.
2010/0151568 A1 6/2010 D'Amour et al.
2011/0125286 A1 5/2011 Selden et al.
2011/0151564 A1 6/2011 Menu et al.
2011/0218512 A1 9/2011 Tullis et al.
2011/0231942 A1 9/2011 He et al.
2011/0294735 A1 12/2011 Marsh et al.
2011/0300543 A1 12/2011 Wang
2012/0009086 A1 1/2012 Nyberg et al.
2012/0009618 A1 1/2012 Yu et al.
2012/0070419 A1 3/2012 Christiansen-Weber
2012/0071451 A1 3/2012 Spenard et al.
2012/0135519 A1 5/2012 Ameri et al.
2012/0149630 A1 6/2012 Zugates et al.
2012/0196275 A1 8/2012 Mezghanni et al.
2012/0196312 A1 8/2012 Sato et al.
2012/0201890 A1 8/2012 Williams et al.
2012/0264209 A1 10/2012 Odorico et al.
2012/0270295 A1 10/2012 Choo et al.
2012/0291096 A1 11/2012 Boldyrev et al.
2013/0031645 A1 1/2013 Touboul et al.
2013/0095567 A1 4/2013 Brolen et al.
2013/0115673 A1 5/2013 West et al.
2013/0137030 A1 5/2013 Sato et al.
2013/0137130 A1 5/2013 Wells et al.
2013/0189327 A1 7/2013 Ortega et al.
2013/0217005 A1 8/2013 Snoeck et al.
2013/0281374 A1 10/2013 Levy et al.
2013/0316442 A1 11/2013 Meurville et al.
2013/0330823 A1 12/2013 Rezania
2014/0038279 A1 2/2014 Ingber et al.
2014/0044713 A1 2/2014 De Lau et al.
2014/0141509 A1 5/2014 Gadue et al.
2014/0193905 A1 7/2014 Kelly et al.
2014/0212910 A1 7/2014 Bhatia et al.
2014/0234953 A1 8/2014 Vacanti et al.
2014/0242693 A1 8/2014 Fryer et al.
2014/0243227 A1 8/2014 Clevers et al.
2014/0273210 A1 9/2014 Baker et al.
2014/0302491 A1 10/2014 Nadauld et al.
2014/0308695 A1 10/2014 Bruce et al.
2014/0328808 A1 11/2014 Watanabe et al.
2014/0336282 A1 11/2014 Ewald et al.
2014/0369973 A1 12/2014 Bernstein et al.
2015/0017140 A1 1/2015 Bhatia et al.
2015/0151297 A1 6/2015 Williamson et al.
2015/0153326 A1 6/2015 Kogel et al.
2015/0185714 A1 7/2015 Geveci
2015/0197802 A1 7/2015 Zink et al.
2015/0201588 A1 7/2015 Kamb et al.
2015/0238656 A1 8/2015 Orlando et al.
2015/0247124 A1 9/2015 Snoeck et al.
2015/0273071 A1 10/2015 Green et al.
2015/0273127 A1 10/2015 Flieg et al.
2015/0290154 A1 10/2015 Roberts et al.
2015/0330970 A1 11/2015 Knoblich et al.
2015/0343018 A1 12/2015 Sansonetti et al.
2015/0359849 A1 12/2015 Greenberg et al.
2015/0361393 A1 12/2015 Nicholas et al.
2016/0002602 A1 1/2016 Almeida-Porada et al.

(56) References Cited

U.S. PATENT DOCUMENTS

| | | | |
|---|---|---|---|
| 2016/0022873 | A1 | 1/2016 | Besner et al. |
| 2016/0046905 | A1 | 2/2016 | Inoue et al. |
| 2016/0060707 | A1 | 3/2016 | Goldenberg et al. |
| 2016/0068805 | A1 | 3/2016 | Martin et al. |
| 2016/0101133 | A1 | 4/2016 | Basu et al. |
| 2016/0102289 | A1 | 4/2016 | Yu et al. |
| 2016/0121023 | A1 | 5/2016 | Edelman et al. |
| 2016/0122722 | A1 | 5/2016 | Ejiri et al. |
| 2016/0143949 | A1 | 5/2016 | Ingber et al. |
| 2016/0177270 | A1 | 6/2016 | Takebe et al. |
| 2016/0184387 | A1 | 6/2016 | Charmot et al. |
| 2016/0186140 | A1 | 6/2016 | Dalton et al. |
| 2016/0206664 | A1 | 7/2016 | Sokal et al. |
| 2016/0215014 | A1 | 7/2016 | Steiner et al. |
| 2016/0237400 | A1 | 8/2016 | Xian |
| 2016/0237401 | A1 | 8/2016 | Vallier et al. |
| 2016/0237409 | A1 | 8/2016 | Little et al. |
| 2016/0244724 | A1 | 8/2016 | Ferro |
| 2016/0245653 | A1 | 8/2016 | Park et al. |
| 2016/0256672 | A1 | 9/2016 | Arumugaswami et al. |
| 2016/0257937 | A1 | 9/2016 | Wauthier et al. |
| 2016/0263098 | A1 | 9/2016 | Mantzoros |
| 2016/0289635 | A1 | 10/2016 | Sasai et al. |
| 2016/0296599 | A1 | 10/2016 | Dinh et al. |
| 2016/0298087 | A1 | 10/2016 | Qu et al. |
| 2016/0312181 | A1 | 10/2016 | Freed et al. |
| 2016/0312190 | A1 | 10/2016 | Ghaedi et al. |
| 2016/0312191 | A1 | 10/2016 | Spence et al. |
| 2016/0319240 | A1 | 11/2016 | Chan et al. |
| 2016/0340645 | A1 | 11/2016 | D'Amour et al. |
| 2016/0340749 | A1 | 11/2016 | Stelzer et al. |
| 2016/0354408 | A1 | 12/2016 | Hariri et al. |
| 2016/0361466 | A1 | 12/2016 | Yanagawa et al. |
| 2016/0376557 | A1 | 12/2016 | Dubart Kupperschmitt et al. |
| 2017/0002330 | A1 | 1/2017 | Vunjak-Novakovic et al. |
| 2017/0027994 | A1 | 2/2017 | Kotton et al. |
| 2017/0035661 | A1 | 2/2017 | Kyrkanides et al. |
| 2017/0035784 | A1 | 2/2017 | Lancaster et al. |
| 2017/0037043 | A1 | 2/2017 | Liu |
| 2017/0067014 | A1 | 3/2017 | Takebe et al. |
| 2017/0101628 | A1 | 4/2017 | Ingber et al. |
| 2017/0107469 | A1 | 4/2017 | Costa et al. |
| 2017/0107483 | A1 | 4/2017 | Pendergraft et al. |
| 2017/0107498 | A1 | 4/2017 | Sareen et al. |
| 2017/0128625 | A1 | 5/2017 | Bhatia et al. |
| 2017/0151049 | A1 | 6/2017 | La Francesca et al. |
| 2017/0152486 | A1 | 6/2017 | Shen et al. |
| 2017/0152528 | A1 | 6/2017 | Zhang |
| 2017/0184569 | A1 | 6/2017 | Keshavarzian et al. |
| 2017/0191030 | A1 | 7/2017 | Huch Ortega et al. |
| 2017/0198261 | A1 | 7/2017 | Sabaawy et al. |
| 2017/0202885 | A1 | 7/2017 | Agulnick |
| 2017/0204375 | A1 | 7/2017 | Accili et al. |
| 2017/0205396 | A1 | 7/2017 | Izpisua Belmonte et al. |
| 2017/0205398 | A1 | 7/2017 | Bruce et al. |
| 2017/0239262 | A1 | 8/2017 | Lefebvre |
| 2017/0240863 | A1 | 8/2017 | Sokal et al. |
| 2017/0240866 | A1 | 8/2017 | Wells et al. |
| 2017/0240964 | A1 | 8/2017 | Leung et al. |
| 2017/0242035 | A1 | 8/2017 | Kiehntopf et al. |
| 2017/0258772 | A1 | 9/2017 | Sabatini et al. |
| 2017/0260501 | A1 | 9/2017 | Semechkin et al. |
| 2017/0260509 | A1 | 9/2017 | Hung et al. |
| 2017/0266145 | A1 | 9/2017 | Nahmias et al. |
| 2017/0267970 | A1 | 9/2017 | Gupta et al. |
| 2017/0267977 | A1 | 9/2017 | Huang et al. |
| 2017/0275592 | A1 | 9/2017 | Sachs et al. |
| 2017/0285002 | A1 | 10/2017 | Taniguchi et al. |
| 2017/0292116 | A1 | 10/2017 | Wells et al. |
| 2017/0296621 | A1 | 10/2017 | Sansonetti et al. |
| 2017/0304294 | A1 | 10/2017 | Wu et al. |
| 2017/0304369 | A1 | 10/2017 | Ang et al. |
| 2017/0319548 | A1 | 11/2017 | Lefebvre |
| 2017/0321188 | A1 | 11/2017 | Viczian et al. |
| 2017/0321191 | A1 | 11/2017 | Kojima |
| 2017/0335283 | A1 | 11/2017 | Wang et al. |
| 2017/0342385 | A1 | 11/2017 | Sachs et al. |
| 2017/0348433 | A1 | 12/2017 | Kay et al. |
| 2017/0349659 | A1 | 12/2017 | Garcia et al. |
| 2017/0349884 | A1 | 12/2017 | Karp et al. |
| 2017/0360962 | A1 | 12/2017 | Kay et al. |
| 2017/0362573 | A1 | 12/2017 | Wells et al. |
| 2017/0362574 | A1 | 12/2017 | Sareen et al. |
| 2018/0021341 | A1 | 1/2018 | Harriman et al. |
| 2018/0030409 | A1 | 2/2018 | Lewis et al. |
| 2018/0030410 | A1 | 2/2018 | Loh et al. |
| 2018/0042970 | A1 | 2/2018 | Rossen et al. |
| 2018/0043357 | A1 | 2/2018 | Bocchi et al. |
| 2018/0059119 | A1 | 3/2018 | Takats et al. |
| 2018/0112187 | A1 | 4/2018 | Smith et al. |
| 2018/0142206 | A1 | 5/2018 | Kime et al. |
| 2018/0171302 | A1 | 6/2018 | Accili |
| 2018/0179496 | A1 | 6/2018 | Rajesh et al. |
| 2018/0193421 | A1 | 7/2018 | Soula |
| 2018/0250410 | A1 | 9/2018 | Borros Gomez et al. |
| 2018/0258400 | A1 | 9/2018 | Ng et al. |
| 2018/0344901 | A1 | 12/2018 | Spence et al. |
| 2019/0031992 | A1 | 1/2019 | Kerns et al. |
| 2019/0078055 | A1 | 3/2019 | Wells et al. |
| 2019/0093076 | A1 | 3/2019 | Schulz |
| 2019/0153395 | A1 | 5/2019 | Barrett et al. |
| 2019/0153397 | A1 | 5/2019 | Wells et al. |
| 2019/0211310 | A1 | 7/2019 | Evans et al. |
| 2019/0298775 | A1 | 10/2019 | Takebe et al. |
| 2019/0300849 | A1 | 10/2019 | Carpino et al. |
| 2019/0314387 | A1 | 10/2019 | Takebe et al. |
| 2019/0367882 | A1 | 12/2019 | Wells et al. |
| 2020/0040309 | A1 | 2/2020 | Takebe et al. |
| 2020/0056157 | A1 | 2/2020 | Takebe et al. |
| 2020/0102543 | A1 | 4/2020 | Okazaki et al. |
| 2020/0149004 | A1 | 5/2020 | Spence et al. |
| 2020/0190478 | A1 | 6/2020 | Wells et al. |
| 2020/0199538 | A1 | 6/2020 | Ng et al. |
| 2020/0339957 | A1 | 10/2020 | Takasato et al. |
| 2021/0008123 | A1 | 1/2021 | Takebe et al. |
| 2021/0030811 | A1 | 2/2021 | Kim et al. |
| 2021/0096026 | A1 | 4/2021 | Azana et al. |
| 2021/0096126 | A1 | 4/2021 | Takebe et al. |
| 2021/0115366 | A1 | 4/2021 | Mahe et al. |
| 2021/0180026 | A1 | 6/2021 | Takebe et al. |
| 2021/0189349 | A1 | 6/2021 | Wells et al. |
| 2021/0292714 | A1 | 9/2021 | Takebe et al. |
| 2021/0324334 | A1 | 10/2021 | Takebe et al. |
| 2021/0363490 | A1 | 11/2021 | Yoshihara et al. |
| 2021/0371815 | A1 | 12/2021 | Holloway et al. |
| 2021/0395679 | A1 | 12/2021 | Asai |
| 2021/0395695 | A1 | 12/2021 | Kim et al. |
| 2022/0041684 | A1 | 2/2022 | Patterson |
| 2022/0056420 | A1 | 2/2022 | Wells et al. |
| 2022/0090011 | A1 | 3/2022 | Ngan et al. |
| 2022/0233605 | A1 | 7/2022 | Ogawa et al. |
| 2022/0275345 | A1 | 9/2022 | Mayhew et al. |
| 2022/0298485 | A1 | 9/2022 | Masuda et al. |
| 2022/0380732 | A1 | 12/2022 | Osafune et al. |
| 2023/0220353 | A1 | 7/2023 | Yue et al. |
| 2023/0399623 | A1 | 12/2023 | Sullivan et al. |

FOREIGN PATENT DOCUMENTS

| | | | |
|---|---|---|---|
| CA | 2968065 | A1 | 6/2016 |
| CA | 3149805 | A1 | 2/2021 |
| CN | 1299408 | A | 6/2001 |
| CN | 101361968 | A | 2/2009 |
| CN | 101600461 | A | 12/2009 |
| CN | 101855554 | A | 10/2010 |
| CN | 102307990 | A | 1/2012 |
| CN | 102439135 | A | 5/2012 |
| CN | 102459574 | A | 5/2012 |
| CN | 102740888 | A | 10/2012 |
| CN | 103068970 | A | 4/2013 |
| CN | 103154237 | A | 6/2013 |
| CN | 103561751 | A | 2/2014 |
| CN | 104387451 | A | 3/2015 |
| CN | 105209605 | A | 12/2015 |

(56) References Cited

FOREIGN PATENT DOCUMENTS

| | | | | |
|---|---|---|---|---|
| CN | 105985395 | A | 10/2016 | |
| CN | 109415685 | A | 3/2019 | |
| CN | 110371967 | A | 10/2019 | |
| CN | 110381967 | A | 10/2019 | |
| CN | 110582564 | A | 12/2019 | |
| CN | 113667603 | A | 11/2021 | |
| EP | 1063289 | A1 | 12/2000 | |
| EP | 2393917 | A2 | 12/2011 | |
| EP | 2393917 | B1 | 4/2016 | |
| EP | 3228306 | A1 | 10/2017 | |
| JP | 2003521673 | A | 7/2003 | |
| JP | 2004166717 | A | 6/2004 | |
| JP | 2006519015 | A | 8/2006 | |
| JP | 2008503203 | A | 2/2008 | |
| JP | 2008505638 | A | 2/2008 | |
| JP | 2012516685 | A | 7/2012 | |
| JP | 2012254081 | A | 12/2012 | |
| JP | 2013066414 | A | 4/2013 | |
| JP | 2013511969 | A | 4/2013 | |
| JP | 2013521810 | A | 6/2013 | |
| JP | 2013528397 | A | 7/2013 | |
| JP | 2013535201 | A | 9/2013 | |
| JP | 2014514918 | A | 6/2014 | |
| JP | 2014516562 | A | 7/2014 | |
| JP | 2014233281 | A | 12/2014 | |
| JP | 2016198033 | A | 12/2016 | |
| JP | 2017532964 | A | 11/2017 | |
| JP | 2018518312 | A | 7/2018 | |
| JP | 2019000014 | A | 1/2019 | |
| JP | 2020516247 | A | 6/2020 | |
| JP | 2020523000 | A | 8/2020 | |
| JP | 7068305 | B2 | 5/2022 | |
| JP | 7148552 | B2 | 10/2022 | |
| KR | 20060114355 | A | 11/2006 | |
| WO | WO-9207615 | A1 | 5/1992 | |
| WO | WO-9821312 | A1 | 5/1998 | |
| WO | 9945100 | A1 | 9/1999 | |
| WO | WO-9949807 | A2 | 10/1999 | |
| WO | 03046141 | A2 | 6/2003 | |
| WO | WO-03082201 | A2 | 10/2003 | |
| WO | WO-2004020614 | A1 | 3/2004 | |
| WO | WO-2005001072 | A1 | 1/2005 | |
| WO | 2005063971 | A2 | 7/2005 | |
| WO | WO-2005081970 | A2 | 9/2005 | |
| WO | WO-2005097974 | A2 | 10/2005 | |
| WO | WO-2005113747 | A2 | 12/2005 | |
| WO | 2006115682 | A2 | 11/2006 | |
| WO | WO-2006126236 | A1 | 11/2006 | |
| WO | 2008073352 | A1 | 6/2008 | |
| WO | WO-2008075339 | A2 | 6/2008 | |
| WO | 2008123614 | A1 | 10/2008 | |
| WO | WO-2009022907 | A2 | 2/2009 | |
| WO | WO-2009086596 | A1 | 7/2009 | |
| WO | WO-2009146911 | A2 | 12/2009 | |
| WO | WO-2010008905 | A2 | 1/2010 | |
| WO | WO-2010090513 | A2 | 8/2010 | |
| WO | WO-2010094694 | A1 | 8/2010 | |
| WO | WO-2010127399 | A1 | 11/2010 | |
| WO | 2010136583 | A2 | 12/2010 | |
| WO | WO-2010143747 | A1 | 12/2010 | |
| WO | WO-2011050672 | A1 | 5/2011 | |
| WO | 2011064309 | A1 | 6/2011 | |
| WO | WO-2011116930 | A1 | 9/2011 | |
| WO | WO-2011139628 | A1 | 11/2011 | |
| WO | WO-2011140441 | A2 | 11/2011 | |
| WO | WO-2012014076 | A2 | 2/2012 | |
| WO | WO-2012027474 | A1 | 3/2012 | |
| WO | WO-2012089669 | A1 | 7/2012 | |
| WO | 2012126013 | A2 | 9/2012 | |
| WO | WO-2012118799 | A2 | 9/2012 | |
| WO | WO-2012154834 | A1 | 11/2012 | |
| WO | WO-2012155110 | A1 | 11/2012 | |
| WO | WO-2012166903 | A1 | 12/2012 | |
| WO | WO-2012168930 | A2 | 12/2012 | |
| WO | WO-2012178215 | A1 | 12/2012 | |
| WO | WO-2013040087 | A2 | 3/2013 | |
| WO | WO-2013067498 | A1 | 5/2013 | |
| WO | WO-2013086486 | A1 | 6/2013 | |
| WO | WO-2013086502 | A1 | 6/2013 | |
| WO | WO-2013093812 | A2 | 6/2013 | |
| WO | WO-2013096741 | A2 | 6/2013 | |
| WO | WO-2013127921 | A1 | 9/2013 | |
| WO | WO-2013155060 | A1 | 10/2013 | |
| WO | WO-2013174794 | A1 | 11/2013 | |
| WO | WO-2013176772 | A1 | 11/2013 | |
| WO | WO-2013192290 | A1 | 12/2013 | |
| WO | WO-2014013334 | A2 | 1/2014 | |
| WO | WO-2014018691 | A1 | 1/2014 | |
| WO | WO-2014048637 | A1 | 4/2014 | |
| WO | WO-2014053596 | A1 | 4/2014 | |
| WO | WO-2014062138 | A1 * | 4/2014 | ........... C12N 5/0603 |
| WO | WO-2014082096 | A1 | 5/2014 | |
| WO | WO-2014083132 | A1 | 6/2014 | |
| WO | WO-2014090993 | A1 | 6/2014 | |
| WO | WO-2014093595 | A1 | 6/2014 | |
| WO | WO-2014093622 | A2 | 6/2014 | |
| WO | WO-2014093655 | A2 | 6/2014 | |
| WO | WO-2014093661 | A2 | 6/2014 | |
| WO | WO-2014093712 | A1 | 6/2014 | |
| WO | WO-2014127170 | A1 | 8/2014 | |
| WO | 2014/151921 | * | 9/2014 | ............. C12N 5/071 |
| WO | 2014148646 | A1 | 9/2014 | |
| WO | WO-2014151921 | A1 * | 9/2014 | ................ A61P 1/16 |
| WO | WO-2014153230 | A1 | 9/2014 | |
| WO | WO-2014153294 | A1 | 9/2014 | |
| WO | WO-2014159356 | A1 | 10/2014 | |
| WO | WO-2014173907 | A1 | 10/2014 | |
| WO | WO-2014182885 | A2 | 11/2014 | |
| WO | WO-2014197934 | A1 | 12/2014 | |
| WO | WO-2014199622 | A1 | 12/2014 | |
| WO | WO-2014204728 | A1 | 12/2014 | |
| WO | WO-2014204729 | A1 | 12/2014 | |
| WO | WO-2015021358 | A2 | 2/2015 | |
| WO | WO-2015060790 | A1 | 4/2015 | |
| WO | WO-2015071474 | A2 | 5/2015 | |
| WO | WO-2015075175 | A1 | 5/2015 | |
| WO | WO-2015076388 | A1 | 5/2015 | |
| WO | WO-2015108893 | A1 | 7/2015 | |
| WO | WO-2015123183 | A1 | 8/2015 | |
| WO | WO-2015129822 | A1 | 9/2015 | |
| WO | WO-2015130919 | A1 | 9/2015 | |
| WO | WO-2015135893 | A1 | 9/2015 | |
| WO | WO-2015138032 | A2 | 9/2015 | |
| WO | WO-2015152954 | A1 | 10/2015 | |
| WO | WO-2015156929 | A1 | 10/2015 | |
| WO | WO-2015157163 | A1 | 10/2015 | |
| WO | WO-2015168022 | A1 | 11/2015 | |
| WO | WO-2015173425 | A1 | 11/2015 | |
| WO | 2015189320 | A1 | 12/2015 | |
| WO | WO-2015183920 | A2 | 12/2015 | |
| WO | WO-2015184273 | A1 | 12/2015 | |
| WO | WO-2015184375 | A2 | 12/2015 | |
| WO | WO-2015185714 | A1 | 12/2015 | |
| WO | WO-2015196012 | A1 | 12/2015 | |
| WO | WO-2015200901 | A1 | 12/2015 | |
| WO | 2016008895 | A1 | 1/2016 | |
| WO | WO-2016011377 | A1 | 1/2016 | |
| WO | WO-2016015158 | A1 | 2/2016 | |
| WO | WO-2016030525 | A1 | 3/2016 | |
| WO | WO-2016033163 | A1 | 3/2016 | |
| WO | WO-2016056999 | A1 | 4/2016 | |
| WO | WO-2016057571 | A1 | 4/2016 | |
| WO | WO-2016061464 | A1 | 4/2016 | |
| WO | WO-2016073989 | A2 | 5/2016 | |
| WO | WO-2016083612 | A1 | 6/2016 | |
| WO | WO-2016083613 | A2 | 6/2016 | |
| WO | WO-2016085765 | A1 | 6/2016 | |
| WO | WO-2016094948 | A1 | 6/2016 | |
| WO | WO-2016103002 | A1 | 6/2016 | |
| WO | WO-2016103269 | A1 | 6/2016 | |
| WO | WO-2016115326 | A1 | 7/2016 | |
| WO | WO-2016121512 | A1 | 8/2016 | |
| WO | 2016/141137 | * | 9/2016 | ........... A61K 35/545 |
| WO | 2016141131 | A1 | 9/2016 | |

(56) References Cited

FOREIGN PATENT DOCUMENTS

| | | | | |
|---|---|---|---|---|
| WO | 2016148253 | A1 | 9/2016 | |
| WO | WO-2016140716 | A1 | 9/2016 | |
| WO | WO-2016141084 | A1 | 9/2016 | |
| WO | WO-2016141137 | A1 * | 9/2016 | ........... A61K 35/545 |
| WO | WO-2016141224 | A1 | 9/2016 | |
| WO | WO-2016144769 | A1 | 9/2016 | |
| WO | WO-2016164413 | A1 | 10/2016 | |
| WO | WO-2016168950 | A1 | 10/2016 | |
| WO | WO-2016174604 | A1 | 11/2016 | |
| WO | WO-2016176208 | A1 | 11/2016 | |
| WO | WO-2016183143 | A1 | 11/2016 | |
| WO | 2016204809 | A1 | 12/2016 | |
| WO | 2016210322 | A1 | 12/2016 | |
| WO | WO-2016193441 | A2 | 12/2016 | |
| WO | WO-2016207621 | A1 | 12/2016 | |
| WO | WO-2016210313 | A1 | 12/2016 | |
| WO | WO-2016210416 | A2 | 12/2016 | |
| WO | WO-2017009263 | A1 | 1/2017 | |
| WO | WO-2017023803 | A1 | 2/2017 | |
| WO | WO-2017036533 | A1 | 3/2017 | |
| WO | WO-2017037295 | A1 | 3/2017 | |
| WO | WO-2017041041 | A1 | 3/2017 | |
| WO | WO-2017048193 | A1 | 3/2017 | |
| WO | WO-2017048322 | A1 | 3/2017 | |
| WO | WO-2017049243 | A1 | 3/2017 | |
| WO | WO-2017059171 | A1 | 4/2017 | |
| WO | WO-2017060884 | A1 | 4/2017 | |
| WO | WO-2017066507 | A1 | 4/2017 | |
| WO | WO-2017066659 | A1 | 4/2017 | |
| WO | WO-2017070007 | A2 | 4/2017 | |
| WO | WO-2017070224 | A1 | 4/2017 | |
| WO | WO-2017070337 | A1 | 4/2017 | |
| WO | WO-2017070471 | A1 | 4/2017 | |
| WO | WO-2017070506 | A1 | 4/2017 | |
| WO | WO-2017070633 | A2 | 4/2017 | |
| WO | 2017083696 | A1 | 5/2017 | |
| WO | WO-2017075389 | A1 | 5/2017 | |
| WO | WO-2017077535 | A1 | 5/2017 | |
| WO | WO-2017079632 | A1 | 5/2017 | |
| WO | WO-2017083705 | A1 | 5/2017 | |
| WO | WO-2017083838 | A1 | 5/2017 | |
| WO | WO-2017096192 | A1 | 6/2017 | |
| WO | WO-2017096282 | A1 | 6/2017 | |
| WO | WO-2017112901 | A1 | 6/2017 | |
| WO | WO-2017115982 | A1 | 7/2017 | |
| WO | WO-2017117333 | A1 | 7/2017 | |
| WO | WO-2017117547 | A1 | 7/2017 | |
| WO | WO-2017117571 | A1 | 7/2017 | |
| WO | WO-2017120543 | A1 | 7/2017 | |
| WO | WO-2017121754 | A1 | 7/2017 | |
| WO | WO-2017123791 | A1 | 7/2017 | |
| WO | 2017136162 | A1 | 8/2017 | |
| WO | WO-2017136462 | A2 | 8/2017 | |
| WO | WO-2017136479 | A1 | 8/2017 | |
| WO | WO-2017139455 | A1 | 8/2017 | |
| WO | WO-2017139638 | A1 | 8/2017 | |
| WO | WO-2017142069 | A1 | 8/2017 | |
| WO | WO-2017143100 | A1 | 8/2017 | |
| WO | WO-2017149025 | A1 | 9/2017 | |
| WO | WO-2017153992 | A1 | 9/2017 | |
| WO | WO-2017160234 | A1 | 9/2017 | |
| WO | WO-2017160671 | A1 | 9/2017 | |
| WO | WO-2017172638 | A1 | 10/2017 | |
| WO | WO-2017174609 | A1 | 10/2017 | |
| WO | WO-2017175876 | A1 | 10/2017 | |
| WO | WO-2017176810 | A1 | 10/2017 | |
| WO | WO-2017184586 | A1 | 10/2017 | |
| WO | WO-2017192997 | A1 | 11/2017 | |
| WO | WO-2017205511 | A1 | 11/2017 | |
| WO | WO-2017218287 | A1 | 12/2017 | |
| WO | WO-2017220586 | A1 | 12/2017 | |
| WO | WO-2018011558 | A1 | 1/2018 | |
| WO | WO-2018019704 | A1 | 2/2018 | |
| WO | WO-2018026947 | A1 | 2/2018 | |
| WO | WO-2018027023 | A1 | 2/2018 | |
| WO | WO-2018027112 | A1 | 2/2018 | |
| WO | WO-2018035574 | A1 | 3/2018 | |
| WO | WO-2018038042 | A1 | 3/2018 | |
| WO | WO-2018044685 | A1 | 3/2018 | |
| WO | WO-2018044885 | A1 | 3/2018 | |
| WO | WO-2018044937 | A2 | 3/2018 | |
| WO | WO-2018044940 | A1 | 3/2018 | |
| WO | WO-2018085615 | A1 | 5/2018 | |
| WO | WO-2018085622 | A1 | 5/2018 | |
| WO | WO-2018085623 | A1 | 5/2018 | |
| WO | WO-2018091677 | A1 | 5/2018 | |
| WO | WO-2018094522 | A1 | 5/2018 | |
| WO | WO-2018106628 | A1 | 6/2018 | |
| WO | WO-2018115852 | A1 | 6/2018 | |
| WO | 2018170280 | A1 | 9/2018 | |
| WO | WO-2018191673 | A1 | 10/2018 | |
| WO | 2018207714 | A1 | 11/2018 | |
| WO | WO-2018197544 | A1 | 11/2018 | |
| WO | WO-2018200481 | A1 | 11/2018 | |
| WO | WO-2018226267 | A1 | 12/2018 | |
| WO | WO-2018229251 | A1 | 12/2018 | |
| WO | WO-2019060336 | A1 | 3/2019 | |
| WO | WO-2019074793 | A1 | 4/2019 | |
| WO | WO-2019126626 | A1 | 6/2019 | |
| WO | 2019140151 | A1 | 7/2019 | |
| WO | WO-2020023245 | A1 | 1/2020 | |
| WO | WO-2020056158 | A1 | 3/2020 | |
| WO | WO-2020069285 | A1 | 4/2020 | |
| WO | 2020097369 | A1 | 5/2020 | |
| WO | WO-2020100481 | A1 | 5/2020 | |
| WO | WO-2020154374 | A1 | 7/2020 | |
| WO | WO-2020160371 | A1 | 8/2020 | |
| WO | WO-2020227711 | A1 | 11/2020 | |
| WO | 2020243613 | A1 | 12/2020 | |
| WO | WO-2020243633 | A1 | 12/2020 | |
| WO | WO-2020247528 | A1 | 12/2020 | |
| WO | WO-2021030373 | A1 | 2/2021 | |
| WO | WO-2021041443 | A2 | 3/2021 | |
| WO | 2021087508 | A1 | 5/2021 | |
| WO | WO-2021262676 | A1 | 12/2021 | |
| WO | 2022111571 | A1 | 6/2022 | |
| WO | 2022261471 | A2 | 12/2022 | |
| WO | 2023278676 | A1 | 1/2023 | |
| WO | 2023023180 | A1 | 2/2023 | |
| WO | WO-2023030158 | A1 | 3/2023 | |
| WO | 2023102133 | A1 | 6/2023 | |
| WO | 2024063531 | A1 | 3/2024 | |
| WO | 2024063999 | A1 | 3/2024 | |

OTHER PUBLICATIONS

Ajmera V., et al., "Novel Plasma Biomarkers Associated with Liver Disease Severity in Adults with Nonalcoholic Fatty Liver Disease," Hepatology, Jan. 2017, vol. 65 (1), pp. 65-77.

Aleo M.D., et al., "Human Drug-Induced Liver Injury Severity is Highly Associated with Dual Inhibition of Liver Mitochondrial Function and Bile Salt Export Pump," Hepatology, 2014, vol. 60 (3), pp. 1015-1022.

Alessi D.R., et al., "LKB1-Dependent Signaling Pathways," Annual Review of Biochemistry, 2006, vol. 75, pp. 137-163.

Allard J., et al., "Immunohistochemical Toolkit for Tracking and Quantifying Xenotransplanted Human Stem Cells," Regenerative Medicine, 2014, vol. 9(4), pp. 437-452.

Altman G. H., et al., "Cell Differentiation by Mechanical Stress," The FASEB Journal, 2001, vol. 16 (2), pp. 270-272.

Ameri J., et al., "FGF2 Specifies HESC-Derived Definitive Endoderm into Foregut/Midgut Cell Lineages in a Concentration-Dependent Manner," Stem Cells, Nov. 2009, vol. 28 (1), pp. 45-56.

Amieva M.R., et al., "Helicobacter Pylori Enter and Survive within Multivesicular Vacuoles of Epithelial cells," Cellular Microbiology, Oct. 4, 2002, vol. 4 (10), pp. 677-690.

An W.F, et al., "Discovery of Potent and Highly Selective Inhibitors of GSK3b," Molecular Libraries, Probe Report, May 2014, 115 Pages.

Anderson G., et al., "Loss of Enteric Dopaminergic Neurons and Associated Changes in Colon Motility in an MPTP Mouse Model of Parkinson's Disease," Experimental Neurology, Sep. 2007, vol. 207 (4-12), 16 pages.

(56) References Cited

OTHER PUBLICATIONS

Andrews P.W., et al., “Embryonic Stem (ES) cells and Embryonal Carcinoma (EC) Cells: Opposite Sides of the same Coin” Biochemical Society Transactions, 2005, vol. 33 (6), pp. 1526-1530.
Ang S.L., et al., “The Formation and Maintenance of the Definitive Endoderm Lineage in the Mouse: Involvement of HNF3/Forkhead Proteins,” Development, Company of Biologist Limited, 1993, vol. 119, pp. 1301-1315.
Anlauf M., et al., “Chemical Coding of the Human Gastrointestinal Nervous System: Cholinergic, VIPergic, and Catecholaminergic Phenotypes,” The Journal of Comparative Neurology, 2003, vol. 459, pp. 90-111.
Aronson B.E., et al., “GATA4 Represses an ileal Program of Gene Expression in the Proximal Small Intestine by Inhibiting the Acetylation of Histone H3, Lysine 27,” Biochimica et Biophysica Acta, Nov. 2014, vol. 1839 (11), pp. 1273-1282.
Arora N., et al., “A Process Engineering Approach to Increase Organoid Yield,” Technical and Resources, 2017, vol. 144, pp. 1128-1136.
Arroyo J.D., et al., “Argonaute2 Complexes Carry a Population of Circulating MicroRNAs Independent of Vesicles in Human Plasma,” PNAS, 2011, vol. 108 (12), pp. 5003-5008.
Asai A., et al., “Paracrine Signals Regulate Human Liver Organoid Maturation from Induced Pluripotent Stem Cells,” Human Development, 2017, vol. 144, pp. 1056-1064.
Aurora M., et al., “HPSC-Derived Lung and Intestinal Organoids as Models of Human Fetal Tissue,” Developmental Biology, 2016, vol. 420, pp. 230-238.
Avansino J.R., et al., “Orthotopic Transplantation of Intestinal Mucosal Organoids in Rodents,” Surgery, Sep. 2006, vol. 140 (3), pp. 423-434.
Baetge G., et al., “Transient Catecholaminergic (TC) Cells in the Vagus Nerves and Bowel of Fetal Mice: Relationship to the Development of Enteric Neurons,” Developmental Biology, 1989, vol. 132, pp. 189-211.
Halpern K.B., et al., “Single-cell Spatial Reconstruction Reveals Global Division of Labor in the Mammalian Liver,” Nature, 2017, vol. 542, No. 7641, pp. 352-356.
Bain G., “Embryonic Stem Cells Express Neuronal Properties in Vitro,” Developmental Biology, 1995, vol. 168, pp. 842-357.
Bajpai R., et al., “CHD7 Cooperates with PBAF to Control Multipotent Neural Crest Formation,” Nature, Feb. 18, 2010, vol. 463, pp. 958-962.
Bansal D., et al., “An Ex-Vivo Human Intestinal Model to Study Entamoeba Histolytica Pathogenesis,” PLoS Neglected Tropical Diseases, Nov. 17, 2009, vol. 3 (11), 11 pages.
Baptista P.M., et al., “The Use of Whole Organ Decellularization for the Generation of a Vascularized Liver Organoid,” Hepatology, 2011, vol. 53 (2), pp. 604-617.
Bar-Ephraim Y.E., et al., “Modelling Cancer Immunomodulation using Epithelial Organoid Cultures,” bioRxiv, Aug. 7, 2018, pp. 1-13.
Barker N., et al., “Lgr5$^{+ve}$ Stem Cells Drive Self-Renewal in the Stomach and Build Long-Lived Gastric Units In Vitro,” Cell Stem Cell, Jan. 8, 2010, vol. 6, pp. 25-36.
Barker N., et al., “Tissue-Resident Adult Stem Cell Populations of Rapidly Self-Renewing Organs,” Cell Stem Cell, Dec. 3, 2010, vol. 7, pp. 656-670.
Barlow A.J., et al., “Critical Nos. of Neural Crest Cells are Required in the Pathways from the Neural Tube to the Foregut to Ensure Complete Enteric Nervous System Formation,” Development, 2008, vol. 135, pp. 1681-1691.
Bartfeld S., et al., “In Vitro Expansion of Human Gastric Epithelial Stem Cells and Their Responses to Bacterial Infection,” Gastroenterology, Jan. 2015, vol. 148 (1), pp. 126-136.
Bartfeld S., et al., “Stem Cell-Derived Organoids and their Application for Medical Research and Patient Treatment,” Journal of Molecular Medicine, 2017, vol. 95, pp. 729-738.
Barth CA., et al., “Transcellular Transport of Fluorescein in Hepatocyte Monolayers: Evidence for Functional Polarity of Cells in Culture,” Proceedings of the National Academy of Sciences USA, 1982, vol. 79, pp. 4985-4987.
Bastide P., et al., “Sox9 Regulates Cell Proliferation and is required for Paneth Cell Differentiation in the Intestinal Epithelium,” JCB, 2007, vol. 178, Issue 4, pp. 635-648.
Battle M A., et al., “GATA4 is Essential for Jejunal Function in Mice,” Gastroenterology, 2008, vol. 135, pp. 1676-1686.
Baumann K., “Colonic Organoids for Drug Testing and Colorectal Disease Modelling,” Nature Reviews Molecular Cell Biology, Jul. 2017, vol. 18, No. 8, p. 467.
Beck F, et al., “Expression of Cdx-2 in the Mouse Embryo and Placenta: Possible Role in Patterning of the Extra-Embryonic Membranes,” Dev Dyn, 1995, vol. 204, pp. 219-227.
Begriche K., et al., “Drug-induced Toxicity on Mitochondria and Lipid Metabolism: Mechanistic Diversity and Deleterious Consequences for the Liver,” Journal of Hepatology, 2011, vol. 54, pp. 773-794.
Bell L.N., et al., “Epidemiology of Idiosyncratic Drug-Induced Liver Injury,” Seminars in Liver Disease, 2009, vol. 29, Issue 4, pp. 337-347.
Bergeles C, et al., “From Passive Tool Holders to Microsurgeons: Safer, Smaller, Smarter Surgical Robots,” IEEE Transactions on Biomedical Engineering, 2014, vol. 61, Issue 5, pp. 1565-1576.
Bergner A.J., et al., “Birthdating of Myenteric Neuron Subtypes in the Small Intestine of the Mouse,” The Journal of Comparative Neurology, 2014, vol. 522, pp. 514-527.
Bernadi P., “The Permeability Transition Pore. Control Points of a Cyclosporin A-Sensitive Mitochondrial Channel Involved in Cell Death,” Biochimica et Biophysica Acta, 1996, vol. 1275, pp. 5-9.
Bernstein B.E., et al., “The NIH Roadmap Epigenomics Mapping Consortium,” Nature Biotechnology, 2010, vol. 28, Issue 10, pp. 1045-1048.
Beuling E., et al., “Co-Localization of Gata4 and Hnfl alpha in the Gastrointestinal Tract is Restricted to the Distal Stomach and Proximal Small Intestine,” Gastroenterology, AGA Abstracts, Abstract T1933, 2007, vol. 132, p. A586.
Beuling E., et al., “Conditional Gata4 Deletion in Mice Induces Bile Acid absorption in the Proximal Small Intestine,” Gut, 2010, vol. 59, Issue 7, pp. 888-895.
Beuling E., et al., “Fog Cofactors Partially Mediate Gata4 Function in the Adult Mouse Small Intestine,” Gastroenterology, AGA Abstracts, Abstract W1467, 2007, vol. 132, pp. A692-A693.
Beuling E., et al., “GATA4 Mediates Gene Repression in the Mature Mouse Small Intestine through Interactions with Friend of GATA (FOG) Cofactors,” Developmental Biology, 2008, vol. 322, Issue 1, pp. 179-189.
Beuling E., et al., “The Absence of GATA4 in the Distal Small Intestine Defines the Ileal Phenotype,” Gastroenterology, ABA Abstract, Abstract 602, 2008, vol. 134, pp. A83-A84.
Bharadwaj S., et al., “Current Status of Intestinal and Multivisceral Transplantation,” Gastroentrerol Rep (Oxf), 2017, vol. 5, Issue 1, pp. 20-28.
Bhutani N., et al., “Reprogramming towards Pluripotency Requires AID-Dependent DNA Demethylation,” Nature, 2010, vol. 463, Issue 7284, pp. 1042-1047.
Bitar K.N., et al., “Intestinal Tissue Engineering: Current Concepts and Future Vision of Regenerative Medicine in the Gut,” Neurogastroenterology & Motility, Jan. 2012, vol. 24, Issue 1, pp. 7-19.
Blaugrund E., et al., “Distinct Subpopulations of Enteric Neuronal Progenitors Defined by Time of Development, Sympathoadrenal Lineage Markers and Mash-1-Dependence,” Development, vol. 122, 1996, pp. 309-320.
Bohan T.P., et al., “Effect of L-Carnitine Treatment for Valproate-Induced Hepatotoxicity,” Neurology, 2001, vol. 56, pp. 1405-1409.
Bohorquez D.V., et al., “An Enteroendocrine Cell-Enteric Glia Connection Revealed by 3D Electron Microscopy,” PLOS One, Feb. 2014, vol. 9, Issue 2, e89881, 13 pages.
Bonilla-Claudio M., et al., “Bmp Signaling Regulates a Dose-Dependent Transcriptional Program to Control Facial Skeletal Development,” Development, 2012, vol. 139, pp. 709-719.

(56) References Cited

OTHER PUBLICATIONS

Boroviak T., et al., "Single Cell Transcriptome Analysis of Human, Marmoset and Mouse Embryos Reveals Common and Divergent Features of Preimplantation Development," Development, 2018, vol. 145, Issue 21, 18 pages.
Bort R., et al., "Diclofenac Toxicity to Hepatocytes: A Role for Drug Metabolism in Cell Toxicity," Journal of Pharmacology and Experimental Therapeutics, 1998, vol. 288, Issue 1 , pp. 65-72.
Bosse T., et al., "Gata4 and Hnfl Alpha are partially required for the Expression of Specific Intestinal Genes during Development," American Journal of Physiology: Gastrointestinal and Liver Physiology, May 2007, vol. 292, pp. G1302-G1314.
Bouchi R., et al., "FOXO1 Inhibition Yields Functional Insulin-Producing Cells in Human Gut Organoid Cultures," Nature Communications, 2014, vol. 5, Issue 4242, 24 pages.
Boullata J.I., et al., "A.S.P.E.N. Clinical Guidelines: Parental Nutrition Ordering, Order Review, Compounding, Labeling and Dispensing," The Journal of Parenteral and Enteral Nutrition, 2014, vol. 38, Issue 3, pp. 334-377.
Bragdon B., et al., "Bone Morphogenetic Proteins: A Critical Review," Cellular Signalling, 2011, vol. 23, pp. 609-620.
Bravo P., et al., "Efficient In Vitro Vectorial Transport of a Fluorescent Conjugated Bile Acid Analogue by Polarized Hepatic Hybrid WIF-B and WIF-B9 Cells," Hepatology, 1998, vol. 27, pp. 576-583.
Brevini T.A.L et al., "No shortcuts to Pig Embryonic Stem Cells," Theriogenology, 2010, vol. 74, pp. 544-550.
Broda T.R., et al., "Generation of Human Antral and Fundic Gastric Organoids from Pluripotent Stem Cells," Nature Protocols, Nov. 2018. vol. 14(1), pp. 28-50.
Browning J.D., et al., "Molecular Mediators of Hepatic Steatosis and Liver Injury," Journal of Clinical Investigation, 2004, vol. 114, Issue 2, pp. 147-152.
Bruens L., et al., "Expanding the Tissue Toolbox: Deriving Colon Tissue from Human Pluripotent Stem Cells," Cell Stem Cell, Jul. 2017, vol. 21, Issue 1, pp. 3-5.
Brugmann S.A., et al., "Building Additional Complexity to in Vitro-Derived Intestinal Tissues," Stem Cell Research & Therapy, 2013, vol. 4, Issue Suppl 1, p. S1, 5 pages.
Burke P., et al., "Towards a Single-Chip, Implantable RFID System: is a Single-Cell Radio Possible?," Biomed Microdevices, 2010, vol. 12, pp. 589-596.
Burn S.F, et al., "Left-right Asymmetry in Gut Development: what happens next?," BioEssays, 2009, vol. 31, pp. 1026-1037.
Burnicka-Turek O., et al., "INSL5-Deficient Mice Display an Alteration in Glucose Homeostasis and an Impaired Fertility," Endocrinology, Oct. 2012, vol. 153, Issue 10, pp. 4655-4665.
Burns A J., et al., "In Ovo Transplantation of Enteric Nervous System Precursors From Vagal to Sacral Neural Crest Results in Extensive Hindgut Colonisation," Development, 2002, Issue 129, pp. 2785-2796.
Burns A J., et al., "Neural Stem Cell Therapies for Enteric Nervous System Disorders," Nature Reviews/Gastroenterology & Hepatology, May 2014, Issue11, pp. 317-328.
Burns A.J., et al., "Enteric Nervous System Development: Analysis of the Selective Developmental Potentialities of Vagal and Sacral Neural Crest Cells using Quail-Chick Chimeras," The Anatomical Record, 2001, vol. 262, pp. 16-28.
Burrin D., et al., "Enteral Obeticholic Acid Prevents Hepatic Cholestasis in Total Parenteral Nutrition-Fed Neonatal Pigs," Hepatology, vol. 62, Oct. 2015, p. 307A.
Buta C, et al., "Reconsidering Pluripotency Tests: Do We Still Need Teratoma Assays?," Stem Cell Research, 2013, vol. 11, pp. 552-562 (11 pages).
Cabezas J., et al., "Nonalcoholic Fatty Liver Disease: A Pathological View," Chapter 8, in Liver Biopsy—Indications, Procedures Results, N. Tagaya (Ed.), InTechOpen, Nov. 21, 2012, pp. 161-188.
Campbell FC, et al., "Transplantation of Cultured Small Bowel Enterocytes," Gut, Sep. 1993, vol. 34, Issue 9, pp. 1153-1155.
Caneparo L., et al., "Intercellular Bridges in Vertebrate Gastrulation," PloS ONE, 2011, vol. 6, Issue 5, e20230, 6 pages.
Cao L., et al., "Development of Intestinal Organoids as Tissue Surrogates: Cell Composition and the Epigenetic Control of Differentiation," Molecular Carcinogenesis, 2015, vol. 54, pp. 189-202.
Capeling M.M., et al., "Nonadhesive Alginate Hydrogels Support Growth of Pluripotent Stem Cell-Derived Intestinal Organoids," Stem Cell Reports, Feb. 2019, vol. 12, Issue 2, pp. 381-394.
Chai P.R., et al., "Ingestible Biosensors for Real-Time Medical Adherence Monitoring: MyTMed," Processing Hawaii International Conference on System Sciences, Jan. 2016, pp. 3416-3423.
CHAI p. R., et al., "Utilizing an Ingestible Biosensor to Assess Real-Time Medication Adherence," Journal of Medical Toxicology, 2015, vol. 11, pp. 439-444.
Chang H.M., et al., "BMP15 Suppresses Progesterone Production by Down-Regulating STAR via ALK3 in Human Granulosa Cells," Molecular Endocrinology, 2013, vol. 27, pp. 2093-2104.
Chang J.H., et al., "Evaluating the In Vitro Inhibition of UGT1A1, OATP1B1, OATP1B3, MRP2, and BSEP in Predicting Drug-Induced Hyperbilirubinemia," Molecular Pharmaceutics, 2013, vol. 10, pp. 3067-3075.
Chatterjee S., et al., "Hepatocyte-Based in Vitro Model for Assessment of Drug-Induced Cholestasis," Toxicology and Applied Pharmacology, 2014, vol. 274, pp. 124-136.
Chauhan R.K., et al., "Genetic and Functional Studies of Hirschsprung Disease," Doctoral Thesis: Department of Clinical Genetics, Erasmus University Rotterdam, the Netherlands, 2016, 202 pages.
Chen B., et al., "Dynamic Imaging of Genomic Loci in Living Human Cells by an Optimized CRISPR/Cas System," Cell, 2013, vol. 155, Issue 7, pp. 1479-1491.
Chen C., et al., "Pdx1 Inactivation Restricted to the Intestinal Epithelium in Mice alters Duodenal Gene Expression in Enterocytes and Enteroendocrine Cells," American Journal of Physiology Gastrointestinal and Liver Physiology, 2009, vol. 297, pp. G1126-G1137.
Chen L.Y., et al., "Mass Fabrication and Delivery of 3D Multilayer μTags into Living cells," Scientific Reports, 2013, vol. 3, Issue 2295, 6 pages.
Chen T.W., et al., "Ultrasensitive Fluorescent Proteins for Imaging Neuronal Activity," Nature, Jul. 18, 2013, vol. 499, pp. 295-300.
Chen Y., et al., "Retinoic Acid Signaling is Essential for Pancreas Development and Promotes Endocrine at the Expense of Exocrine Cell Differentiation in Xenopus," Developmental Biology, 2004, vol. 271, pp. 144-160.
Cheng X., et al., "Self-Renewing Endodermal Progenitor Lines Generated from Human Pluripotent Stem Cells," Cell Stem Cell, Apr. 6, 2012, vol. 10, pp. 371-384.
Choi E., et al., "Cell Lineage Distribution Atlas of the Human Stomach Reveals Heterogeneous Gland Populations in the Gastric Antrum," Gut, 2014, vol. 63, Issue 11, pp. 1711-1720.
Choi E., et al., "Expression of Activated Ras in Gastric Chief Cells of Mice Leads to the Full Spectrum of Metaplastic Lineage Transitions". Gastroenterology, Apr. 2016, vol. 150, Issue 4, pp. 918-930.
Christoffersson J., et al., "Developing Organ-on-a-chip Concepts Using Bio-Mechatronic Design Methodology," Biofabrication, May 26, 2017, vol. 9, Issue 2, 14 pages.
Chughlay M.F., et al., "N-Acetylcysteine for Non-Paracetamol Drug-Induced Liver Injury: a Systematic Review," British Journal of Clinical Pharmacology, 2016, vol. 81, pp. 1021-1029.
Churin Y., et al., "Helicobacter Pylori CagA Protein Targets the c-Met Receptor and Enhances the Motogenic Response," Journal of Cell Biology, 2003, vol. 161, No. 2, pp. 249-255.
Cieslar-Pobuda A., et al., "The Expression Pattern of PFKFB3 Enzyme Distinguishes Between Induced-Pluripotent Stem Cells and Cancer Stem Cells," Oncotarget, Aug. 13, 2015, vol. 6, Issue 30, pp. 29753-29770.
Cincinnati Children's Hospital Medical Center, "Scientists Grow Human Esophagus in Lab: Tiny Organoids Enable Personalized Disease Diagnosis, Regenerative Therapies," CCHMC Public Press Release, Sep. 20, 2018, 2 pages.
Clarke L.L., "A Guide to Using Chamber Studies of Mouse Intestine," American Journal of Physiology: Gastrointestinal and Liver Physiology, Jun. 2009, vol. 296, issue 6, pp. G1151-G1166.

(56) References Cited

OTHER PUBLICATIONS

Clevers H., "Modeling Development and Disease with Organoids," Cell, Jun. 16, 2016, vol. 165, Issue 7, pp. 1586-1597.
Coghlan M., et al., "Selective Small Molecule Inhibitors of Glycogen Synthase Kinase-3 Modulate Glycogen Metabolism and Gene Transcription," Chemistry & Biology, Oct. 2000, vol. 7, Issue 10, pp. 793-803.
Collier A.J., et al., "Comprehensive Cell Surface Protein Profiling Identifies Specific Markers of Human Naive and Primed Pluripotent States," Cell Stem Cell, Jun. 1, 2017, vol. 20, pp. 874-890.
Correria C., et al., "Combining Hypoxia and Bioreactor Hydrodynamics Boosts Induced Pluripotent Stem Cell Differentiation towards Cardiomyocytes," Stem Cell Reviews and Reports, Dec. 2014, vol. 10, pp. 786-801.
Cortez a R., et al., "Transplantation of Human Intestinal Organoids into the Mouse Mesentery: A More Physiological and Anatomic Engraftment Site," Surgery, 2018, vol. 164, pp. 643-650.
Costa M., et al., "A Method for Genetic Modification of Human Embryonic Stem Cells using Electroporation," Nature Protocols, Apr. 5, 2007, vol. 2, pp. 792-796.
Couzin J., "Small RNAs Make Big Splash," Science, Dec. 20, 2002, vol. 298, pp. 2296-2297.
Covacci A., et al., "Molecular Characterization of the 128-kDa Immunodominant Antigen of Helicobacter Pylori Associated with Cytotoxicity and Duodenal Ulcer," Proceedings of the National Academy of Sciences USA, Jun. 15, 1993, vol. 90, pp. 5791-5795.
Crespo M., et al., "Colonic Organoids Derived from Human Induced Pluripotent Stem Cells for Modeling Colorectal Cancer and Drug Testing," Nature Medicine, vol. 23, No. 7, Jun. 19, 2017, pp. 878-884.
Crocenzi FA., et al., "$Ca^{2+}$-Dependent Protein Kinase C Isoforms are Critical to Estradiol 17beta-D-Glucuronide-Induced Cholestasis in the Rat," Hepatology, Dec. 2008, vol. 48, pp. 1885-1895.
Cunningham T.J., et al., "Mechanisms of Retinoic Acid Signalling and its Roles in Organ and Limb Development," Nature Reviews Molecular Cell Biology, vol. 16, No. 2, Jan. 5, 2015, pp. 110-123.
Curchoe CL., et al., "Early Acquisition of Neural Crest Competence During hESCs Neuralization," PloS One, Nov. 2010, vol. 5, pp. 1-17.
Cutrin J.C., et al., "Reperfusion Damage to the Bile Canaliculi in Transplanted Human Liver," Hematology, 1996, vol. 24, pp. 1053-1057.
Dahl A., et al., "Translational Regenerative Medicine-Hepatic Systems," Chapter 34, Clinical Aspects of Regenerative Medicine, eds. A. Atala, M.D. and J. Allickson, PhD, Elsevier, Inc, 2015, pp. 469-484.
D'amour K A., et al., "Production of Pancreatic Hormone-Expressing Endocrine Cells from Human Embryonic Stem Cells," Nature Biotechnology, 2006, vol. 24, pp. 1392-1401.
D'amour K.A et al., "Efficient Differentiation of Human Embryonic Stem Cells to Definitive Endoderm," Nature Biotechnology, Dec. 2005, vol. 23, No. 12, pp. 1534-1541.
Das R., "RFID Forecasts, Players and Opportunities 2017-2027," IDTechEx, 2017, downloaded from https://www.idtechex.com/en/research-report/rfid-forecasts-players-and-opportunities-2017-2027/546, 8 pages.
Dash A., et al., "Pharmacotoxicology of Clinically-Relevant Concentrations of Obeticholic Acid in an Organotypic Human Hepatocyte System," Toxicol in Vitro, 2017, vol. 39, pp. 93-103.
Date S., et al., "Mini-Gut Organoids: Reconstitution of the Stem Cell Niche," Annual Review of Cell and Developmental Biology, Nov. 2015, vol. 31, pp. 269-289.
Davenport C., et al., "Anterior-Posterior Patterning of Definitive Endoderm Generated from Human Embryonic Stem Cells Depends on the Differential Signaling of Retinoic Acid, Wnt-, and BMP-Signaling," Stem Cells, 2016, vol. 34, pp. 2635-2647.
Davidson M.D., et al., "Long-Term Exposure to Abnormal Glucose Levels Alters Drug Metabolism Pathways and Insulin Sensitivity in Primary Human Hepatocytes," Scientific Reports, 2016, vol. 6, 28178, 11 pages.
De Santa Barbara P., et al., "Bone Morphogenetic Protein Signaling Pathway Plays Multiple Roles During Gastrointestinal Tract Development," Developmental Dynamics, 2005, vol. 234, pp. 312-322.
De Santa Barbara P., et al., "Development and Differentiation of the Intestinal Epithelium," Cellular and Molecular Life Sciences, 2003, vol. 60, issue 7, pp. 1322-1332.
DEDHIA p. H., et al., "Organoid Models of Human Gastrointestinal Development and Disease," Gastroenterology, Jan. 14, 2016, vol. 150, pp. 1098-1112 (15 pages).
Dekaney C.M., et al., "Expansion of Intestinal Stem Cells Associated with Long-Term Adaptation Following lleocecal Resection in Mice," American Journal of Physiology: Gastrointestinal and Liver Physiology, Sep. 13, 2007, vol. 293, pp. G1013-G1022.
Dekkers J F, et al., "A Functional CFTR Assay Using Primary Cystic Fibrosis Intestinal Organoids," Nature Medicine, vol. 19, No. 7, Jul. 2013, pp. 939-945.
Demehri F.R., et al., "Development of an Endoluminal Intestinal Lengthening Device using a Geometric Intestinal Attachment Approach," Surgery, 2015, vol. 158, pp. 802-811.
Demehri F.R., et al., "Development of an Endolurninal Intestinal Attachment for Clinically Applicable Distraction Enterogenesis Device," Journal of Pediatric Surgery, Jan. 2016, vol. 51, pp. 101-106.
Deng H., et al., "Effects of All-Trans Retinoic Acid on the Differentiation of Neural Stem Cells and the Expression of c-myc Gene," Chinese Journal of Tissue Engineering Research, Mar. 18, 2007, vol. 11, pp. 2039-2042.
Deng H., "Mechanisms of Retinoic Acid on the Induction of Differentiation of Neural Stem Cells for Newborn Rat Striatum," Chinese Doctoral and Master Dissertations Full-Text Database (Doctoral) Basic Science, Issue 4, May 20, 2005, pp. 1-91. (Translation).
Denham M., et al., "Multipotent Caudal Neural Progenitors derived from Human Pluripotent Stem Cells that give Rise to Lineages of the Central and Peripheral Nervous System," Stem Cells, Mar. 5, 2015, vol. 33, pp. 1759-1770.
Dessimoz J., et al., "FGF Signaling is Necessary for Establishing Gut Tube Domains along the Anterior-Posterior Axis in Vivo," Mech Dev, 2006, vol. 123, pp. 42-55.
DeWard A.D., et al., "Cellular Heterogeneity in the Mouse Esophagus Implicates the Presence of a Nonquiescent Epithelial Stem Cell Population," Cell Reports, Oct. 23, 2014, vol. 9, No. 2, pp. 701-711.
Discher D.E., et al., "Growth Factors, Matrices, and Forces Combine and Control Stem Cells," Science, Jun. 2009, vol. 324, pp. 1673-1677.
Dobreva G., et al., "SATB2 Is a Multifunctional Determinant of Craniofacial Patterning and Osteoblast Differentiation," Cell, 2006, vol. 125, Issue 5, pp. 971-986.
Driver I., et al., "Specification of regional intestinal stem cell identity during *Drosophila* metamorphosis," Development, 2014, vol. 141, pp. 1848-1856.
Duluc I., et al., "Fetal Endoderm Primarily Holds the Temporal and Positional Information Required for Mammalian Intestinal Development," The Journal of Cell Biology, 1994, vol. 126, pp. 211-221.
Dumortier G., et al., "Tolérance hépatique des antipsychotiques atypiques, [Hepatic Tolerance of Atypical Antipsychotic Drugs]," L'Encephale, 2002, vol. 28, pp. 542-551.
Dunn, "Cationic Nanoparticles for the Targeting and Delivery of Nucleic Acids to the Pulmonary Endothelium," University of Cincinnati, Sep. 19, 2018, Doctoral Thesis; downloaded from https://etd.ohiolink.edu/apexprod/rws_olink/r/1501/10?clear=10&p10_accession_num=ucin1544098242321181; 160 pages.
Dvir-Ginzberg M., et al., "Liver Tissue Engineering within Alginate Scaffolds: Effects of Cell-Seeding Density on Hepatocyte Viability, Morphology, and Function," Tissue Engineering, 2003, vol. 9, pp. 757-766.
Eberhard J., et al., "A Cohort Study of the Prognostic and Treatment Predictive Value of SATB2 Expression in Colorectal Cancer," British Journal of Cancer, 2012, vol. 106, pp. 931-938.
Edling Y., et al., "Increased Sensitivity for Troglitazone-Induced Cytotoxicity using a Human in Vitro Co-Culture Model," Toxicol in Vitro, 2009, vol. 23, pp. 1387-1395.

(56) References Cited

OTHER PUBLICATIONS

Eicher A.K., et al., "Translating Developmental Principles to Generate Human Gastric Organoids," Cellular and Molecular Gastroenterology and Hepatology, 2018, vol. 5, pp. 353-363.
Ekser B., et al., "Comparable Outcomes in Intestinal Retransplantation: Single-Center Cohort Study," The Journal of Clinical and Translational Research, 2018, vol. 32, e13290, 10 pages.
El Kasmi K.C., et al., "Phytosterols Promote Liver Injury and Kupffer Cell Activation in Parenteral Nutrition-Associated Disease," Science Translational Medicine, 2013, vol. 5, 206ra137, 10 pages.
El Taghdouini A., et al., "In Vitro Reversion of Activated Primary Human Hepatic Stellate Cells," Fibrogenesis & Tissue Repair, 2015, vol. 8(14), 15 pages.
Elbashir S.M., et al., "Functional anatomy of siRNAs for Mediating Efficient RNAi in *Drosophila melanogaster* Embryo Lysate," EMBO J., 2001, vol. 20, pp. 6877-6888.
Engmann J., et al., "Fluid Mechanics of Eating, Swallowing and Digestion-Overview and Perspectives," Food & Function, 2013, vol. 4, pp. 443-447.
Evans M.J., et al., "Establishment in Culture of Pluripotent Cells from Mouse Embryos," Nature, 1981, vol. 292, pp. 154-156.
Ezashi T., et al., "Low $O_2$ Tensions and the Prevention of Differentiation of hES Cells," PNAS, Mar. 2005, vol. 102, Issue 13, pp. 4783-4788.
Fagerberg L., et al., "Analysis of the Human Tissue-specific Expression by Genome-wide Integration of Transcriptomics and Antibody-based proteomics," Molecular & Cellular Proteomics, 2014, vol. 13, pp. 397-406.
Fahrmayr C., et al., "Phase I and II Metabolism and MRP2-Mediated Export of Bosentan in a MDCKII-OATP1B1-CYP3A4-UGT1A1-MRP2 quadruple-Transfected Cell Line," British Journal of Pharmacology, 2013, vol. 169, pp. 21-33.
Falasca L., et al., "The Effect of Retinoic Acid on the re-establishment of Differentiated Hepatocyte Phenotype in Primary Culture," Cell Tissue Res, Aug. 1998, vol. 293, pp. 337-347.
Fatehullah A., et al., "Organoids as an in Vitro Model of Human Development and Disease," Nature Cell Biology, Mar. 2016, vol. 18, Issue 3, pp. 246-254.
Finkbeiner S.R., et al., "A Gutsy Task: Generating Intestinal Tissue from Human Pluripotent Stem Cells," Digestive Diseases and Sciences, 2013, vol. 58, pp. 1176-1184.
Finkbeiner S.R., et al., "Stem Cell-Derived Human Intestinal Organoids as an Infection Model for Rotaviruses," mBio, Jul./Aug. 2012, vol. 3, issue 4, e00159-12, 6 pages.
Finkbeiner S.R., et al., "Transcriptome-wide Analysis Reveals Hallmarks of Human Intestine Development and Maturation in Vitro and In Vivo," Stem Cell Reports, Jun. 3, 2015, vol. 4, pp. 1140-1155.
Finkenzeller K., "RFID Handbook: Fundamentals and Applications in Contactless Smart Cards, Radio Frequency Identification and Near-Field Communication," Third Edition, John Wiley & Sons, Ltd., 2010, 8 pages.
Fisher A., et al., "Entacapone-Induced Hepatotoxicity and Hepatic Dysfunction," Movement Disorders, 2002, vol. 17, pp. 1362-1365.
Fitzpatrick D R., et al., "Identification of SATB2 as the Cleft Palate Gene on 2q32-q33," Human Molecular Genetics, 2003, vol. 12, Issue 19, pp. 2491-2501.
Fon Tacer K., et al., "Research Resource: Comprehensive Expression Atlas of the Fibroblast Growth Factor System in Adult Mouse," Molecular Endocrinology, 2010, vol. 24, Issue 10, pp. 2050-2064.
Fordham R.P., et al., "Transplantation of Expanded Fetal Intestinal Progenitors Contributes to Colon Regeneration after Injury," Cell Stem Cell, Dec. 5, 2013, vol. 13, pp. 734-744.
Fromenty B., "Drug-induced liver injury in obesity," Journal of Hepatology, 2013, vol. 58, pp. 824-826.
Fu M., et al., "Embryonic Development of the Ganglion Plexuses and the Concentric Layer Structure of Human Gut: a Topographical Study," Anatomy and Embryology, Feb. 27, 2004, vol. 208, pp. 33-41.
Fu M., et al., "HOXB5 expression is spatially and temporarily Regulated in Human Embryonic Gut during Neural Crest Cell Colonization and Differentiation of Enteric Neuroblasts," Developmental Dynamics, 2003, vol. 228, pp. 1-10.
Furness J.B., "The Enteric Nervous System and Neurogastroenterology," Nature Reviews/Gastroenterology & Hepatology, May 2012, vol. 9, pp. 286-294.
Gafni O., et al., "Derivation of Novel Human Ground State Naive Pluripotent Stem Cells," Nature, Oct. 29, 2013, vol. 504, pp. 282-286.
Geerts A., et al., "Formation of Normal Desmin Intermediate Filaments in Mouse Hepatic Stellate Cells Requires Vimentin," Hepatology, Oct. 2001, vol. 33, pp. 177-188.
Genthe J.R., et al., "Ventromorphins: A New Class of Small Molecule Activators of the Canonical BMP Signaling Pathways," ACS Chemical Biology, 2017, vol. 12, Issue 9, pp. 2436-2447.
Georgas K M., et al., "An illustrated Anatomical Ontology of the Developing Mouse Lower Urogenital Tract," Development, May 15, 2015, vol. 142, pp. 1893-1908.
Gerdes H.H., et al., "Tunneling Nanotubes, an Emerging Intercellular Communication Route in Development," 2013, vol. 130, pp. 381-387.
Gessner R.C., et al., "Functional Ultrasound Imaging for Assessment of Extracellular Matrix Scaffolds used for Liver Organoid Formation," Biomaterials, 2013, vol. 34, pp. 9341-9351.
Giles D.A., et al., "Thermoneutral Housing Exacerbates Nonalcoholic Fatty Liver Disease in Mice and Allows for Sex-Independent Disease Modeling," Nature Medicine, 2017, vol. 23, Issue 7, pp. 829-838.
Ginestet C., Book Review in the Journal of the Royal Statistical Society. Series A (Statistics in Society) (2011), of ggplot2: Elegant Graphics for Data Analysis, by H. Wickham, 2009, vol. 174, Issue 1, p. 245 (2 pages).
Glorioso J.M., et al., "Pivotal Preclinical Trial of the Spheroid Reservoir Bioartificial Liver," Journal of Hepatology, 2015, vol. 63, Issue 2, pp. 388-398.
Goldenring J.R., et al., "Differentiation of the Gastric Mucosa: III. Animal Models of Oxyntic Atrophy and Metaplasia," American Journal of Physiology—Gastrointestinal and Liver Physiology, 2006, vol. 291, pp. G999-G1004.
Goldenring J.R., et al., "Overexpression of Transforming Growth Factor-alpha Alters Differentiation of Gastric Cell Lineages," Digestive Diseases and Sciences, 1996, vol. 41, Issue 4, pp. 773-784.
Goldstein A.M., et al., "BMP Signaling is Necessary for Neural Crest Cell Migration and Ganglion Formation in the Enteric Nervous System," Mechanisms of Development, 2005, vol. 122, pp. 821-833.
Gomez M.C., et al., "Derivation of Cat Embryonic Stem-Like Cells from in Vitro-Produced Blastocysts on Homologous and Heterologous Feeder Cells," Theriogenology, Sep. 1, 2010, vol. 74, Issue 4, pp. 498-515.
Gomez-Pinilla P.J., et al., "Ano1 is a Selective Marker of Interstitial Cells of Cajal in the Human and Mouse Gastrointestinal Tract," American Journal of Physiology: Gastrointestinal and Liver Physiology, 2009, vol. 296, Issue 6, pp. G1370-G1381.
Gori M., et al., "Investigating Nonalcoholic Fatty Liver Disease in a Liver-on-a-Chip Microfluidic Device," PLOS One, Jul. 2016, vol. 11, Issue 7, e0159729, 15 pages.
Gouon-Evans V., et al., "BMP-4 is Required for Hepatic Specification of Mouse Embryonic Stem Cell-Derived Definitive Endoderm," Nature Biotechnology, Nov. 2006, vol. 24, Issue 11, pp. 1402-1411.
Gracz A.D., et al., "Brief report: CD24 and CD44 Mark Human Intestinal Epithelial Cell Populations with Characteristics of Active and Facultative Stem Cells," Stem Cells, Apr. 4, 2013, vol. 31, pp. 2024-2030.
Gracz A.D., et al., "Sox9 Expression Marks a Subset of CD24-Expressing Small Intestine Epithelial Stem Cells that Form Organoids in Vitro," American Journal of Physiology: Gastrointestinal and Liver Physiology, 2010, vol. 298, Issue 5, pp. G590-G600.
Gradwohl G., et al., "Neurogenin3 is Required for the Development of the Four Endocrine Cell Lineages of the Pancreas," Proceedings of the National Academy of Sciences USA, 2000, vol. 97, Issue 4, pp. 1607-1611.

(56) References Cited

OTHER PUBLICATIONS

Grapin Botton A., "Three-Dimensional Pancreas Organogenesis Models," Diabetes Obesity and Metabolism, Sep. 2016, vol. 18 (Suppl 1), pp. 33-40.
Green M.D., et al., "Generation of Anterior Foregut Endoderm from Human Embryonic and Induced pluripotent Stem Cells," Nature Biotechnology, Mar. 2011, vol. 29, Issue 3, pp. 267-272.
Gregersen H., et al., "The Zero-Stress State of the Gastrointestinal Tract: Biomechanical and Functional Implications," Digestive Diseases and Sciences, Dec. 2000, vol. 45(12), pp. 2271-2281.
Gregorieff A., et al., "Wnt Signaling in the Intestinal Epithelium: from Endoderm to Cancer," Genes & Development, 2005, vol. 19, pp. 877-890.
Groneberg D.A., et al., "Intestinal Peptide Transport: Ex Vivo Uptake Studies and Localization of Peptide Carrier PEPT1," American Journal of Physiology: Gastrointestinal and Liver Physiology, Sep. 2001, vol. 281, pp. G697-G704.
Grosse A.S., et al., "Cell Dynamics in Fetal Intestinal Epithelium: Implications for Intestinal Growth and Morphogenesis," Development, 2011, vol. 138, pp. 4423-4432.
Guan Y., et al., "Human Hepatic Organoids for the Analysis of Human Genetic Diseases," JCI Insight, Sep. 7, 2017, vol. 2, Issue 17, e94954; 17 pages.
Guilak F, et al., "Control of Stem Cell Fate by Physical Interactions with the Extracellular Matrix," Cell Stem Cell, Jul. 2009, vol. 5, pp. 17-26.
Guo G., et al., "Epigenetic Resetting of Human Pluripotency," Development, 2017, vol. 144, pp. 2748-2763.
Guo Z., et al., "Injury-Induced BMP Signaling Negatively Regulates *Drosophila* Midgut Homeostasis," Journal of Cell Biology, 2013, vol. 201, Issue 6, pp. 945-961.
Gurdon J.B., "Adult Frogs Derived from the Nuclei of Single Somatic Cells," Developmental Biology, 1962, vol. 4, pp. 256-273.
Gurken A. "Advances in Small Bowel Transplantation," Turkish Journal of Surgery, 2017, vol. 33, Issue 3, pp. 135-141.
Gyorgy A.B., et al., "SATB2 Interacts with Chromatin-Remodeling Molecules in Differentiating Cortical Neurons," European Journal of Neuroscience, 2008, vol. 27, pp. 865-873.
Haimovich G., et al., "Intercellular mRNA Trafficking via Membrane Nanotube-Like Extensions in Mammalian Cells," PNAS, 2017, vol. 114, Issue 46, pp. E9873-E9882.
Han B., et al., "Microbiological Safety of a Novel Bio-Artificial Liver support System Based on Porcine Hepatocytes: an Experimental Study," European Journal of Medical Research, 2012, vol. 17, Issue 1, Journal 13, 8 pages.
Han M E., et al., "Gastric Stem Cells and Gastric Cancer Stem Cells," Anatomy & Cell Biology, 2013, vol. 46, Issue 1, pp. 8-18.
Hannon G.J., "RNA Interference," Nature, 2002, vol. 418, Issue 6894, pp. 244-251.
Hannon N.R.F, et al., "Generation of Multipotent Foregut Stem Cells from Human Pluripotent Stem Cells," Stem Cell Reports, Oct. 2013, vol. 1, Issue 4, pp. 293-306.
Hao M.M., et al., "Development of Enteric Neuron Diversity," Journal of Cellular and Molecular Medicine, 2009, vol. 13, Issue 7, pp. 1193-1210.
Haramis A.P.G., et al., "De Novo Crypt Formation and Juvenile Polyposis on BMP Inhibition in Mouse Intestine," Science, 2004, vol. 303, Issue 5664, pp. 1684-1686.
Hardwick J.C.H., et al., "Bone Morphogenetic Protein 2 Is Expressed by, and Acts Upon, Mature Epithelial Cells in the Colon," Gastroenterology, 2004, vol. 126, Issue 1, pp. 111-121.
Hardy T., et al., "Nonalcoholic Fatty Liver Disease: New Treatments," Current Opinion in Gastroenterology, May 2015, vol. 31, Issue 3, pp. 175-183.
Hassan W., et al., "Reduced Oxidative Stress Contributes to the Lipid Lowering Effects of Isoquercitrin in Free Fatty Acids Induced Hepatocytes," Oxidative Medicine and Cellular Longevity, 2014, vol. 2014, 313602, 18 pages.
Haveri H., et al., "Transcription Factors GATA-4 and GATA-6 in Normal and Neoplastic Human Gastrointestinal Mucosa," BMC Gastroenterology, 2008, vol. 8, Issue 9, 13 pages.
He X.C., et al., "BMP Signaling Inhibits Intestinal Stem Cell Self-Renewal through Suppression of Wnt-beta-Catenin Signaling," Nature Genetics, 2004, vol. 36, Issue 10, pp. 1117-1121.
Heidari R., et al., "Factors Affecting Drug-Induced Liver Injury: Antithyroid Drugs as Instances," Clinical and Molecular Hepatology, 2014, vol. 20, Issue 3, pp. 237-248.
Hernandez F., et al., "Refining Indications for Intestinal Retransplantation," International Small Bowel Symposium 2013; Abstract 12.241, retrieved from https://www.tts.org/component/tts/view=presentation&id=13241, Accessed, Jun. 12, 2017, 3 pages.
Higuchi Y., et al., "Gastrointestinal Fibroblasts Have Specialized, Diverse Transcriptional Phenotypes: A Comprehensive Gene Expression Analysis of Human Fibroblasts," PLOS One, Jun. 2015, vol. 10, Issue 6, 19 pages.
Hockemeyer D., et al., "Genetic Engineering of Human ES and iPS Cells using TALE Nucleases," Nature Biotechnology, 2012, vol. 29, Issue 8, pp. 731-734.
Hoffmann W., "Current Status on Stem Cells and Cancers of the Gastric Epithelium," International Journal of Molecular Sciences, 2015, vol. 16, Issue 8, pp. 19153-19169.
Holland P.W.H., et al., "Classification and Nomenclature of all Human Homeobox Genes," BMC Biology, 2007, vol. 5, Issue 47, 29 pages.
Hooton D., et al., "The Secretion and Action of Brush Border Enzymes in the Mammalian Small Intestine," Reviews of Physiology, Biochemistry and Pharmacology, 2015, vol. 168, pp. 59-118.
Hou P., et al., "Pluripotent Stem Cells Induced from Mouse Somatic Cells by Small-Molecule Compounds," Science, 2013, vol. 341, Issue 6146, pp. 651-654.
Howell J.C., et al., "Generating Intestinal tissue from Stem Cells: Potential for Research and Therapy," Regenerative Medicine, Nov. 2011, vol. 6, Issue 6, pp. 743-755.
Hsu F., et al., "The UCSC Known Genes," Bioinformatics, 2006, vol. 22, Issue 9, pp. 1036-1046.
Hu H., et al., "Long-Term Expansion of Functional Mouse and Human Hepatocytes as 3D Organoids," Cell, 2018, vol. 175, Issue 6, pp. 1591-1606.
Hu X., et al., "Micrometer-Scale Magnetic-Resonance-Coupled Radio-Frequency Identification and Transceivers for Wireless Sensors in Cells," Physical Review Applied, 2017, Issue 8, pp. 014031-1; 13 pages.
Huang H., "Differentiation of Human Embryonic Stem Cells into Smooth Muscle Cells in Adherent Monolayer Culture," Biochemical and Biophysical Research Communications, 2006, vol. 351 pp. 321-327.
Huch M., et al., "$Lgr^5$+ Liver Stem Cells, Hepatic Organoids and Regenerative medicine," Regenerative Medicine, 2013, vol. 8, Issue 4, pp. 385-387.
Huch M., et al., "Long-Term Culture of Genome-Stable Bipotent Stem Cells from Adult Human Liver," Cell, 2015, Issue 160, pp. 299-312.
Huch M., et al., "Modeling mouse and Human development using Organoid cultures," Development, 2015, Issue 142, pp. 3113-3125.
Huebsch N., et al., "Automated Video-Based Analysis of Contractility and Calcium Flux in Human-Induced Pluripotent Stem Cell-Derived Cardiomyocytes Cultured Over Different Spatial Scales," Tissue Engineering: Part C, 2015, vol. 21, No. 5, pp. 467-479.
Huh W.J., et al., " Ménétrier's Disease: Its Mimickers and Pathogenesis," Journal of Pathology and Translational Medicine, 2016, vol. 50, Issue 1, pp. 10-16.
Hutvagner G., et al., "A microRNA in a Multiple-Turnover RNAi Enzyme Complex," Science, Sep. 20, 2002, vol. 297, No. 5589, pp. 2056-2060.
Hynds R.E., et al., "The Relevance of Human Stem Cell-Derived Organoid Models for Epithelial Translational Medicine," Stem Cells, 2013, vol. 31, No. 3, pp. 417-422.
Ijpenberg., et al., "Wt1 and Retinoic Acid Signaling are Essential for Stellate cell development and Liver Morphogenesis," Developmental Biology, Dec. 2007, vol. 312, No. 1, pp. 157-170.

(56) References Cited

OTHER PUBLICATIONS

Inoue H., et al., "IPS Cells: A game Changer for Future Medicine," EMBO Journal, 2014, vol. 33, No. 5, pp. 409-417.
Ito K., et al., "Temporal Transition of Mechanical Characteristics of HUVEC/MSC Spheroids Using a Microfluidic Chip with Force Sensor Probes," Micromachines, 2016, vol. 7(221), 14 pages.
Jalan-Sakrikar N., et al., "Hedgehog Signaling Overcomes an EZH2-Dependent Epigenetic Barrier to Promote Cholangiocyte Expansion," PLoS One, 2016, vol. 11(12), e0168266, 19 pages.
Jean C., et al., "Pluripotent Genes in Avian Stem Cells," Develop. Growth Differ., 2013, vol. 55, pp. 41-51.
Jeejeebhoy K.N., "Short Bowel Syndrome: A Nutritional and Medical Approach," CMAJ, 2002, vol. 166, Issue 10, pp. 1297-1302.
Jenny M., et al., "Neurogenin3 is differentially Required for Endocrine Cell Fate Specification in the Intestinal and Gastric Epithelium," EMBO J, 2002, vol. 21, Issue 23, pp. 6338-6347.
Johannesson M., et al., "FGF4 and Retinoic Acid Direct Differentiation of hESCs into PDX1-Expressing Foregut Endoderm in a Time- and Concentration-Dependent Manlier," PLoS One, Mar. 2009, vol. 4, Issue 3, pp. 1-13.
Johansson K.A., et al., "Temporal Control of Neurogenin3 Activity in Pancreas Progenitors Reveals Competence Windows for the Generation of Different Endocrine Cell Types," Dev Cell, 2007, vol. 12, pp. 457-465.
Johnson L.R., et al., "Stimulation of Rat Oxyntic Gland Mucosal Growth by Epidermal Growth Factor," American Journal of Physiology, 1980, vol. 238, Issue G, pp. 45-49.
Johnston T.B., et al., "Extroversion of the Bladder, Complicated by the Presence of Intestinal Openings on the Surface of the Extroverted Area," Journal of Anatomy, 1913, vol. 48, Issue 1, pp. 89-106.
Jones P., et al., "Stromal Expression of Jagged 1 Promotes Colony Formation by Fetal Hematopoietic Progenitor Cells," Blood, Sep. 1, 1998, vol. 92, No. 5, pp. 1505-1511.
Jung P., et al., "Isolation and in Vitro Expansion of Human Colonic Stem Cells," Nature Medicine, Oct. 2011, vol. 17, pp. 1225-1227.
Juno R J., et al., "A serum factor(s) after Small Bowel Resection Induces Intestinal Epithelial Cell Proliferation: Effects of Timing, Site, and Extent of Resection," Journal of Pediatric Surgery, Jun. 2003, vol. 38, pp. 868-874.
Juno R.J., et al., "A Serum Factor after Intestinal Resection Stimulates Epidermal Growth Factor Receptor Signaling and Proliferation in Intestinal Epithelial Cells," Surgery, Aug. 2002, vol. 132, pp. 377-383.
Kabouridis P.S., et al., "Microbiota Controls the Homeostasis of Glial Cells in the Gut Lamina Propria," Neuron, Jan. 21, 2015, vol. 85, pp. 289-295.
Kaji K., et al., "Virus Free Induction of Pluripotency and Subsequent Excision of Reprogramming Factors," Nature, Apr. 2009, vol. 458, Issue 7239, pp. 771-775.
Kanuri G., et al., "In Vitro and in Vivo Models of Non-Alcoholic Fatty Liver Disease (NAFLD)," International Journal of Molecular Sciences, 2013, vol. 14, pp. 11963-11980.
Karlikow M., et al., "*Drosophila* Cells Use Nanotube-like Structures to Transfer dsRNA and RNAi Machinery Between Cells," Scientific Reports, 2016, vol. 6, Issue 27085, 9 pages.
Katoh M., "WNT Signaling in Stem Cell Biology and Regenerative Medicine," Current Drug Targets, 2008, vol. 9, Issue 7, pp. 565-570.
Kawaguchi J., et al., "Isolation and propagation of enteric neural crest progenitor cells from mouse embryonic stem cells and embryos," Development, 2010, vol. 137, pp. 693-704.
Kawaguchi Y., et al., "The Role of the Transcriptional Regulator Ptf1a in Converting Intestinal to Pancreatic Progenitors," Nature Genetics, 2002, vol. 32, pp. 128-134.
Keeley T.M., et al., "Cytodifferentiation of the postnatal mouse stomach in normal and Huntingtin-interacting protein 1-related-deficient mice," American Journal of Physiology: Gastrointestinal and Liver Physiology, 2010, vol. 299, pp. G1241-G1251.
Keitel V., et al., "De Novo Bile Salt Transporter Antibodies as a Possible Cause of Recurrent Graft Failure after Liver Transplantation: A Novel Mechanism of Cholestasis," Hepatology, 2009, vol. 50, pp. 510-517.
Kelly G.M., et al., "Retinoic Acid and the Development of the Endoderm," Journal Developmental Biology, 2015, vol. 3, pp. 25-56.
Keung A.J., et al., "Presentation Counts: Microenvironmental Regulation of Stem Cells by Biophysical and Material Cues," Annual Review of Cell and Developmental Biology, 2010, vol. 26, pp. 533-556.
Khan FA., et al., "Overview of Intestinal and Multivisceral Transplantation," UpToDate, Sep. 2018 retrieved from https://www.uptodate.com/contents/overview-of-intestinal-and-multiviscera-l-transplantation/print], 32 pages.
Kilens S., et al., "Parallel Derivation of Isogenic Human Primed and Naive Induced Pluripotent Stem Cells," Nature Communications, 2018, vol. 9, Issue 360, 13 pages.
Kilpinen H., et al., "Common Genetic Variation Drives Molecular Heterogeneity in Human iPSCs," Nature, 2017, vol. 546, Issue 7658, pp. 370-375.
Kim B.M., et al., "Regulation of Mouse Stomach Development and Barx1 Expression by specific microRNAs," Development, 2011, vol. 138, pp. 1081-1086.
Kim B.M., et al., "The Stomach Mesenchymal Transcription Factor Barx1 Specifies Gastric Epithelial Identity through Inhibition of Transient Wnt Signaling," Developmental Cell, 2005, vol. 8, pp. 611-622.
Kim D., et al., "HISAT: a Fast Spliced Aligner with Low Memory Requirements," Nature Methods, 2015, vol. 12, Issue 4, pp. 357-360.
Kim T.H., et al., "Stomach Development, Stem Cells and Disease," Development, 2016, vol. 143, pp. 554-565.
Klimanskaya I., et al., "Human Embryonic Stem Cells Derived without Feeder Cells," Lancet, 2005, vol. 365, Issue 9471, pp. 1636-1641.
Kock K., et al., "A Perspective on Efflux Transport Proteins in the Liver," Clinical Pharmacology & Therapeutics, 2012, vol. 92, Issue 5, pp. 599-612.
Koehler E.M., et al., "Presence of Diabetes Mellitus and Steatosis Is Associated with Liver Stiffness in a General Population: The Rotterdam Study," Hepatology, 2016, vol. 63, pp. 138-147.
Kohlnhofer B.M., et al., "GATA4 Regulates Epithelial Cell Proliferation to Control Intestinal Growth and Development in Mice," Cellular and Molecular Gastroenterology and Hepatology, 2016, vol. 2(2), pp. 189-209.
Koike M., et al., "Effects of mechanical strain on proliferation and differentiation of bone marrow stromal cell line ST2," Journal of Bone and Mineral Metabolism, 2005, vol. 23, pp. 219-225.
Kolahchi A.R., et al., "Microfluidic-Based Multi-Organ Platforms for Drug Discovery," Micromachines, 2016, vol. 7, Issue 162, pp. 1-33.
Kolodny G.M., "Evidence for Transfer of Macromolecular RNA Between Mammalian Cells in Culture," Experimental Cell Research, 1971, vol. 65, pp. 313-324.
Koo B-K., et al., "Controlled Gene Expression in Primary Lgr5 Organoid Cultures," Nature Methods, Jan. 1, 2012, vol. 9, No. 1, pp. 81-83.
Kordes C., et al., "Hepatic Stellate Cells Contribute to Progenitor Cells and Liver Regeneration," Journal of Clinical Investigation, 2014, vol. 124, Issue 12, pp. 5503-5515.
Kosinski C., et al., "Indian Hedgehog Regulates Intestinal Stem Cell Fate through Epithelial-Mesenchymal Interactions during Development," Gastroenterology, Sep. 2010, vol. 139, pp. 893-903.
Kostrzewski T., et al., "Three-dimensional Perfused Human in Vitro Model of Non-Alcoholic Fatty Liver Disease," World Journal of Gastroenterology, 2017, vol. 23, Issue 2, pp. 204-215.
Kovalenko P.L., et al., "The Correlation between the Expression of Differentiation Markers in rat Small Intestinal Mucosa and the Transcript Levels of Schlafen 3," JAMA Surgery, Sep. 4, 2013, vol. 148, pp. 1013-1019.

(56) References Cited

OTHER PUBLICATIONS

Krahenbuhl S., et al., "Toxicity of Bile Acids on the Electron Transport Chain of Isolated Rat Liver Mitochondria," Hepatology, 1994, vol. 19, pp. 471-479.
Kraus M.R.C., et al., "Patterning and Shaping the Endoderm in Vivo and in Culture," Current Opinion Genetics & Development, 2012, vol. 22, pp. 347-353.
Krausova M., et al., "Wnt Signaling in Adult Intestinal Stem Cells and Cancer," Cellular Signalling, 2014, vol. 26, pp. 570-579.
Kretzschmar K., et al., "Organoids: Modeling Development and the Stem Cell Niche in a Dish," Developmental Cell, Sep. 2016, vol. 38, pp. 590-600.
Kroon E., et al., "Pancreatic Endoderm Derived From Human Embryonic Stem Cells Generates Glucose-Responsive Insulin Secreting Cells In Vivo," Nature Biotechnology, 2008, vol. 26, Issue 4, pp. 443-452.
Kruitwagen H.S., et al., "SCH-O-5 Long-Term Adult Feline Liver Organoid Cultures for Disease Modelling of Hepatic Lipidosis," Research Communications of the 26th ECVIM-CA Congress, Sep. 2016, ECVIM Abstracts pp. 203-204.
Kruitwagen H.S., et al., "Long-Term Adult Feline Liver Organoid Cultures for Disease Modeling of Hepatic Steatosis," Stem Cell Reports, Apr. 2017, vol. 8(4), pp. 822-830.
Kubal C.A., et al., "Challenges with Intestine and Multivisceral Re-Transplantation: Importance of Timing of Re-Transplantation and Optimal Immunosuppression," Ann Transplant, 2018, vol. 23, pp. 98-104.
Kubo A., et al., "Development of Definitive Endoderm from Embryonic Stem Cells in Culture," Development, 2004, vol. 131, Issue 7, pp. 1651-1662.
Kudoh T., et al., "Distinct Roles for Fgf, Wnt and Retinoic Acid in Posteriorizing the Neural Ectoderm," Development, 2002, vol. 129, pp. 4335-4346.
Kullak-Ublick G.A., et al., "Drug-Induced Liver Injury: Recent Advantages in Diagnosis and Risk Assessment," Gut, 2017, vol. 66, pp. 1154-1164.
Kumar J.A., et al., "Controversies in the Mechanism of Total Parenteral Nutrition Induced Pathology," Children, 2015, vol. 2, Issue 3, pp. 358-370.
Kumar M., et al., "Signals from Lateral Plate Mesoderm Instruct Endoderm toward a Pancreatic Fate," Dev Biol, 2003, vol. 259, Issue 1, pp. 109-122.
Kuratnik A., et al., "Intestinal Organoids as Tissue Surrogates for Toxicological and Pharmacological Studies," Biochemical Pharmacology, 2013, vol. 85, Issue 12, pp. 1721-1726.
Kurpios N.A., et al., "The Direction of Gut Looping is Established by Changes in the Extracellular Matrix and in Cell: Cell Adhesion," PNAS, 2008, vol. 105, Issue 25, pp. 8499-8506.
Lachmann N., et al., "Large-Scale Hematopoietic Differentiation of Human Induced Pluripotent Stem Cells Provides Granulocytes or Macrophages for Cell Replacement Therapies," Stem Cell Report, Feb. 10, 2015, vol. 4, pp. 282-296.
Lahar N., et al., "Intestinal Subepithelial Myofibroblasts Support in Vitro and in Vivo Growth of Human Small Intestinal Epithelium," PLoS One, Nov. 2011, vol. 6(11), e26898, 9 pages.
Lai F.P-L., et al., "Correction of Hirschsprung-Associated Mutations in Human Induced Pluripotent Stem Cells via Clustered Regularly Interspaced Short Palindromic Repeats/Cas9, Restores Neural Crest Cell Function," Gastroenterology, 2017, vol. 153, No. 1, pp. 139-153.
Lambert P.F., et al., "Using an Immortalized Cell Line to Study the HPV Life Cycle in Organotypic "Raft" Cultures," Methods Molecular Medicine, 2005, vol. 119, pp. 141-155.
Lambrecht N.W.G., et al., "Identification of the K Efflux Channel Coupled to the Gastric H-K-Atpase During Acid Secretion," Physiological Genomics, 2005, vol. 21, Issue 1, pp. 81-91.
Lameris A.L., et al., "Expression Profiling of Claudins in the Human Gastrointestinal Tract in Health and During Inflammatory Bowel Disease," Scandinavian Journal of Gastroenterology, 2013, vol. 48, Issue 1, pp. 58-69.
Lancaster M.A., et al., "Organogenesis in a Dish: Modeling Development and Disease Using Organoid Technologies," Science, 2014, vol. 345, Issue 6194, 1247125, 9 pages.
Langmead G., et al., "Ultrafast and Memory-Efficient Alignment of Short DNA Sequences to the Human Genome," Genome Biology, 2009, vol. 10, 10 pages.
Lavial F., et al., "Chicken Embryonic Stem Cells as a Non-Mammalian Embryonic Stem Cell Model," Development, Growth & Differentiation, 2010, vol. 52, pp. 101-114.
Le Douarin N.M., et al., "Neural Crest Cell Plasticity and its Limits," Development 131, 2004, pp. 4637-4650.
Le S., et al., "FactoMineR: An R Package for Multivariate Analysis," Journal of Statistical Software, 2008, vol. 25, Issue 1, pp. 1-18.
Le Vee M., et al., "Polarized Expression of Drug Transporters in Differentiated Human Hepatoma HepaRG Cells," Toxicol in Vitro, 2013, vol. 27, pp. 1979-1986.
Lechner C., et al., "Development of a Fluorescence-Based Assay for Drug Interactions with Human Multidrug Resistance Related Protein (MRP2; ABCC2) in MDCKII-MRP2 Membrane Vesicles," European Journal of Pharmaceutics and Biopharmaceutics, 2010, vol. 75, pp. 284-290.
Lee C.S., et al., "Neurogenin 3 Is Essential for the Proper Specification of Gastric Enteroendocrine Cells and the Maintenance of Gastric Epithelial Cell Identity," Genes Dev, 2002, vol. 16, pp. 1488-1497.
Lee G., et al., "Isolation And Directed Differentiation of Neural Crest Stem Cells Derived from Human Embryonic Stem Cells," Nature Biotechnology, Dec. 2007, vol. 25, pp. 1468-1475.
Lee W.M., et al., "Intravenous N-Acetylcysteine Improves Transplant-Free Survival in Early Stage Non-Acetaminophen Acute Liver Failure," Gastroenterology, 2009, vol. 137, Issue 3, pp. 856-864.
Lennerz J.K.M., et al., "The Transcription Factor MIST1 Is a Novel Human Gastric Chief Cell Marker Whose Expression Is Lost in Metaplasia, Dysplasia, and Carcinoma," The American Journal of Pathology, 2010, vol. 177, Issue 3, pp. 1514-1533.
Leslie E.M., et al., "Differential Inhibition of Rat and Human Na+-Dependent Taurocholate Cotransporting Polypeptide (NTCP/SLC10A1) by Bosentan: A Mechanism for Species Differences in Hepatotoxicity," Journal of Pharmacology and Experimental Therapeutics, 2007, vol. 321, Issue 3, pp. 1170-1178.
Leung A.A., et al., "Tolerance Testing of Passive Radio Frequency Identification Tags for Solvent, Temperature, and Pressure Conditions Encountered in an Anatomic Pathology or Biorepository Setting," Journal of Pathology Informatics, 2010, vol. 1, 6 pages.
Levin D.E., et al., "Human Tissue-Engineered Small Intestine Forms from Postnatal Progenitor Cells," Journal of Pediatric Surgery, 2013, vol. 48, pp. 129-137.
Li H., et al., "Treefam: A Curated Database of Phylogenetic Trees of Animal Gene Families," Nucleic Acids Research, 2006, vol. 34, pp. D572-D580.
Li L., "BMP Signaling Inhibits Intestinal Stem Cell Self-Renewal through Antagonizing Wnt Signaling," Gastroenterology, AASLD Abstracts, Abstract S1223, 2005, vol. 128, p. A702.
Li N., et al., "A Systematic Assessment of Mitochondrial Function Identified Novel Signatures for Drug-Induced Mitochondrial Disruption in Cells," Toxicological Sciences, 2014, vol. 142, Issue 1, pp. 261-273.
Li Y., et al., "In Vitro Organogenesis from Pluripotent Stem Cells," Organogenesis, Jun. 2014, vol. 10, Issue 2, pp. 159-163.
Li Z., et al., "SATB2 is a Sensitive Marker for Lower Gastrointestinal Well-Differentiated Neuroendocrine Tumors," International Journal of Clinical and Experimental Pathology, vol. 8, No. 6, Jan. 2015, pp. 7072-7082.
Lim D.A., et al., "Noggin Antagonizes BMP Signaling to Create a Niche for Adult Neurogenesis," Neuron, Dec. 2000, vol. 28, pp. 713-726.
Lin C., et al., "The Application of Engineered Liver Tissues for Novel Drug Discovery," Expert Opinion on Drug Discovery, 2015, vol. 10, Issue 5, pp. 519-540.
Lin Y., et al., "Differentiation, Evaluation, and Application of Human Induced Pluripotent Stem Cell-Derived Endothelial Cells," Arteriosclerosis, Thrombosis, and Vascular Biology, 2017, vol. 37, pp. 2014-2025.

(56) References Cited

OTHER PUBLICATIONS

Lindley R.M., et al., "Human and Mouse Enteric Nervous System Neurosphere Transplants Regulate the Function of Aganglionic Embryonic Distal Colon," Gastroenterology, Jul. 2008, vol. 135, No. 1, pp. 205-216.
Liu J., et al., "A Small-Molecule Agonist of the Wnt Signaling Pathway," Angewandte Chemie International Edition Engl., 2005, vol. 44, issue 13, pp. 1987-1990.
Liu J.A-J., et al., "Identification of GLI Mutations in Patients with Hirschsprung Disease that Disrupt Enteric Nervous System Development in Mice," Gastroenterology, 2015, vol. 149, No. 7, pp. 1837-1848.
Liu L., et al., "A Review of Locomotion Systems for Capsule Endoscopy," IEEE Reviews in Biomedical Engineering, 2015, vol. 8, pp. 138-151.
Logan C.Y., et al., "The Wnt Signaling Pathway in Development and Disease," Annual Review of Cell and Developmental Biology, 2004, vol. 20, pp. 781-810.
Loike J.D., et al., "Opinion: Develop Organoids, Not Chimeras, for Transplantation," The Scientist Magazine, Aug. 2019, (online: http://www.the-scientist.com/news-opinion/opinion--develop-Organoids--not--chimeras--for-transplantation-66339), 3 pages.
Longmire T.A., et al., "Efficient Derivation of Purified Lung and Thyroid Progenitors from Embryonic Stem Cells," Stem Cell, 2012, vol. 10, pp. 398-411.
Lopez-Diaz L., et al., "Intestinal Neurogenin 3 Directs Differentiation of a Bipotential Secretory Progenitor to Endocrine Cell Rather than Goblet Cell Fate," Developmental Biology, 2007, vol. 309, pp. 298-305.
Love M.I., et al., "Moderated Estimation of Fold Change and Dispersion for RNA-seq Data with DESeq2," Genome Biology, 2014, vol. 15, No. 12, pp. 1-21.
Low L.A., et al., "Organs-on-Chips: Progress, Challenges, and Future Directions," Experimental Biology and Medicine, 2017, vol. 242, pp. 1573-1578.
Lu Y., et al., "A Novel 3D Liver Organoid System for Elucidation of Hepatic Glucose Metabolism," Biotechnology and Bioengineering, Feb. 2012, vol. 109, Issue 2, pp. 595-604.
Ludwig T.E., et al., "Derivation of Human Embryonic Stem Cells in Defined Conditions," Nature Biotechnology, Feb. 2006, vol. 24, pp. 185-187.
Ludwig T.E., et al., "Feeder-Independent Culture of Human Embryonic Stem Cells," Nat Methods, Aug. 2006, vol. 3, pp. 637-646.
Lui V.C.H., et al., "Perturbation of Hoxb5 Signaling in Vagal Neural Crests Down-regulates Ret Leading to Intestinal Hypoganglionosis in Mice," Gastroenterology, Apr. 2008, vol. 134, pp. 1104-1115.
Luntz J., et al., "Mechanical Extension Implants for Short-Bowel Syndrome," Smart Structures and Materials 2006: Smart Structures and Integrated Systems, Proceedings of SPIE, 2006, vol. 6173, pp. 617309-1-617309-11.
Luo X., et al., "Generation of Endoderm Lineages from Pluripotent Stem Cells," Regenerative Medicine, 2017, vol. 12, Issue 1, pp. 77-89.
Macparland S.A., et al., "Single Cell RNA Sequencing of Human Liver Reveals Distinct Intrahepatic Macrophage Populations," Nature Communications, Oct. 2018, vol. 9, Issue 4383, 21 pages.
Mahe M.M., et al., "Establishment of Gastrointestinal Epithelial Organoids," Current Protocols in Mouse Biology, 2013, vol. 3, issue 4, pp. 217-240.
Mahe M.M., et al., "In Vivo Model of Small Intestine," Methods in Molecular Biology, 2017, vol. 1597, pp. 229-245.
Majumdar A.P., "Postnatal Undernutrition: Effect of Epidermal Growth Factor on Growth and Function of the Gastrointestinal Tract in Rats," Journal of Pediatric Gastroenterology and Nutrition, 1984, vol. 3, pp. 618-625.
Makin A.J., et al., "A 7-Year Experience of Severe Acetaminophen-Induced Hepatotoxicity (1987-1993)," Gastroenterology, Dec. 1995, vol. 109, Issue. 6, pp. 1907-1916.
Malinen M.M., et al., "Differentiation of Liver Progenitor Cell Line to Functional Organotypic Cultures in 3D Nanofibrillar Cellulose and Hyaluronan-gelatin Hydrogels," Biomaterials, Jun. 2014, vol. 35, pp. 5110-5121.
Mammoto A., et al., "Mechanosensitive Mechanisms in Transcriptional Regulation," Journal of Cell Science, 2012, vol. 125, pp. 3061-3073.
Marcum Z.A., et al., "Medication Adherence to Multi-Drug Regimens," Clinics in Geriatric Medicine, May 2012, vol. 28, Issue 2, pp. 287-300.
Marini F, et al., "pcaExplorer: an R/Bioconductor Package for Interacting with RNA-seq Principal Components," BMC Bioinformatics, Jun. 2019, vol. 20, Issue 1, pp. 1-8.
Marini F, "pcaExplorer: Interactive Visualization of RNA-seq Data Using a Principal Components Approach," Bioconductor.org, R package version 2.3.0, 2017, 7 pages.
Markova S.M., et al., "Association of CYP2C9*2 with Bosentan-Induced Liver Injury," Clinical Pharmacology & Therapeutics, Dec. 2013, vol. 94, Issue 6, pp. 678-686.
Marsh M.N., et al., "A Study of the Small Intestinal Mucosa Using the Scanning Electron Microscope," Gut, 1969, vol. 10, pp. 940-949.
Martin G.R., "Teratocarcinomas and Mammalian Embryogenesis," Science, Aug. 1980, vol. 209, Issue 4458, pp. 768-776.
Martin M., et al., "Dorsal Pancreas Agenesis in Retinoic Acid-deficient Raldh2 Mutant Mice," Developmental Biology, Aug. 2005, vol. 284, pp. 399-411.
McCauley H.A., et al., "Pluripotent Stem Cell-derived Organoids: Using Principles of Developmental Biology to Grow Human Tissues in a Dish," Development, Mar. 2017, vol. 144, pp. 958-962.
McCracken K.W., et al., "Erratum: Wnt/β-catenin promotes gastric fundus specification in mice and humans," Nature, 2017, vol. 543, Issue 136, 1 page.
McCracken K.W., et al., "Generating Human Intestinal Tissue from Pluripotent Stem Cells in Vitro," Nature Protocols, Nov. 2011, vol. 6, Issue 12, pp. 1920-1928.
McCracken K.W., et al., "Mechanism of Embryonic Stomach Development," Seminars in Cell & Development Biology, 2017, vol. 66, pp. 36-42.
McCracken K.W., et al., "Modelling Human Development and Disease in Pluripotent Stem-Cell-Derived Gastric Organoids," Nature, Oct. 2014, vol. 516, Issue 7531, pp. 400-404.
McCracken K.W., et al., "Wnt/β-Catenin Promotes Gastric Fundus Specification in Mice and Humans," Nature, Jan. 2017, vol. 541, Issue 7636, pp. 182-187.
McCracken K.W., "Mechanisms of Endoderm Patterning and Directed Differentiation of Human Stem Cells into Foregut Tissues," Dissertation, Graduate School of the University of Cincinnati, Jun. 19, 2014, 185 pages.
McGovern D.P.B., et al., "Genome-Wide Association Identifies Multiple Ulcerative Colitis Susceptibility Loci," Nature Genetics, Apr. 2010, vol. 42, Issue 4, pp. 332-337.
McKenzie T.J., et al., "Artificial and Bioartificial Liver Support," Seminars in Liver Disease, May 2008, vol. 28, Issue 2, pp. 210-217.
McKeown S.J., et al., "Hirschsprung Disease: A Developmental Disorder of the Enteric Nervous System," Wiley Interdisciplinary Reviews Developmental Biology, Jan.-Feb. 2013, vol. 2, pp. 113-129.
McLin V.A., et al., "Repression of Wnt/β-Catenin Signaling in the Anterior Endoderm is Essential for Liver and Pancreas Development," Development, Jun. 2007, vol. 134, pp. 2207-2217.
McLin V.A., et al., "The Role of the Visceral Mesoderm in the Development of the Gastrointestinal Tract," Gastroenterology, Jun. 2009, vol. 136, pp. 2074-2091.
McMahon J.A., et al., "Noggin-Mediated Antagonism of BMP Signaling is required for Growth and Patterning of the Neural Tube and Somite," Genes & Development, May 1998, vol. 12, pp. 1438-1452.
McManus M.T., et al., "Gene Silencing in Mammals by Small Interfering RNAs," Nature Reviews Genetics, Oct. 2002, vol. 3, pp. 737-747.

(56) References Cited

OTHER PUBLICATIONS

Meerbrey K.L., et al., "The pINDUCER Lentiviral Toolkit for Inducible RNA Interference in Vitro and in Vivo," Proceedings of the National Academy of Sciences USA, Mar. 2011, vol. 108, pp. 3665-3670.
Mercaldi C.J., et al., "Methods to Identify and Compare Parenteral Nutrition Administered from Hospital-Compounded and Premixed Multichamber Bags in a Retrospective Hospital Claims Database," Journal of Parenteral and Enteral Nutrition, May 2012, vol. 36, Issue 3, pp. 330-336.
Merker S.R., et al., "Gastrointestinal Organoids: How they Gut it out," Developmental Biology, Dec 2016, vol. 420, pp. 239-250.
Mica Y., et al., "Modeling Neural Crest Induction, Melanocyte Specification and Disease-Related Pigmentation Defects in hESCs and Patient-Specific iPSCs," Cell Reports, Apr. 25, 2013, vol. 3, pp. 1140-1152.
Micallef S.J., et al., "Endocrine Cells Develop within Pancreatic Bud-like Structures Derived from Mouse ES Cells Differentiated in Response to BMP4 and Retinoic Acid," Stem Cell Research, Oct. 2007, vol. 1, pp. 25-36.
Michaut A., et al., "A Cellular Model to Study Drug-Induced Liver Injury in Nonalcoholic Fatty Liver Disease: Application of Acetaminophen," Toxicology and Applied Pharmacology, Feb. 2016, vol. 292, pp. 40-55.
Miki T., et al., "Hepatic Differentiation of Human Embryonic Stem Cells Is Promoted by Three-Dimensional Dynamic Perfusion Culture Conditions," Tissue Engineering: Part C Methods, May 2011, vol. 17, Issue 5, pp. 557-568.
Mills J C., et al., "Gastric Epithelial Stem Cells," Gastroenterology, Feb. 2011, vol. 140, pp. 412-424.
Miyabayashi T., et al., "Wnt/beta-Catenin/CBP Signaling Maintains Long-Term Murine Embryonic Stem Cell Pluripotency," Proceedings of the National Academy of Sciences USA, Mar. 2007, vol. 104, issue 13, pp. 5668-5673.
Múnera J.O., et al., "Differentiation of Human Pluripotent Stem Cells into Colonic Organoids via Transient Activation of BMP Signaling," Cell Stem Cell, Jul. 6, 2017, vol. 21, No. 1, pp. 51-64.
Molodecky N.A., et al., "Increasing Incidence and Prevalence of the Inflammatory Bowel Diseases With Time, Based on Systematic Review," Gastroenterology, Jan. 2012, vol. 142, pp. 46-54.
Molotkov A., et al., "Retinoic Acid Generated by Raldh2 in Mesoderm is required for Mouse Dorsal Endodermal Pancreas Development," Developmental Dynamics, Apr. 2005, vol. 232, pp. 950-957.
Mori R., et al., "Micropatterned Organoid Culture of Rat Hepatocytes and HepG2 Cells," Journal of Bioscience and Bioengineering, Sep. 2008, vol. 106(3), pp. 237-242.
Mork L.M., et al., "Comparison Culture Media for Bile Acid Transport Studies in Primary Human Hepatocytes," Journal of Clinical and Experimental Hepatology, 2012, vol. 2, pp. 315-322.
Moser A.R., et al., "A Dominant Mutation that Predisposes to Multiple Intestinal Neoplasia in the Mouse," Science, Jan. 1990, vol. 247, Issue 4940, pp. 322-324.
Mosher J T., et al., "Intrinsic Differences among Spatially Distinct Neural Crest Stem Cells in Terms of Migratory Properties, Fate-Determination, and Ability to Colonize the Enteric Nervous System," Developmental Biology, Mar. 2007, vol. 303, issue 1, pp. 1-15.
Mou H., et al., "Generation of Multipotent Lung and Airway Progenitors from Mouse ESCs and Patient-Specific Cystic Fibrosis iPSCs," Stem Cell, Apr. 2012, vol. 10, pp. 385-397.
Mudaliar S., et al., "Efficacy and Safety of the Farnesoid X Receptor Agonist Obeticholic Acid in Patients with Type 2 Diabetes and Nonalcoholic Fatty Liver Disease," Gastroenterology, Sep. 2013, vol. 145, pp. 574-582.
Mullin E., "Tiny Human Esophagus Grown in the Lab-Here's Why: Miniature Version of the Organ that Guides Food to the Stomach could Help Scientists Treat a Variety of Medical Ailments," National Geographic, Sep. 20, 2018, downloaded from https://www.nationalgeographiccom/science/2018/news-human-esophagus-grown-lab-stem-cells-cancer-health.html, 5 pages.
Munera J.O., et al., "Generation of Gastrointestinal Organoids from Human Pluripotent Stem Cells, Organ Regeneration," In: Tsuji T., (eds), Organ Regeneration, Methods in Molecular Biology, Humana Press, New York, NY, 2017, vol. 1597, 11 pages.
Munoz M., et al., "Conventional Pluripotency Markers are Unspecific for Bovine Embryonic-Derived Cell-Lines," Theriogenology, 2008, vol. 69, pp. 1159-1164.
Nakamura T., et al., "Advancing Intestinal Organoid Technology toward Regenerative Medicine," Cellular and Molecular Gastroenterology and Hepatology, 2018, vol. 5, pp. 51-60.
Nandivada P., et al., "Treatment of Parenteral Nutrition-Associated Liver Disease: The Role of Lipid Emulsions," Advances in Nutrition, Nov. 2013, vol. 4, No. 6, pp. 711-717.
Nantasanti S., et al., "Concise Review: Organoids are a Powerful Tool for the Study of Liver Disease and Personalized Treatment Design in Humans and Animals: Organoids for Disease Modeling and Therapy," Stem Cells Translational Medicine, Jan. 21, 2016, vol. 5(3), pp. 325-330.
Navarro V J., et al., "Drug-Related Hepatotoxicity," New England Journal of Medicine, 2006, vol. 354, pp. 731-739.
Negishi T., et al., "Retinoic Acid Signaling Positively Regulates Liver Specification by Inducing wnt2bb Gene Expression in Medaka," Hepatology, 2010, vol. 51, pp. 1037-1045.
Neiiendam J L., et al., "An NCAM-derived FGF-receptor Agonist, the FGL-peptide, Induces Neurite Outgrowth and Neuronal Survival in Primary Rat Neurons," Journal of Neurochemistry, 2004, vol. 91, issue 4, pp. 920-935.
Nelson B J., et al., "Microrobots for Minimally Invasive Medicine," Annual Review of Biomedical Engineering, 2010, vol. 15, issue 12, pp. 55-85.
Nelson C M., "On Buckling Morphogenesis," Journal of Biomechanical Engineering, 2016, vol. 138, pp. 021005-1-021005-6.
Neuschwander-Tetri B A., et al., "Farnesoid X Nuclear Receptor Ligand Obeticholic Acid for Non-Cirrhotic, Non-Alcoholic Steatohepatitis (FLINT): A Multicentre, Randomised, Placebo-Controlled Trial," Lancet, 2015, vol. 385, Issue 9972, pp. 956-965.
Ni X., et al. "Functional Human Induced Hepatocytes (hiHeps) with Bile Acid Synthesis and Transport Capacities: A Novel in Vitro Cholestatic Model," Scientific Reports, 2016, vol. 6, Issue 38694, 16 pages.
Nielsen C., et al., "Gizzard Formation and the Role of Bapx1," Developmental Biology, 2001, vol. 231, Issue 1, pp. 164-174.
Nishida T., et al., "Rat Liver Canalicular Membrane Vesicles Contain an ATP-Dependent Bile Acid Transport System," Proceedings of the National Academy of Sciences USA, Aug. 1991, vol. 88, Issue 15, pp. 6590-6594.
Noguchi T-A.K., et al., "Generation of Stomach Tissue from Mouse Embryonic Stem Cells," Nature Cell Biology, 2015, vol. 17, Issue 8, pp. 984-993.
Nomura S., et al., "Evidence for Repatteming of the Gastric Fundic Epithelium Associated With Menetrier's Disease and TGFα Overexpression," Gastroenterology, May 2005, vol. 128, Issue 5, pp. 1292-1305.
Obermayr F, et al., "Development and Developmental Disorders of the Enteric Nervous System," Nature Reviews/Gastroenterology & Hepatology, Jan. 2013, vol. 10, Issue 1, pp. 43-57.
Ogaki S., et al., "Wnt and Notch Signals Guide Embryonic Stem Cell Differentiation into the Intestinal Lineages," Stem Cells, Jun. 2013, vol. 31, Issue 6, pp. 1086-1096.
Okada Y., et al., "Retinoic-Acid-Concentration-Dependent Acquisition of Neural Cell Identity during in Vitro Differentiation of Mouse Embryonic Stem Cells," Developmental Biology, 2004, vol. 275, Issue 1, pp. 124-142.
Okita K., et al., "An Efficient Nonviral Method to Generate Integration-Free Human-Induced Pluripotent Stem Cells from Cord Blood and Peripheral Blood Cells," Stem Cells, Mar. 2013, vol. 31, Issue 3, pp. 458-466.
Okita K., et al., "Generation of Mouse Induced Pluripotent Stem Cells without Viral Vectors," Science, Nov. 7, 2008, vol. 322, Issue 5903, pp. 949-953.

(56) References Cited

OTHER PUBLICATIONS

Olbe L., et al., "A Mechanism by which Helicobacter Pylori Infection of the Antrum Contributes to the Development of Duodenal Ulcer," Gastroenterology, 1996, vol. 110, Issue 5, pp. 1386-1394.
Oorts M., et al., "Drug-induced cholestasis risk assessment in sandwich-cultured human hepatocytes," Toxicol in Vitro, 2016, vol. 34, pp. 179-186.
Ootani A., et al., "Sustained in Vitro Intestinal Epithelial Culture within a Wnt-Dependent Stem Cell Niche," Nature Medicine, 2009, vol. 15, Issue 6, pp. 701-706.
Ornitz D.M., et al., "FGF Signaling Pathways in Endochondral and Intramembranous Bone Development and Human Genetic Disease," Genes & Development, 2002, vol. 16, Issue 12, pp. 1446-1465.
Ornitz D.M., et al., "The Fibroblast Growth Factor Signaling Pathway," Wiley Interdisciplinary Reviews Developmental Biology, 2015, vol. 4, Issue 3, pp. 215-266.
Orso G., et al., "Pediatric Parenteral Nutrition-Associated Liver Disease and Cholestasis: Novel Advances in Pathomechanisms-based Prevention and Treatment," Dig Liver Dis, 2016, vol. 48, Issue 3, pp. 215-222.
Ouchi R., et al., "Modeling Steatohepatitis in Humans with Pluripotent Stem Cell-Derived Organoids," Cell Metabolism, Aug. 6, 2019, vol. 30, Issue 2, pp. 374-384.
Paddison P.J., et al., "Short Hairpin Activated Gene Silencing in Mammalian Cells," Methods in Molecular Biology, 2004, vol. 265, pp. 85-100.
Paddison P.J., et al., "RNA interference: the new somatic cell genetics?," Cancer Cell, 2002, vol. 2, Issue 1, pp. 17-23.
Pai R., et al., "Deoxycholic acid activates beta-catenin Signaling Pathway and Increases Colon Cell Cancer Growth and Invasiveness," Molecular Biology of the Cell, 2004, vol. 15, Issue 5, pp. 2156-2163.
Pan Q., "University of Science and Technology of China Press," Physiology, Jan. 31, 2014, pp. 149-150.
Pardal M.L., et al., "Towards the Internet of Things: An Introduction to RFID Technology," RFID Technology—Concepts, Applications, Challenges, Proceedings of the 4th International Workshop, IWRT 2010, In conjunction with ICEIS, 2010, pp. 69-78.
Paris D.B.B.P., et al., "Equine Embryos and Embryonic Stem Cells: Defining Reliable Markers of Pluripotency," Theriogenology, 2010, vol. 74, Issue 4, pp. 516-524.
Park H.R., et al., "Lipotoxicity of Palmitic Acid on Neural Progenitor Cells and Hippocampal Neurogenesis," Toxicological Research, Jun. 2011, vol. 27, Issue 2, pp. 103-110.
Park J.S., et al., "Differential Effects of Equiaxial and Uniaxial Strain on Mesenchymal Stem Cells," Biotechnology and Bioengineering, 2004, vol. 88, Issue 3, pp. 359-368.
Park J.S., et al., "The effect of Matrix Stiffness on the Differentiation of Mesenchymal Stem Cells in Response to TGF-β," Biomaterials, 2011, vol. 32, Issue 16, pp. 3921-3930.
Park K.I., et al., "Acute Injury Directs the Migration, Proliferation, and Differentiation of Solid Organ Stem Cells: Evidence for the Effect of Hypoxia-Ischemia in the CNS on Clonal "reporter" Neural Stem Cells," Experimental Neurology, 2006, vol. 199, Issue 1, pp. 156-178.
Park Y.H., et al., "Review of Atrophic Gastritis and Intestinal Metaplasia as a Premalignant Lesion of Gastric Cancer," Journal of Cancer Prevention, 2015, vol. 20, Issue 1, pp. 25-40.
Parkin D.M., "The Global Health Burden of Infection-Associated Cancers in the Year 2002," International Journal of Cancer, 2006, vol. 118, Issue 12, pp. 3030-3044.
Pastor W.A., et al., "TFAP2C Regulates Transcription in Human Naive Pluripotency by Opening Enhancers," Nature Cell Biology, 2018, vol. 20, Issue 5, pp. 553-564.
Pastula A., et al., "Three-Dimensional Gastrointestinal Organoid Culture in Combination with Nerves or Fibroblasts: A Method to Characterize the Gastrointestinal Stem Cell Niche," Stem Cells International, 2016, 16 pages.
Patankar J.V., et al., "Intestinal Deficiency of Gata4 Protects from Diet-Induced Hepatic Steatosis by Suppressing De Novo Lipogenesis and Gluconeogenesis in Mice," Journal of Hepatology, Posters, Abstract 1253, 2012, vol. 56, p. S496.
Patankar J.V., et al., "Intestinal GATA4 Deficiency Protects from Diet-Induced Hepatic Steatosis," Journal of Hepatology, 2012, vol. 57, Issue 5, pp. 1061-1068.
Peek Jr., R.M., et al., "Helicobacter pylori cagA+ Strains and Dissociation of Gastric Epithelial Cell Proliferation from Apoptosis," Journal of the National Cancer, 1997, vol. 89, Issue 12, pp. 863-868.
Peek Jr., R.M., "Helicobacter Pylori Infection and Disease: from Humans to Animal Models," Disease Models & Mechanisms, 2008, vol. 1, Issue 1, pp. 50-55.
Pennisi C.P., et al., "Uniaxial Cyclic Strain Drives Assembly and Differentiation of Skeletal Myocytes," Tissue Engineering: Part A, 2011, vol. 17, pp. 2543-2550.
Pereira C.F., et al., "Heterokaryon-Based Reprogramming of Human B Lymphocytes for Pluripotency Requires Oct4 but Not Sox2," PLoS Genet, 2008, vol. 4, Issue 9, el000170, 14 pages.
Pessayre D., et al., "Central Role of Mitochondria in Drug-Induced Liver Injury," Drug Metabolism Reviews, 2012, vol. 44, Issue 1, pp. 34-87.
Pessayre D., et al., "Mitochondrial involvement in Drug-Induced Liver Injury," in Adverse Drug Reaction, J. Uetrecht (ed.). Handbook of Experimental Pharmacology, 2010, pp. 311-365.
Petitte J.N., et al., "Avian Pluripotent Stem Cells," Mechanisms of Development, 2004, vol. 121, Issue 9, pp. 1159-1168.
Poling H.M., et al., "Mechanically Induced Development and Maturation of Human Intestinal Organoids in Vivo," Nature Biomedical Engineering, 2018, vol. 2, Issue 6, pp. 429-442.
Polson J., et al., "AASLD Position Paper: The Management of Acute Liver Failure," Hepatology, 2005, vol. 41, Issue 5, pp. 1179-1197.
Pompaiah M., et al., "Gastric Organoids: An Emerging Model System to Study Helicobacter pylori Pathogenesis," Current Topics in Microbiology and Immunology, 2017, vol. 400, pp. 149-168.
Prakash R., "Regulation of WNT Genes in Stem Cells Development and Organogenesis," IJP, Jun. 2014, vol. 1, Issue 6, pp. 366-372.
Pulikkot S., "Establishment of a 3D Culture Model of Gastric Stem Cells Supporting Their Differentiation into Mucous Cells Using Microfibrous Polycaprolactone Scaffold," Dissertation, United Arab Emirates University, College of Medicine and Health Sciences, May 2015, 187 pages.
Purton L E., et al., "All-Trans Retinoic Acid Enhances the Long-Term Repopulating Activity of Cultured Hematopoietic Stem Cells," Blood, 2000, vol. 95, Issue 2, pp. 470-477.
Qi M-C., et al., "Mechanical Strain induces Osteogenic Differentiation: Cbfa1 and Ets-1 Expression in Stretched Rat Mesenchymal Stem Cells," International Journal of Oral and Maxillofacial Surgery, 2008, vol. 37, pp. 453-458.
Que J., et al., "Morphogenesis of the Trachea and Esophagus: Current Players and New Roles for Noggin and Bmps," Differentiation, 2006, vol. 74, pp. 422-437.
Rachek LI., et al., "Troglitazone, but not Rosiglitazone, Damages Mitochondrial DNA and induces Mitochondrial Dysfunction and Cell Death in Human Hepatocytes," Toxicology and Applied Pharmacology, 2009, vol. 240, Issue 3, pp. 348-354.
Raju R., et al., "A Network Map of FGF-1/FGFR Signaling System," Journal of Signal Transduction, Apr. 2014, Article ID 962962, 16 pages.
Ramachandran S.D., et al., "In Vitro Generation of Functional Liver Organoid-Like Structures Using Adult Human Cells," PLoS One, Oct. 21, 2015, vol. 10, No. 10, pp. 1-14.
Ramalingam S., et al., "Distinct Levels of Sox9 Expression Mark Colon Epithelial Stem Cells that form Colonoids in Culture," The American Journal of Physiology: Gastrointestinal and Liver Physiology, 2012, vol. 302, Issue 1, pp. G10-G20.
Ramirez-Weber F-A., et al., "Cytonemes: Cellular Processes that Project to the Principal Signaling Center in *Drosophila* Imaginal Discs," Cell, 1999, vol. 97, pp. 599-607.

(56) References Cited

OTHER PUBLICATIONS

Ramsey V.G., et al., "The Maturation of Mucus-Secreting Gastric Epithelial Progenitors: into Digestive-Enzyme Secreting Zymogenic Cells Requires Mist1," Development, 2007, vol. 134, Issue 1, pp. 211-222.
Rane A., et al., "Drug Metabolism in the Human Fetus and Newborn Infant," Pediatric Clinics of North America, 1972, vol. 19, Issue 1, pp. 37-49.
Rankin S.A., et al., "A Molecular Atlas of Xenopus Respiratory System Development," Developmental Dynamics, 2015, vol. 244, pp. 69-85.
Rankin S.A., et al., Timing is everything: Reiterative Wnt, BMP and RA Signaling Regulate Developmental Competence during Endoderm Organogenesis, Developmental Biology, Feb. 1, 2018, vol. 434, Issue 1, pp. 121-132.
Rankin S.A., et al., "Suppression of Bmp4 Signaling by the Zinc-Finger Repressors OsrI and Osr2 is required for Wnt/beta-Catenin-Mediated Lung Specification in Xenopus," Development, 2012, vol. 139, Issue 16, pp. 3010-3020.
Rao R.R., et al., "Gene Expression Profiling of Embryonic Stem Cells Leads to Greater Understanding of Pluripotency and Early Developmental Events," Biology of Reproduction, 2004, vol. 71, pp. 1772-1778.
Ratineau C., et al., "Endoderm- and Mesenchyme-Dependent Commitment of the Differentiated Epithelial Cell Types in the Developing Intestine of Rat," Differentiation, 2003, vol. 71, pp. 163-169.
Ray K., "Engineering Human Intestinal Organoids with a Functional ENS," Nature Reviews Gastroenterology & Hematology, Nov. 2016, 1 page.
Rector, R.S., et al., "Mitochondrial Dysfunction Precedes Insulin Resistance and Hepatic Steatosis and Contributes to the Natural History of Non-Alcoholic Fatty Liver Disease in an Obese Rodent Model," Journal of Hepatology, 2010, vol. 52, Issue 5, pp. 727-736.
Reilly G C., et al., "Intrinsic Extracellular Matrix Properties Regulate Stem Cell Differentiation," Journal of Biomechanics, Jan. 2010, vol. 43, Issue 1, pp. 55-62.
Rennert K., et al., "A Microfluidically Perfused Three Dimensional Human Liver Model," Biomaterials, 2015, vol. 71, pp. 119-131.
Reuben A., et al., "Drug-Induced Acute Liver Failure: Results of a U.S. Multicenter, Prospective Study," Hepatology, 2010, vol. 52, pp. 2065-2076.
Ricchi M., et al., "Differential Effect of Oleic and Palmitic Acid on Lipid Accumulation and Apoptosis in Cultured Hepatocytes," Journal of Gastroenterology and Hepatology, May 2009, vol. 24, Issue 5, pp. 830-840.
Richards M et al., "The Transcriptome Profile of Human Embryonic Stem Cells as Defined by SAGE," Stem Cells, 2004, vol. 22, pp. 51-64.
Riedinger, et al., "Reversible Shutdown of Replicon Initiation by Transient Hypoxia in Ehrlich ascites Cells: Dependence of Initiation on Short-Lived Protein," European Journal of Biochemistry, Dec. 1992, vol. 210, Issue 2, pp. 389-398.
Roberts A., et al., "Identification of Novel Transcripts in Annotated Genomes using RNA-Seq," Bioinformatics, 2011, vol. 27, Issue 17, pp. 2325-2329.
Roberts A., et al., "Improving RNA-Seq Expression Estimates by Correcting for Fragment Bias," Genome Biology, 2011, vol. 12, 14 pages.
Roberts D.J., et al., "Sonic Hedgehog is an Endodermal Signal inducing Bmp-4 and Hox genes during Induction and Regionalization of the Chick hindgut," Development, 1995, vol. 121, pp. 3163-3174.
Rodriguez, P., et al., "BMP Signaling in the Development of the Mouse Esophagus and Forestomach," Development, 2010, vol. 137, Issue 24, pp. 4171-4176.
Rodriguez-Pineiro A.M., et al., "Studies of Mucus in Mouse Stomach, Small Intestine, and Colon. II. Gastrointestinal Mucus Proteome Reveals Muc2 and Muc5ac Accompanied by a set of Core Proteins," American Journal of Physiology: Gastrointestinal and Liver Physiology, 2013, vol. 305, pp. G348-G356.
Rohrschneider, M.R., et al., "Polarity and Cell Fate Specification in the Control of C. Elegans Gastrulation," Developmental Dynamics, 2009, vol. 238, Issue 4, pp. 789-796.
Ronn R.E., et al., "Retinoic Acid Regulates Hematopoietic Development from Human Pluripotent Stem Cells," Stem Cell Reports. 2015, vol. 4, pp. 269-281.
Roth, R.B., et al., "Gene Expression Analyses Reveal Molecular Relationships among 20 Regions of the Human CNS," Neurogenetics, 2006, vol. 7, pp. 67-80.
Rouch J.D., et al., "Scalability of an Endoluminal Spring for Distraction Enterogenesis," Journal of Pediatric Surgery, 2016, vol. 51, pp. 1988-1992.
Roy S., et al., "Cytoneme-Mediated Contact-Dependent Transport of the *Drosophila* Decapentaplegic Signaling Protein," Science, 2014, vol. 343, pp. 1244624-1 to 1244624-10.
Russo M. W., et al., "Liver Transplantation for Acute Liver Failure From Drug Induced Liver Injury in the United States," Liver Transplantation, 2004, vol. 10, Issue 8, pp. 1018-1023.
Sachs N., et al., "A Living Biobank of Breast Cancer Organoids Captures Disease Heterogeneity," Cell, 2018, vol. 172, pp. 373-386.
Saenz J.B., et al., "Stomach Growth in a Dish," Nature, Jan. 2017, vol. 541, No. 7636, pp. 160-161.
Saffrey M J., "Cellular Changes in the Enteric Nervous System During Ageing," Developmental Biology, 2013, vol. 382, pp. 344-355.
Saha S., et al., "Inhibition of Human Embryonic Stem Cell Differentiation by Medical Strain," Journal of Cellular Physiology, 2006, vol. 206, pp. 126-137.
Saini A., "Cystic Fibrosis Patients Benefit from Mini Guts," Cell Stem Cell, 2016, vol. 19, pp. 425-427.
Saito M., et al., "Reconstruction of Liver Organoid using a Bioreactor," World Journal of Gastroenterology, Mar. 2006, vol. 12, Issue 12, pp. 1881-1888.
Salas-Vidal E., et al., "Imaging Filopodia Dynamics in the Mouse Blastocyst," Developmental Biology, 2004, vol. 265, pp. 75-89.
Sampaziotis F., et al., "Potential of Human Induced Pluripotent Stem Cells in Studies of Liver Disease," Hepatology, 2015, vol. 62, Issue 1, pp. 303-311.
Sancho E., et al., "Signaling Pathways in Intestinal Development and Cancer," Annual Review of Cell and Developmental Biology, 2004, vol. 20, pp. 695-723.
Sandoiu A., "Scientists Create Human Esophagus in Stem Cell First," Medical News Today, Downloaded from https://www.medicalnewstoday.com/articles/323118.phpSep. 21, 2018, 4 pages.
Sartori-Rupp A., et al., "Correlative Cryo-Electron Microscopy Reveals the Structure of TNTs in Neuronal Cells," Nature Communications, 2019, vol. 10, 16 pages.
Sasai Y., "Cytosystems Dynamics in Self-Organization of Tissue Architecture," Nature, 2013, vol. 493, pp. 318-326.
Sasai Y., "Next-Generation Regenerative Medicine: Organogenesis from Stem Cells in 3D Culture," Cell Stem Cell, May 2013, vol. 12, pp. 520-530.
Sasselli V., et al., "The Enteric Nervous System," Developmental Biology, Jan. 2012, vol. 366, pp. 64-73.
Sato T., et al., "Single Lgr5 Stem Cells Build Crypt-Villus Structures in Vitro without a Mesenchymal Niche," Nature, 2009, vol. 459, pp. 262-265.
Sato T., et al., "Long-term Expansion of Epithelial Organoids from Human Colon, Adenoma, Adenocarcinoma, and Barrett's Epithelium," Gastroenterology, Nov. 1, 2011, vol. 141, pp. 1762-1772.
Sato T., et al., "Snapshot: Growing Organoids from Stem Cells," Cell, 2015, vol. 161, pp. 1700-1700e1.
Savidge T.C., et al., "Human Intestinal Development in a Severe-Combined Immunodeficient Xenograft model," Differentiation, 1995, vol. 58, pp. 361-371.
Savin T., et al., "On the Growth and Form of the Gut," Nature, Aug. 3, 2011, vol. 476, pp. 57-62.
Schlieve C.R., et al., "Created of Warm Blood and Nerves: Restoring an Enteric Nervous System in Organoids," Cell Stem Cell, Jan. 2017, vol. 20, pp. 5-7.

(56) References Cited

OTHER PUBLICATIONS

Schmelter M., et al., "Embryonic Stem Cells Utilize Reactive Oxygen Species as Transducers of Mechanical Strain-induced Cardiovascular Differentiation," The FASEB Journal, Jun. 2006, vol. 20, Issue 8, pp. 1182-1184.
Schonhoff S E., et al., "Neurogenin 3-expressing Progenitor Cells in the Gastrointestinal Tract Differentiate into both Endocrine and Non-Endocrine Cell Types," Dev Biol, Jun. 2004, vol. 270, Issue 2, pp. 443-454.
Schumacher M A., et al., "Gastric Sonic Hedgehog Acts as a Macrophage Chemoattractant during the Immune Response to Helicobacter pylori," Gastroenterology, May 2012, vol. 142, Issue 5, pp. 1150-1159.
Schumacher M.A., et al., "The Use of Murine-derived Fundic Organoids in Studies of Gastric Physiology," J. Physiol., Apr. 15, 2015, vol. 593, Issue 8, pp. 1809-1827.
Schuppan D., et al., "Non-alcoholic Steatohepatitis: Pathogenesis and Novel Therapeutic Approaches," Journal of Gastroenterology and Hepatology, Aug. 2013, vol. 28, Suppl. 1, pp. 68-76.
Serviddio G., et al., "Ursodeoxycholic Acid Protects Against Secondary Biliary Cirrhosis in Rats by Preventing Mitochondrial Oxidative Stress," Hepatology, 2004, vol. 39, pp. 711-720.
Shah S.B., et al., "Cellular Self-assembly and Biomaterials-based Organoid Models of Development and Diseases," Acta Biomaterialia, Apr. 15, 2017, vol. 53, pp. 29-45.
Shahbazi M N., et al., "Self-organization of the human embryo in the absence of maternal tissues," Nature Cell Biology, May 4, 2016, vol. 18, Issue 6, pp. 700-708.
Shan J., et al., "Identification of a Specific Inhibitor of the Dishevelled PDZ Domain," Biochemistry, 2005, vol. 44, Issue 47, pp. 15495-15503.
Sheehan-Rooney K., et al., "Bmp and Shh Signaling Mediate the Expression of satb2 in the Pharyngeal Arches," PLoS One, Mar. 21, 2013, vol. 8, Issue 3, e59533, 10 pages.
Shekherdimian S., et al., "The Feasibility of using an Endoluminal Device for Intestinal Lengthening," Journal of Pediatric Surgery, Aug. 2010, vol. 45, Issue 8, pp. 1575-1580.
Sherwood R I., et al., "Transcriptional Dynamics of Endodermal Organ Formation," Developmental Dynamics, Jan. 2009, vol. 238, Issue 1, pp. 29-42.
Sherwood R I., et al., "Wnt Signaling Specifies and Patterns Intestinal Endoderm," Mechanisms of Development, Sep. 2011, vol. 128, pp. 387-400.
Shi X L., et al., "Evaluation of a Novel Hybrid Bioartificial Liver Based on a Multi-Layer Flat-Plate Bioreactor," World Journal of Gastroenterology, Jul. 28, 2012, vol. 18, Issue 28, pp. 3752-3760.
Shi X-L., et al., "Effects of Membrane Molecular Weight Cut-off on Performance of a Novel Bioartificial Liver," Artificial Organs, Mar. 2011, vol. 35, Issue, 3, pp. E40-E46.
Shimizu N., et al., "Cyclic Strain Induces Mouse Embryonic Stem Cell Differentiation into Vascular Smooth Muscle Cells by Activating PDGF Receptor Beta," Journal of Applied Physiology, Mar. 2008, vol. 104, pp. 766-772.
Shyer A.E., et al., "Bending Gradients: How the Intestinal Stem Cell Gets Its Home," Cell, Apr. 23, 2015, vol. 161, Issue 3, pp. 569-580.
Shyer A.E., et al., "Villification: How the Gut Gets its Villi," Science, Oct. 11, 2013, vol. 342, pp. 212-218.
Siegel R., et al., "Colorectal Cancer Statistics, 2014," CA Cancer Journal for Clinicians, Apr. 2014, vol. 64, Issue 2, pp. 104-117.
Sigalet D L., "The Role of the Enteric Neuronal System in Controlling Intestinal Function," Clinical Surgery Society Magazine, 2003, vol. 64, p. 214.
Siller R., et al., "Small-Molecule-Driven Hepatocyte Differentiation of Human Pluripotent Stem Cells," Stem Cell Reports, May 2015, vol. 4, No. 5, pp. 939-952.
Sim Y.J., et al., "2i Maintains a Naive Ground State in ESCs through Two Distinct Epigenetic Mechanisms," Stem Cell Reports, May 9, 2017, vol. 8, Issues. 5, pp. 1312-1328.
Simkin J.E., et al., "Retinoic Acid Upregulates Ret and Induces Chain Migration and Population Expansion in Vagal Neural Crest Cells to Colonise the Embryonic Gut", PLoS ONE, May 2013, vol. 8(5), e64077, pp. 1-12.
Simon-Assmann P., et al., "In Vitro Models of Intestinal Epithelial Cell Differentiation," Cell Biology and Toxicology, Jul. 2007, vol. 23, Issue 4, pp. 241-256.
Sinagoga K.L., et al., "Generating Human Intestinal Tissues from Pluripotent Stem Cells to Study Development and Disease," The EMBO Journal, May 5, 2015, vol. 34, Issue 9, pp. 1149-1163.
Singh S., et al., "Comparative Effectiveness of Pharmacological Interventions for Nonalcoholic Steatohepatitis: A Systematic Review and Network Meta-analysis," Hepatology, Nov. 2015, vol. 62, Issue 5, pp. 1417-1432.
Si-Tayeb K., et al., "Highly Efficient Generation of Human Hepatocyte-Like Cell from Induced Pluripotent Stem Cells," Hepatology, Jan. 2010, vol. 51, Issue 1, pp. 297-305.
Sitti M., et al., "Biomedical Applications of Untethered Mobile Milli/Microrobots," The Proceedings of the IEEE Institution of Electrical Engineers, Feb. 2015, vol. 103, Issue 2, pp. 205-224.
Skardal A., et al., "Organoid-on-a-Chip and Body-on-a-Chip Systems for Drug Screening and Disease Modeling," Drug Discovery Today, Sep. 2016, vol. 21, Issue 9, pp. 1399-1411.
Slaymaker I M., et al., "Rationally Engineered Cas9 Nucleases with Improved Specificity," Science, Jan. 1, 2016, vol. 351, issue 6268, pp. 84-88.
Sloan C A., et al., "ENCODE Data at the ENCODE Portal," Nucleic Acids Research, Jan. 4, 2016, vol. 44, Issue. D1, pp. D726-D732.
Sneddon I.N., "The Relation between Load and Penetration in the Axisymmetric Boussinesq Problem for a Punch of Arbitrary Profile," International Journal of Engineering Science, May 1965, vol. 3, Issue 1, pp. 47-57.
Snoeck H W., "Generation of Anterior Foregut Derivatives from Pluripotent Stem Cells," Stem Cells Handbook, S. Sell (ed.), Jul. 3, 2013, pp. 161-175.
Snykers S., et al., "In Vitro Differentiation of Embryonic and Adult Stem Cells into Hepatocytes: State of the Art," Stem Cells, Mar. 2009, vol. 27, Issue 3, pp. 577-605.
Soffers J H M., et al., "The Growth Pattern of the Human Intestine and its Mesentery," BMC Developmental Biology, Aug. 22, 2015, vol. 15, Issue 31, 16 pages.
Song W., et al., "Engraftment of Human Induced Pluripotent Stem cell-Derived Hepatocytes in Immunocompetent Mice via 3D Co-aggregation and Encapsulation," Scientific Reports, 2015, vol. 5, Issue 16884, 13 pages.
Song Z., et al., "Efficient Generation of Hepatocyte-like cells from Human Induced Pluripotent Stem Cells," Cell Res, Nov. 2009, vol. 19, Issue 11, pp. 1233-1241.
Sonntag F., et al., "Design and Prototyping of a Chip-based Multi-micro-Organoid Culture System for Substance Testing, Predictive to Human (substance) Exposure," Journal of Biotechnology, Jul. 1, 2010, vol. 148, Issue 1, pp. 70-75.
Soto-Gutierrez A., et al., "Engineering of an Hepatic Organoid to Develop Liver Assist Devices," Cell Transplant, 2010, vol. 19, Issue 6, pp. 815-822.
Spear P C., et al., "Interkinetic Nuclear Migration: A Mysterious Process in Search of a Function," Develop. Growth Differ, Apr. 2012, vol. 54, Issue 3, pp. 306-316.
Speer A L., et al., "Fibroblast Growth Factor 10-Fibroblast Growth Factor Receptor 2b Mediated Signaling is not Required for Adult Glandular Stomach Homeostasis," PLoS ONE, Nov. 2012, vol. 7, Issue 11, e49127, 12 pages.
Speer A L., et al., "Murine Tissue-Engineered Stomach Demonstrates Epithelial Differentiation," Journal of Surgical Research, Mar. 22, 2011, vol. 171, Issue 1, pp. 6-14.
Spence J R., et al., "Vertebrate Intestinal Endoderm Development," Developmental Dynamics, Mar. 2011, vol. 240, Issue 3, pp. 501-520.
Spence J R., et al., "Translational Embryology: Using Embryonic Principles to Generate Pancreatic Endocrine cells from Embryonic Stem Cells," Developmental Dynamics, Dec. 2007, vol. 236, issue 12, pp. 3218-3227.

(56) References Cited

OTHER PUBLICATIONS

Spence J.R., et al., “Directed Differentiation of Human Pluripotent Stem Cells into Intestinal Tissue in Vitro,” Nature (London), Feb. 3, 2011, vol. 470, Issue 7332, pp. 105-109.
Stadtfeld M., et al., “Induced Pluripotent Stem Cells Generated without Viral Integration,” Science, Nov. 7, 2008, vol. 322, issue 5903, pp. 945-949.
Stafford D., et al., “A Conserved Role for Retinoid Signaling in Vertebrate Pancreas Development,” Development Genes and Evolution, Sep. 2004, vol. 214, Issue 9, pp. 432-441.
Stange D E., et al., “Differentiated Troy$^+$ Chief Cells act as ‘Reserve’ Stem cells to Generate all Lineages of the Stomach Epithelium,” Cell, Oct. 10, 2013, vol. 155, Issue 2, pp. 357-368.
Stark R., et al., “Development of an Endoluminal Intestinal Lengthening Capsule,” Journal of Pediatric Surgery, Jan. 2012, vol. 47, Issue 1, pp. 136-141.
Stender S., et al., “Adiposity Amplifies the Genetic Risk of Fatty Liver Disease Conferred by Multiple Loci,” Nat Genet, Jun. 2017, vol. 49, Issue 6, pp. 842-847.
Stevens J L., et al., “The Future of Drug Safety Testing: Expanding the View and Narrowing the Focus,” Drug Discovery Today, Feb. 2009, vol. 14, Issue 3-4, pp. 162-167.
Stuart T., et al., “Comprehensive Integration of Single-Cell Data,” Cell, Jun. 13, 2019, vol. 177, pp. 1888-1902.
Su N., et al., “Role of FGF/FGFR Signaling in Skeletal Development and Homeostasis: Learning from Mouse Models,” Bone Research, Apr. 29, 2014, vol. 2, No. 1, 24 pages.
Sugawara T., et al., “Organoids Recapitulate Organs?,” Stem Cell Investigation, Jan. 2018, vol. 5(3), 4 pages.
Sugimoto S., et al., “Reconstruction of the Human Colon Epithelium in Vivo,” Cell Stem Cell, 2018, vol. 22, pp. 171-176.
Sui L., et al., “Signaling Pathways During Maintenance and Definitive Endoderm Differentiation of Embryonic Stem Cells,” The International Journal of Developmental Biology, 2013, vol. 57(1), pp. 1-12.
Sun Y., et al., “Genome Engineering of Stem Cell Organoids for Disease Modeling,” Protein Cell, May 2017, vol. 8(5), pp. 315-327.
Suzuki A., et al., “Clonal Identification and Characterization of Self-renewing Pluripotent Stem Cells in the Developing Liver,” The Journal of Cell Biology, Jan. 7, 2002, vol. 156(1), pp. 173-184.
Tada M., et al., “Embryonic Germ Cells Induce Epigenetic Reprogramming of Somatic Nucleus in Hybrid Cells,” EMBO Journal, 1997, vol. 16(21), pp. 6510-6520.
Taipale J., et al., “The Hedgehog and Wnt signalling pathways in cancer,” Nature, May 17, 2001, vol. 411, pp. 349-354.
Tait I.S., et al., “Colonic Mucosal Replacement by Syngeneic Small Intestinal Stem Cell Transplantation,” The American Journal of Surgery, Jan. 1994, vol. 167(1), pp. 67-72.
Tait I.S., et al., “Generation of Neomucosa in Vivo by Transplantation of Dissociated Rat Postnatal Small Intestinal Epithelium,” Differentiation, Apr. 1994 Vol. 56,(1-2), pp. 91-100.
Takahashi K., et al., “Induction of Pluripotent Stem Cells from Adult Human Fibroblasts by Defined Factors,” Cell, Nov. 30, 2007, vol. 131(5), pp. 861-872.
Takahashi K., et al., “Induction of Pluripotent Stem Cells from Mouse Embryonic and Adult Fibroblast Cultures by Defined Factors,” Cell, Aug. 25, 2006, vol. 126(4), pp. 663-676.
Takahashi S., et al., “Epigenetic Differences between Naive and Primed Pluripotent Stem Cells,” Cellular and Molecular Life Sciences, Apr. 2018, vol. 75(7), pp. 1191-1203.
Takaki M., et al., “In Vitro Formation of Enteric Neural Network Structure in a Gut-Like Organ Differentiated from Mouse Embryonic Stem Cells,” Stem Cells, Jun. 9, 2006, vol. 24(6), pp. 1414-1422.
Takashima Y., et al., “Resetting Transcription Factor Control Circuitry toward Ground-State Pluripotency in Human,” Cell, Sep. 11, 2014, vol. 158(6), pp. 1254-1269.
Takebe T., et al., “Generation of a Vascularized and Functional Human Liver from an iPSC-derived Organ Bud Transplant,” Nature Protocols, Feb. 2014, vol. 9(2), pp. 396-409.
Takebe T., et al., “Human iPSC-Derived Miniature Organs: A Tool for Drug Studies,” Clinical Pharmacology & Therapeutics, Sep. 2014, vol. 96(3), pp. 310-313.
Takebe T., et al., “Massive and Reproducible Production of Liver Buds Entirely from Human Pluripotent Stem Cells,” Cell Reports, Dec. 5, 2017, vol. 21(10), pp. 2661-2670.
Takebe T., et al., “Vascularized and Complex Organ Buds from Diverse Tissues via Mesenchymal Cell-Driven Condensation,” Cell Stem Cell, May 7, 2015, vol. 16(5), pp. 556-565.
Takebe T., et al., “Vascularized and Functional Human Liver from an iPSC-derived Organ bud Transplant,” Nature, Jul. 25, 2013, vol. 499(7459), pp. 481-484.
Tamm C., et al., “A Comparative Study of Protocols for Mouse Embryonic Stem Cell Culturing,” PLoS ONE, Dec. 10, 2013, vol. 8(12), e81156, 10 pages.
Tamminen K., et al., “Intestinal Commitment and Maturation of Human Pluripotent Stem Cells Is Independent for Exogenous FGF4 and R-spondin1,” PLOS One, Jul. 31, 2015, vol. 10(7), e0134551, 19 pages.
Tang W., et al., “Faithful Expression of Multiple Proteins via 2A-Peptide Self-processing: a Versatile and Reliable method for Manipulating Brain Circuits,” The Journal of Neuroscience, Jul. 8, 2009, vol. 29(27), pp. 8621-8629.
Teo A K.K., et al., “Activin and BMP4 Synergistically Promote Formation of Definitive Endoderm in Human Embryonic Stem Cells,” Stem Cells, Apr. 2012, vol. 30(4), pp. 631-642.
Terry B.S., et al., “Preliminary Mechanical Characterization of the Small Bowel for In Vivo Robotic Mobility,” Journal of Biomechanical Engineering, Sep. 2011, vol. 133(9), 091010-1-09101-7.
Thanasupawat, T., et al., “INSL5 is a Novel Marker for Human Enteroendocrine Cells of the Large Intestine and Neuroendocrine Tumours,” Oncology Reports, 2013, vol. 29, No. 1., pp. 149-154.
The ENCODE Project Consortium, “An Integrated Encyclopedia of DNA Elements in the Human Genome,” Nature, Sep. 5, 2012, vol. 489, pp. 57-74.
The United States Pharmacopeia: The National Formulary (USP 24 NF 19), United States Pharmacopoeial Convention, Inc., Rockville, MD, 1999, 4 pages.
The WNT Homepage, “Small molecules in Wnt signaling,” Nusse Lab, Jan. 2019, 2 pages.
Theunissen T.W., et al., “Systematic Identification of Culture Conditions for Induction and Maintenance of Naive Human Pluripotency,” Cell Stem Cell, Oct. 2, 2014, vol. 15(4), pp. 471-487.
Thomson J.A., et al., “Embryonic Stem Cell Lines Derived from Human Blastocysts,” Science, Nov. 6, 1998, vol. 282(5391), pp. 1145-1147.
Tian X., et al., “Modulation of Multidrug Resistance-Associated Protein 2 (Mrp2) and Mrp3 Expression and Function with Small Interfering RNA in Sandwich-Cultured Rat Hepatocytes,” Molecular Pharmacology, Oct. 2004, vol. 66(4), pp. 1004-1010.
Tiso N., et al., “BMP Signalling Regulates Anteroposterior Endoderm Patterning in Zebrafish,” Mech Dev, Oct. 2002, vol. 118, pp. 29-37.
Toivonen S., et al., “Activin A and Wnt-dependent Specification of Human Definitive Endoderm Cells,” Experimental Cell Research, Aug. 2013, vol. 319(17), pp. 2535-2544.
Tran K., et al., “Evaluation of Regional and Whole Gut Motility using the Wireless Motility Capsule: Relevance in Clinical Practice,” Therapeutic Advances in Gastroenterology, Jul. 2012, vol. 5(4), pp. 249-260.
Trapnell C., et al., “Differential gene and Transcript Expression Analysis of RNA-seq Experiments with TopHat and Cufflinks,” Nature Protocols, 2013, vol. 7(3), pp. 562-578.
Trapnell C., et al., “Transcript Assembly and Quantification by RNA-Seq reveals Unannotated Transcripts and Isoform Switching during Cell Differentiation,” Nature Biotechnology, May 2, 2010, vol. 28(5), pp. 511-515.
Trisno S.L., et al., “Esophageal Organoids from Human Pluripotent Stem Cells Delineate Sox2 Functions during Esophageal Specification,” Cell Stem Cell, Oct. 4, 2018, vol. 23(4), pp. 501-515.
Remington, J.P., (ed.), “Remington: The Science and Practice of Pharmacy,” 2006, Lippincott, Williams & Wilkens, Baltimore, MD, 2006, Table of Contents in 6 pages.

(56) References Cited

OTHER PUBLICATIONS

Tsakmaki A., et al., "3D Intestinal Organoids in Metabolic Research: Virtual Reality in a Dish," Current Opinion in Pharmacology, 2017, vol. 37, pp. 51-58.
Tsedensodnom O., et al. "ROS: Redux and Paradox in Fatty Liver Disease, " Hepatology, 2013, vol. 58(4), pp. 1210-1212.
Tsukada N., et al., "The Structure and Organization of the Bile Canalicular Cytoskeleton with Special Reference to Actin and Actin-Binding Proteins," Hepatology, 1995, vol. 21, No. 4, pp. 1106-1113.
Tuschl T. et al., "Targeted mRNA degradation by Double-Stranded RNA in vitro," Genes & Development., 1999, vol. 13, pp. 3191-3197.
Tyml K., et al., "Lipopolysaccharide Reduces Intercellular Coupling in Vitro and Arteriolar Conducted Response in Vivo," American Journal of Physiology-Heart and Circulatory Physiology, 2001, vol. 281, pp. H1397-H1406.
Uppal K., et al., "Meckel's Diverticulum: A Review," Clinical Anatomy, 2011, vol. 24, pp. 416-422.
Valadi H., et al., "Exosome-Mediated Transfer of mRNAs and MicroRNAs is a Novel mechanism of Genetic Exchange between Cells," Nature Cell Biology, 2007, vol. 9, No. 6, pp. 654-659.
Van Breemen R.B., et al., "Caco-2 Cell Permeability Assays to Measure Drug Absorption," Expert Opinion on Drug Metabolism & Toxicology, Aug. 2005, vol. 1, No. 2, pp. 175-185.
Van De Garde M.D., et al., "Liver Monocytes and Kupffer Cells Remain Transcriptionally Distinct during Chronic Viral Infection," PLoS One, Nov. 3, 2016, vol. 11, No. 11, 16 pages.
Van Dop W.A., et al., "Depletion of the Colonic Epithelial Precursor Cell Compartment upon Conditional Activation of the Hedgehog Pathway," Gastroenterology, 2009, vol. 136, No. 7, pp. 2195-2203.
Van Klinken B.J.W., et al., "MUC5B is the Prominent Mucin in Human Gallbladder and is also Expressed in a Subset of Colonic Goblet Cells," The American Journal of Physiology, 1998, vol. 274, pp. G871-G878.
Venick, R.S., et al., "Unique Technical and Patient Characteristics of Retransplantation: A Detailed Single-Center Analysis of Intestinal Transplantation," International Small Bowel Symposium 2013; Abstract 5.203, retrieved from https://www.tts.org/component/ts/?view=presentation&id=13190, accessed Jun. 12, 2017, 4 pages.
Verma S., et al., "Diagnosis, Management and Prevention of Drug-Induced Liver Injury," Gut, 2009, vol. 58, pp. 1555-1564.
Verzi M.P., et al., "Role of the Homeodomain Transcription Factor Bapx1 in Mouse Distal Stomach Development," Gastroenterology, 2009, vol. 136, No. 5, pp. 1701-1710.
Vosough M., et al. "Generation of Functional Hepatocyte-Like Cells from Human Pluripotent Stem Cells in a Scalable Suspension Culture," Stem Cells and Development, 2013, vol. 22, No. 20, pp. 2693-2705.
Vu J., et al., "Regulation of Appetite, Body Composition and Metabolic Hormones by Vasoactive Intestinal Polypeptide (VIP)," Journal of Molecular Neuroscience, Apr. 23, 2015, vol. 56, No. 2, pp. 377-387.
Wakayama T., et al., "Full-term Development of Mice from Enucleated Oocytes Injected with Cumulus Cell Nuclei," Nature, Jul. 23, 1998, vol. 394, pp. 369-374.
Walker E.M., et al., "GATA4 and GATA6 Regulate Intestinal Epithelial Cytodifferentiation during Development," Developmental Biology, 2014, vol. 392, pp. 283-294.
Wallace A S., et al., "Development of the Enteric Nervous System, Smooth Muscle and Interstitial cells of Cajal in the Human Gastrointestinal Tract," Cell and Tissue Research, Jan. 26, 2005, vol. 319, pp. 367-382.
Walton K.D., et al., "Epithelial Hedgehog Signals Direct Mesenchymal Villus Patterning through BMP," Abstracts / Developmental Biology, 2009, vol. 331, p. 489.
Walton K.D., et al., "Hedgehog-Responsive Mesenchymal Clusters Direct Patterning and Emergence of Intestinal Villi," PNAS, Sep. 25, 2012, vol. 109, No. 39, pp. 15817-15822.
Walton K.D., et al., "Villification in the Mouse: Bmp Signals Control Intestinal Villus Patterning," Development, 2016, vol. 143, pp. 427-436.
Wan W., et al., "The Role of wnt Signaling in the Development of Alzheimer's disease: A Potential Therapeutic Target?," BioMed Research International, 2014, vol. 2014, pp. 1-9.
Wang A., et al., "Generating Cells of the Gastrointestinal system: Current Approaches and Applications for the Differentiation of Human Pluripotent Stem Cells," Journal of Molecular Medicine, Jun. 20, 2012, vol. 90, pp. 763-771.
Wang F., et al., "Isolation and Characterization of Intestinal Stem Cells based on Surface Marker Combinations and Colony-Formation Assay," Gastroenterology, 2013, vol. 145, No. 2, pp. 383-395.
Wang J., et al., "Mutant Neurogenin-3 in Congenital Malabsorptive Diarrhea," New England Journal of Medicine, Jul. 20, 2006, vol. 355, pp. 270-280.
Wang S., (Ed.), "The role of Homologous Genes in the Development of Appendages," in Basis of Developmental Biology, Press of East China University of Science and Technology, 2014, pp. 184-185.
Wang X., et al., "Cloning and Variation of Ground State Intestinal Stem Cells," Nature, Jun. 11, 2015, vol. 522, pp. 173-178.
Wang Y., et al., "Hepatic Stellate Cells, Liver Innate Immunity, and Hepatitis C Virus," Journal of Gastroenterology and Hepatology, 2013, vol. 28(1), pp. 112-115.
Wang Z., et al., "Retinoic Acid Regulates Morphogenesis and Patterning of Posterior Foregut Derivatives," Developmental Biology, May 23, 2006, vol. 297, pp. 433-445.
Want R., "An Introduction to RFID Technology," IEEE Pervasive Computing, 2006, vol. 5, pp. 25-33.
Ward D.F Jr., et al., "Mechanical Strain Enhances Extracellular Matrix-Induced Gene Focusing and Promotes Osteogenic Differentiation of Human Mesenchymal Stem Cells Through an Extracellular-Related Kinase-Dependent Pathway," Stem Cells and Development, 2007, vol. 16, pp. 467-479.
Ware C.B., "Concise Review: Lessons from Naive Human Pluripotent Cells," Stem Cells, 2017, vol. 35, pp. 35-41.
Warlich E., et al., "Lentiviral Vector Design and Imaging Approaches to Visualize the Early Stages of Cellular Reprogramming," Molecular Therapy, Apr. 2011, vol. 19, No. 4, pp. 782-789.
Warren C.R., et al., "Induced Pluripotent Stem Cell Differentiation Enables Functional Validation of GWAS Variants in Metabolic Disease," Cell Stem Cell, Apr. 6, 2017, vol. 20, pp. 547-557.
Warren C.R., et al., "The NextGen Genetic Association Studies Consortium: A Foray into In Vitro Population Genetics," Cell Stem Cell, 2017, vol. 20, pp. 431-433.
Watson C.L., et al., "An in Vivo Model of Human Small Intestine Using Pluripotent Stem Cells," Nature Medicine, Oct. 19, 2014, vol. 20, No. 11, pp. 1310-1314.
Wehkamp J., et al., "Paneth Cell Antimicrobial Peptides: Topographical Distribution and Quantification in Human Gastrointestinal Tissues," FEBS Letters, 2006, vol. 580, pp. 5344-5350.
Weis V.G., et al., "Current Understanding of SPEM and its Standing in the Preneoplastic Process," Gastric Cancer, 2009, vol. 12, pp. 189-197.
Wells J.M., et al., "Early Mouse Endoderm is Patterned by Soluble Factors from Adjacent Germ Layers," Development, Mar. 21, 2000, vol. 127, pp. 1563-1572.
Wells J.M., et al., "How to Make and Intestine," Development, vol. 141, No. 4, Feb. 15, 2014, pp. 752-760.
Wen S., et al., "Helicobacter Pylori Virulence Factors in Gastric Carcinogenesis," Cancer Letters, 2009, vol. 282, pp. 1-8.
Wernig M., et al., "In Vitro Reprogramming of Fibroblasts into a Pluripotent ES-cell-like State," Nature, 2007, vol. 448, pp. 318-324.
Whissell G., et al., "The Transcription Factor GATA6 Enables Self-Renewal of Colon Adenoma Stem Cells by Repressing BMP Gene Expression," Nature Cell Biology, 2014, vol. 16, No. 7, pp. 695-707.
Wieck M.M., et al., "Prolonged Absence of Mechanoluminal Stimulation in Human Intestine Alters the Transcriptome and Intestinal Stem Cell Niche," Cell Mol Gastroenterol Hepatol, 2017, vol. 3, No. 3, pp. 367-388.

(56) References Cited

OTHER PUBLICATIONS

Wiley L.A., et al., "cGMP Production of Patient-Specific iPSCs and Photoreceptor Precursor Cells to Treat Retinal Degenerative Blindness," Scientific Reports, 2016, vol. 6(30742), 16 pages.
Willet S.G., et al., "Stomach Organ and Cell Lineage Differentiation: From Embryogenesis to Adult Homeostasis," Cellular and Molecular Gastroenterology and Hepatology, Sep. 2016, vol. 2, pp. 546-559.
Williamson R.C.N., et al., "Humoral Stimulation of Cell Proliferation in Small Bowel after Transection and Resection in Rats," Gastroenterology, 1978, vol. 75, No. 2, pp. 249-254.
Wills A., et al., "Bmp Signaling is necessary and sufficient for Ventrolateral Endoderm Specification in Xenopus," Developmental Dynamics, 2008, vol. 237(8), pp. 2177-2186.
Wilmut I., et al., "Viable Offspring Derived from Fetal and Adult Mammalian Cells," Nature, Feb. 27, 1997, vol. 385, pp. 810-813.
Woltjen K., et al., "piggyBac transposition reprograms fibroblasts to induced pluripotent stem cells," Nature, Apr. 9, 2009, vol. 458, pp. 766-770.
Workman M.J., et al., "Engineered Human Pluripotent-Stem-Cell-derived Intestinal tissues with a functional Enteric Nervous System," Nature Medicine, Jan. 2017, vol. 23(1), pp. 49-59.
Workman M.J., "Generating 3D Human Intestinal Organoids with an Enteric Nervous System," Thesis, Graduate School of the University of Cincinnati, 2014, 60 pages.
Xia H.H.X., et al., "Antral-Type Mucosa in the Gastric Incisura, Body, and Fundus (Antralization): A Link Between Helicobacter pylori Infection and Intestinal Metaplasia?," American Journal of Gastroenterology, 2000, vol. 95, No. 1, pp. 114-121.
Xinaris C, et al., "Organoid Models and Applications in Biomedical Research," Nephron Jun. 25, 2015, Issue 130, pp. 191-199.
Xu R., et al., "Association between Patatin-Like Phospholipase Domain Containing 3 Gene (PNPLA3) Polymorphisms and Non-alcoholic Fatty Liver Disease: A Huge Review and Meta-Analysis," Scientific Reports, Mar. 20, 2015, vol. 5(9284), 11 pages.
Xu R., et al. (Eds), "Retinoic Acid Receptor" in Basis and Clinic of Receptor, Shanghai Science and Technology Press, 1992, pp. 129-131.
Xue X., et al., "Endothelial PAS Domain Protein 1 Activates the Inflammatory Response in the Intestinal Epithelium to Promote Colitis in Mice," Gastroenterology, 2013, vol. 145, No. 4, pp. 831-841.
Yahagi N., et al., "Position-Specific Expression of Hox Genes along the Gastrointestinal Tract," Congenital Anomalies, 2004, vol. 44, pp. 18-26.
Yamada S., et al. "Differentiation of Immature Enterocytes into Enteroendocrine Cells by Pdx1 Overexpression," American Journal of Physiology: Gastrointestinal and Liver Physiology, 2001, vol. 281, No. 1, pp. G229-G236.
Yamaguchi Y., et al., "Purified Interleukin 5 Supports the Terminal Differentiation and Proliferation of Murine Eosinophilic Precursors," Journal of Experimental Medicine, Jan. 1988, vol. 167, No. 1, pp. 43-56.
Yanagimachi M.D., et al., "Robust and Highly-Efficient Differentiation of Functional Monocytic Cells from Human Pluripotent Stem Cells Under Serum- and Feeder Cell-Free Conditions," PLoS One, 2013, vol. 8(4), e59243, 9 pages.
Yanagita M., "Modulator of Bone Morphogenetic Protein Activity in the Progression of Kidney Diseases," Kidney International, 2006, vol. 70, pp. 989-993.
Yang K., et al., "Systems Pharmacology Modeling Predicts Delayed Presentation and Species Differences in Bile Acid-Mediated Troglitazone Hepatotoxicity," Clinical Pharmacology & Therapeutics, 2014, vol. 96(5), pp. 589-598.
Yin C., et al., "Hepatic Stellate Cells in Liver Development, Regeneration, and Cancer," The Journal of Clinical Investigation, May 2013, vol. 123, No. 5, pp. 1902-1910.
Yoneda M., et al., "Noninvasive Assessment of Liver Fibrosis by Measurement of Stiffness in Patients with Nonalcoholic Fatty Liver Disease (NAFLD)," Dig Liver Dis, 2008, vol. 40, pp. 371-378.
Young H.M., et al., "Expression of Ret-, p75(NTR)-, Phox2a-, Phox2b-, and Tyrosine Hydroxylase-Immunoreactivity by Undifferentiated Neural Crest-Derived Cells and Different Classes of Enteric Neurons in the Embryonic Mouse Gut," Developmental Dynamics, 1999, vol. 216, pp. 137-152.
Young H.M., et al., "GDNF is a Chemoattractant for Enteric Neural Cells," Developmental biology, Dec. 19, 2000, vol. 229, pp. 503-516.
Yu H., et al., "The Contributions of Human Mini-Intestines to the Study of Intestinal Physiology and Pathophysiology," Annual Review of Physiology, Feb. 10, 2017, vol. 79, pp. 291-312.
Yuan Y., et al., "Peptic ulcer disease today," Nature Clinical Practice Gastroenterology & Hepatology, Feb. 2006, vol. 3, No. 2, pp. 80-89.
Yui S., et al., "Functional Engraftment of Colon Epithelium Expanded in Vitro from a Single Adult Lgr5(+) stem cell," Nature Medicine, Mar. 11, 2012, vol. 18, No. 4, pp. 618-623.
Zachos N.C., et al., "Human Enteroids/Colonoids and Intestinal Organoids Functionally Recapitulate Normal Intestinal Physiology and Pathophysiology," The Journal of Biological Chemistry, Feb. 19, 2016, vol. 29, No. 18, pp. 3759-3766.
Zain S.M., et al., "A Common Variant in the Glucokinase Regulatory Gene rs780094 and Risk of Nonalcoholic Fatty Liver Disease: A Meta-Analysis," Journal of Gastroenterology & Hepatology, 2015, vol. 30, pp. 21-27.
Zambrano E., et al., "Total parenteral Nutrition Induced Liver Pathology: An Autopsy Series of 24 Newborn Cases," Pediatric and Developmental Pathology, 2004, vol. 7, pp. 425-432.
Zborowski J., et al., "Induction of Swelling of Liver Mitochondria by Fatty Acids of Various Chain Length," Biochimica et Biophysica Acta, Oct. 22, 1963, vol. 70, pp. 596-598.
Zbuk K.M., et al., "Hamartomatous polyposis syndromes," Nature Clinical Practice Gastroenterology & Hepatology, 2007, vol. 4, No. 9, pp. 492-502.
Zhang D., et al., "Neural Crest Regionalisation for Enteric Nervous System Formation: Implications for Hirschsprung's Disease and Stem Cell Therapy," Developmental Biology, Mar. 15, 2010, vol. 339, pp. 280-294.
Zhang H., et al., "The Existence of Epithelial-to-Mesenchymal Cells with the Ability to Support Hematopoiesis in Human Fetal Liver," Cell Biology International, Mar. 2005, vol. 29, No. 3, pp. 213-219.
Zhang Q, et al., "Small-Molecule Synergist of the Wnt/β-catenin Signaling Pathway," PNAS, May 1, 2007, vol. 104, No. 18, pp. 7444-7448.
Zhang R.R., et al., "Human iPSC-Derived Posterior Gut Progenitors are Expandable and Capable of Forming Gut and Liver Organoids," Stem Cell Reports, Mar. 13, 2018, vol. 10, pp. 780-793.
Zhang W., et al., "Elastomeric Free-Form Blood Vessels for Interconnecting Organs on Chip Systems," Lab Chip, Apr. 26, 2016, vol. 16, No. 9, pp. 1579-1586.
Zhang Y.S., et al., "Seeking the Right Context for Evaluating Nanomedicine: from Tissue Models in Petri Dishes to Microfluidic Organs-on-a-chip," Nanomedicine (Lond.), 2015, vol. 10, No. 5, pp. 685-688.
Zhang Y.S., et al., "Multisensor-Integrated Organs-on-Chips Platform for Automated and Continual in Situ Monitoring of Organoid behaviors," Proceedings of the National Academy of Sciences USA, 2017, vol. 114, pp. E2293-E2302.
Zhao Y., et al., "A XEN-like State Bridges Somatic Cells to Pluripotency during Chemical Reprogramming," Cell, 2015, vol. 163, pp. 1678-1691.
Zhong J., et al., "Continuous-Wave Laser-Assisted Injection of Single Magnetic Nanobeads into Living Cells," Sensors and Actuators B: Chemical, 2016, vol. 230, pp. 298-305.
Zhou H., et al., "Generation of Induced Pluripotent Stem Cells Using Recombinant Proteins," Cell Stem Cell, May 8, 2009, vol. 4, pp. 381-384.
Zhou J., et al., "The Potential for Gut Organoid Derived Interstitial Cells of Cajal in Replacement Therapy," International Journal of Molecular Sciences, Sep. 26, 2017, vol. 18, No. 10, p. 2059 in 17 pages.
Zhou Q., et al., "In Vivo Reprogramming of Adult Pancreatic Exocrine Cells to β-Cells," Nature, 2008, vol. 455, pp. 627-632.

(56) References Cited

OTHER PUBLICATIONS

Zorn A.M., et al., "Vertebrate Endoderm Development and Organ Formation," Annual Review of Cell and Developmental Biology, 2009, vol. 25, pp. 221-251.
Alkhatatbeh M.J., et al., "Low Simvastatin Concentrations Reduce Oleic Acid-Induced Steatosis in HepG2 Cells: An In Vitro Model of Non-Alcoholic Fatty Liver Disease," Experimental and Therapeutic Medicine, 2016, vol. 11 (4), pp. 1487-1492.
Bain C.C., et al., "Constant Replenishment from Circulating Monocytes Maintains the Macrophage Pool in Adult Intestine," Nat Immunol, Oct. 2014, vol. 15 (10), pp. 929-937.
Bain C.C., et al., "Resident and Pro-Inflammatory Macrophages in the Colon Represent Alternative Context-Dependent Fates of the Same Ly6Chi Monocyte Precursors," Mucosal Immunology, May 2013, vol. 6 (3), pp. 498-510.
Bayha E., et al., "Retinoic Acid Signaling Organizes Endodermal Organ Specification Along the Entire Antero-Posterior Axis," PLoS one, Jun. 10, 2009, vol. 4 (6), e5845, 15 pages.
Bort R., et al., "Hex Homeobox Gene-Dependent Tissue Positioning is Required for Organogenesis of the Ventral Pancreas," Development, Jan. 2004, vol. 131 (4), pp. 797-806.
Bujko A., et al., "Transcriptional and Functional Profiling Defines Human Small Intestinal Macrophage Subsets," Journal of Experimental Medicine, 2018, vol. 215 (2), pp. 441-458.
Bulmer J.N., et al., "Macrophage Populations in the Human Placenta and Amniochorion," Clinical Experimental Immunology, 1984, vol. 57 (2), pp. 393-403.
Camp J.G., et al., "Multilineage Communication Regulates Human Liver Bud Development from Pluripotency," Nature, 2017, vol. 546 (7659), pp. 533-538.
Campbell E.L., et al., "Transmigrating Neutrophils Shape the Mucosal Microenvironment Through Localized Oxygen Depletion to Influence Resolution of Inflammation," Immunity, 2014, vol. 40 (1), pp. 66-77.
Choi K.D., et al., "Identification of the Hemogenic Endothelial Progenitor and Its Direct Precursor in Human Pluripotent Stem Cell Differentiation Cultures," Cell Reports, Sep. 27, 2012, vol. 2(3), pp. 553-567.
Cumano A., et al., "Lymphoid Potential, Probed before Circulation in Mouse, Is Restricted to Caudal Intraembryonic Splanchnopleura," Cell, Sep. 20, 1996, vol. 86 (6), pp. 907-916.
Davies L.C., et al., "Tissue-Resident Macrophages," Nat Immunol, Oct. 2013, vol. 14 (10), pp. 986-995.
Dekkers R., et al., "A Bioassay Using Intestinal Organoids to Measure CFTR Modulators in Human Plasma," Journal of Cystic Fibrosis, 2015, vol. 14 (2), pp. 178-181.
DeSchepper S., et al., "Self-Maintaining Gut Macrophages Are Essential for Intestinal Homeostasis," Cell, Oct. 4, 2018, vol. 175 (2), pp. 400-415.
Feldstein A.E., et al., "Free Fatty Acids Promote Hepatic Lipotoxicity By Stimulating TNF-α Expression via a Lysosomal Pathway," Hepatology, Jul. 2004, vol. 40 (1), pp. 185-194.
Fukuda A., et al., "Ectopic Pancreas Formation in Hes1-Knockout Mice Reveals Plasticity of Endodermal Progenitors of the Gut, Bile Duct, and Pancreas," The Journal of Clinical Investigation, Jun. 2006, vol. 116 (6), pp. 1484-1493.
Glocker E.O., et al., "Inflammatory Bowel Disease and Mutations Affecting the Interleukin-10 Receptor," N Engl J Med, Nov. 19, 2009, vol. 361 (21), pp. 2033-2045.
Hentsch B., et al., "Hlx Homeo Box Gene is Essential for an Inductive Tissue Interaction that Drives Expansion of Embryonic Liver and Gut," Genes & Development, 1996, vol. 10 (1), pp. 70-79.
Higashiyama H., et al., "Embryonic Cholecystitis and Defective Gallbladder Contraction in the Sox17-Haploinsufficient Model of Biliary Atresia," Development, 2017, vol. 144 (10), pp. 1906-1917.
Hoeffel G., et al., "C-Myb+ Erythro-Myeloid Progenitor-Derived Fetal Monocytes Give Rise to Adult Tissue-Resident Macrophages," Immunity, Apr. 21, 2015, vol. 42 (4), pp. 665-678.
Iacovino M., et al., "HoxA3 is an Apical Regulator of Hemogenic Endothelium," Nat Cell Biol, Jan. 2011, vol. 13 (1), pp. 72-78.
Jørgensen M.C., et al., "Neurog3-Dependent Pancreas Dysgenesis Causes Ectopic Pancreas in Hes1 Mutant Mice," Development, 2018, vol. 145 (17), 11 pages.
Kennedy M., et al., "T Lymphocyte Potential Marks the Emergence of Definitive Hematopoietic Progenitors in Human Pluripotent Stem Cell Differentiation Cultures," Cell Reports, Dec. 27, 2012, vol. 2 (6), pp. 1722-1735.
Kuci Z., et al., "Mesenchymal Stromal Cells from Pooled Mononuclear Cells of Multiple Bone Marrow Donors as Rescue Therapy in Pediatric Severe Steroid-Refractory Graft-Versus-Host Disease: A Multicenter Survey," Haematologica, 2016, vol. 101 (8), pp. 985-994.
Lanctot P.M., et al., "The Glycans of Stem Cells," Curr Opin Chem Biol, Aug. 2007, vol. 11(4), pp. 373-380.
Maeno M., et al., "The Role of BMP-4 and GATA-2 in the Induction and Differentiation of Hematopoietic Mesoderm in Xenopus Laevis," Blood, Sep. 15, 1996, vol. 88 (6), pp. 1965-1972.
Maheshwari A., et al., "TGF-β2 Suppresses Macrophage Cytokine Production and Mucosal Inflammatory Responses in the Developing Intestine," Gastroenterology, 2011, vol. 140 (1), pp. 242-253.
Man A.L., et al., "CX3CR1+ Cell-Mediated Salmonella Exclusion Protects the Intestinal Mucosa during the Initial Stage of Infection," The Journal Immunology, 2017, vol. 198 (1), pp. 335-343.
Martin M.J., et al., "Human Embryonic Stem Cells Express an Immunogenic Nonhuman Sialic Acid," Nature Medicine, Feb. 2005, vol. 11(2), pp. 228-232.
Miller A.J., et al., "Generation of Lung Organoids from Human Pluripotent Stem Cells in Vitro," Nature Protocols, Feb. 28, 2019, vol. 14, No. 2, pp. 518-540.
Montalbano G., et al., "Synthesis of Bioinspired Collagen/Alginate/Fibrin Based Hydrogels for Soft Tissue Engineering," Material Science & Engineering, C 91, 2018, pp. 236-246.
Nissim S., et al., "Iterative Use of Nuclear Receptor Nr5a2 Regulates Multiple Stages of Liver and Pancreas Development," Development Biology, Jul. 26, 2016, vol. 418 (1), pp. 108-123.
Palaria A., et al., "Patterning of the Hepato-Pancreatobiliary Boundary by BMP Reveals Heterogeneity Within the Murine Liver Bud," Hepatology, Jul. 2018, vol. 68 (1), pp. 274-288.
Perdiguero E.G., et al., "Development and Maintenance of Resident Macrophages," Nature Immunology, Jan. 2016, vol. 17 (1), pp. 2-8.
Perdiguero E.G., et al., "Tissue-Resident Macrophages Originate from Yolk-Sac-Derived Erythro-Myeloid Progenitors," Nature, Feb. 26, 2015, vol. 518 (7540), pp. 547-551.
Rankin S.A., et al., "A Retinoic Acid-Hedgehog Cascade Coordinates Mesoderm-Inducing Signals and Endoderm Competence During Lung Specification," Cell Reports, Jun. 28, 2016, vol. 16 (1), pp. 66-78.
San Roman A.K., et al., "Boundaries, Junctions and Transitions in the Gastrointestinal Tract," Exp Cell Res, Nov. 15, 2011, vol. 317 (19), pp. 2711-2718.
Shaw T.N., et al., "Tissue-Resident Macrophages in the Intestine are Long Lived and Defined by Tim-4 and CD4 Expression," Journal of Experimental Medicine, 2018, vol. 215 (6), pp. 1507-1518.
Sheng J., et al., "Most Tissue-Resident Macrophages Except Microglia Are Derived from Fetal Hematopoietic Stem Cells," Immunity, Aug. 18, 2015, vol. 43 (2), pp. 382-393.
Shibata Y., et al., "Prediction of Hepatic Clearance and Availability by Cryopreserved Human Hepatocytes: An Application of Serum Incubation Method," Drug Metabolism and Disposition, 2002, vol. 30(8), pp. 892-896.
Shih H.P., et al., "A Gene Regulatory Network Cooperatively Controlled by Pdx1 and Sox9 Governs Lineage Allocation of Foregut Progenitor Cells," Cell Reports, Oct. 13, 2015, vol. 13 (2), 326-336.
Smith D.M., et al., "Roles of BMP Signaling and Nkx2.5 in Patterning at the Chick Midgut-Foregut Boundary," Development, 2000, vol. 127 (17), pp. 3671-3681.
Smith P.D., et al., "Intestinal Macrophages Lack CD14 and CD89 and Consequently are Down-Regulated for LPS- and IgA-Mediated Activities," The Journal of Immunology, 2001, vol. 167 (5), pp. 2651-2656.

(56) References Cited

OTHER PUBLICATIONS

Spence J.R., et al., "Sox17 Regulates Organ Lineage Segregation of Ventral Foregut Progenitor Cells," Dev Cell, Jul. 2009, vol. 17 (1), pp. 62-74.
Stresser D.M., et al., "Validation of Pooled Cryopreserved Human Hepatocytes as a Model for Metabolism Studies," BD Biosciences, Jan. 1, 2004, Retrieved from https://www.researchgate.net/profile/David-Stresser/publication/268359224_Validation_of_Pooled_Cryopreserved_Human_Hepatocytes_as_a_Model_for_Metabolism_Studies/links/54ed49710cf2465f5330eddc/Validation-of-Pooled-Cryopreserved-Human-Hepatocytes-as-a-Model-for-Metabolism-Studies.pdf on Jan. 15, 2021, 2 pages.
Sturgeon C.M., et al., "Wnt Signaling Controls the Specification of Definitive and Primitive Hematopoiesis from Human Pluripotent Stem Cells," Natural Biotechnology, Jun. 2014, vol. 32 (6), pp. 554-561.
Sumazaki R., et al., "Conversion of Biliary System to Pancreatic Tissue in Hes1-Deficient Mice," Nature Genetics, Jan. 2004, vol. 36 (1), pp. 83-87.
Takata K., et al., "Induced-Pluripotent-Stem-Cell-Derived Primitive Macrophages Provide a Platform for Modeling Tissue-Resident Macrophage Differentiation and Function," Immunity, Jul. 18, 2017, vol. 47 (1), pp. 183-198.
Tepass U., et al., "Epithelium Formation in the *Drosophila* Midgut Depends on the Interaction of Endoderm and Mesoderm," Development, 1994, vol. 120 (3), pp. 579-590.
Thamm K., et al., "Notch Signaling During Larval and Juvenile Development in the Polychaete Annelid *Capitella* sp. I," Developmental Biology, 2008, vol. 320 (1), pp. 304-318.
Tugizov S.M., et al., "Differential Transmission of HIV Traversing Fetal Oral/Intestinal Epithelia and Adult Oral Epithelia," Journal of Virology, 2012, vol. 86 (5), pp. 2556-2570.
Udager A., et al., "Dividing the Tubular Gut: Generation of Organ Boundaries at the Pylorus," Progress in Molecular Biology and Translational Science, 2010, vol. 96, pp. 35-62.
Uhlén M., et al., "A Human Protein Atlas for Normal and Cancer Tissues Based on Antibody Proteomics," Molecular & and Cellular Proteomics, Aug. 27, 2005, vol. 4 (12), pp. 1920-1932.
Yeung E.N.W., et al., "Fibrinogen Production is Enhanced in an In-Vitro Model of Non-Alcoholic Fatty Liver Disease: An Isolated Risk Factor for Cardiovascular Events?," Lipids in Health and Disease, 2015, vol. 14 (86), 8 pages.
Zhang Y., et al., "Development and Stem Cells of the Esophagus," Seminars in Cell & Developmental Biology, Dec. 19, 2016, vol. 66, pp. 25-35.
Zhang Y., et al., "Palmitic and Linoleic Acids Induce ER Stress and Apoptosis in Hepatoma Cells," Lipids in Health and Disease, 2012, vol. 11 (1), 8 pages.
Zhang Z., et al., "Syndecan4 Coordinates Wnt/JNK and BMP Signaling to Regulate Foregut Progenitor Development," Developmental Biology, 2016, vol. 416 (1), pp. 187-199.
Abe T., et al., "Reporter Mouse Lines for Fluorescence Imaging," Development, Growth & Differentiation, May 2013, vol. 55, No. 4, pp. 390-405.
Adam M., et al., Psychrophilic Proteases Dramatically Reduce Single-Cell RNA-Seq Artifacts: a Molecular Atlas of Kidney Development, Development, Oct. 1, 2017, vol. 144, No. 19, pp. 3625-3632.
Arora R., et al., Multiple Roles and Interactions of Tbx4 and Tbx5 in Development of the Respiratory System, PLoS Genetics, Aug. 2, 2012, vol. 8, No. 8, e1002866, 14 pages.
Asahina K., et al., Septum Transversum-Derived Mesothelium gives rise to Hepatic Stellate Cells and Perivascular Mesenchymal Cells in Developing Mouse Liver, Hepatology, Mar. 2011, vol. 53, No. 3, pp. 983-995.
Baptista P.M., et al., "Transplantable Liver Organoids, Too Many Cell Types to Choose: a Need for Scientific Self-Organization," Current Transplantation Reports, Feb. 15, 2020, vol. 7, pp. 18-23.
Barnes R.M., et al., "Analysis of the Hand1 Cell Lineage Reveals Novel Contributions to Cardiovascular, Neural Crest, Extra-Embryonic, and Lateral Mesoderm Derivatives," Developmental Dynamics, vol. 239, 2010, pp. 3086-3097.
Baron M., et al., A Single-Cell Transcriptomic Map of the Human and Mouse Pancreas Reveals Inter- and Intra-cell Population Structure, Cell Systems, Oct. 26, 2016, vol. 3, No. 4, pp. 346-360.
Bauwens C.L., et al., "Control of Human Embryonic Stem Cell Colony and Aggregate Size Heterogeneity Influences Differentiation Trajectories," Stem Cells, vol. 26, No. 9, Sep. 2008, pp. 2300-2310.
Brandenberg N., et al., "High-Throughput Automated Organoid Culture via Stem-Cell Aggregation in Microcavity Arrays," Nature Biomedical Engineering, 2020, vol. 4, pp. 863-874.
Briggs J.A., et al., The Dynamics of Gene Expression in Vertebrate Embryogenesis at SingleCell Resolution, Science, Jun. 1, 2018, vol. 360, No. 6392, eaar5780, 23 pages.
Bult C.J., et al., Mouse Genome Database (MGD) 2019, Nucleic Acids Research, Jan. 8, 2019, vol. 47, No. D1, pp. D801-D806.
Calder, L.E., Retinoic Acid-mediated Regulation of GLI3 Enables High Yield Motoneuron Derivation from Human Embryonic Stem Cells Independent of Extrinsic Activation of SHH Signaling, Dissertation, Jan. 2015, 24 pages.
Cao J., et al., The Single-Cell Transcriptional Landscape of Mammalian Organogenesis, Nature, Feb. 2019, vol. 566, No. 7745, pp. 496-502.
Carpenedo R.L., et al., "Homogeneous and Organized Differentiation Within Embryoid Bodies Induced by Microsphere-mediated Delivery of Small Molecules," Biomaterials, May 2009, vol. 30, No. 13, pp. 2507-2515.
Carpenedo R.L., et al., "Rotary Suspension Culture Enhances the Efficiency, Yield, and Homogeneity of Embryoid Body Differentiation," Stem Cells, 2007, vol. 25, pp. 2224-2234.
Carpenedo R.L., "Microsphere-Mediated Control of Embryoid Body Microenvironments," May 2010, 24 pages.
Chambers M. S., et al., Highly Efficient Neural Conversion of Human ES and IPS Cells by Dual Inhibition of SMAD Signaling, Nature Biotechnol., Mar. 2009, vol. 27(3), pp. 275-280.
Chen Y., et al., "Robust Bioengineered 3D Functional Human Intestinal Epithelium," Scientific Reports, vol. 5 (13708), Sep. 16, 2015, XP055454950, DOI: 10.1038/srep13708, 11 pages.
Chua C.C., et al., "Single Luminal Epithelial Progenitors Can Generate Prostate Organoids in Culture," Nature Cell Biology, Oct. 2014, vol. 16(10), 26 pages.
Cohen M., et al., Lung Single-Cell Signaling Interaction Map Reveals Basophil Role in Macrophage Imprinting, Cell, Nov. 1, 2018, vol. 175, No. 4, pp. 1031-1044.
Conley B.J., et al., "Derivation, Propagation and Differentiation of Human Embryonic Stem Cells," The International Journal of Biochemistry & Cell Biology, 2004, vol. 36, pp. 555-567.
De Soysa T.Y., et al., Single-cell Analysis of Cardiogenesis Reveals Basis for Organ-level Developmental Defects, Nature, Aug. 2019, vol. 572, No. 7767, pp. 120-124.
Dolle L., et al., "EpCAM and the Biology of Hepatic Stem/Progenitor Cells," American Journal of physiology gastrointestinal liver physiology, 2015, vol. 308, pp. G233-G250.
Duh G., et al., "EGF Regulates Early Embryonic Mouse Gut Development in Chemically Defined Organ Culture," International Pediatric Research Foundation, 2000, vol. 48, No. 6, pp. 794-802.
Dye B.R., et al., "Take a Deep Breath and Digest the Material: Organoids and Biomaterials of the Respiratory and Digestive Systems," Materials Research Society, Sep. 2017, vol. 7, No. 3, pp. 502-514.
El Sebae G.K., et al., "Single-Cell Murine Genetic Fate Mapping Reveals Bipotential Hepatoblasts and Novel Multi-organ Endoderm Progenitors," Development, Oct. 1, 2018, vol. 145, No. 19, dev168658, 7 pages.
Erkan M., etal., Organ-, Inflammation- and Cancer Specific Transcriptional Fingerprints of Pancreatic and Hepatic Stellate Cells,. Molecular Cancer, Dec. 2010, vol. 9, No. 1, pp. 1-15.
Farrell J.A., et al., Single-Cell Reconstruction of Developmental Trajectories During Zebrafish Embryogenesis, Science, Jun. 1, 2018, vol. 360, No. 6392, eaar3131, 18 pages.

(56) References Cited

OTHER PUBLICATIONS

Fattahi F., et al., Deriving Human ENS Lineages for Cell Therapy and Drug Discovery in Hirschsprung Disease, Nature, Feb. 2016, vol. 531 (7592), pp. 105-109.
Ferretti E., et al., Mesoderm Specification and Diversification: From Single Cells to Emergent Tissues,. Current Opinion in Cell Biology, Dec. 2019, vol. 61, pp. 110-116.
Forster R., et al., "Human Intestinal Tissue with Adult Stem Cell Properties Derived from Pluripotent Stem Cells," Stem Cell Reports, Jun. 3, 2014, vol. 2, No. 6, pp. 838-852.
Foulke-Abel J., et al., Human Enteroids as a Model of Upper Small Intestinal Ion Transport Physiology and Pathophysiology, Gastroenterology, Mar. 2016, vol. 150, No. 3, pp. 638-649.
Francou A., et al., Second Heart Field Cardiac Progenitor Cells in the Early Mouse Embryo, Biochimica et Biophysica Acta, Apr. 1, 2013, vol. 1833, No. 4, pp. 795-798.
Franklin V., et al., Regionalisation of the Endoderm Progenitors and Morphogenesis of the Gut Portals of the Mouse Embryo,. Mechanisms of Development, Jul. 1, 2008, vol. 125, No. 7, pp. 587-600.
Gao S., et al., Fetal Liver: An Ideal Niche for Hematopoietic Stem Cell Expansion, Science China, Life Sciences, Review, Aug. 2018, vol. 61 (8), pp. 885-892.
Gissen P., et al., "Structural and Functional Hepatocyte Polarity and Liver Disease," Journal of Hepatology, 2015, vol. 63, pp. 1023-1037.
Godoy P., et al., "Recent Advances in 2D and 3D in vitro Systems Using Primary Hepatocytes, Alternative Hepatocyte Sources and Non-parenchymal Liver Cells and their use in Investigating Mechanisms of Hepatotoxicity Cell Signaling and ADME," Arch Toxicol, Aug. 2013, vol. 87, 216 pages.
Graffmann N., et al., "Modeling Nonalcoholic Fatty Liver Disease With Human Pluripotent Stem Cell-Derived Immature Hepatocyte-Like Cells Reveals Activation of PLIN2 and Confirms Regulatory Functions of Peroxisome Proliferator-Activated Receptor Alpha," Stem Cells and Development, vol. 25 (15), 2016, pp. 1119-1133.
Grand R. J., et al., "Development of the Human Gastrointestinal Tract—A Review," Gastroenterology, May 1976, vol. 70, No. 5, pp. 790-810.
Grapin-Botton A., Antero-posterior Patterning of the Vertebrate Digestive Tract: 40 Years After Nicole Le Douarin's PhD Thesis, The International Journal of Developmental Biology, Jan. 1, 2005, vol. 49, Nos. 2-3, pp. 335-347.
Griffin O.D., et al., "Human B1 Cells in Umbilical Cord and Adult Peripheral Blood Express the Novel Phenotype CD20+CD27+CD43+ CD70-," Journal of Experimental Medicine, 2011, vol. 208(1), pp. 67-80.
Han L., et al., Single Cell Transcriptomics Identifies a Signaling Network Coordinating Endoderm and Mesoderm Diversification during Foregut Organogenesis, Nature Communications, Aug. 2020, vol. 11, No. 4158, pp. 1-16.
Hill D R., et al., "Bacterial Colonization Stimulates a Complex Physiological Response in the Immature Human Intestinal Epithelium," Developmental Biology, Microbiology and Infectious Disease, Tools and Resources, Nov. 7, 2017, XP055822977, retrieved from the Internet: https://elifesciences.org/articles/29132,35 pages.
Hoffmann A.D., et al., Sonic Hedgehog Is required in Pulmonary Endoderm for Atrial Septation, Development, 2009, vol. 136, pp. 1761 1770.
Horie M., et al., TBX4 is involved in the Super-Enhancer-Driven Transcriptional Programs Underlying Features Specific to Lung Fibroblasts,. The American Journal of Physiology—Lung Cellular and Molecular Physiology, Jan. 1, 2018, vol. 314, No. 1, pp. L177-L191.
Huss J. M., et al., "Constitutive Activities of Estrogen-Related Receptors: Transcriptional Regulation of Metabolism by the ERR Pathways in Health and Disease," Biochimica et Biophysica Acta, 2015, vol. 1852, 2015, pp. 1912-1927.
Huynh N., et al., "61.06 Feasibility and Scalability of Spring Parameters in Distraction Enterogenesis in a Murine Model," 2017, 3 pages, Retrieved from Internet: URL: https://www.asc-abstracts.org/abs2017/61-06-feasibility-and-scalability-of-spring- parameters-in- distraction-enterogenesis-in-a-murine-model/, Retrieved on Jun. 4, 2022.
Ibarra-Soria X. et al., Defining Murine Organogenesis at Single-Cell Resolution Reveals a Role for the Leukotriene Pathway in Regulating Blood Progenitor Formation,. Nature Cell Biology, Feb. 2018, vol. 20, No. 2, pp. 127-134.
Khan J.A., et al., "Fetal Liver Hematopoietic Stem Cell Niches Associate With Portal Vessels," Science, Jan. 8, 2016, vol. 351 (6269), pp. 176-180.
Kharchenko V. P., et al., Bayesian Approach to Single-cell Differential Expression Analysis, Nature Methods, Jul. 2014, vol. 11, No. 7, pp. 740-742.
Kim E., et al., Isl1 Regulation of Nkx2.1 in the Early Foregut Epithelium Is Required for Trachea-Esophageal Separation and Lung Lobation, Developmental Cell, Dec. 16, 2019, vol. 51, No. 6, pp. 675-683.
Kimura M., et al., "Digitalized Human Organoid for Wireless Phenotyping," iScience, cell press, XP055822469, DOI: 10.1016/j.isci.2018.05.007, retrieved from the Internet: https://www.ncbi.nlm.nih.gov/pmc/articles/PMC6147234/, Jun. 29, 2018, vol. 4, pp. 294-301.
Kiselev Y. V., et al., SCmap—A Tool for Unsupervised Projection of Single Cell RNA-seq data, Nature Methods, May 2018, vol. 15 (5), pp. 359-362.
Koike H., et al., "Engineering Human Hepato-Biliary-Pancreatic Organoids from Pluripotent Stem Cells," Nature Protocols, Feb. 2021, vol. 16(2), pp. 919-936.
Koike H., et al., Modeling human hepato-biliary-pancreatic organogenesis from the foregut-midgut boundary, Nature, Oct. 2019, vol. 574(7776), pp. 112-116.
Langfelder P., et aL, WGCNA: An R package for weighted correlation network analysis, BMC Bioinformatics, Dec. 2008, vol. 9 (1), pp. 1-13.
Langmead B., et al., Fast Gapped-read Alignment with Bowtie 2, Nature Methods, Apr. 2012, vol. 9 (4), pp. 357-359.
Le Douarin N., et al., Role of the Mesoderm in the Induction of the Synthesis of Glycogen During Differentiation of the Hepatic Endoderm, CR Acad Hebd Seances Acad Sci D, 1967, vol. 264, pp. 1872-1874.
Lee G., et al., "Derivation of Neural Crest Cells From Human Pluripotent Stem Cells," Nature Protocols, Mar. 18, 2010, vol. 5(4), pp. 688-701.
Li et al., RSEM: Accurate Transcript Quantification from RNA-Seq data with or without a Reference Genome, BMC Bioinformatics Aug. 2011, vol. 12, No. 323, 16 pages.
Li L.C., et al., Single-Cell Transcriptomic Analyses Reveal Distinct Dorsal/Ventral Pancreatic Programs,. EMBO Reports, Oct. 2018, vol. 19, No. 10, e46148, 14 pages.
Lis R., et al., "Conversion of Adult Endothelium to Immunocompetent Haematopoietic Stem Cells," Nature, May 2017, vol. 545 (7655), pp. 439-445.
Loh K. M., et al., Mapping the Pairwise Choices Leading From Pluripotency to Human Bone, Heart, and Other Mesoderm Cell Types, Cell, Jul. 14, 2016, vol. 166, No. 2, pp. 451-467.
Manno L. G., et al., Molecular Diversity of Midbrain Development in Mouse, Human and Stem Cells, Cell, Oct. 6, 2016, vol. 167, (2), pp. 566-580.
Mashima H., et al., INSL5 may be a Unique Marker of Colorectal Endocrine Cells and Neuroendocrine Tumors, Biochemical and Biophysical Research Communications, 2013, vol. 432, pp. 586-592.
Mccann C.J., et al., "Enteric Neural Stem Cell Therapies for Enteric Neuropathies," Neurogastroenterology and Motility, vol. 30, e13369, 2018, doi: 10.1111/nmo. 13369, pp. 1-9.
MCGrath P.S., et al., The Basic Helix-Loop-Helix Transcription Factor NEUROG3 Is Required for Development of the Human Endocrine Pancreas, Diabetes, Jul. 2015, vol. 64, pp. 2497-2505.
McIntyre B., et al., "Gli3-mediated hedgehog inhibition in human pluripotent stem cells initiates and augments developmental programming of adult hematopoiesis," The American Society of Hematology, Feb. 28, 2013, vol. 121 (9), pp. 1543-1552.
McKimpson W.M., et al., "A Fluorescent Reporter Assay of Differential Gene Expression Response to Insulin in Hepatocytes,"

(56) References Cited

OTHER PUBLICATIONS

Methods in Cell Physiology, American Journal of Physiology Cell Physiology, May 15, 2019, vol. 317, pp. C143-C151.
Menendez L., et al., Directed differentiation of human pluripotent cells to neural crest stem cells, Nature Protocols, Jan. 2013, vol. 8 (1), pp. 203-212.
Mitaka T., "Reconstruction of Hepatic Organoid by Hepatic Stem Cells," Journal of Hepatobiliary Pancreatic Surgery, 2002, vol. 9 (6), pp. 697-703.
Moignard V., et al., Decoding the Regulatory Network of Early Blood Development From Single-Cell Gene Expression Measurements, Nature Biotechnology, Mar. 2015, vol. 33, No. 3, pp. 269-276.
Montecino-Rodriguez E., et al., "Identification of a B-1 B Cell-Specified Progenitor," Natural Immunology, Mar. 2006, vol. 7(3), pp. 293-301.
Morrison A. J., et al., Single-cell transcriptome analysis of avian neural crest migration reveals signatures of invasion and molecular transitions, eLife., Dec. 2017, vol. 6, 27 pages.
Moschidou D., et al., "Human Mid-Trimester Amniotic Fluid Stem Cells Cultured under Embryonic Stem Cell Conditions with Valproic Acid Acquire Pluripotent Characteristics," Stem Cells and Development, Feb. 1, 2013, vol. 22, No. 3, pp. 444-458.
Nantasanti S., et al., Disease Modeling and Gene Therapy of Copper Storage Disease in Canine Hepatic Organoids, Stem Cell Reports, 2015, vol. 5, pp. 895-907.
Nasr T., et al., Endosome-Mediated Epithelial Remodeling Downstream of Hedgehog-Gli Is Required for Tracheoesophageal Separation, Developmental Cell, Dec. 16, 2019, vol. 51, No. 6, pp. 665-674.
Naujok O., et al., Cytotoxicity and Activation of the WNT/Beta-Catenin Pathway in Mouse Embryonic Stem Cells Treated with Four GSK3 Inhibitors, BMC Research Notes, 2014, vol. 7, No. 273, pp. 1-8.
Ng S., et al., "Human iPSC-Derived Hepatocyte-Like Cells Support Plasmodium Liver-Stage Infection In Vitro," Stem cell reports, Mar. 10, 2015, vol. 4, pp. 348-359.
Nowotschin S., et al., The Emergent Landscape of the Mouse Gut Endoderm at Single-Cell Resolution, Nature, May 2019, vol. 569, No. 7756, pp. 361-367.
Ogaki S., et al., A Cost-Effective System for Differentiation of Intestinal Epithelium from Human Induced Pluripotent Stem Cells, Scientific Reports, Nov. 30, 2015, 11 pages.
Payushina O.V., Hematopoietic Microenvironment in the Fetal Liver: Roles of Different Cell Populations, Review Article, International Scholarly Research Network Cell Biology, 2012, 8 pages.
Pedersen J.K., et al., Endodermal Expression of Nkx6 Genes depends differentially on Pdx1, Developmental Biology, Dec. 15, 2005, vol. 288, No. 2, pp. 487-501.
Peng T., et al., Coordination of Heart and Lung Co-development by a Multipotent Cardiopulmonary Progenitor, Nature, Aug. 2013, vol. 500, No. 7464, pp. 589-592.
Pijuan-Sala B., et al., A Single-Cell Molecular Map of Mouse Gastrulation and Early Organogenesis, Nature, Feb. 2019, vol. 566, No. 7745, pp. 490-495.
Que J., et al., Mesothelium Contributes to Vascular Smooth Muscle and Mesenchyme During Lung Development, Proceedings of the National Academy of Sciences USA, Oct. 28, 2008, vol. 105, No. 43, pp. 16626-16630.
Rana M.S., et al., A Molecular and Genetic Outline of Cardiac Morphogenesis, Acta Physiologica (Oxf), Apr. 2013, vol. 207, No. 4, pp. 588-615.
Riehl T., et al., "CD44 and TLR4 Mediate Hyaluronic Acid Regulation of Lgr5+ Stem Cell Proliferation, Crypt Fission, and Intestinal Growth in Postnatal and Adult Mice," The American Journal of Physiology—Gastrointestinal and Liver Physiology, Dec. 1, 2015, vol. 309, No. 11, pp. G874-G887.
Robert-Moreno A., et al., "Impaired Embryonic Haematopoiesis Yet Normal Arterial Development in the Absence of the Notch ligand Jagged1," EMBO Journal, 2008, vol. 27(13), pp. 1886-1895.
Robert-Moreno A., et al., " RBPjκ-dependent Notch Function Regulates Gata2 and is Essential for the Formation of Intra-embryonic Hematopoietic Cells," Development and disease, 2005, vol. 132(5), pp. 1117-1126.
Rothstein L.T., et al., "Human B-1 cells take the stage," Annals of the New York Academy of Sciences, May 2013, vol. 1285, pp. 97-114.
Rubin L.L., et al., Targeting the Hedgehog Pathway in Cancer, Nature Reviews Drug Discovery, 2006, vol. 5, pp. 1026-1033.
Sanchez-Valle V., et al., "Role of Oxidative Stress and Molecular Changes in Liver Fibrosis: A Review," Current Medicinal Chemistry, 2012, vol. 19, No. 28, pp. 4850-4860.
Sander M., et al., Homeobox Gene Nkx6.1 lies Downstream of Nkx2.2 in the major Pathway of Beta-Cell formation in the Pancreas, Development, Dec. 15, 2000, vol. 127, No. 24, pp. 5533-5540.
Sathananthan A.H., et al., "Human Embryonic Stem Cells and their Spontaneous Differentiation," Italian Journal of Anatomy and Embryology, 2005, vol. 110 (Supplement 1), No. 2, pp. 151-157.
Sauka-Spengler T et al., Snapshot: Neural Crest, Cell, Oct. 2010, vol. 143, No. 3, 486-486. e1.
Schlieve C. R., et al., Neural Crest Cell Implantation Restores Enteric Nervous System Function and Alters the Gastrointestinal Transcriptome in Human Tissue-Engineered Small Intestine, Stem Cell Reports, ISSCR, Sep. 12, 2017, vol. 9, pp. 883-896.
Scialdone A., et al., Resolving Early Mesoderm Diversification Through Single-Cell Expression Profiling, Nature, Jul. 2016, vol. 535, No. 7611, pp. 289-293.
Scott A., et al., "Repeated Mechanical Lengthening of Intestinal Segments in a Novel Model," Journal of Pediatric Surgery, Jun. 2015, vol. 50, No. 6, pp. 954-957.
Seet C.S., et al., Generation of Mature T Cells from Human Hematopoietic Stem/Progenitor Cells in Artificial Thymic Organoids, Nature Methods, May 2017, vol. 14 (5), pp. 521-530.
Semrau S., et al., Dynamics of lineage commitment revealed by single-cell transcriptomics of differentiating embryonic stem cells, Nature Communications, Oct. 2017, vol. 8 (1), pp. 1-16.
Simões F.C., et al., "The Ontogeny, Activation and Function of the Epicardium During Heart Development and Regeneration," Development, Apr. 1, 2018, vol. 145, No. 7, dev155994; 13 pages.
Soldatow V. Y., et al., "In Vitro Models for Liver Toxicity Testing," Toxicology Research 2.1, 2013, vol. 2, pp. 23-39.
Sugimura R., et al., "Haemotopoietic Stem and Progenitor Cells from Human Pluripotent Stem Cells," Nature, May 25, 2017, vol. 545 (7655), pp. 432-438.
Sullins V. F., et al., "Intestinal Lengthening in an Innovative Rodent Surgical Model," Journal of Pediatric Surgery, Dec. 2014, vol. 49, No. 12, pp. 1791-1794.
Sweetman D., et al., The Migration of Paraxial and Lateral Plate Mesoderm Cells Emerging From the Late Primitive Streak Is Controlled by Different Wnt Signals, BMC Developmental Biology, Dec. 2008, vol. 8, No. 1, pp. 1-15.
Tanaka M., "Molecular and Evolutionary Basis of Limb Field Specification and Limb Initiation," Development, Growth & Differentiation, Jan. 2013, vol. 55, No. 1, pp. 149-163.
Tang X. et al. Transcriptome Regulation and Chromatin Occupancy by E2F3 and MYC in Mice, Scientific Data, Feb. 16, 2016, vol. 3, No. 1, pp. 1-8.
Testaz S., et al., Sonic hedgehog restricts adhesion and migration of neural crest cells independently of the Patched-Smoothened-Gli signaling pathway, PNAS, Oct. 23, 2001, vol. 98 (22), pp. 12521-12526.
Ueda T., et al., "Expansion of Human NOD/SCID-repopulating Cells by Stem Cell Factor Flk2/Flt3 ligand, thrombopoietin, IL-6, and soluble IL-6 receptor," Journal of Clinical Investment, 2000, vol. 105(7), pp. 1013-1021.
Uenishi I.G., et al., "NOTCH Signaling Specifies Arterial-type Definitive Hemogenic Endothelium from Human Pluripotent Stem Cells," Nature Communication, 2018, 14 pages.
Wagner D.E., et al., Lineage Tracing Meets Single-cell Omics: Opportunities and Challenges, Nature Reviews Genetics, Jul. 2020, vol. 21, No. 7, pp. 410-427.

(56) References Cited

OTHER PUBLICATIONS

Wang, et al., "Spatially Monitoring Oxygen Level in 3D Microfabricated Cell Culture Systems Using Optical Oxygen Sensing Beads," Lab on a Chip, 2013, vol. 13, pp. 1586-1592.
Wang J., et al., WebGestalt 2017: A more comprehensive, powerful, flexible and interactive gene set enrichment analysis toolkit, Nucleic Acids Research, Jul. 2017, vol. 45, 8 pages.
Wang L., et al., "The Maintenance and Generation of Membrane Polarity in Hepatocytes," Hepatology, 2004, vol. 39, No. 4, pp. 892-899.
Weinreb C., et al., Lineage tracing on transcriptional landscapes links state to fate during differentiation, Science, Feb. 14, 2020, vol. 367, (6479), 48 pages.
Weinreb C., et al., SPRING: A Kinetic Interface for Visualizing High Dimensional Single-cell Expression Data, Bioinformatics, Apr. 2018, vol. 34 (7), pp. 1246-1248.
Weisenberg, E. M.D., "Esophagus—General Histology"; Pathology Outlines, Copyright 2003-2023, 2023,3 Pages.
Wilkinson C. A., et al., "Long-term Ex-vivo Haematopoietic-stem-Cell Expansion Allows Nonconditioned Transplantation," Nature, 2019, vol. 571 (7763), pp. 117-121.
Xie T., et al., Single-Cell Deconvolution of Fibroblast Heterogeneity in Mouse Pulmonary Fibrosis, Cell Reports, Mar. 27, 2018, vol. 22, No. 13, pp. 3625-3640.
Yao S., et al., Long-Term Self-Renewal and Directed Differentiation of Human Embryonic Stem Cells in Chemically Defined Conditions, PNAS, 2006, vol. 103, No. 18, pp. 6907-6912.
Yu G., et al., ClusterProfiler: An R package for Comparing Biological Themes Among Gene Clusters, Omics: A Journal Integrative Biology, May 2012, vol. 16 (5), pp. 284-287.
Yuelei C., et al., BMP Signaling Pathway and Colon Cancer, CNKI, Oct. 15, 2009, 1 page.
Zaret K.S., From Endoderm to Liver Bud: Paradigms of Cell Type Specification and Tissue Morphogenesis, Current Topics in Developmental Biology, Jan. 2016, vol. 117, pp. 647-669.
Zeltner N., et al., Feeder-free derivation of neural crest progenitor cells from human pluripotent stem cells, Journal of Visualized Experiments, May 2014, vol. 87, 9 pages.
Zhang C., et al., "Angiopoietin-like 5 and IGFBP2 Stimulate Ex-vivo Expansion of Human Cord Blood Hematopoietic Stem Cells as Assayed by NOD/SCID transplantation," Hematopoiesis and stem Cells, 2008, vol. 111 (7), pp. 3415-3423.
Zhang X., et al., A Comprehensive Structure-Function Study of Neurogenin3 Disease-Causing Alleles during Human Pancreas and Intestinal Organoid Development, Developmental Cell, Aug. 5, 2019, vol. 50, pp. 367-380.
Abo., K.M., et al., Human iPSC-Derived Alveolar and Airway Epithelial Cells Can Be Cultured at Air-liquid Interface and Express SARS-CoV-2 Host Factors. Biorxiv, Jun. 4, 2020, 27 pages.
Adachi S., et al., "Three Distinctive Steps in Peyer's Patch Formation of Murine Embryo," International Immunology, Apr. 1997, vol. 9(4), pp. 507-514.
Anderson C.M.H., et al., "Inhibition of Intestinal Dipeptide Transport by the Neuropeptide VIP is an Anti-absorptive Effect via the VPAC1 Receptor in a Human Enterocyte-like Cell Line (Caco-2)," British Journal of Pharmacology, 2003, vol. 138, No. 4, pp. 564-573.
Ang L.T., et al., "A Roadmap for Human Liver Differentiation from Pluripotent Stem Cells," Cell Reports, Feb. 20, 2018, vol. 22, pp. 2190-2205.
Baker C., et al., "Hypoganglionosis in the Gastric Antrum Causes Delayed Gastric Emptying," Neurogastroenterology and Motility, May 2020, vol. 32(5): e13766, 18 pages.
Balbinot C., et al., "Fine-tuning and Autoregulation of the Intestinal Determinant and Tumor Suppressor Homeobox Gene CDX2 by Alternative Splicing," Cell Death and Differentiation, 2017, vol. 24, No. 12, pp. 2173-2186.
Barber K., et al., "Derivation of Enteric Neuron Lineages from Human Pluripotent Stem Cells," Nature Protocols, Apr. 2019, vol. 14, No. 4, pp. 1261-1279.
Bar-Ephraim Y.E., et al., "Organoids in Immunological Research,". Nature Reviews Immunology, May 2020, vol. 20(5), pp. 279-293.
Barkauskas C. E. et al. "Lung Organoids: Current Uses and Future Promise," Development, Mar. 15, 2017, vol. 144(6), pp. 986-997.
Barkauskas C.E., et al., Type 2 alveolar Cells Are Stem Cells in Adult Lung. The Journal of Clinical Investigation, Jul. 1, 2013, vol. 123(7), pp. 3025-3036.
Barnes P.J., et al., "Chronic Lung Diseases: Prospects for Regeneration and Repair," European Respiratory Review, Mar. 31, 2021, vol. 30(159), 14 pages.
Basil, M. C., et al., "The Cellular and Physiological Basis for Lung Repair and Regeneration: Past, Present, and Future," Apr. 2, 2020, vol. 26(4, pp. 482-502.
Batterham R.L., et al., "Gut Hormone PYY3-36 Physiologically Inhibits Food Intake," Nature, Aug. 8, 2002, vol. 418, pp. 650-654.
Beckett E.A.H., et al., "Inhibitory Responses Mediated by Vagal Nerve Stimulation are Diminished in Stomachs of Mice with Reduced Intramuscular Interstitial Cells of Cajal," Mar. 20, 2017, Scientific Reports, vol. 7, No. 44759, 11 pages.
Beers M.F., et al., "Alveolar Type 2 Epithelial Cell Quality Control Responses to Pulmonary Fibrosis Related SFTPC Mutations Are Dysfunctional and Substrate Specific," The FASEB Journal, Apr. 2020, vol. 34(S1), 1 page (Abstract Only).
Bergen V., et al., "Generalizing RNA Velocity to Transient Cell States Through Dynamical Modeling," Nature Biotechnology, Oct. 28, 2019, vol. 38(12), 26 pages.
Bharat A., et al., "Lung Transplantation for Patients with Severe COVID-19," Science Translational Medicine, Dec. 16, 2020, vol. 12(574):eabe4282, 13 pages.
Blanchard J.W., et al., "Reconstruction of the Human Blood-Brain Barrier in vitro reveals a Pathogenic Mechanism of APOE4 in Pericytes," Nature Medicine, Jun. 2020, vol. 26, No. 6, pp. 952-963.
Bohorquez D.V., et al., "Neuroepithelial Circuit Formed by Innervation of Sensory Enteroendocrine Cells," The Journal of Clinical Investigation, 2015, vol. 125, No. 2, pp. 782-786.
Bolte C., et al., "FOXF1 Transcription Factor Promotes Lung Regeneration After Partial Pneumonectomy," Scientific Reports, Sep. 6, 2017, vol. 7(1):10690, 14 pages.
Braegger C.P., et al., "Ontogenetic Aspects of the Intestinal Immune System in Man," International Journal of Clinical and Laboratory Research, 1992, vol. 22(1), pp. 1-4.
Breit S., et al., "Vagus Nerve as Modulator of the Brain-Gut Axis in Psychiatric and Inflammatory Disorders," Frontiers in Psychiatry, Mar. 13, 2018, vol. 9, Article. 44, 15 pages.
Brookes S.J.H., et al., "Extrinsic Primary Afferent Signaling in the Gut," Nature Rev Gastroenter Hepatol., 2013, vol. 10, No. 5, pp. 286-296.
Brosch M., et al., "Epigenomic Map of Human Liver Reveals Principles of Zonated Morphogenic and Metabolic Control," Nature Communications, 2018, vol. 9, Article. 4150, 13 pages.
Buning J.W., et al., "Higher Hydrocortisone Dose Increases Bilirubin in Hypopituitary Patients- results from an RCT," European Journal of Clinical Investigation, 2016, vol. 46, No. 5, pp. 475-480.
Burleigh D.E., et al., "Stimulation of Intestinal Secretion by Vasoactive Intestinal Peptide and Cholera Toxin," Autonomic Neuroscience: Basic and Clinical, 2007, vol. 133, pp. 64-75.
Bykov V.L., "Paneth Cells: History of Discovery, Structural and Functional Characteristics and the Role in the Maintenance of Homeostasis in the Small Intestine," Morfologiia, 2014, vol. 145, No. 1, pp. 67-80.
Cakir B., et al., "Development of Human Brain Organoids with Functional Vascular-like System," Nature Methods, Nov. 2019, vol. 16, No. 11, pp. 1169-1176.
Cao J., et al., "A Human Cell Atlas of Fetal Gene Expression," Science, Nov. 13, 2020, vol. 370(6518), 42 pages.
Cardenas-Diaz F. L., et al., Temporal and Spatial Staging of Lung Alveolar Regeneration Is Determined by the Grainyhead Transcription Factor Tfcp211, Cell Reports, May 30, 2023, vol. 42(5), 21 pages.
Cardoso W.V., et al., "Regulation of Early Lung Morphogenesis: Questions, Facts and Controversies," Development, 2006, vol. 133, pp. 1611-1624.

(56) References Cited

OTHER PUBLICATIONS

Chandrasekaran A., et al., "Astrocyte Differentiation of Human Pluripotent Stem Cells: New Tools for Neurological Disorder Research," Frontiers in Cellular Neuroscience, Sep. 26, 2016, vol. 10, Article. 215, 27 pages.
Chassaing B., et al., "Mammalian Gut Immunity," Biomedical Journal, Sep. 2014, vol. 37(5) p. 246 in 22 pages.
Chen M., et al., "Gene Ablation for PEPTI in Mice Abolishes the Effects of Dipeptides on Small Intestinal Fluid Absorption, Short Circuit Current and Intracellular pH," American Journal of Physiology—Gastrointestinal and Liver Physiology, Apr. 29, 2010, 33 pages.
Cheng Y., et al., "Current Development Status of MEK Inhibitors," Molecules, 2017, vol. 22, pp. 1-20.
Choi J., et al., "Inflammatory Signals Induce AT2 Cell-Derived Damage-Associated Transient Progenitors that Mediate Alveolar Regeneration," Cell stem cell, Sep. 3, 2020 , vol. 27(3), pp. 366-382.
Chung C., et al., "Hippo-Foxa2 Signaling Pathway Plays a Role in Peripheral Lung Maturation and Surfactant Homeostasis." Proceedings of the National Academy of Sciences of the United States of America, May 7, 2013, vol. 110(19), pp. 7732-7737.
Chung, M. I., et al., "Niche-mediated BMP/SMAD Signaling Regulates Lung Alveolar Stem Cell Proliferation and Differentiation," Development, May 1, 2018, vol. 145(9):dev 163014, 23 pages.
Cox H.M., et al., "Peptide YY Is Critical for Acylethanolamine Receptor Gpr119-Induced Activation of Gastrointestinal Mucosal Responses," Cell Metabolism, Jun. 9, 2010, vol. 11, pp. 532-542.
Cox H.M., "Neuroendocrine Peptide Mechanisms Controlling Intestinal Epithelial Function," Current Opinion in Pharmacology, 2016, vol. 31, pp. 50-56.
Creeden J.F., et al., "Bilirubin as a Metabolic Hormone: the Physiological Relevance of Low Levels," American Journal of Physiology—Endocrinology and Metabolism, 2021, vol. 320, No. 2, 59 pages.
Daviaud N., et aL, "Vascularization and Engraftment of Transplanted Human Cerebral Organoids in Mouse Cortex," Disorders of the Nervous System, Nov./Dec. 2018, vol. 5, No. 6, 18 pages.
De Carvalho A.L.R.T., et al., "Glycogen Synthase Kinase 3 Induces Multilineage Maturation of Human Pluripotent Stem Cell-derived Lung Progenitors in 3D Culture," Development. Jan. 15, 2019, vol. 146(2):dev171652, 34 pages.
De Carvalho A.L.R.T et al., "The in Vitro Multi-Lineage Differentiation and Maturation of Lung and Airway Cells from Human Pluripotent Stem Cell-derived Lung Progenitors in 3D," Nature Protocols, Apr. 2021, 16(4), pp. 1802-1829.
De Lau W., et al., "Peyer's Patch M Cells Derived from Lgr5+ Stem Cells Require SpiB and are Induced by RankL in Cultured Miniguts,". Molecular and Cellular Biology, Sep. 2012, vol. 32(18), pp. 3639-3647.
De Souza H.S.P., et al., "Immunopathogenesis of IBD: Current State of the Art," Nature Reviews Gastroenterology & Hepatology, Jan. 2016, vol. 13(1), pp. 13-27.
Dekkers J.F., et al., "High-resolution 3D Imaging of Fixed and Cleared Organoids," Nature protocol, Jun. 2019, vol. 14(6), pp. 1756-1771.
Duren Z., et al., "Modeling Gene Regulation from Paired Expression and Chromatin Accessibility Data,". Proceedings of the National Academy of Sciences of the United States of America, Jun. 2, 2017, vol. 114(25), pp. E4914-E4923.
Eberl G., et al., "An Essential Function for the Nuclear Receptor RORgamma(t) in the Generation of Fetal Lymphoid Tissue Inducer Cells," Nature Immunology, Dec. 21, 2003, vol. 5(1), pp. 64-73.
Egerod K.L., et al., "A Major Lineage of Enteroendocrine Cells Coexpress CCK, Secretin, GIP, GLP-1, PYY, and Neurotensin but Not Somatostatin," Endocrinology, Dec. 1, 2012, vol. 153, No. 12, pp. 5782-5795.
Egerod K.L., et al., "Profiling of G Protein-coupled Receptors in Vagal Afferents Reveals Novel Gut-to-brain Sensing Mechanisms," Molecular Metabolism, 2018, vol. 12, pp. 62-75.
Faure S., et al., "Endogenous Patterns of BMP Signaling During Early Chick Development," Developmental Biology, Apr. 1, 2002, vol. 244(1), pp. 44-65.
Faure S., et al., "Enteric Neural Crest Cells Regulate Vertebrate Stomach Patterning and Differentiation," Development, 2015, vol. 142, pp. 331-342.
Faure S., et al., "Expression Pattern of the Homeotic Gene Bapx1 During Early Chick Gastrointestinal Tract Development," Gene Expression Patterns, Dec. 2013, vol. 13(8), 7 pages.
Finn J., et al., DIk1-Mediated Temporal Regulation of Notch Signaling Is Required for Differentiation of Alveolar Type II to Type I Cells during Repair, Cell Reports, Mar. 12, 2019, vol. 26(11), pp. 2942-2954.
Flodby P., et al., "Cell-Specific Expression of Aquaporin-5 (Aqp5) in Alveolar Epithelium Is Directed by GATA6/Spl via Histone Acetylation," Scientific Reports, Jun. 14, 2017, vol. 7(1):3473, 12 pages.
Fomin M.E., et al., "Human Fetal Liver Cultures Support Multiple Cell Lineages That Can Engraft Immunodeficient Mice," Open Biology, 2017, 16 pages.
Frank D. B., et al., "Emergence of a Wave of Wnt Signaling that Regulates Lung Alveologenesis by Controlling Epithelial Self-Renewal and Differentiation," Cell Reports, Nov. 22, 2016, vol. 17(9), pp. 2312-2325.
Freddo A.M., et al., "Coordination of Signaling and Tissue Mechanics During Morphogenesis of Murine Intestinal Villi: A Role for Mitotic Cell Rounding," Integrative Biol., Sep. 12, 2016;8(9):918-928.
Fukuda M., et al., "Small Intestinal Stem Cell Identity Is Maintained with Functional Paneth Cells in Heterotopically Grafted Epithelium Onto the Colon," Genes & Development, 2014, vol. 28, No. 16, pp. 1752-1757.
Furness J.B., et al., "The Identification of Neuronal Control Pathways Supplying Effector Tissues in the Stomach," Cell and Tissue Research, Dec. 2020, vol. 382, No. 3, pp. 433-445.
Gage B.K., et al., "Generation of Functional Liver Sinusoidal Endothelial Cells from Human Pluripotent Stem-Cell Derived Venous Angioblasts," Cell Stem Cell, Aug. 6, 2020, vol. 27, pp. 254-269.
Galand G., "Brush Border Membrane Sucrase-Isomaltase, Maltase-Glucoamylase and Trehalase in Mammals. Comparative Development, Effects of Glucocorticoids, Molecular Mechanisms, and Phylogenetic Implications," Comparative Biochemistry & Physiology, 1989, vol. 94B, No. 1, 11 pages.
Gaskill C.F., et al., "Disruption of Lineage Specification in Adult Pulmonary Mesenchymal Progenitor Cells Promotes Microvascular Dysfunction," Journal of Clinical Investigation, Jun. 1, 2017, vol. 127(6), pp. 2262-2276.
Gerdes H-H., et al., "Intercellular Transfer Mediated by Tunneling Nanotubes," Current Opinion in Cell Biology, 2008, vol. 20, pp. 470-475.
Gibbs C.S., et al., "High-performance Single-cell Gene Regulatory Network Inference at Scale: the Inferelator 3.0," Bioinformatics, May 1, 2022, vol. 38(9), pp. 2519-2528.
Gilbert M.A., et al., "Protein-Elongating Mutations in MYH11 Are Implicated in a Dominantly Inherited Smooth Muscle Dysmotility Syndrome with Severe Esophageal, Gastric, and Intestinal Disease," Human Mutation, 2020, vol. 41, pp. 973-982.
Gillich A., et al., "Capillary Cell Type Specialization in the Alveolus," Nature, Oct. 2020, 586(7831), pp. 785-789.
Gokey J.J., et al., "Active Epithelial Hippo Signaling in Idiopathic Pulmonary Fibrosis," JCI insight, Mar. 3, 2018, vol. 3(6), 14 pages.
Gonzales L.W., et al., "Differentiation of Human Pulmonary Type II Cells in Vitro by Glucocorticoid Plus Cyclic Amp," AJP—Lung Articles in Press, 2002, 45 pages.
Goodwin K., et al., "Smooth Muscle Differentiation Shapes Domain Branches During Mouse Lung Development," Development, Nov. 15, 2019, 146(22), 37 pages.
Gorin G., et al., "Protein Velocity and Acceleration from Single-cell Multiomics Experiments," Genome Biology, (2020)21 :39, 6 pages.
Gorin G., et al., "RNA Velocity Unraveled," PLOS Computational Biology, Sep. 12, 2022, vol. 18(9):e1010492, 55 pages.
Granja J.M., et al., "ArchR is a Scalable Software Package for Integrative Single-Cell Chromatin Accessibility Analysis," Nature Genetics, Mar. 2021, vol. 53(3), pp. 403-411.

(56) References Cited

OTHER PUBLICATIONS

Grant R.A., et al., "Circuits Between Infected Macrophages and T cells in Sars-CoV-2 Pneumonia," Nature, Feb. 25, 2021, vol. 590(7847), pp. 635-641.
Green J., et al., "Diversity of Interstitial Lung Fibroblasts Is Regulated by Platelet-derived Growth Factor Receptor Alpha Kinase Activity," American Journal of Respiratory Cell and Molecular Biology, Apr. 2016, vol. 54(4), pp. 532-545.
Gribble F.M., et al., "Function and Mechanisms of Enteroendocrine Cells and Gut Hormones in Metabolism," Reviews, Apr. 2019, vol. 15, pp. 226-237.
Guo M., et al., "Single Cell RNA Analysis Identifies Cellular Heterogeneity and Adaptive Responses of the Lung at Birth," Nature Communications, Jan. 3, 2019; vol. 10(1):37, 16 pages.
Guye P., et al., "Genetically Engineering Self-organization of Human Pluripotent Stem Cells into a Liver Bud-like Tissue Using Gata6," Nature Communications, Jan. 6, 2016, 12 pages.
Ham O., et al., "Blood Vessel Formation in Cerebral Organoids Formed From Human Embryonic Stem Cells," Biochemical and Biophysical Research Communications, 2020, vol. 521, pp. 84-90.
Hamilton T.G., et al., "Evolutionary Divergence of Platelet-derived Growth Factor Alpha Receptor Signaling Mechanisms," Molecular and Cellular Biology, Jun. 1, 2003, vol. 23(11), pp. 4013-4025.
Hao Y., et al., "Integrated Analysis of Multimodal Single-cell Data," Cell, Jun. 24, 2021, ;vol. 184(13), pp. 3573-3587.
Harrison S.P., et al., "Liver Organoids: Recent Developments, Limitations and Potential," Frontiers in Medicine, May 2021, vol. 8, 18 pages.
Hawkins F., et al., "Prospective Isolation of NKX2-1-Expressing Human Lung Progenitors Derived from Pluripotent Stem Cells," The Journal of Clinical Investigation, Jun. 1, 2017; 127(6), pp. 2277-2294.
He B., et al., "Understanding Transcriptional Regulatory Networks Using Computational Models," Current Opinion in Genetics & Development, Apr. 1, 2016, vol. 37, pp. 101-108.
Herriges M.J., et al., "Long Noncoding RNAs are Spatially Correlated with Transcription Factors and Regulate Lung Development," Genes & Development, Jun. 15, 2014, vol. 28(12), pp. 1363-1379.
Holloway E.M., et al., "Differentiation of Human Intestinal Organoids with Endogenous Vascular Endothelial Cells," Developmental Cell, 2020, vol. 54, pp. 516-528.
Homan K.A., et al., "Flow-Enhanced Vascularization and Maturation of Kidney Organoids in Vitro," Nature Methods, 2019, 16(3), pp. 255-262.
Hu S., et al., "Wnt/β-Catenin Signaling and Liver Regeneration: Circuit, Biology, and Opportunities," Gene expression, 2021, vol. 20(3), pp. 189-199.
Hu Y., et al., "Wnt/β-Catenin Signaling Is Critical for Regenerative Potential of Distal Lung Epithelial Progenitor Cells in Homeostasis and Emphysema," Stem Cells, Nov. 2020, vol. 38(11), pp. 1467-1478.
Huang W-K., et al., "Generation of Hypothalamic Arcuate Organoids From Human Induced Pluripotent Stem Cells," Cell Stem Cell, 2021, pp. 1657-1670.
Huycke T.R., et al., "Genetic and Mechanical Regulation of Intestinal Smooth Muscle Development," Cell, 2019, vol. 179, No. 1, pp. 90-105.
Hyland N.P., et al., "Functional Consequences of Neuropeptide Y Y2 Receptor Knockout and Y2 Antagonism in Mouse and Human Colonic Tissues," British Journal of Pharmacology, 2003, vol. 139, pp. 863-871.
Iino S., et al., "Interstitial Cells of Cajal Are Involved in Neurotransmission in the Gastrointestinal Tract," The Japan Society of Histochemistry and Cytochemistry, 2006, 39 (6), pp. 145-153.
Ikegami., M. et al. "Surfactant Protein D Influences Surfactant Ultrastructure and Uptake by Alveolar Type Ii Cells," American Journal of Physiology—Lung Cellular and Molecular Physiology, Mar. 2005, vol. 288(3), pp. L552-L561.
Jacob A., et al., "Derivation of Self-Renewing Lung Alveolar Epithelial Type II Cells From Human Pluripotent Stem Cells," Nature Protocols, 2019, 14(12), pp. 3303-3332.
Jacob A., et al., "Differentiation of Human Pluripotent Stem Cells into Functional Lung Alveolar Epithelial Cells," Cell Stem Cell, Oct. 5, 2017, vol. 21(4), pp. 472-488.
Jacob F, et al., "Human Pluripotent Stem Cell-Derived Neural Cells and Brain Organoids Reveal SARS-CoV-2 Neurotropism Predominates in Choroid Plexus Epithelium," Cell Stem Cell, 2020, vol. 27, pp. 937-950.
Jain R., et al., "Plasticity of Hopx (+) Type I Alveolar Cells to Regenerate Type Ii Cells in the Lung," Nature Communications, 2015, vol. 13;6(1):6727, 20 pages.
Jin S., et al., "Inference and Analysis of Cell-cell Communication Using Cellchat," Nature Communications, Feb. 17, 2021, vol. 12(1):1088, 20 pages.
Kaelberer M.M., et al., "A Gut-Brain Neural Circuit for Nutrient Sensory Transduction," Science, Sep. 21, 2018, vol. 361, No. 6408, 18 pages.
Kalucka J., et al., "Single-Cell Transcriptome Atlas of Murine Endothelial Cells," Cell, 2020, vol. 180, pp. 764-779.
Kathiriya, J.J., et al., "Human Alveolar Type 2 Epithelium Transdifferentiates into Metaplastic KRT5+ Basal Cells," Nature Cell Biology, Jan. 2022, vol. 24(1), pp. 10-23.
Khalil H.A., et al., "Intestinal Epithelial Replacement by Transplantation of Cultured Murine and Human Cells Into the Small Intestine," Plos One, May 31, 2019, vol. 14, No. 5, 13 pages.
Kim S., et al., "Engraftment Potential of Spheroid-Forming Hepatic Endoderm Derived from Human Embryonic Stem Cells," Stem Cells Development. Jun. 15, 2013, vol. 22(12), pp. 1818-1829.
Kinchen J., et al., "Structural Remodeling of the Human Colonic Mesenchyme in Inflammatory Bowel Disease," Cell, 2018, vol. 175, No. 2, pp. 372-388.
Kitano K., et al., "Bioengineering of Functional Human Induced Pluripotent Stem Cell-derived Intestinal Grafts," Nature Communications, 2017, vol. 8, No. 765, 13 pages.
Knox S.M., et al., "Parasympathetic Innervation Maintains Epithelial Progenitor Cells During Salivary Organogenesis," Science, Sep. 24 2010, vol. 329, No. 5999, pp. 1645-1647.
Kobayashi Y., et al., "Persistence of a Regeneration-associated, Transitional Alveolar Epithelial Cell State in Pulmonary Fibrosis," Nature Cell Biology, Aug. 2020, vol. 22(8), pp. 934-946.
Koboziev I., et al., "Use of Humanized Mice to Study the Pathogenesis of Autoimmune and Inflammatory Diseases," Inflammatory Bowel Diseases, Jul. 1, 2015, 21 (7), pp. 1652-1673.
Koslowski M., et al., "MS4A12 Is a Colon-Selective Store-Operated Calcium Channel Promoting Malignant Cell Processes," Cancer Research, May 1, 2008, vol. 68, No. 9, 3458-3466.
Kotobank, "Encyclopedia—Basement Membrane," Machine translated by Google, 2023, 6 pages.
Kuna L., et al., "Peptic Ulcer Disease: A Brief Review of Conventional Therapy and Herbal Treatment Options," Journal of Clinical Medicine, 2019, vol. 8, No. 2, 19 pages.
Kusakabe T., et al., "Thyroid-Specific Enhancer-binding Protein/NKX2.1 is Required for the Maintenance of Ordered Architecture and Function of the Differentiated Thyroid," Molecular Endocrinology, Aug. 2006, vol. 20(8), pp. 1796-1809.
Lacanna R., et al., "Yap/Taz Regulate Alveolar Regeneration and Resolution of Lung Inflammation," Journal of Clinical Investigation, May 1, 2019, vol. 129(5), pp. 2107-2122.
Lanas A., et al., "Peptic Ulcer Disease," vol. 390, Aug. 5, 2017, pp. 613-624.
Lange M., et al., "CellRank for Directed Single-cell Fate Mapping," Nature Methods, Feb. 2022, vol. 19(2), pp. 159-170.
Lasrado R., et al., "Lineage-Dependent Spatial and Functional Organization of the Mammalian Enteric Nervous System," Science, 2017, vol. 356, No. 6339, pp. 722-726.
Laughney A.M., et al., "Regenerative Lineages and Immune-mediated Pruning in Lung Cancer Metastasis," Nature Medicine, Feb. 2020, vol. 26(2), pp. 259-269.

(56) References Cited

OTHER PUBLICATIONS

Le Guen L., et al., "Mesenchymal-Epithelial Interactions During Digestive Tract Development and Epithelial Stem Cell Regeneration," Cellular and Molecular Life Sciences, 2015, vol. 72, No. 20, pp. 3883-3896.
Lee J., et al., "IL-25 and CD4(+) TH2 Cells Enhance Type 2 Innate Lymphoid Cell-derived IL-13 Production, Which Promotes IgE-mediated Experimental Food Allergy," The Journal of Allergy and Clinical Immunology, Apr. 1, 2016, vol. 137(4), pp. 1216-1225.
Lee J.H. et al., "Anatomically and Functionally Distinct Lung Mesenchymal Populations Marked by Lgr5 and Lgr6," Cell, Sep. 7, 2017, vol. 170(6), pp. 1149-1163.
Li N., et al., Early-Life Compartmentalization of Immune Cells in Human Fetal Tissues Revealed by High-Dimensional Mass Cytometry, Frontiers in Immunology, Aug. 14, 2019; vol. 10(1932), 13 pages.
Li N., et al., Mass cytometry reveals innate lymphoid cell differentiation pathways in the human fetal intestine. Journal of Experimental Medicine, May 7, 2018, vol. 215(5), pp. 1383-1396.
Li N., et al., "Memory CD4+ T Cells Are Generated in the Human Fetal Intestine," Nature Immunology, Mar. 2019, vol. 20(3), pp. 301-312.
Li Z., et al., "Essential Roles of Enteric Neuronal Serotonin in Gastrointestinal Motility and the Development/Survival of Enteric Dopaminergic Neurons," The Journal of Neuroscience, Jun. 15, 2011, vol. 31, No. 24, pp. 8998-9009.
Lian X., et al., "Robust Cardiomyocyte Differentiation from Human Pluripotent Stem Cells via Temporal Modulation of Canonical Wnt Signaling," PNAS, May 29, 2012, pp. E1848-E1857.
Liang, W., et al., "MEF2C Alleviates Acute Lung Injury in Cecal Ligation and Puncture (CLP)-induced Sepsis Rats by Up-regulating AQP1," Allergologia et Immunopathologia, Sep. 1, 2021, vol. 49(5), pp. 117-124.
Lignitto L., et al., "Nrf2 Activation Promotes Lung Cancer Metastasis by Inhibiting the Degradation of Bach 1," Cell, Jul. 11, 2019, vol. 178(2), pp. 316-329.
Lippmann E.S., et al., "Human Blood-Brain Barrier Endothelial Cells Derived from Pluripotent Stem Cells," Nature Biotechnology, Aug. 2012, 30(8), pp. 783-791.
Little D.R., et al., "Differential Chromatin Binding of the Lung Lineage Transcription Factor NKX2-1 Resolves Opposing Murine Alveolar Cell Fates in Vivo," Nat Comm. May 2021; vol. 12, No. 1, 18 pages.
Loh K.M., et al., "Efficient Endoderm Induction from Human Pluripotent Stem Cells by Logically Directing Signals Controlling Lineage Bifurcations," Cell Stem Cell, Feb. 6, 2014, vol. 14(2), pp. 237-252.
Ma T.Y., et al., "IEC-18, A Nontransformed Small Intestinal Cell Line for Studying Epithelial Permeability," Journal of Laboratory and Clinical Medicine, Aug. 1992, vol. 120, No. 2, pp. 329-341.
Mabbott N.A., et al., "Microfold (M) Cells: Important Immunosurveillance Posts in the Intestinal Epithelium," Mucosal Immunology, Jul. 1, 2013, vol. 6(4), pp. 666-677.
Maeda Y., et al., Kras(G12D) and Nkx2-1 Haploinsufficiency Induce Mucinous Adenocarcinoma of the Lung. Journal of Clinical Investigation, Dec. 3, 2012, vol. 122(12), pp. 4388-4400.
Mahe M., et al., "Establishment of Human Epithelial Enteroids and Colonoids from Whole Tissue and Biopsy," Journal of Visualized Experiments, Mar. 6, 2015, vol. 97, 13 pages.
Manno., L.G., et al., "RNA Velocity of Single Cells," Nature, Aug. 2018, vol. 560 (7719), pp. 494-498.
Mansour A.A., et al., "An In Vivo Model of Functional and Vascularized Human Brain Organoids," Nature Biotechnology, Jun. 2018, 36(5), pp. 432-441.
Maruyama E.O., et al., "Cell-Specific Cre Strains for Genetic Manipulation in Salivary Glands," PLOS ONE, Jan. 11, 2016, vol. 11(1):e0146711, 12 pages.
Mccauley H.A., "Enteroendocrine Regulation of Nutrient Absorption," The Journal of Nutrition, 2019, pp. 10-21.
Mccauley H.A., et al., "Enteroendocrine Cells Couple Nutrient Sensing to Nutrient Absorption by Regulating Ion Transport," Nature Communications, 2020, vol. 11,10 pages.
Mccauley K.B., et al., "Efficient Derivation of Functional Human Airway Epithelium from Pluripotent Stem Cells via Temporal Regulation of Wnt Signaling," Cell Stem Cell, 2017, vol. 20, pp. 844-857.
Mccauley K.B., et al., "Single-Cell Transcriptomic Profiling of Pluripotent Stem Cell-Derived SCGB3A2+ Airway Epithelium," Stem Cell Reports, 2018, vol. 10, pp. 1579-1595.
Mcginnis C.S., et al., "DoubletFinder: Doublet Detection in Single-Cell RNA Sequencing Data Using Artificial Nearest Neighbors," Cell Systems, Apr. 24, 2019, vol. 8(4), pp. 329-337.
Mellitzer G., et al., "Loss of Enteroendocrine Cells in Mice Alters Lipid Absorption and Glucose Homeostasis and Impairs Postnatal Survival," The Journal of Clinical Investigation, vol. 120, No. 5, May 2010, pp. 1708-1721.
Menoret S., et al., "Generation of Immunodeficient Rats With Rag1 and Il2rg Gene Deletions and Human Tissue Grafting Models," Transplantation, Aug. 2018, vol. 102, No. 8, pp. 1271-1278.
Mentlein R., et al., "Proteolytic Processing of Neuropeptide Y and Peptide YY by Dipeptidyl Peptidase IV," Regulatory Peptides, 1993, vol. 49, pp. 133-144.
Miraldi E.R., et al., Leveraging Chromatin Accessibility for Transcriptional Regulatory Network Inference in T Helper 17 Cells. Genome Research, Mar. 1, 2019, vol. 29(3), pp. 449-463.
Miranda J., et al., "A Novel Mutation in FOXF1 Gene Associated with Alveolar Capillary Dysplasia with Misalignment of Pulmonary Veins, Intestinal Malrotation and Annular Pancreas," Neonatology, 2013, vol. 103, pp. 241-245.
Mitaka., et al., "Characterization of Hepatic-organoid Cultures," Drug Metabolism Reviews, 2010, vol. 42, No. 3, pp. 472-481.
Mizumoto H., et al., "Hybrid Artificial Liver Using Hepatocyte Organoids," Regenerative Medicine, 2006, vol. 5 No. 3, pp. 81-86.
Mollaoglu G., et al., "The Lineage-Defining Transcription Factors SOX2 and NKX2-1 Determine Lung Cancer Cell Fate and Shape the Tumor Immune Microenvironment," Immunity, Oct. 16, 2018, vol. 49(4), pp. 764-779.
Moniot B., et al., "SOX9 Specifies the Pyloric Sphincter Epithelium Through Mesenchymal-epithelial Signals," Development, Aug. 2004, vol. 131, No. 15, pp. 3795-3804.
Moodaley R., et al., "Agonism of Free Fatty Acid Receptors 1 and 4 Generates Peptide YY-Mediated Inhibitory Responses in Mouse Colon," British journal of Pharmacology, 2017, vol. 174, pp. 4508-4522.
Morrisey E.E., et al., "Preparing for the First Breath: Genetic and Cellular Mechanisms in Lung Development," Developmental Cell, Jan. 19, 2010, vol. 18, pp. 8-23.
Mowat A., et al., "Regional Specialization Within the Intestinal Immune System," Nature Reviews Immunology, Oct. 2014, vol. 14(10), pp. 667-685.
Nabhan A., et al., "A Single Cell Wnt Signaling Niche Maintains Stemness of Alveolar Type 2 Cells," Science, Mar. 9, 2018; vol. 359(6380), pp. 1118-1123.
Nagy N., et al., "Enteric Nervous System Development: a Crest Cell's Journey From Neural Tube to Colon," Seminars in Cell & Developmental Biology, 2017, vol. 66, pp. 94-106.
Nagy N., et al., "Sonic Hedgehog Controls Enteric Nervous System Development by Patterning the Extracellular Matrix," Development, 2016, 143(2), pp. 264-275.
Nakahara T., et al., "Human Papillomavirus Type 16 E1e4 Contributes to Multiple Facets of the Papillomavirus Life Cycle," Journal of Virology, Oct. 31, 2005, vol. 79, No. 20, pp. 13150-13165.
Nakamura T., et al., "Intestinal Stem Cell Transplantation," Journal of Gastroenterology, 2017, vol. 52, pp. 151-157.
Nedvetsky P.I., et al., "Parasympathetic Innervation Regulates Tubulogenesis in the Developing Salivary Gland," Developmental Cell, 2014, vol. 30, pp. 449-462.
Negretti N. M., et al., "A Single-cell Atlas of Mouse Lung Development," Development Dec. 15, 2021, vol. 148(24), 30 pages.
Nguyen J., et al., "The Next Generation of Endothelial Differentiation: Tissue-Specific ECs," Cell Stem Cell, Jul. 1, 2021, vol. 28(7), pp. 1188-1204.

(56) References Cited

OTHER PUBLICATIONS

Nochi T., et al., "Cryptopatches are essential for the development of human GALT," Cell Reports, Jun. 27, 2013, vol. 3(6), vol. 1874-1884.
Noel G., et al., "A Primary Human Macrophage-enteroid Co-culture Model to Investigate Mucosal Gut Physiology and Host-pathogen Interactions," Scientific Reports, Mar. 27, 2017, vol. 7(45270), 13 pages.
Norlen P., et al., "The Vagus Regulates Histamine Mobilization from Rat Stomach ECL Cells by Controlling Their Sensitivity to Gastrin," The Journal of Physiology, 2005, 564(Pt 3), pp. 895-905.
Oceguera-Yanez F., et al., "Engineering the AAVS1 Locus for Consistent and Scalable Transgene Expression in Human iPSCs and their Differentiated Derivatives," Methods, 2015, 13 pages.
Ohashi S., et al., "Epidermal Growth Factor Receptor and Mutant p53 Expand an Esophageal Cellular Subpopulation Capable of Epithelial-to-Mesenchymal Transition through ZEB Transcription Factors," Tumor and Stem Cell Biology, Apr. 27, 2010, vol. 70, No. 10, pp. 4147-4184.
Ostrin E. J., et al., "β-Catenin Maintains Lung Epithelial Progenitors After Lung Specification," Development, Mar. 1, 2018, vol. 145(5), 32 pages.
Paik D.T., et al., "Single-cell RNA-Seq Unveils Unique Transcriptomic Signatures of Organ-Specific Endothelial Cells," Circulation, Nov. 10, 2020, 142(19), pp. 1848-1862.
Palikuqi B., et al., "Adaptable Haemodynamic Endothelial Cells for Organogenesis and Tumorigenesis," Nature, Sep. 17, 2020, vol. 585, 33 pages.
Panaro B.L., et al., "The Melanocortin-4 Receptor Is Expressed in Enteroendocrine L Cells and Regulates the Release of Peptide YY and Glucagon-like Peptide 1 In Vivo," Cell Metabolism, Dec. 2, 2014, vol. 20, pp. 1018-1029.
Paris A.J., et al., "STAT3—BDNF-TrkB Signaling Promotes Alveolar Epithelial Regeneration After Lung Injury," Nature Cell Biology, Oct. 2020, vol. 22(10), pp. 1197-1210.
Park B., et al., "Hematopoietic Stem Cell Expansion and Generation: the Ways to Make a Breakthrough," Blood Research, Dec. 2015, vol. 50, No. 4, 10 pages.
Penkala I.J., et al., "Age-Dependent Alveolar Epithelial Plasticity Orchestrates Lung Homeostasis and Regeneration," Cell Stem Cell, Oct. 7, 2021, vol. 28, pp. 1775-1789.
Perriot S., et al., "Differentiation of Functional Astrocytes From Human-Induced Pluripotent Stem Cells in Chemically Defined Media," STAR Protocols, Dec. 17, 2021,2(4):100902, 13 pages.
Perriot S., et al., "Human Induced Pluripotent Stem Cell-Derived Astrocytes Are Differentially Activated by Multiple Sclerosis-Associated Cytokines," Stem Cell Reports, Nov. 13, 2018, vol. 11, pp. 1199-1210.
Pradhan A., et al., "The S52F FOXF1 Mutation Inhibits STAT3 Signaling and Causes Alveolar Capillary Dysplasia," American Journal of Respiratory and Critical Care Medicine, Oct. 15, 2019, vol. 200, No. 8, pp. 1045-1056.
Qian X., et al., "Brain-Region-Specific Organoids Using Mini-bioreactors for Modeling ZIKV Exposure," Cell, 2016, vol. 165, pp. 1238-1254.
Qian X., et al., "Generation of Human Brain Region-specific Organoids Using a Miniaturized Spinning Bioreactor," Nature Protocols, Mar. 2018, 13(3), pp. 565-580.
Qin X., "Why is Damage Limited to the Mucosa in Ulcerative Colitis but Transmural in Crohn's Disease", World Journal of Gastrointestinal Pathophysiology, Aug. 15, 2013, vol. 4, No. 3, pp. 63-64.
Rakhilin N., et al., "Simultaneous Optical and Electrical in Vivo Analysis of the Enteric Nervous System," Nature Communications, Jun. 7, 2016, 7:11800, 7 pages.
Ran F.A., et al., "Genome Engineering using the CRISPR-Cas9 System," Nature Protocols, Nov. 2013, 8(11), pp. 2281-2308.
Ranganathan S., et al., "Evaluating *Shigella flexneri* Pathogenesis in the Human Enteroid Model," Infection and Immunity, Apr. 2019, vol. 87(4), 14 pages.
Rice A.C., et al., "A New Animal Model of Hemolytic Hyperbilirubinemia-Induced Bilirubin Encephalopathy (Kernicterus)," Pediatric Research, 2008, vol. 64, No. 3, pp. 265-269.
Riemondy K. A., et al., "Single Cell RNA Sequencing Identifies TGF-β as a Key Regenerative Cue Following LPS-induced Lung Injury," JCI Insight, Apr. 4, 2019, vol. 4(8), 18 pages.
Rindler T.N., et al., "Efficient Transduction of Alveolar Type 2 Cells with Adeno-associated Virus for the Study of Lung Regeneration," American Journal of Respiratory Cell and Molecular Biology, Jul. 2021, vol. 65(1), pp. 118-121.
Roberts D.J., et al., "Epithelial-mesenchymal Signaling During the Regionalization of the Chick Gut," Development, 1998, vol. 125, No. 15, pp. 2791-2801.
Rodriguez-Castillo J. A., et al., "Understanding Alveolarization to Induce Lung Regeneration," Respiratory Research, Dec. 2018, vol. 19:1-1, 11 pages.
Rouch J.D., et al., "Development of Functional Microfold (M) Cells from Intestinal Stem Cells in Primary Human Enteroids," PLOS One . Jan. 28, 2016, vol. 11(1), 16 pages.
Ruppert C.. et al., "Role of HGF in the healthy and injured lung," European Respiratory Journal, 2015, vol. 46, 2 pages.
Rydning A., et al., "Mast Cell Derived Histamine is Involved in Gastric Vasodilation During Acid Back Diffusion via Activation of Sensory Neurons," Am J Physiol Gastrointest Liver Physiol., Sep. 1, 2002, vol. 283, vol. 3, 36 pages.
Salahudeen A. A., et al., "Progenitor Identification and SARS-CoV-2 Infection in Human Distal Lung Organoids," Nature, Dec. 24, 2020, vol. 588(7839), pp. 670-675.
Scavuzzo M.A., et al., "Organotypic Pancreatoids with Native Mesenchyme Develop Insulin Producing Endocrine Cells," Scientific Reports, Sep. 7, 2017, pp. 1-12.
Serra M., et al., "Pluripotent Stem Cell Differentiation Reveals Distinct Developmental Pathways Regulating Lung-Versus Thyroid-lineage Specification," Development, Nov. 1, 2017, vol. 144(21), pp. 3879-3893.
Shacham-Silverberg V., et al., "Generation of Esophageal Organoids and Organotypic Raft Cultures from Human Pluripotent Stem Cells," Methods of Cell Biology, May 13, 2020, vol. 159, pp. 1-23.
Shaylor L.A., et al., "Convergence of Inhibitory Neural Inputs Regulate Motor Activity in the Murine and Monkey Stomach," Am J Physiol Gastrointest Liver Physiol., Nov. 1, 2016, vol. 311, No. 5, pp. G838-G851.
Shi Y., et al., "Vascularized Human Cortical Organoids (vOrganoids) Model Cortical Development in Vivo," PloS Biology, 2020, 8(5), 29 pages.
Shin Y., et al., "Blood-Brain Barrier Dysfunction in a 3D In Vitro Model of Alzheimer's Disease," Advanced Science, 2019, 6(20), 10 pages.
Shinozawa T., et al., "High-Fidelity Drug-Induced Liver Injury Screen Using Human Pluripotent Stem Cell-Derived Organoids," Gastroenterology. Feb. 2021, vol. 160(3), pp. 831-846.
Simian M., et al., "Organoids: A Historical Perspective of Thinking in Three Dimensions," Journal of Cell Biology, 2017, vol. 216, No. 1, pp. 31-40.
Singh A., et al., "Evaluation of Transplantation Sites for Human Intestinal Organoids," Plos One, Aug. 27, 2020, 15(8), 12 pages.
Singh A., et al., "Gastrointestinal Organoids: a Next-Generation Tool for Modeling Human Development," American Journal of Physiology—gastrointestinal and Liver Physiology, 2020, 319(3), pp. G375-G381.
Smith D.M., et al., "BMP Signaling Specifies the Pyloric Sphincter," Nature, Dec 16, 1999, vol. 402, No. 6763, pp. 748-749.
Song L., et al., "Assembly of Human Stem Cell Derived Cortical Spheroids and Vascular Spheroids to Model 3-D Brain-like Tissues," 2019, Scientific Reports, vol. 9, No. 5977, 16 pages.
Spencer J., et al., "T Cell Subclasses in Fetal Human Ileum," Clinical and Experimental Immunology, 1986, pp. 553-558.
Spencer J., et al., "The Development of Gut Associated Lymphoid Tissue in the Terminal lleum of Fetal Human Intestine," Clinical and Experimental Immunology, 1986, pp. 536-543.
Srinivas S., et al., "Cre Reporter Strains Produced by Targeted Insertion of EYFP and ECFP into the ROSA26 Locus," BMC Developmental Biology, Dec. 2001, vol. 1 (4), 8 pages.

(56) References Cited

OTHER PUBLICATIONS

Srinivasan B., et al., "TEER Measurement Techniques for in Vitro Barrier Model Systems," Journal of Laboratory Automation, 2015, 20 (2), 20 pages.
Staab J.F, et al., "Co-Culture System of Human Enteroids/Colonoids with Innate Immune Cells,". Current Protocols in Immunology, Dec. 2020, vol. 131(1), 23 pages.
Stevens M.L., et al., "Genomic Integration of Wnt/-catenin and BMP/smad1 Signaling Coordinates Foregut and Hindgut Transcriptional Programs," Development, 2017, 144(7), pp. 1283-1295.
Stras., et al., "Maturation of the Human Intestinal Immune System Occurs Early in Fetal Development," Developmental Cell, Nov. 4, 2019, vol. 51(3), pp. 357-373.
Strauss K.A., et al., "Crigler-Najjar Syndrome Type 1: Pathophysiology, Natural History, and Therapeutic Frontier," Hepatology, 2020, 71(6), pp. 1923-1939.
Street K., et al., "Slingshot: Cell Lineage and Pseudotime Inference for Single-cell Transcriptomics," BMC Genomics, Dec. 2018, vol. 19, pp. 1-16.
Strikoudis A., et al., "Modeling of Fibrotic Lung Disease Using 3D Organoids Derived from Human Pluripotent Stem Cells," Cell Reports, Jun. 18, 2019, vol. 27(12), pp. 3709-3723.
Strunz M., et al., "Alveolar Regeneration Through a Krt8+ Transitional Stem Cell State That Persists in Human Lung Fibrosis," Nature Communications, Jul. 16, 2020, vol. 11(1):3559, 20 pages.
Sucre J. M.S., et al., "Hyperoxia Injury in the Developing Lung is Mediated by Mesenchymal Expression of Wnt5A," American Journal of Respiratory and Critical Care Medicine, May 15, 2020, vol. 201(10), pp. 1249-1262.
Sugimoto S., et al., "An Organoid-based Organ-Repurposing Approach to Treat Short Bowel Syndrome," Nature, Apr. 2021, vol. 99, 26 pages.
Sun X., et al., "A Census of the Lung: CellCards from LungMAP," Developmental Cell, Jan. 10, 2022, vol. 57(1), pp. 112-145.
Sun X-Y., et al., "Generation of Vascularized Brain Organoids to Study Neurovascular Interactions," eLife, 2022, vol. 11,28 pages.
Sung T.S., et al., "The Cells and Conductance Mediating Cholinergic Neurotransmission in the Murine Proximal Stomach," The Journal of Physiology, 2018, 596(9), pp. 1549-1574.
Tan S.H., et al., "AQP5 Enriches for Stem Cells and Cancer Origins in the Distal Stomach," Nature, 2020, 578 (7795), pp. 437-443.
Tanimizu N., et al., "Generation of Functional Liver Organoids on Combining Hepatocytes and Cholangiocytes with Hepatobiliary Connections Ex Vivo," Nature Communications, Jun. 2021, 12 pages.
Tanimizu N., et al., "Tissue Structure Formation by Liver Epithelial Cells," 2012, vol. 84, No. 8, pp. 658-665.
Tata P.R., et al., "Developmental History Provides a Roadmap for the Emergence of Tumor Plasticity," Developmental Cell, Mar. 26, 2018, vol. 44(6), pp. 679-693.
TCW J. et al., "An Efficient Platform for Astrocyte Differentiation from Human Induced Pluripotent Stem Cells," Stem Cell Reports, vol. 9, 2017, pp. 600-614.
Teixeira V., et al., "Neonatal Vitamin C and Cysteine Deficiencies Program Adult Hepatic Glutathione and Specific Activities of Glucokinase, Phosphofructokinase, and Acetyl-CoA Carboxylase in Guinea Pigs' Livers," 2021, Antioxidants, 10, 953, 17 pages.
Theodosiou N.A., et al., "Sox9 and Nkx2. 5 Determine the Pyloric Sphincter Epithelium Under the Control of BMP Signaling," Developmental Biology, 2005, 279, pp. 481-490.
Thompson CA., et al., "GATA4 Is Sufficient to Establish Jejunal Versus lleal Identity in the Small Intestine," Cellular and Molecular Gastroenterology and Hepatology, May 2017, 3(3), pp. 422-446.
Thwaites D.T., et al., "H+/Dipeptide Absorption Across the Human Intestinal Epithelium Is Controlled Indirectly via a Functional Na+/H+ Exchanger," Gastroenterology, 2002, vol. 122, pp. 1322-1333.
Toth A., et al., "Alveolar Epithelial Progenitor Cells Drive Lung Regeneration via Dynamic Changes in Chromatin Topology Modulated by Lineage-specific Nkx2-1 Activity," bioRxiv, 2022, 31 pages.
Toth A., et al., "Alveolar Epithelial Stem Cells in Homeostasis and Repair," Chapter 10 in Lung Stem Cells in Development, Health and Disease, European Respiratory Society, 2021, pp. 122-133.
Tough I.R., et al., "Endogenous Peptide YY and Neuropeptide Y Inhibit Colonic lon Transport, Contractility and Transit Differentially via Y1 and Y2 Receptors," British journal of Pharmacology, 2011, vol. 164, pp. 471-484.
Traber M.G., et al., "Vitamins C and E: Beneficial Effects from a Mechanistic Perspective," Free Radical Biology and Medicine, 2011,51 (5), pp. 1000-1013.
Travaglini K.J., et al., "A Molecular Cell Atlas of the Human Lung from Single-cell RNA Sequencing," Nature, Nov. 26, 2020, vol. 587(7835), pp. 619-625.
Tsai Y-H., et al., "In Vitro Patterning of Pluripotent Stem Cell-Derived Intestine Recapitulates in Vivo Human Development," Development, 2016, 144(6), 57 pages.
Ustiyan V., et al., "FOXF1 Transcription Factor Promotes Lung Morphogenesis by Inducing Cellular Proliferation in Fetal Lung Mesenchyme," Developmental Biology, 2018, 443(1), pp. 50-63.
Vallicelli C., et al., "Small Bowel Emergency Surgery: Literature's Review," World Journal of Emergency Surgery, 2011, vol. 6, No. 1,8 pages.
Van De Steeg E., et al., "Complete OATP1B1 and OATP1B3 Deficiency Causes Human Rotor Syndrome by Interrupting Conjugated Bilirubin Reuptake Into the Liver," The Journal of Clinical Investigation, 2012, vol. 122, No. 2, pp. 519-528.
Van Lieshout., L.P., et al., "A Novel Triple-Mutant AAV6 Capsid Induces Rapid and Potent Transgene Expression in the Muscle and Respiratory Tract of Mice," Molecular Therapy- Methods and Clinical Development, Open Access Jun. 15, 2018, vol. 9, pp. 323-329.
Vannucchi M.G., "The Telocytes: Ten Years after Their Introduction in the Scientific Literature. An Update on Their Morphology, Distribution, and Potential Roles in the Gut," International Journal of Molecular Sciences, 2020, vol. 21, 15 pages.
Verheyden J.M., et al., "A Transitional Stem Cell State in the Lung," Nature Cell Biology, Sep. 2020, vol. 22(9), pp. 1025-1026.
Vila Ellis L., et al., "Epithelial Vegfa Specifies a Distinct Endothelial Population in the Mouse Lung," Developmental Cell, 2020, 52, pp. 617-630.
Walsh K.T., et al., "The Enteric Nervous System for Epithelial Researchers: Basic Anatomy, Techniques, and Interactions with the Epithelium," Cellular and Molecular Gastroenterology and Hepatology, 2019, vol. 8, No. 3, pp. 369-378.
Wang Y., et al., "Loss of Lrig1 Leads to Expansion of Brunner Glands Followed by Duodenal Adenomas with Gastric Metaplasia," Am J Pathol., Apr. 2015, vol. 185, No. 4, pp. 1123-1134.
Ward S.M., et al., "Involvement of Intramuscular Interstitial Cells of Cajal in Neuroeffector Transmission in the Gastrointestinal Tract," The Journal of Physiology, 2006, vol. 576, pp. 675-682.
Weigmann B., et al., Isolation and Subsequent Analysis of Murine Lamina Propria Mononuclear Cells from Colonic Tissue, Nature Protocols, Oct. 2007, vol. 2(10), 2307-2311.
Weng A., et al., "Lung Injury Induces Alveolar Type 2 Cell Hypertrophy and Polyploidy with Implications for Repair and Regeneration," American Journal of Respiratory Cell and Molecular Biology, May 2022, vol. 66(5), pp. 564-576.
Westfal M.L., et al., "Pediatric Enteric Neuropathies: Diagnosis and Current Management," Current Opinion in Pediatrics, 2017, 29(3), pp. 347-353.
Wiel C, et al., "BACH1 Stabilization by Antioxidants Stimulates Lung Cancer Metastasis," Cell, Jul. 11, 2019, vol. 178(2), pp. 330-345.
Wimmer R.A., et al., "Generation of Blood Vessel Organoids from Human Pluripotent Stem Cells," Nature Protocols, 2019, vol. 14, pp. 3082-3100.
Wimmer R.A., et al., "Human Blood Vessel Organoids as a Model of Diabetic Vasculopathy," Nature, 2019, 565(7740), 41 pages.

(56) References Cited

OTHER PUBLICATIONS

Wong G.L.H., et al., "High Incidence of Mortality and Recurrent Bleeding in Patients With Helicobacter Pylori-Negative Idiopathic Bleeding Ulcers," Gastroenterology, 2009, vol. 137, pp. 525-531.
Wright E.M., et al., "Biology of Human Sodium Glucose Transporters," Physiological Reviews, 2011, vol. 91,62 pages.
Wright E.M., et al., "Regulation of Na+/Glucose Cotransporters," The Journal of Experimental Biology, 1997, vol. 200, pp. 287-293.
Wunderlich M., et al., "AML Xenograft Efficiency Is Significantly Improved in Nod/Scid-IL2RG Mice Constitutively Expressing Human SCF, GM-CSF and IL-3," Leukemia, Oct. 2010, vol. 24(10) pp. 1785-1788.
Wunderlich M., et al., "Improved Multilineage Human Hematopoietic Reconstitution and Function in NSGS Mice," PLOS One, Dec. 12, 2018, vol. 13(12), 20 pages.
Yamaguchi T., et al., "NKX2-1/TTF-1: An Enigmatic Oncogene That Functions as a Double-edged Sword for Cancer Cell Survival and Progression," Cancer Cell, Jun. 10, 2013, vol. 23(6), pp. 718-723.
Yang Y., et al., "Transcription Factor C/EBP Homologous Protein in Health and Diseases," Frontiers in Immunology, Nov. 27, 2017, vol. 8:1612, 18 pages.
Yu Q., et al., "Charting Human Development Using a Multi-Endodermal Organ Atlas and Organoid Models," Cell, 2021, vol. 184, pp. 3281-3298.
Yuan T., et al., "Fgf10 Signaling in Lung Development, Homeostasis, Disease, and Repair After Injury," Frontiers in Genetics, Sep. 25, 2018, vol. 9(418), 8 pages.
Yun C.H.C., et al., "CAMP-mediated Inhibition of the Epithelial Brush Border Na +/H+ exchanger, NHE3, requires an Associated Regulatory Protein," PNAS, 1997, vol. 94, pp. 3010-3015.
Zacharias W.J., et al., "Regeneration of the Lung Alveolus by an Evolutionarily Conserved Epithelial Progenitor," Nature, Mar. 8, 2018, vol. 555(7695), pp. 251-255.
Zepp J.A., et al., "Distinct Mesenchymal Lineages and Niches Promote Epithelial Self-Renewal and Myofibrogenesis in the Lung," Cell, Sep. 7, 2017, vol. 170(6), pp. 1134-1148.
Zhang S., et al., "Vascularized Organoids on a Chip: Strategies for Engineering Organoids with Functional Vasculature," Lab Chip, 2021,21 (3), pp. 473-488.
Zhao C-M., et al., "Control of Gastric Acid Secretion in Somatostatin Receptor 2 Deficient Mice: Shift from Endocrine/Paracrine to Neurocrine Pathways," Endocrinology, 2008, 149(2), pp. 498-505.
Zhou B., et al., "Comprehensive Epigenomic Profiling of Human Alveolar Epithelial Differentiation Identifies Key Epigenetic States and Transcription Factor Co-regulatory Networks for Maintenance of Distal Lung Identity," BMC Genomics, Dec. 2021, vol. 22(906), 25 pages.
Mammen J. M., et al., "Mucosal Repair in the Gastrointestinal Tract," Critical Care Medicine, 2003, vol. 31, pp. S532-537. DOI: 10.1097/01.CCM.0000081429.89277.AF.
Mammoto A., et al., "Vascular Niche in Lung Alveolar Development, Homeostasis, and Regeneration," Frontiers in Bioengineering and Biotechnology, Nov. 2019, vol. 7, No. 318. doi: 10.3389/fbioe.2019.00318.
Mammoto, T., et al., "Mechanical control of tissue and organ development," Development, 2010, vol. 137, No. 9, pp. 1407-1420.
Mandegar M. A., et al., "CRISPR Interference Efficiently Induces Specific and Reversible Gene Silencing in Human iPSCs," Cell Stem Cell, 2016, 18(4), pp. 541-553.
Marable, S.S., et al., "Hnf4a deletion in the mouse kidney phenocopies Fanconi renotubular syndrome," JCI Insight, 2018, vol. 3, 12 Pages.
Mari L. et al., "A pSMAD/CDX2 complex is essential for the intestinalization of epithelial metaplasia," Cell Reports, 2014, 7(4), 1197-1210.
Marino G. et al., "Self-consumption: the interplay of autophagy and apoptosis", Nature reviews Molecular cell biology, 2014, vol. 15, No. 2, pp. 81-94.
Mariotti, V., et al., "Animal models of biliary injury and altered bile acid metabolism," Biochimica et Biophysica Acta (BBA)—Molecular Basis of Disease, 2018, vol. 1864, pp. 1254-1261.
Martin M. "Cutadapt Removes Adapter Sequences From High-Throughput Sequencing Reads," EMBnet.journal, 2011 17, 10-12.
Martindale J.L., et al., "Ribonucleoprotein Immunoprecipitation (RIP) Analysis," Bio Protoc, 2020, vol. 10, No. 2, e3488. doi: 10.21769/BioProtoc3488.
Matrka M. C., et al., "Overexpression of the Human DEK Oncogene Reprograms Cellular Metabolism and Promotes Glycolysis," PLoS One, 2017, vol. 12, e0177952.
Matsuda S., et al., "Brain-Derived Neurotrophic Factor Induces Migration of Endothelial Cells Through a TrkB-ERK-Integrin V3-FAK Cascade." Journal of Cellular Physiology, 227, 2012, pp. 2123-2129.
Matt N. et al., "Retinoic acid-induced developmental defects are mediated by RARI3/RXR heterodimers in the pharyngeal endoderm," Development, 2003, 130(10), 2083-2093.
Mayor S., et al., "Pathways of Clathrin-independent Endocytosis," Nature Reviews, Molecular Cell Biology, 2007, vol. 8(8), pp. 603-612.
Mccarty, W. J., et al., "A Microfabricated Platform for Generating Physiologically-Relevant Hepatocyte Zonation," Scientific Reports, 2016, vol. 6, 26868, 10 Pages.
McMahon H.T., et al., "Molecular Mechanism and Physiological Functions of Clathrin-mediated Endocytosis," Nature Reviews Molecular Cell Biology, Aug. 2011, vol. 12(8), pp. 517-533.
Mcnaughton, L., et al., "Distribution of nitric oxide synthase in normal and cirrhotic human liver," Proceedings of the National Academy of Sciences, 2002, vol. 99, pp. 17161-17166.
Mendelsohn C. et al., "Developmental analsyis of the retinoic acid-inducible RARb2 promoter in transgenic animals," Development, 1991, 113, 723-734.
Meng G., et al., "Optimizing Human Induced Pluripotent Stem Cell Expansion in Stirred-Suspension Culture," Stem Cells and Development, Dec. 15, 2017, vol. 26, No. 24, pp. 1804-1817, DOI: 10.1089/scd.2017.0090, Retrieved from the Internet URL: https://www.liebertpub.com/doi/pdf/10.1089/scd.2017.0090casatoken=4jmtPMYfDEcAAAAA:3nd2OwOrb6Kyltkq641ZOmaNdxD4fHqdAl8it6DjaU7EuxXp4qO09t16ps7WJfgbo9HkQEJU.
Miao Y., et al., "Enhancer-Associated Long Non-Coding RNA LEENE Regulates Endothelial Nitric Oxide Synthase and Endothelial Function," Nature Communications, Jan. 2018, vol. 9, No. 1, doi: 10.1038/s41467-017-02113-y.
Miao Y., et al., "Intrinsic Endocardial Defects in Hypoplastic Left Heart Syndrome," Cell Stem Cell, Jul. 2020. doi: 10.1016/j.stem.2020.07.015.
Miao Z., et al., "Single Cell Regulatory Landscape of the Mouse Kidney Highlights Cellular Differentiation Programs and Disease Targets," Nature Communications, 2021, vol. 12, No. 2277.
Michael A., et al., "Optimized Mouse ES Cell Culture System by Suspension Growth in a Fully Defined Medium", Nature Protocols, May 1, 2008, vol. 3, No. 6, pp. 1013-1017, DOI: 10.1038/nprot.2008.65.
Midendorp S., et al., "Adult Stem Cells in the Small Intestine Are Intrinsically Programmed with Their Location-Specific Function," Stem Cells, 2014, vol. 32, pp. 1083-1091. DOI: 10.1002/stem.1655.
Miller J. L., et al., "Emergence of Oropharyngeal, Laryngeal and Swallowing Activity in the Developing Fetal Upper Aerodigestive Tract: An Ultrasound Evaluation." Early Human Development, 71, 2003, pp. 61-87.
Minoo P. et al., "Defects in tracheoesophageal and lung morphogenesis in Nkx2.1 (-/-) mouse embryos," Dev. Biol., 1999, 209, 60-71.
Mitani, S., et al., "Human ESC/iPSC-Derived Hepatocyte-like Cells Achieve Zone-Specific Hepatic Properties by Modulation of WNT Signaling," Mol Ther, 2017, vol. 25, pp. 1420-1433.
Miyoshi H., et al., "In Vitro Expansion and Genetic Modification of Gastrointestinal Stem Cells in Spheroid Culture," Nature Protocols, 2013, vol. 8(12), pp. 2471-2482.
Moffett, J.R., et al., "Acetate Revisited: A Key Biomolecule at the Nexus of Metabolism, Epigenetics and OncogenesisPart 1: Acetyl-

(56) References Cited

OTHER PUBLICATIONS

CoA, Acetogenesis and Acyl-CoA Short-Chain Synthetases," Frontiers in Physiology, 2020, vol. 11.
Moon C. et al., "Development of a primary mouse intestinal epithelial cell monolayer culture system to evaluate factors that modulate IgA transcytosis," Mucosal Immunol, 2014, 7, 818-828.
Moorefield E.C., et al., "Generation of renewable mouse intestinal epithelial cell monolayers and organoids for functional analyses," BMC Cell Biol, Aug. 15, 2018, vol. 19(1):15.
Mootha V.K et al., "PGC-1alpha-responsive genes involved in oxidative phosphorylation are coordinately downregulated in human diabetes," Nat Genet 34, 267-273 (2003).
Morizane R., et al., "Differentiation of Murine Embryonic Stem and Induced Pluripotent Stem Cells to Renal Lineage In Vitro." Biochemical and Biophysical Research Communications, 390, 2009, pp. 1334-1339.
Morizane R., et al., "Generation of Nephron Progenitor Cells and Kidney Organoids from Human Pluripotent Stem Cells," Nature Protocols, 2017, vol. 12, pp. 195-207.
Morizane R., et al., "Kidney Organoids: A Translational Journey," Trends in Molecular Medicine, 2017, vol. 23, pp. 246-263.
Morizane R., et al., "Nephron Organoids Derived from Human Pluripotent Stem Cells Model Kidney Development and Injury." Nature Biotechnology, 33(11), 2015, pp. 1193-1200. https://doi.org/10.1038/nbt.3392.
Morris M. E., et al., "SLC and ABC Transporters: Expression, Localization, and Species Differences at the Blood-Brain and the Blood-Cerebrospinal Fluid Barriers," AAPS Journal, 2017, vol. 19, pp. 1317-1331.
Mounier F., et al., "Ontogenesis of Angiotensin-I Converting Enzyme in Human Kidney," Kidney International, 1987, vol. 32, pp. 684-690.
Murphy C. L., et al., "HIF-Mediated Articular Chondrocyte Function: Prospects for Cartilage Repair," Arthritis Research Therapy, 2009, vol. 11, p. 213. DOI: 10.1186/ar2574.
Murphy P.A., et al., "Alternative RNA Splicing in the Endothelium Mediated in Part by Rbfox2 Regulates the Arterial Response to Low Flow," eLife, Jan. 2018, vol. 7, e29494. doi: 10.7554/eLife.29494.
Navin N., et al., "Tumor Evolution Inferred by Single-cell Sequencing," Nature, Apr. 7, 2011, vol. 472(7341), pp. 90-94.
Neal E.H., et al., "A Simplified, Fully Defined Differentiation Scheme for Producing Blood-Brain Barrier Endothelial Cells from Human iPSCs," Stem Cell Reports, 2019, vol. 12, pp. 1380-1388.
Nebert D. W., et al., "Letter to the Editor for 'Update of the Human and Mouse Fanconi Anemia Genes,'" Human Genomics, 2016, vol. 10, No. 1, 25 pages.
Nejak-Bowen, K., et al., "Beta-catenin regulates vitamin C biosynthesis and cell survival in murine liver," J Biol Chem, 2009, vol. 284, pp. 28115-28127.
Nelson L.J., et al., "Low-Shear Modelled Microgravity Environment Maintains Morphology and Differentiated Functionality of Primary Porcine Hepatocyte Cultures," Cells Tissues Organs, 2010, vol. 192, pp. 125-140.
Niederreither K. "Embryonic retinoic acid synthesis is essential for early mouse post-implantation development," Nature Genetics, 1999, 21(4), 444-448.
Niethamer T.K., et al., "Defining the Role of Pulmonary Endothelial Cell Heterogeneity in the Response to Acute Lung Injury," eLife, Feb. 2020, vol. 9, No. e53072. doi: 10.7554/eLife.53072.
Nishinakamura R., "Human Kidney Organoids: Progress and Remaining Challenges," Nature Reviews Nephrology, 2019, vol. 15, pp. 613-624.
Nonn, O., et al., "Maternal Angiotensin Increases Placental Leptin in Early Gestation via an Alternative Renin-Angiotensin System Pathway: Suggesting a Link to Preeclampsia," Hypertension, 2021, vol. 77, pp. 1723-1736.
Nozaki, Y., et al., "Metabolic Control Analysis of Hepatic Glycogen Synthesis In Vivo," Proceedings of the National Academy of Sciences of the United States of America, 2020, vol. 117, pp. 8166-8176.
Efremova I., et al., "CellPhoneDB: Inferring Cell-Cell Communication from Combined Expression of Multi-Subunit Receptor-Ligand Complexes," Nature Protocols, 2020, vol. 15, pp. 1484-1506.
Eicher A.K., et al., "Functional Human Gastrointestinal Organoids Can Be Engineered from Three Primary Germ Layers Derived Separately from Pluripotent Stem Cells," Cell Stem Cell, 2022, vol. 29, pp. 36-51.e6. doi: 10.1016/j.stem.2021.10.010.
Engelstoft, M. S. et al., "Enteroendocrine Cell Types Revisited". Current Opinion in Pharmacology, 2013, vol. 13, pp. 912-921.
Everhart J. E., et al., "Fatty Liver: Think Globally," Hepatology, 2010, vol. 51, pp. 1491-1493.
Fan Y., et al., "Bioengineering Thymus Organoids to Restore Thymic Function and Induce Donor-Specific Immune Tolerance to Allografts", The American Society of Gene Cell Therapy, vol. 23, No. 7, Jul. 2015, pp. 1262-1277.
Fang M., et al., "Ulinastatin Ameliorates Pulmonary Capillary Endothelial Permeability Induced by Sepsis Through Protection of Tight Junctions via Inhibition of TNFalpha and Related Pathways," Frontiers in Pharmacology, Sep. 2018, vol. 9, doi: 10.3389/fphar.2018.00823.
Fantes J. et al., "Mutations in SOX2 cause anophthalmia," Nature Genetics, 2003, 33(4), 461-463.
Fausett S. R. et al., "Compartmentalization of the foregut tube: developmental origins of the trachea and esophagus," Wiley Interdisciplinary eviews. Developmental Biology, 2012, (2), 184-202.
Fausett S.R., et al., "BMP antagonism by Noggin is required in presumptive notochord cells for mammalian foregut morphogenesis," Developmental Biology, 2014, 391(1), 111-24.
Feliers D., et al., "Mechanism of VEGF Expression by High Glucose in Proximal Tubule Epithelial Cells," Molecular and Cellular Endocrinology, 2010, vol. 314, pp. 136-142.
Ferguson, D., et al., "Emerging Therapeutic Approaches for the Treatment of NAFLD and Type 2 Diabetes Mellitus," Nature Reviews Endocrinology, 2021, vol. 17, pp. 484-495.
Fermini, B., et al., "Clinical Trials in a Dish: A Perspective on the Coming Revolution in Drug Development," SLAS Discovery, 2018, vol. 23, pp. 765-776.
Fischer B., et al., "Oxygen Tension in the Oviduct and Uterus of Rhesus Monkeys, Hamsters and Rabbits," Journal of Reproduction and Fertility, 1993, vol. 99, pp. 673-679.
Freedman B.S., "Physiology Assays in Human Kidney Organoids," American Journal of Physiology—Renal Physiology, 2022, vol. 322, pp. F625-F638.
Freund J.B. et al., "Fluid flows and forces in development: functions, features and biophysical principles," Development, 2012, 139(7), 1229-1245.
Fujita Y. et al., "Pax6 and Pdx1 are required for production of glucose-dependent insulinotropic polypeptide in proglucagon-expressing L cells," Am J Physiol Endocrinol Metab, 2008, 295, E648-657.
Funakoshi, K., et al., "Highly Sensitive and Specific Alu-Based Quantification of Human Cells Among Rodent Cells," Scientific Reports, 2017, vol. 7, Article 13202. DOI: 10.1038/s41598-017-13402-3.
Furuta G. T. et al., "Eosinophilic Esophagitis," New England Journal of Medicine, 2015, 373(17), 1640-1648.
Gang, X., et al., "P300 Acetyltransferase Regulates Fatty Acid Synthase Expression, Lipid Metabolism and Prostate Cancer Growth," Oncotarget, 2016, vol. 7, No. 11, pp. 15135-15149.
Gao C, et al., "RBFox1-Mediated RNA Splicing Regulates Cardiac Hypertrophy and Heart Failure," Journal of Clinical Investigation, 2016, vol. 126, pp. 195-206.
Gao et al., "Highly Branched Poly (-amino esters) for Non-Viral Gene Delivery: High Transfection Efficiency and Low Toxicity Achieved by Increasing Molecular Weight", Biomacromolecules, 2016, vol. 17(11), pp. 3640-3647.
Gao, H., et al., "Association of GCKR Gene Polymorphisms with the Risk of Nonalcoholic Fatty Liver Disease and Coronary Artery Disease in a Chinese Northern Han Population," Journal of Clinical and Translational Hepatology, 2019, vol. 7, pp. 297-303.

(56) References Cited

OTHER PUBLICATIONS

Garca-Surez, O., et al., "TrkB is Necessary for the Normal Development of the Lung." Respiratory Physiology & Neurobiology, vol. 167, No. 3, Jul. 31, 2009, pp. 281-291.
Garcia-Martinez, S., et al., "Mimicking physiological 02 tension in the female reproductive tract improves assisted reproduction outcomes in pig," Molecular Human Reproduction, 2018, vol. 24, pp. 260-270.
Garlanda C. et al., "Heterogeneity of endothelial cells. Specific markers" Arterioscler Thromb Vasc Biol, 1997, 17, 1193-1202.
Gazzin, S., et al., "Bilirubin Accumulation and Cyp mRNA Expression in Selected Brain Regions of Jaundiced Gunn Rat Pups," Pediatric Research, 2012, vol. 71, No. 6, pp. 653-660.
German-Diaz, M., et al., "A New Case of Congenital Malabsorptive Diarrhea and Diabetes Secondary to Mutant Neurogenin," Pediatrics, 2017, vol. 140, No. 2, 8 pages.
Ghatak S. et al., "Bile acid at low pH reduces squamous differentiation and activates EGFR signaling in esophageal squamous cells in 3-D culture," Journal of Gastrointestinal Surgery: Official Journal of the Society for Surgery of the Alimentary Tract, 2013, 17(10), 1723-31.
Ginestet C., "ggplot2: Elegant Graphics for Data Analysis," J R Stat Soc a Stat, 2011 174, 245,245.
Glass, L. L., et al., "Single-cell RNA-sequencing reveals a distinct population of proglucagon-expressing cells specific to the mouse upper small intestine," Molecular Metabolism, 2017, vol. 6, pp. 1296-1303.
Gololow N., et al., "Epitheliomesenchymal Interaction in Pancreatic Morphogenesis," Developmental Biology, 1962, vol. 4, pp. 242-255.
Gordillo M., et al., "Orchestrating liver development," Development, Jun. 2015, vol. 142(12), pp. 2094-2108.
Goss A.M., "Wnt2/2b and beta-catenin signaling are necessary and sufficient to specify lung progenitors in the foregut," Developmental Cell, 2009, 17(2), 290-8.
Gotoh S. et al. "Generation of Alveolar Epithelial Spheroids via Isolated Progenitor Cells from Human Pluripotent Stem cells" Stem Cell Reports (2014) 3(3):394-403.
Greene, A. S., et al., "Microvascular Angiogenesis and the Renin-Angiotensin System." Current Hypertension Reports, vol. 4, No. 1, Feb. 2002, pp. 56-62.
Greene Y. J., et al., "Ascorbic Acid Regulation of 3-Hydroxy-3-Methylglutaryl Coenzyme A Reductase Activity and Cholesterol Synthesis in Guinea Pig Liver." Biochimica et Biophysica Acta, 834(1), 1985, pp. 134-138.
Greggio C., et al., "Artificial Three-Dimensional Niches Deconstruct Pancreas Development In Vitro," Development, 2013, vol. 140, pp. 4452-4462.
Gribble, F. M., et al., "Enteroendocrine Cells: Chemosensors in the Intestinal Epithelium," Annu Rev Physiol, 2016, vol. 78, pp. 277-299.
Gribouval O., et al., "Mutations in Genes in the Renin-Angiotensin System Are Associated with Autosomal Recessive Renal Tubular Dysgenesis," Nature Genetics, 2005, vol. 37, pp. 964-968.
Gribouval, O., et al., "Spectrum of Mutations in the Renin-Angiotensin System Genes in Autosomal Recessive Renal Tubular Dysgenesis." Human Mutation, vol. 33, No. 2, Feb. 2012, pp. 316-326.
Gu G., et al., "Global expression analysis of gene regulatory pathways during endocrine pancreatic development," Development, 2004, 131, 165-179.
Gu M., et al., "iPSC-Endothelial Cell Phenotypic Drug Screening and In Silico Analyses Identify Tyrphostin-AG1296 for Pulmonary Arterial Hypertension," Science Translational Medicine, 2021, vol. 13, No. 592. doi: 10.1126/scitranslmed.aba6480.
Gu M., et al., "Microfluidic Single-Cell Analysis Shows That Porcine Induced Pluripotent Stem Cell-Derived Endothelial Cells Improve Myocardial Function by Paracrine Activation," Circulation Research, 2012, vol. 111, pp. 882-893.
Gu M., et al., "Patient-Specific iPSC-Derived Endothelial Cells Uncover Pathways that Protect Against Pulmonary Hypertension in BMPR2 Mutation Carriers," Cell Stem Cell, 2017, vol. 20, pp. 490-504.
Gualdi R., et al., "Hepatic Specification of the Gut Endoderm In Vitro: Cell Signaling and Transcriptional Control," Genes Development, 1996, vol. 10, pp. 1670-1682 (14 Pages).
Guan X. et al., "GLP-2 receptor localizes to enteric neurons and endocrine cells expressing vasoactive peptides and mediates increased blood flow," Gastroenterology, 2006, 130, 150-164.
Guarino, M., et al., "Nicotinamide and NAFLD: Is There Nothing New Under the Sun?" Metabolites, 2019, vol. 9.
Gubler M. C., et al., "Renin-Angiotensin System in Kidney Development: Renal Tubular Dysgenesis," Kidney International, 2010, vol. 77, pp. 400-406.
Gubler M. C., "Renal Tubular Dysgenesis," Pediatric Nephrology, 2014, vol. 29, pp. 51-59.
Guo L., et al., "The Adrenal Stress Response is an Essential Host Response Against Therapy-Induced Lethal Immune Activation," Science Signaling, 2023, vol. 16, eadd4900. doi: 10.1126/scisignal.add4900.
Concepcion J. P., et al., "Neonatal Diabetes, Gallbladder Agenesis, Duodenal Atresia, and Intestinal Malrotation Caused by a Novel Homozygous Mutation in RFX6," Pediatric Diabetes, 2014, vol. 15, pp. 67-72.
Coon S. D. et al., "Glucose-dependent insulinotropic polypeptide-mediated signaling pathways enhance apical PepT1 expression in intestinal epithelial cells," Am J Physiol Gastrointest Liver Physiol, 2015, 308, G56-62.
Cormier J.T., et al., "Expansion of Undifferentiated Murine Embryonic Stem Cells as Aggregates in Suspension Culture Bioreactors," Tissue Engineering, Nov. 1, 2006, vol. 12, No. 11, pp. 3233-3245, Retrieved from the Internet URL: https://www.liebertpub.com/doi/epdf/10.1089/ten.2006.12.3233.
Cortina, G., et al., "Enteroendocrine Cell Dysgenesis and Malabsorption, a Histopathologic and Immunohistochemical Characterization," Human Pathology, 2007, vol. 38, pp. 570-580.
Coskun T. et al., "Activation of Prostaglandin E Receptor 4 Triggers Secretion of Gut Hormone Peptides GLP-1, GLP-2, and PYY," Endocrinology, 2013, 154, 45-53.
Cox H. M., "Endogenous PYY and NPY mediate tonic Y(1)- and Y(2)-mediated absorption in human and mouse colon," Nutrition, 2008, 24, 900-906.
Creane M., et al., "Biodistribution and Retention of Locally Administered Human Mesenchymal Stromal Cells: Quantitative Polymerase Chain Reaction-Based Detection of Human DNA in Murine Organs," Cytotherapy, 2017, vol. 19, pp. 384-394. DOI: 10.1016/j.jcyt.2016.12.003.
Crisera C. A., et al., "Expression and Role of Laminin-1 in Mouse Pancreatic Organogenesis," Diabetes, 2000, vol. 49, pp. 936-944.
Cruz, N. M., et al., "Differentiation of Human Kidney Organoids from Pluripotent Stem Cells." In Methods in Cell Biology, vol. 153, Chapter 7, 2019, pp. 133-150.
Cucullo L., et al., "The role of shear stress in Blood-Brain Barrier endothelial physiology," BMC Neurosci, 2011, 40, 15 pages.
Cuevas I., et al., "Sustained Endothelial Expression of HoxA5 In Vivo Impairs Pathological Angiogenesis and Tumor Progression," PLoS One, 2015, vol. 10, e0121720.
Cui, J., et al., "Progressive Pseudogenization: Vitamin C Synthesis and Its Loss in Bats," Molecular Biology and Evolution, 2011, vol. 28, No. 4, pp. 1025-1031.
Cunningham, R.P., et al., "Liver Zonation—Revisiting Old Questions With New Technologies," Frontiers in Physiology, 2021, vol. 12, 732929.
Dahlman et al., "Barcoded Nanoparticles for High Throughput in Vivo Discovery of Targeted Therapeutics", PNAS, U.S.A., 2017, vol. 114(8), pp. 2060-2065.
Daneman R., et al., "The Blood-Brain Barrier," Cold Spring Harbor Perspectives in Biology, 2015, vol. 7, a020412.
Daniel K.E., et al., "Scalable Stirred-Suspension Bioreactor Culture of Human Pluripotent Stem Cells," Tissue Engineering, Jan. 1, 2010, vol. 16, No. 2, pp. 405-421, DOI: 10.1089/ten.tea.2009.0454.

(56) References Cited

OTHER PUBLICATIONS

Daniely Y et al., "Critical role of p63 in the development of a normal esophageal and tracheobronchial epithelium," American Journal of Physiology, Cell Physiology, 2004, 287(1), C171-C181.
Dathan N. et al., "Distribution of the titf2/foxel gene product is consistent with an important role in the development of foregut endoderm, palate, and hair," Dev. Dyn., 2002, 224, 450-456.
Davidson L. M., et al., "Bronchopulmonary Dysplasia: Chronic Lung Disease of Infancy and Long-Term Pulmonary Outcomes," Journal of Clinical Medicine, 2017, vol. 6, p. 20.
Davis B. P., et al., "Eosinophilic Esophagitis-Linked Calpain 14 is an IL-13-Induced Protease that Mediates Esophageal Epithelial Barrier Impairment," JCI Insight, 2016, 1(4), 11 pages.
Dawkins H.U.S., et al., "Progress in rare diseases research 2010-2016: An IRDiRC Perspective," Clinical and Translational Science. Jan. 2018;11(1):11-20.
De Felice, M. et al., "A mouse model for hereditary thyroid dysgenesis and cleft palate," Nat. Genet., 1998, 19, 395-398.
De Jong E. M. et al., Etiology of esophageal atresia and tracheoesophageal fistula: 'Mind the gap', Current Gastroenterology Reports, 2010, 12(3), 215-222.
De Paepe M. E., et al., "Growth of Pulmonary Microvasculature in Ventilated Preterm Infants," American Journal of Respiratory and Critical Care Medicine, 2006, vol. 173, pp. 204-211.
De Santa Barbara P., et al., "Molecular Etiology of Gut Malformations and Diseases," American Journal of Medical Genetics, Dec. 3, 20020; vol. 115(4), pp. 221-230.
De Santa Barbara, P., et al., "Tail gut endoderm and gut/genitourinary/tail development: a new tissue-specific role for Hoxa13," Development, 2002, vol. 129, pp. 551-561.
Demirgan E.B., et al., "AGTR1-related Renal Tubular Dysgeneses May Not Be Fatal," Kidney International Reports, 2021, vol. 6, pp. 846-852.
Distefano P.V. et al., "KRIT1 protein depletion modifies endothelial cell behavior via increased vascular endothelial growth factor (VEGF)signaling," J Biol Chem, 2014, 289, 33054-33065.
D'Mello R. J., et al., "LRRC31 is Induced by IL-13 and Regulates Kallikrein Expression and Barrier Function in the Esophageal Epithelium," Mucosal Immunology, 2016, 9(3), pp. 744-756.
Dolinay T., et al., "Integrated Stress Response Mediates Epithelial Injury in Mechanical Ventilation," American Journal of Respiratory Cell and Molecular Biology, 2017, 57, pp. 193-203.
Dollard S. C, et al., "Production of Human Papillomavirus and Modulation of the Infectious Program in Epithelial Raft Cultures." Genes & Development, 6, 1992, pp. 1131-1142.
Domyan E.T. et al., "Signaling through BMP receptors promotes respiratory identity in the foregut via repression of Sox2," Development (Cambridge, England), 2011, 138(5), 971-981.
Donati, B., et al., "The rs2294918 E434K Variant Modulates Patatin-Like Phospholipase Domain-Containing 3 Expression and Liver Damage." Hepatology, vol. 63, No. 3, Mar. 2016, pp. 787-798.
Dong R., et al., "SpatialDWLS: Accurate Deconvolution of Spatial Transcriptomic Data." Genome Biology, 22, 145, 2021, 10 pages. https://doi.org/10.1186/s13059-021-02362-7.
Dorison A., et al., "What Can We Learn from Kidney Organoids?" Kidney International, 102, 2022, pp. 1013-1029. https://doi.org/10.1016/j.kint.2022.06.032.
Dougherty, E., "Tackling the common denominator in liver disease," Novartis, Jun. 16, 2016, https://www.novartis.com/stories/tackling-common-denominator-liver-disease.
Doupe D. P. et al., "A Single Progenitor Population Switches Behavior to Maintain and Repair Esophageal Epithelium," Science, 2012, 337(6098), 1091-1093.
Draheim K. M., et al., "Cerebral Cavernous Malformation Proteins at a Glance," Journal of Cell Science, 2014, vol. 127(4), pp. 701-707.
Drukcer, D. J., "Evolving Concepts and Translational Relevance of Enteroendocrine Cell Biology," J Clin Endocrinol Metab, 2016, vol. 101, No. 3, pp. 778-786.
Du A. et al., "Arx is required for normal enteroendocrine cell development in mice and humans," Developmental biology, 2012, 365, 175-188.
Du Y., et al., "Lung Gene Expression Analysis (LGEA): An Integrative Web Portal for Comprehensive Gene Expression Data Analysis in Lung Development," Thorax, 2017, 72, pp. 481-484.
Du Y. et al., "'LungGENS': a web-based tool for mapping single-cell gene expression in the developing lung," Thorax, 2015, 70, 1092-1094.
Dubrovskyi O., et al., "Measurement of Local Permeability at Subcellular Level in Cell Models of Agonist- and Ventilator-Induced Lung Injury," Laboratory Investigation, 2013, vol. 93, pp. 254-263.
Duluc I., et al., "Changing Intestinal Connective Tissue Interactions Alters Homeobox Gene Expression in Epithelial Cells," Journal of Cell Science, 1997, vol. 110, pp. 1317-1324.
Dunn A., et al., "Poly seq: A poly(J3-amino ester)-based Vector for Multifunctional Cellular Barcoding," Stem Cell Reports. Sep. 2021, vol. 14(2), pp. 2149-2158.
Dunn A., et al., "Polymeric Vectors for Strategic Delivery of Nucleic Acids," Nano Life, 2017, vol. 7, No. 02, 1730003, 12 pages.
Dunn et al., "Highly Efficient In Vivo Targeting of the Pulmonary Endothelium Using Novel Modifications of Polyethylenimine: An Importance of Charge", Advan Health Mater. 2018, vol. 7(23): 1800876, 25 pages.
Duval, K., et al., "Revisiting the role of Notch in nephron segmentation confirms a role for proximal fate selection during mouse and human nephrogenesis," Development, 2022, vol. 149.
Dye B. R., et al., "A Bioengineered Niche Promotes In Vivo Engraftment and Maturation of Pluripotent Stem Cell Derived Human Lung Organoids," eLife 5, 2016, 18 pages.
Dye B.R. et al., "In vitro generation of human pluripotent stem cell derived lung organoids," Elife 4:e05098 (2015), 25 pages.
Vega M. E. et al., "Inhibition of notch signaling enhances transdifferentiation of the esophageal squamous epithelium towards a Barrett's-like metaplasia via KLF4," Cell Cycle, 2014, 13(24), 3857-3866.
Veldman, T., et al., "Human Papillomavirus E6 and Myc Proteins Associate In Vivo and Bind to and Cooperatively Activate the Telomerase Reverse Transcriptase Promoter." Proceedings of the National Academy of Sciences, vol. 100, No. 14, Jul. 8, 2003, pp. 8211-8216.
Verdera H,C., et al., AAV vector immunogenicity in humans: A long journey to successful gene transfer, Mol Thera. Mar. 4, 2020;28(3):723-746.
Verma S.K., et al., "RBFOX2 is Required for Establishing RNA Regulatory Networks Essential for Heart Development," Nucleic Acids Research, 2022, vol. 50, No. 4, 2270-2286. doi: 10.1093/nar/gkac055.
Verscheijden L.F.M., et al., "Differences in P-Glycoprotein Activity in Human and Rodent Blood-Brain Barrier Assessed by Mechanistic Modelling," Archives of Toxicology, 2021, vol. 95, pp. 3015-3029.
Vincent C. C., et al., "Scalable GMP Compliant Suspension Culture System for Human ES cells," Stem Cell Research, May 1, 2012, vol. 8, No. 3, DOI: 10.1016/j.scr.2012.02.001, pp. 388-402.
Vincent K.M., et al., "Expanding the Clinical Spectrum of Autosomal-Recessive Renal Tubular Dysgenesis: Two Siblings with Neonatal Survival and Review of the Literature," Molecular Genetics and Genomic Medicine, 2022, vol. 10, e1920.
Vohwinkel C.U., et al., "Bronchopulmonary Dysplasia: Endothelial Cells in the Driver's Seat," American Journal of Respiratory Cell and Molecular Biology, Apr. 2021, vol. 65, No. 1, pp. 6-7. doi: 10.1165/rcmb.2021-0145ED.
Wagner N., et al., "Coronary Vessel Development Requires Activation of the TrkB Neurotrophin Receptor by the Wilms' Tumor Transcription Factor Wt1," Genes & Development, 2005, vol. 19, pp. 2631-2642.
Wahlestedt C. et al., "Neuropeptide Y Receptor Subtypes, Y1 and Y2," Annals of the New York Academy of Sciences, 1990, 611, 7-26.
Wahlicht, T., et al., "Controlled Functional Zonation of Hepatocytes In Vitro by Engineering of Wnt Signaling." ACS Synthetic Biology, vol. 9, 2020, pp. 1638-1649.

(56) References Cited

OTHER PUBLICATIONS

Walker E.M. et al., "Characterization of the developing small intestine in the absence of either GATA4 or GATA6," BMC Res Notes, 2014, 7, 902, 12 pages.
Wang D. H., et al., "Regulation of Angiotensin Type 1 Receptor and Its Gene Expression: Role in Renal Growth," Journal of the American Society of Nephrology, 1997, vol. 8, pp. 193-198.
Wang D.H. et al., "Aberrant Epithelial-Mesenchymal Hedgehog Signaling Characterizes Barrett's Metaplasia," Gastroenterology 2010, 138(5), 1810-1822.e2.
Wang H., et al., "Recent Progress in microRNA Delivery for Cancer Therapy by Non-Viral Synthetic Vectors," Advanced Drug Delivery Reviews, 2015, vol. 81, pp. 142-160.
Wang K., et al., "ANNOVAR: Functional Annotation of Genetic Variants from High-Throughput Sequencing Data," Nucleic Acids Research, 2010, vol. 38, e164.
Wang Q. et al., "Regulatable in vivo biotinylation expression system in mouse embryonic stem cells," PloS One, 2013, 8, 5, e63532, 7 pages.
Wang S., "Fundamentals of developmental biology", edited by , East China University of 25 Technology Press, Feb. 2014, 1st edition, pp. 184-185 "Role of homologous genes in development of appendages", published on Feb. 28, 2014).
Wang T. et al."Polypeptide Growth Factor and Spinal Cord Injury". Xinjiang Science and Technology Press, Yunnan Science and Technology Press, "Biological Effects of EGF", pp. 88-89, published on Apr. 30, 2003).
Wang X., et al., "A Tropomyosin Receptor Kinase Family Protein, NTRK2, is a Potential Predictive Biomarker for Lung Adenocarcinoma," PeerJ, Jun. 2019, vol. 7, doi: 10.7717/peerj.7125.
Wang, Y., et al., "Metformin Improves Mitochondrial Respiratory Activity through Activation of AMPK," Cell Reports, 2019, vol. 29, pp. 1511-1523 e1515.
Wang, Y., et al., "Transcriptional regulation of hepatic lipogenesis," Nat Rev Mol Cell Biol, 2015, vol. 16, pp. 678-689.
Watanabe H., et al., "SOX2 and p63 colocalize at genetic loci in squamous cell carcinomas," Journal of Clinical Investigation, 2014, 124(4), 1636-1645.
Watanabe M., et al., "Feasibility Study of NMR-Based Serum Metabolomic Profiling to Animal Health Monitoring: A Case Study on Iron Storage Disease in Captive Sumatran Rhinoceros (*Dicerorhinus sumatrensis*)," PLoS One, 2016, vol. 11, e0156318.
Weber R.J., et al., "Efficient Targeting of Fatty-acid modified Oligonucleotides to live Cell Membranes through Stepwise Assembly," Biomacromolecules, 2014, vol. 15(12), pp. 4621-4626.
Wei Y., et al., "Liver Homeostasis is Maintained by Midlobular Zone 2 Hepatocytes," Science, Feb. 2021, vol. 371, No. eabb1625.
Weirauch M. T. et al., "Determination and inference of eukaryotic transcription factor sequence specificity," Cell, 2014, 158, 1431-1443.
Wells J.M. et al., "Wnt/beta-catenin signaling is required for development of the exocrine pancreas," BMC Dev Biol, 2007, 7, 4, 18 pages.
Wesley, B. T., et al., "Single-Cell Atlas of Human Liver Development Reveals Pathways Directing Hepatic Cell Fates," Nature Cell Biology, 2022, vol. 24, No. 10, pp. 14871498.
Wessel J., et al., "Do Genes Determine Our Health? Implications for Designing Lifestyle Interventions and Drug Trials," Circulation: Cardiovascular Genetics, 2016, vol. 9, pp. 2-3.
Wesson, D., et al., "The effect of intrauterine esophageal ligation on growth of fetal rabbits," J Pediatr Surg, 1984, vol. 19, pp. 398-399.
Whitehead K. J., et al., "The Cerebral Cavernous Malformation Signaling Pathway Promotes Vascular Integrity via Rho GTPases," Nature Medicine, 2009, vol. 15, pp. 177-184.
Wieland H.A., et al., "Subtype selectivity of the novel nonpeptide neuropeptide YY1 receptor antagonist BIBO3304 and its effect on feeding in rodents," Br J Pharmacol, Oct. 1998, vol. 125(3), pp. 549-555.
Williamson K. A., et al., "Mutations in SOX2 Cause Anophthalmia-Esophageal-Genital (AEG) Syndrome," Human Molecular Genetics, 2006, 15(9), pp. 1413-1422.
Woo J. et al., "Band -mediated inhibition of Wnt signaling in the mouse thoracic foregut controls tracheo-esophageal septation and epithelial differentiation," PloS One, 2011, 6(7), e22493, 8 pages.
Wu H., et al., "Advantages of Single-Nucleus over Single-Cell RNA Sequencing of Adult Kidney: Rare Cell Types and Novel Cell States Revealed in Fibrosis," Journal of the American Society of Nephrology, Jan. 2019, vol. 30, No. 1, pp. 23-32.
Wu H., et al., "Comparative Analysis and Refinement of Human PSC-Derived Kidney Organoid Differentiation with Single-Cell Transcriptomics," Cell Stem Cell, 2018, vol. 23, pp. 869-881.e868.
Wu X., et al., "Modeling Drug-induced Liver Injury and Screening for Anti-hepatofibrotic Compounds Using Human PSC-derived Organoids,", Cell Regeneration, Biomed Central, vol. 12, No. 1, Mar. 3, 2023, pp. 1-13.
Xia, M.F, et al., "NAFLD and Diabetes: Two Sides of the Same Coin? Rationale for Gene-Based Personalized NAFLD Treatment," Frontiers in Pharmacology, 2019, vol. 10, 877.
Xia Y., et al., "Angiotensin Receptors, Autoimmunity, and Preeclampsia," Journal of Immunology, 2007, vol. 179, pp. 3391-3395.
Xiang Y., et al., "Fusion of Regionally Specified hPSC-Derived Organoids Models Human Brain Development and Interneuron Migration,". Cell Stem Cell, 2017, vol. 21, pp. 383-398.
Xiao C. et al., "Gut peptides are novel regulators of intestinal lipoprotein secretion: experimental and pharmacological manipulation of lipoprotein metabolism," Diabetes, 2015, 64, 2310-2318.
Xiao S., et al., "Gastric Stem Cells: Physiological and Pathological Perspectives," Frontiers in Cell and Developmental Biology, 2020, vol. 8, pp. 1-13.
Xu, C.-R., et al., "Chromatin 'Prepattern' and Histone Modifiers in a Fate Choice for Liver and Pancreas," Science, 2011, vol. 332, pp. 963-966.
Xu R., "Basis and Clinical Applications of Receptors", edited by et al. Shanghai Science and Technology Press, 1st edition, Feb. 1992, Section of "Retinoic Acid Receptors" on pp. 129-131, published on Feb. 29, 1992.
Xu, W., et al., "Hypoxia activates Wnt/-catenin signaling by regulating the expression of BCL9 in human hepatocellular carcinoma," Scientific Reports, 2017, vol. 7, 40446, 13 pages.
Xu, Y., et al., "Ascorbate protects liver from metabolic disorder through inhibition of lipogenesis and suppressor of cytokine signaling 3 (SOCS3)," Nutrition & Metabolism, 2020, vol. 17, 17.
Yanan Y., et al., "Research Progress on Hedgehog Signaling Pathway and Liver Fibrosis," Chinese Journal of Anatomy, 06, Dec. 25, 2019, pp. 589-592.
Yang M., et al., "Angiogenesis-Related Genes May Be a More Important Factor than Matrix Metalloproteinases in Bronchopulmonary Dysplasia Development," Oncotarget, 2017, vol. 8, pp. 18670-18679.
Ye D.Z. et al., "Foxa1 and Foxa2 control the differentiation of goblet and enteroendocrine L- and D-cells in mice," Gastroenterology, 2009, 137, 2052-2062.
Guo M., et al., "Guided Construction of Single Cell Reference for Human and Mouse Lung," Nature Communications, Jul. 29, 2023, 14:4566, 20 pages.
Gupta A. et al., "The great divide: septation and malformation of the cloaca, and its implications for surgeons," Pediatr Surg Int, 2014, 30, 1089-1095.
Ha, T. Y., et al., "Ascorbate Indirectly Stimulates Fatty Acid Utilization in Primary Cultured Guinea Pig Hepatocytes by Enhancing Carnitine Synthesis," The Journal of Nutrition, 1994, vol. 124, pp. 732-737.
Haasdijk R. A., et al., "Cerebral Cavernous Malformations: From Molecular Pathogenesis to Genetic Counselling and Clinical Management," European Journal of Human Genetics, 2012, vol. 20, pp. 134-140.
Habib A. M. et al., "Overlap of endocrine hormone expression in the mouse intestine revealed by transcriptional profiling and flow cytometry," Endocrinology, 2012, 153, 3054-3065.

(56) References Cited

OTHER PUBLICATIONS

Haeussler M., et al., "Evaluation of Off-Target and On-Target Scoring Algorithms and Integration into the Guide RNA Selection Tool CRISPOR," Genome Biology, 2016, vol. 17, No. 148, 12 pages.
Hagan D.M. et al., "Mutation analysis and embryonic expression of the HLXB9 Currarino syndrome gene," Am. J. Hum. Genet., 2000, 66, 1504-1515.
Haigh J. J., et al., "Cortical and Retinal Defects Caused by Dosage-Dependent Reductions in VEGF-A Paracrine Signaling," Developmental Biology, 2003, vol. 262, pp. 225-241.
Hajal C., et al., "Biology and Models of the Blood-Brain Barrier," Annual Review of Biomedical Engineering, 2021, vol. 23, pp. 359-384.
Hale, C., et al., "Molecular Targeting of the GK-GKRP Pathway in Diabetes." Expert Opinion on Therapeutic Targets, vol. 19, No. 1, 2015, pp. 129-139.
Han L., et al., "Osr1 Functions Downstream of Hedgehog Pathway to Regulate Foregut Development," Developmental Biology, 2017, 427, pp. 72-83.
Hansmann G., et al., "Pulmonary Hypertension in Bronchopulmonary Dysplasia," Pediatric Research, Jun. 2020, No. 10.1038/s41390-020-0993-4.
Harris-Johnson K.S. et al., "13-Catenin promotes respiratory progenitor identity in mouse foregut," Proc. Natl. Acad. Sci. U. S. A., 2009, 106, 16287-16292.
Harrison S.A., et al., "Selonsertib for Patients with Bridging Fibrosis or Compensated Cirrhosis Due to NASH: Results from Randomized Phase III STELLAR Trials," Journal of Hepatology, 2020, vol. 73, pp. 26-39.
Haussinger, D., "Nitrogen metabolism in liver: structural and functional organization and physiological relevance," Biochem J, 1990, vol. 267, pp. 281-290.
He, L., et al., "Proliferation tracing reveals regional hepatocyte generation in liver homeostasis and repair," Science, 2021, vol. 371, eabc4346.
Heinz S. et al., "Simple combinations of lineage-determining transcription factors prime cis-regulatory elements required for macrophage and B cell identities," Mol Cell, 2010, 38, 576-589.
Hernaez R., et al., "Association Between Variants in or near PNPLA3, GCKR, and PPP1R3B with Ultrasound-Defined Steatosis Based on Data from the Third National Health and Nutrition Examination Survey," Clinical Gastroenterology and Hepatology, 2013, vol. 11, pp. 1183-1190.e1182.
Hilgers K. F., et al., "Aberrant Renal Vascular Morphology and Renin Expression in Mutant Mice Lacking Angiotensin-Converting Enzyme," Hypertension, 1997, vol. 29, pp. 216-221.
Hill, D. R., et al., "Gastrointestinal Organoids: Understanding the Molecular Basis of the Host-Microbe Interface," Cell Mol Gastroenterol Hepatol, 2017, vol. 3, pp. 138-149.
Hirschhorn, J. N., et al., "Genome-Wide Association Studies for Common Diseases and Complex Traits." Nature Reviews Genetics, vol. 6, 2005, pp. 95-108.
Hirsh A. J., et al., "Effect of Cholecystokinin and Related Peptides on Jejunal Transepithelial Hexose Transport in the Sprague-Dawley Rat," American Journal of Physiology-Gastrointestinal and Liver Physiology, 1996, vol. 271, No. G755-G761.
Hoffmeister K.M., "Desialylated Platelets: A Missing Link in Hepatic Thrombopoietin Regulation," The Hematologist 2015; 12(3), 7 pages.
Hoffmeister K.M., "The role of lectins and glycans in platelet clearance," Journal of Thrombosis and Haemostasis. Jul. 2011;9 (suppl), pp. 35-43.
Hohwieler H., et al., "Human Pluripotent Stem Cell-Derived Acinar/Ductal Organoids Generate Human Pancreas upon Orthotopic Transplantation and Allow Disease Modelling," Gut, 2017, vol. 66, pp. 473-486.
Holt L.M., et al., "Astrocyte Morphogenesis is Dependent on BDNF Signaling via Astrocytic TrkB.T1," eLife, Aug. 2019, vol. 8, No. e44667. doi: 10.7554/eLife.44667.
Homayun B., et al., "Challenges and Recent Progress in Oral Drug Delivery Systems for Biopharmaceuticals," Pharmaceutics, Mar. 1, 20199, vol. 11(3):129.
Hoskins E. E., et al., Fanconi anemia deficiency stimulates HPV-associated hyperplastic growth in organotypic epithelial raft culture. Oncogene, 2009, 28(5), 674-685.
Hotta K., et al., "Association of the rs738409 Polymorphism in PNPLA3 with Liver Damage and the Development of Nonalcoholic Fatty Liver Disease," BMC Medical Genetics, 2010, vol. 11, p. 172.
Hu H., et al., "AnimalTFDB 3.0: A Comprehensive Resource for Annotation and Prediction of Animal Transcription Factors," Nucleic Acids Research, 2019, 47(D1), pp. D33-D38.
Hu Y. et al., "Targeted disruption of peptide transporter Pept1 gene in mice significantly reduces dipeptide absorption in intestine," Molecular pharmaceutics, 2008, 5(6), 1122-1130.
Hu Z. et al., "Generation of Naivetropic Induced Pluripotent Stem Cells from Parkinson's Desease Patients for High-Efficiency Genetic Manipulation oand Disease Modeling," Stem Cells and Development, 2015, vol. 24, No. 21, 2591-2604.
Huang H., et al., "p300-Mediated Lysine 2-Hydroxyisobutyrylation Regulates Glycolysis," Molecular Cell, 2018, vol. 70, pp. 663-678. e666. doi: 10.1016/j.molcel.2018.04.011.
Huang J., et al., "Activation of Wnt/-Catenin Signalling via GSK3 Inhibitors Direct Differentiation of Human Adipose Stem Cells into Functional Hepatocytes," Nature Scientific Reports, 2017, 7, Article No. 40716, 12 pages.
Huang, S. X. L., et al., "Efficient generation of lung and airway epithelial cells from human pluripotent stem cells," Nat. Biotechnol., 2014, vol. 32, No. 1, pp. 84-91.
Hudert, C. A., et al., "Genetic Determinants of Steatosis and Fibrosis Progression in Paediatric NonAlcoholic Fatty Liver Disease." Liver International, vol. 39, 2019, pp. 540-556.
Huo X. et al., "Acid and Bile Salt-Induced CDX2 Expression Differs in Esophageal Squamous Cells From Patients With and Without Barrett's Esophagus," Gastroenterology, 2010, 139(1), 194-203.e1.
Hurr, C., et al., "Liver Sympathetic Denervation Reverses Obesity-Induced Hepatic Steatosis." The Journal of Physiology, vol. 597, No. 17, Sep. 2019, pp. 4565-4580.
Hurskainen M., et al., "Single Cell Transcriptomic Analysis of Murine Lung Development on Hyperoxia-Induced Damage," Nature Communications, Mar. 2021, vol. 12, No. 1565. doi: 10.1038/s41467-021-21865-2.
Husson, A., et al., "Argininosuccinate synthetase from the urea cycle to the citrulline-NO cycle," European Journal of Biochemistry, 2003, vol. 270, pp. 1887-1899.
Huynh N., et al., "Feasibility and Scalability of Spring Parameters in Distraction Enterogenesis in a Murine Model," Journal of Surgical Research, 2017, vol. 215, pp. 219-224.
Iansante, V., et al., "Human hepatocyte transplantation for liver disease: current status and future perspectives," Pediatric Research, 2018, vol. 83, pp. 232-240.
Ikeda, Y., et al., "Bilirubin exerts pro-angiogenic property through Akt-eNOS787 dependent pathway," Hypertension Research, 2015, vol. 38, pp. 733-740.
Illig R. et al., "Spatio-temporal expression of HOX genes in human hindgut development," Developmental dynamics: an official publication of the American Association of Anatomists, 2013, 242, 53-66.
Isosaari L., et al., "Simultaneous Induction of Vasculature and Neuronal Network Formation on a Chip Reveals a Dynamic Interrelationship Between Cell Types," Cell Communication and Signaling, 2023, vol. 21, 132. doi: 10.1186/s12964-023-01159-4.
Iwafuchi-Doi, M. et al., "Pioneer transcription factors in cell reprogramming," Genes Dev 2014, 28, 2679-2692.
Iwasawa K., et al., "Organogenesis In Vitro," Current Opinion in Cell Biology, 2021, 73, pp. 84-91.
Jackerott M. et al., "Immunocytochemical localization of the NPY/PYY Y1 receptor in enteric neurons, endothelial cells, and endocrine-like cells of the rat intestinal tract," J Histochem Cytochem, 1997, 45(12), 1643-1650.

(56) References Cited

OTHER PUBLICATIONS

Jang S. W., et al., "A Selective TrkB Agonist with Potent Neurotrophic Activities by 7,8-Dihydroxyflavone," Proceedings of the National Academy of Sciences of the United States of America, 2010, vol. 107, pp. 2687-2692.
Jaramillo M., et al., "Endothelial Cells Mediate Islet-Specific Maturation of Human Embryonic Stem Cell-Derived Pancreatic Progenitor Cells," Tissue Engineering Part A, 2015, vol. 21, pp. 14-25.
Snowball J. et al., "Endodermal Wnt signaling is required for tracheal cartilage formation," Dev Biol 405, 56-70 (2015).
Soneson C., et al., "Differential Analyses for RNA-Seq: Transcript-Level Estimates Improve Gene-Level Inferences," F1000Research, 2015, vol. 4, p. 1521.
Song H.W., et al., "Transcriptomic Comparison of Human and Mouse Brain Microvessels," Scientific Reports, 2020, vol. 10, 12358. doi: 10.1038/s41598-020-69096-7.
Spangle, J. M., et al., "The Human Papillomavirus Type 16 E6 Oncoprotein Activates mTORC1 Signaling and Increases Protein Synthesis." Journal of Virology, vol. 84, No. 18, Sep. 2010, pp. 9398-9407.
Sparrow D. B., et al., "A Mechanism for Gene-Environment Interaction in the Etiology of Congenital Scoliosis," Cell, 2012, vol. 149, pp. 295-306.
Speliotes E. K., et al., "Genome-Wide Association Analysis Identifies Variants Associated with Nonalcoholic Fatty Liver Disease That Have Distinct Effects on Metabolic Traits," PLoS Genetics, 2011, vol. 7, e1001324.
Spencer-Dene B. et al.," Stomach development is dependent on fibroblast growth factor 10/fibroblast growth factor receptor 2b-mediated signaling," Gastroenterology, 2006, 130, 1233-1244.
Sreter K.B., et al., "Plasma Brain-Derived Neurotrophic Factor (BDNF) Concentration and BDNF/TrkB Gene Polymorphisms in Croatian Adults with Asthma," Journal of Personalized Medicine, Oct. 2020, vol. 10, No. 4, doi: 10.3390/jpm10040189.
Stoeckius M., et al., "Cell Hashing with Barcoded antibodies enables Multiplexing and Doublet Detection for Single Cell Genomics," Genome Biology, 2018, vol. 19(1), pp. 1-12.
Stoffers D. A., et al., "Pancreatic Agenesis Attributable to a Single Nucleotide Deletion in the Human IPF1 Gene Coding Sequence," Nature Genetics, 1997, vol. 15, pp. 106-110.
Stoll B. J., et al., "Neonatal Outcomes of Extremely Preterm Infants from the NICHD Neonatal Research Network," Pediatrics, 2010, vol. 126, pp. 443-456.
Subramanian, A. et al., "Gene set enrichment analysis: A knowledge-based approach for interpreting genome-wide expression profiles," Proceedings of the National Academy of Sciences, 2005, 102(43), 15545-15550.
Sunshine J.C., "Effects of Base Polymer Hydrophobicity and End-Group Modification on Polymeric Gene Delivery," Biomacromolecules 2011, 12, pp. 35923600.
Suprynowicz, F. A., et al., "HPV-16 E5 Oncoprotein Upregulates Lipid Raft Components Caveolin-1 and Ganglioside GM1 at the Plasma Membrane of Cervical Cells." Oncogene, vol. 27, 2008, pp. 1071-1078.
Suzuki, et al., "Directed differentiation of human induced pluripotent stem cells into mature stratified bladder urothelium," Scientific Reports, 2019, vol. 9, 10506.
Takahashi J., et al., Suspension Culture in a Rotating Bioreactor for Efficient Generation of Human Intestinal Organoids, Cell Reports Methods, Nov. 1, 2022, vol. 2, No. 11, 15 pages, DOI: 101-110 10.1016/j.crmeth.2022.100337, Retrieved from the Internet URL: https://www.ncbi.nlm.nih.gov/pmc/articles/PMC9701612/pdf/main.pdf.
Takasato M., et al., "Kidney Organoids from Human iPS Cells Contain Multiple Lineages and Model Human Nephrogenesis," Nature, 2016, vol. 536, p. 238.
Tam P. P., and Loebel D. A., "Gene Function in Mouse Embryogenesis: Get Set for Gastrulation," Nature Reviews Genetics, 2007, 8, pp. 368-381.
Tanaka K., et al., "Structure and Functional Expression of the Cloned Rat Neurotensin Receptor," Neuron, 1990, vol. 4, pp. 847-854.
Tanii, H., et al., "Induction of Cytochrome P450 2A6 by Bilirubin in Human Hepatocytes," Pharmacology & Pharmacy, 2013, vol. 04, pp. 182-190.
Tannenbaum, S.E. et al., "Derivation of Xeno-Free and GMP-Grade Human Embryonic Stem Cells—Platforms for Future Clinical Applications," PLoS ONE, Jun. 2012, vol. 7, No. 6, 16 pages.
Tanwar S. et al., "Validation of terminal peptide of procollagen III for the detection and assessment of nonalcoholic steatohepatitis in patients with nonalcoholic fatty liver disease," Hepatology, 2013, 57, 103-111.
Tarlungeanu D. C., et al., "Impaired Amino Acid Transport at the Blood Brain Barrier Is a Cause of Autism Spectrum Disorder," Cell, 2016, vol. 167, pp. 1481-1494.e1418.
Terry, N. A. et al., "Lipid Malabsorption from Altered Hormonal Signaling Changes Early Gut Microbial Responses". Am J Physiol-Gastrointest Liver Physiol, 2018, 315(6), pp. G990-G1000.
Terry N.A. et al., "Dysgenesis of enteroendocrine cells in Aristaless-Related Homeobox polyalanine expansion mutationsm," J Pediatr Gastroenterol Nutr, 2015, 60, 2, 192-199.
Tessarollo L., et al., "TrkB Truncated Isoform Receptors as Transducers and Determinants of BDNF Functions," Frontiers in Neuroscience, Mar. 2022, vol. 16, doi: 10.3389/fnins.2022.847572.
Thakur, A., et al., "Hepatocyte Nuclear Factor 4-Alpha Is Essential for the Active Epigenetic State at Enhancers in Mouse Liver," Hepatology, 2019, vol. 70, pp. 1360-1376.
The Lancet Gastroenterology, "Headway and hurdles in non-alcoholic fatty liver disease," Lancet Gastroenterology & Hepatology, 2020, vol. 5, 93.
Thebaud B., et al., "Vascular Endothelial Growth Factor Gene Therapy Increases Survival, Promotes Lung Angiogenesis, and Prevents Alveolar Damage in Hyperoxia-Induced Lung Injury: Evidence that Angiogenesis Participates in Alveolarization," Circulation, 2005, vol. 112, pp. 2477-2486.
Thommensen L. et al., "Molecular mechanisms involved in gastrin-mediated regulation of cAMP-responsive promoter elements," Am J Physiol Endocrinol Metab, 2001, 281, E1316-1325.
Thompson F.M., et al., "Epithelial Growth of the Small Intestine Occurs by Both Crypt Fission and Crypt Hyperplasia During Infancy and Childhood in Humans," Journal of Gastroenterology and Hepatology, 2001, 2 Pages.
Tomassoni-Ardori F., et al., "Rbfox1 Up-Regulation Impairs BDNF-Dependent Hippocampal LTP by Dysregulating TrkB Isoform Expression Levels," eLife, Aug. 2019, vol. 8, e49673. doi: 10.7554/eLife.49673.
Totoson P., et al., "Activation of endothelial TrkB receptors induces relaxation of resistance arteries." Vascular Pharmacology, 106, 2018, pp. 46-53.
Touboul T. et al., "Generation of functional hepatocytes from human embryonic stem cells under chemically defined conditions that recapitulate liver development," Hepatology, 2010, 51, 1754-1765.
Traag V.A., et al., "From Louvain to Leiden: Guaranteeing Well-Connected Communities," Scientific Reports, 2019, vol. 9, 5233. doi: 10.1038/s41598-019-41695-z.
Tran M., et al., "Spatial Analysis of Ligand-Receptor Interaction in Skin Cancer at Genome-Wide and Single-Cell Resolution," bioRxiv, Sep. 2021, doi: 10.1101/2020.09.10.290833.
Trapnell C et al., "The dynamics and regulators of cell fate decisions are revealed by pseudotemporal ordering of single cells," Nat Biotechnol, 2014, 32, 381-386.
Tsakmaki A., et al., "Diabetes Through a 3D Lens: Organoid Models," Diabetologia, Springer Berlin Heidelberg, Berlin/heidelberg, vol. 63, No. 6, Mar. 27, 2020, pp. 1093-1102.
Tsankov A. M. et al., "Transcription factor binding dynamics during human ES cell differentiation," Nature, 2015, 518(7539), 344-9.
Tufro-Mcreddie, A., et al., "Angiotensin II Regulates Nephrogenesis and Renal Vascular Development." American Journal of Physiology, vol. 269, No. 1, 1995, pp. F110-F115.
Uchida H., et al., "A Xenogeneic-free System Generating Functional Human Gut Organoids from Pluripotent Stem Cells," JCI Insight, Jan. 12, 2017, vol. 2, No. 1, 13 pages.

(56) References Cited

OTHER PUBLICATIONS

Uchimura, K., et al., "Human Pluripotent Stem Cell-Derived Kidney Organoids with Improved Collecting Duct Maturation and Injury Modeling," Cell Reports, 2020, vol. 33, 108514.
Vales, S., et al., "In Vivo Human PSC-Derived Intestinal Organoids to Study Stem Cell Maintenance." In Methods in Molecular Biology, vol. 2171, Chapter 12, 2020, pp. 201-214.
Van Den Berg C.W., et al., "Renal Subcapsular Transplantation of PSC-Derived Kidney Organoids Induces Neo-vasculogenesis and Significant Glomerular and Tubular Maturation In Vivo," Stem Cell Reports, 2018, vol. 10, pp. 751-765. doi: 10.1016/j.stemcr.2018.01.041.
Van Dop W. A., et al., "Hedgehog Signalling Stimulates Precursor Cell Accumulation and Impairs Epithelial Maturation in the Murine Oesophagus," Gut, 2012, 62(3), pp. 348-357.
Van Hoecke et al., "How mRNA therapeutics are entering the monoclonal antibody field," Journal of Translational Medicine . Feb. 22, 2019;17(1):54 in 14 pages.
Van Raay T. J. et al., "Frizzled 5 signaling governs the neural potential of progenitors in the developing Xenopus retina," Neuron, 2005, 46(1), 23-36.
Van Straten, G., et al., "Aberrant Expression and Distribution of Enzymes of the Urea Cycle and Other Ammonia Metabolizing Pathways in Dogs with Congenital Portosystemic Shunts," PLOS ONE, 2014, vol. 9, e100077, 11 pages.
Vatine G. D., et al., "Modeling Psychomotor Retardation Using iPSCs from MCT8-Deficient Patients Indicates a Prominent Role for the Blood-Brain Barrier," Cell Stem Cell, 2017, vol. 20, pp. 831-843.e835.
Vatine G.D., et al., "Human iPSC-Derived Blood-Brain Barrier Chips Enable Disease Modeling and Personalized Medicine Applications," Cell Stem Cell, 2019, vol. 24, pp. 995-1005.
Blanchard C., et al., "Coordinate Interaction between IL-13 and Epithelial Differentiation Cluster Genes in Eosinophilic Esophagitis," The Journal of Immunology 2010, 184(7), 4033-4041.
Bochkis I.M. et al., "Genome-wide location analysis reveals distinct transcriptional circuitry by paralogous regulators Foxa1 and Foxa2," PLoS genetics, 2012, 8, 6, e1002770, 10 pages.
Boj S.F., et al., "Forskolin-induced Swelling in Intestinal Organoids: An In Vitro Assay for Assessing Drug Response in Cystic Fibrosis Patients," J Vis Exp, Feb. 11, 2017, (120):55159.
Bolger A. M. et al., "Trimmomatic: a flexible trimmer for Illumina sequence data," Bioinformatics, 2014, 30, 2114-2120.
Bolte C., et al., "Nanoparticle Delivery of Proangiogenic Transcription Factors into the Neonatal Neurotrophic Factor-Mediated Alveolar Capillary Injury and Repair Circulation Inhibits Alveolar Simplification Caused by Hyperoxia," American Journal of Respiratory and Critical Care Medicine, Jul. 2020, vol. 202, No. 1, pp. 100-111. doi: 10.1164/ rccm.201906-1232OC.
Boon et al., "Amino Acid Levels Determine Metabolism and CYP450 Function in Hepatocytes and Hepatoma Cell Lines," Nature Communications, 2020, vol. 11, 1393.
Bordi C. et al., "Classification of gastric endocrine cells at the light and electron microscopical levels," Microsc. Res. Tech., 2000, 48, 258-271.
Brafman D.A., et al., "Analysis of SOX2-Expressing Cell Populations Derived from Human Pluripotent Stem Cells," Stem Cell Reports, Nov. 19, 2013, vol. 1, pp. 464-478.
Bray N. L., et al., "Near-Optimal Probabilistic RNA-Seq Quantification," Nature Biotechnology, 2016, vol. 34, pp. 525-527.
Buettner et al., "Computational Analysis of Cell-to-cell Heterogeneity in Single-cell RNA-sequencing Data reveals Hidden Subpopulations of cells", Nature Biotech, 2015, vol. 33(2), pp. 155-160.
Buske P., et al., "On the Biomechanics of Stem Cell Niche Formation in the Gut—Modelling Growing Organoids," The FEBS Journal, 2012, vol. 279, pp. 3475-3487.
Butler, A., et al. Integrating Single-Cell Transcriptomic Data Across Different Conditions, Technologies, and Species. Nature Biotechnology, 2018, 36(4), pp. 411-420.
Cai, W., et al., "Genetic polymorphisms associated with nonalcoholic fatty liver disease in Uyghur population: a case-control study and meta-analysis," Lipids in Health and Disease, 2019, vol. 18, 14.
Cain M.P., et al., "Quantitative Single-Cell Interactomes in Normal and Virus-Infected Mouse Lungs," Disease Models & Mechanisms, May 2020, vol. 13, No. 6, doi: 10.1242/dmm.044404.
Cakir, et al., "Engineering of Human Brain Organoids with a Functional Vascular-Like System," Nature Methods, 2019, vol. 16, No. 11, 1169-1175.
Caldwell J. M., et al., "Novel Immunologic Mechanisms in Eosinophilic Esophagitis," Current Opinion in Immunology, 2017, vol. 48, pp. 114-121.
Candi E. et al., "Differential roles of p63 isoforms in epidermal development: selective genetic complementation in p63 null mice," Cell Death Differ, 2006, 13, 1037-1047.
Capeling M. M., et al., "Suspension Culture Promotes Serosal Mesothelial Development in Human Intestinal Organoids," Cell Reports, Feb. 1, 2022, vol. 38, No. 7, 33 pages, DOI: 10.1016/j.celrep.2022.110379.
Capeling M. M. et al., "Suspension culture promotes serosal mesothelial development in human intestingal organoids," Cell Reports, 2002, 38, 110379, 33 pages.
Carmona R., et al., "Conditional Deletion of WT1 in the Septum Transversum Mesenchyme Causes Congenital Diaphragmatic Hernia in Mice,". eLife, Sep. 19, 2016, vol. 5, No. e16009, pp. 1-17.
Chambers J. C, et al., "Genome-Wide Association Study Identifies Loci Influencing Concentrations of Liver Enzymes in Plasma," Nature Genetics, 2011, vol. 43, pp. 1131-1138.
Chance W.T., et al., "Preservation of Intestine Protein by Peptide YY During Total Parenteral Nutrition," Life Sciences 1996, vol. 58, No. 21, pp. 1785-1794.
Chandran S., et al., "Necrotising Enterocolitis in a Newborn Infant Treated with Octreotide for Chylous Effusion: Is Octreotide Safe?," BMJ Case Reports, 2020, 13, e232062. doi:10.1136/bcr-2019-232062.
Char V.C. et al., "Digestion and absorption of carbohydrates by the fetal lamb in utero," Pediatr Res, 1979, 13, 1018-1023.
Charlton, V. E., et al., "Effects of Gastric Nutritional Supplementation on Fetal Umbilical Uptake of Nutrients," Am J Physiol, 1981, vol. 241, pp. E178-E185.
Chatterjee S., et al., "Tissue-Specific Gene Expression during Productive Human Papillomavirus 16 Infection of Cervical, Foreskin, and Tonsil Epithelium." Journal of Virology, 93(17), 2019, e00915-19.
Chen et al., "A Versatile Polypharmacology Platform Promotes Cryoprotection and Viability of Human Pluripotent and Differentiated Cells," Nature Methods, 2021, vol. 18, pp. 528-541.
Chen, F., et al., "Inhibition of Tgf beta signaling by endogenous retinoic acid is essential for primary lung bud induction," Development, 2007, vol. 134, pp. 2969-2979.
Chen H., et al., "Single-Cell Trajectories Reconstruction, Exploration and Mapping of Omics Data with STREAM," Nature Communications, 2019, vol. 10, Article 1903. doi: 10.1038/s41467-019-09670-4, 14 pages.
Chen H. et al., "Transcript profiling identifies dynamic gene expression patterns and an important role for Nrf2/Keap1 pathway in the developing mouse esophagus," PloS One 2012, 7(5), e36504, 10 pages.
Chen J., et al., "Improved Human Disease Candidate Gene Prioritization Using Mouse Phenotype," BMC Bioinformatics, 2007, vol. 8, p. 392.
Chen J., et al., "ToppGene Suite for Gene List Enrichment Analysis and Candidate Gene Prioritization," Nucleic Acids Research, 2009, vol. 37, pp. W305-W311.
Chen S., et al., "fastp: An Ultra-Fast All-in-One FASTQ Preprocessor," Bioinformatics, 2018, vol. 34, pp. i884-i890.
Chen X., "Aberrant expression of Wnt and Notch signal pathways in Barrett's esophagus," Clinics and Research in Hepatology and Gastroenterology, 2012, 36(5), 473-483.
Chen Y., et al., "A Three-Dimensional Model of Human Lung Development and Disease from Pluripotent Stem Cells," Nature Cell Biology, May 2017, vol. 19, No. 5, pp. 542-557.

(56) References Cited

OTHER PUBLICATIONS

Chen Y. et al., “BMP Signaling pathway and colon cancer,” Journal of Cell Biology 2009, 5, 6 pages (Chinese with machine translation).
Chen, Y., et al., “SOX2 expression inhibits terminal epidermal differentiation,” Exp. Dermatol., 2015, vol. 24, pp. 966-982.
Chen Y., et al., “Regulation of Angiogenesis Through a MicroRNA (miR-130a) That Down-Regulates Antiangiogenic Homeobox Genes GAX and HOXA5,” Blood, 2008, vol. 111, pp. 1217-1226.
Chen Y. et al., “The Molecular Mechanism Governing the Oncogenic Potential of SOX2 in Breast Cancer,” Journal of Biological Chemistry 2008, 283(26), 17969-17978.
Cheung K.C.P., et al., “Preservation of Microvascular Barrier Function Requires CD31 Receptor-Induced Metabolic Reprogramming,” Nature Communications, Jul. 2020, vol. 11, No. 1, doi: 10.1038/s41467-020-17329-8.
Chey, W. Y., et al., “Secretin: historical perspective and current status,” Pancreas, 2014, vol. 43, pp. 162-182.
Chin, A. M., et al., “Morphogenesis and maturation of the embryonic and postnatal intestine,” Seminars in Cell Developmental Biology, 2017, vol. 66, pp. 81-93.
Cho C., et al., “Reck and Gpr124 Are Essential Receptor Cofactors for Wnt7a/Wnt7b-Specific Signaling in Mammalian CNS Angiogenesis and Blood-Brain Barrier Regulation,” Neuron, 2017, vol. 95, pp. 1221-1225.
Cho C. F., et al., “Blood-Brain-Barrier Spheroids as an In Vitro Screening Platform for Brain-Penetrating Agents,” Nature Communications, 2017, vol. 8, p. 15623.
Choi K., et al., “iGEAK: An Interactive Gene Expression Analysis Kit for Seamless Workflow Using the R/Shiny Platform,” BMC Genomics, 2019, vol. 20, p. 177.
Choudhary S.,et al., “Comparison and Evaluation of Statistical Error Models for scRNA-seq,” Genome Biology, 2022, vol. 23, 27. doi: 10.1186/s13059-021-02584-9.
Claesson-Welsh L., et al., “Permeability of the Endothelial Barrier: Identifying and Reconciling Controversies,” Trends in Molecular Medicine, Apr. 2021, vol. 27, No. 4, pp. 314-331.
Claeys, W., et al., “A mouse model of hepatic encephalopathy: bile duct ligation induces brain ammonia overload, glial cell activation and neuroinflammation,” Scientific Reports, 2022, vol. 12, 17558.
Clemmensen, C. et al., “Emerging Hormonal-Based Combination Pharmacotherapies for the Treatment of Metabolic Diseases”. Nat Rev Endocrinol, 2018, 14(10), pp. 670-684.
Collier et al., “Identifying Human Nave Pluripotent Stem Cells—Evaluating State-Specific Reporter Lines and Cell-Surface Markers”, BioEssays. May 2018, 40(5):1700239 in 12 pages.
Ye F., et al., “Fibroblast Growth Factors 7 and 10 Are Expressed in the Human Embryonic Pancreatic Mesenchyme and Promote the Proliferation of Embryonic Pancreatic Epithelial Cells,” Diabetologia, 2005, vol. 48, pp. 277-281.
Yin H., et al., “Non-viral Vectors for Gene-based Therapy,” Nature Reviews Genetics, 2014, vol. 15(8), pp. 541-555.
Yokobori, T., et al., “Intestinal epithelial culture under an air-liquid interface: a tool for studying human and mouse esophagi,” Dis. Esophagus, 2016, vol. 29, pp. 843-847.
Younossi, Z.M., et al., “Economic and Clinical Burden of Nonalcoholic Steatohepatitis in Patients With Type 2 Diabetes in the U.S.,” Diabetes Care, 2020, vol. 43, pp. 283-289.
Yu J., et al., “Induced Pluripotent Stem Cell Lines Derived from Human Somatic Cells,” Science, 2007, vol. 318, pp. 1917-1920.
Yu X. et al., “Lentiviral vectors with two independent internal promoters transfer highlevel expression of multiple transgenes to human hematopoietic stem-progenitor cells,” Mol Ther, 2003, 7, 827-838.
Yu, Y., Chinese Studies on Disease Signaling Pathway and Targeted Therapy, Anhui Science and Technology Press, May 31, 2013, p. 363 [Reference unavailable, citing referencing Search Report, 3 pgs.].
Yu, Y., et al., “A comparative analysis of liver transcriptome suggests divergent liver function among human, mouse and rat,” Genomics, 2010, vol. 96, pp. 281-289.
Yusta B. et al., “Enteroendocrine localization of GLP-2 receptor expression in humans and rodents,” Gastroenterology, 2000, 119, 744-755.
Zanini F., et al., “Developmental Diversity and Unique Sensitivity to Injury of Lung Endothelial Subtypes During Postnatal Growth,” iScience, Mar. 2023, vol. 26, No. 3, doi: 10.1016/j.isci.2023.106097.
Zanini F., et al., “Phenotypic Diversity and Sensitivity to Injury of the Pulmonary Endothelium During a Period of Rapid Postnatal Growth,” bioRxiv, Apr. 2021, doi: 10.1101/2021.04.27.441649.
Zeng, Q., et al., “O-Linked GlcNAcylation Elevated by HPV E6 Mediates Viral Oncogenesis.” Proceedings of the National Academy of Sciences, vol. 113, No. 33, Aug. 16, 2016, pp. 9333-9338.
Zhang, D., et al., “Highly efficient differentiation of human ES cells and iPS cells into mature pancreatic insulin-producing cells,” Cell Res., 2009, vol. 19, pp. 429-438.
Zhang H., et al., “Generation of Quiescent Cardiac Fibroblasts From Human Induced Pluripotent Stem Cells for In Vitro Modeling of Cardiac Fibrosis,” Circulation Research, Sep. 2019, vol. 125, No. 5, pp. 552-566.
Zhang S. L., et al., “Angiotensin II Stimulates Pax-2 in Rat Kidney Proximal Tubular Cells: Impact on Proliferation and Apoptosis,” Kidney International, 2004, vol. 66, pp. 2181-2192.
Zhao Z., et al., “Establishment and Dysfunction of the Blood-Brain Barrier,” Cell, 2015, vol. 163(5), pp. 1064-1078.
Zheng G.X.Y., et al., “Massively Parallel Digital Transcriptional Profiling of Single Cells,” Nature Communications, 2017, vol. 8(1), pp. 1-12.
Zheng, Y., et al., pH-and Temperature-Senstive PCL-Grafted Poly (R-amino ester)-Poly (ethylene glycol)-Poly (R-amino ester) Copolymer Hydrogels, Macromolecular Research, 2010, vol. 18, No. 11, pp. 1096-1102.
Zhou C., et al., “Comprehensive Profiling Reveals Mechanisms of SOX2-Mediated Cell Fate Specification in Human ESCs and NPCs,” Cell Research, 2016, 26(2), pp. 171-189. DOI: 10.1038/cr.2016.15.
Zhou H. J., et al., “Endothelial Exocytosis of Angiopoietin-2 Resulting from CCM3 Deficiency Contributes to Cerebral Cavernous Malformation,” Nature Medicine, 2016, vol. 22, pp. 1033-1042.
Zhou Y., et al., “A Subtype of Oral, Laryngeal, Esophageal, and Lung Squamous Cell Carcinoma with High Levels of TrkB-T1 Neurotrophin Receptor mRNA,” BMC Cancer, Jun. 2019, vol. 19, No. 1, doi: 10.1186/s12885-019-5789-8.
Zhou Z., et al., “Cerebral Cavernous Malformations Arise from Endothelial Gain of MEKK3-KLF2/4 Signaling,” Nature, 2016, vol. 532, pp. 122-126.
Zhu, S., et al., “Liver Endothelial Heg Regulates Vascular/Biliary Network Patterning and Metabolic Zonation via Wnt Signaling,” Cell Molecular Gastroenterology and Hepatology, 2022, vol. 13, pp. 1757-1783.
Zhu Z. et al., “Human pluripotent stem cells: an emerging model in developmental biology,” Development 140, 705-717 (2013).
Zhuo J. L., et al., “Proximal Nephron,” Comprehensive Physiology, 2013, vol. 3, No. 3, pp. 1079-1123.
Ziegler B. L., et al., “KDR Receptor: A Key Marker Defining Hematopoietic Stem Cells,” Science, vol. 285, No. 5433, Sep. 3, 1999, pp. 1553-1558.
Zwerschke, W., et al., “Modulation of Type M2 Pyruvate Kinase Activity by the Human Papillomavirus Type 16 E7 Oncoprotein.” Proceedings of the National Academy of Sciences USA, vol. 96, Feb. 1999, pp. 1291-1296.
Krishnan, U., et al., “Evaluation and Management of Pulmonary Hypertension in Children with Bronchopulmonary Dysplasia.” The Journal of Pediatrics, vol. 188, Sep. 2017, pp. 24-34.e1.
Kuhnert F. et al., “Essential regulation of CNS angiogenesis by the orphan G protein-coupled receptor GPR124,” Science, 2010, 330, 985-989. 10.1126/science.1196554.
Kumagai et al., “A bilirubin-inducible fluorescent protein from eel muscle,” Cell (2013) 153(7):1602-11.

(56) References Cited

OTHER PUBLICATIONS

Kumar A., et al., “Specification and Diversification of Pericytes and Smooth Muscle Cells from Mesenchymoangioblasts,” Cell Reports, 2017, vol. 19, pp. 1902-1916.
Kumari, D., “States of Pluripotency: Nave and Primed Pluripotent Stem Cells,” InTech Open, vol. 1, Chapter 3, 2016, pp. 31-45.
Kurz H., “Cell Lineages and Early Patterns of Embryonic CNS Vascularization,” Cell Adhesion & Migration, 2009, vol. 3, pp. 205-210.
Kuzmichev A. N.et al., “Sox2 acts through Sox21 to regulate transcription in pluripotent and differentiated cells,” Cuurrent Biology, 22(18), 2012, 1705-1710.
Kwapiszewska G., et al., “BDNF/TrkB Signaling Augments Smooth Muscle Cell Proliferation in Pulmonary Hypertension,” American Journal of Pathology, 2012, vol. 181, pp. 2018-2029.
L. Landsman, et al., “Pancreatic Mesenchyme Regulates Epithelial Organogenesis Throughout Development,” PLoS Biology, 2011, vol. 9, Article e1001143, 14 pages.
Lammert E., “Induction of Pancreatic Differentiation by Signals from Blood Vessels,” Science, 2001, vol. 294, pp. 564-567.
Lancaster M. A., et al., “Cerebral Organoids Model Human Brain Development and Microcephaly,” Nature, 2013, vol. 501(7467), pp. 373-379.
Landin, B. H., et al., “Labeled Lectin Studies of Renal Tubular Dysgenesis and Renal Tubular Atrophy of Postnatal Renal Ischemia and End-Stage Kidney Disease.” Pediatric Pathology, vol. 14, No. 1, 1994, pp. 87-99.
Langen U.H., et al., “Development and Cell Biology of the Blood-Brain Barrier,” Annual Review of Cell and Developmental Biology, 2019, vol. 35, pp. 591-613.
Langer R., “Tissue Engineering,” Science, 1990, vol. 249, pp. 1527-1533.
Lau J. Y., et al., “Systematic Review of the Epidemiology of Complicated Peptic Ulcer Disease: Incidence, Recurrence, Risk Factors and Mortality,” Digestion, 2011, vol. 84, pp. 102-113. DOI: 10.1159/000323958.
Leblanc G. G., et al., “Biology of Vascular Malformations of the Brain,” Stroke, 2009, vol. 40, pp. e694-e702.
Leedham S. J. et al., “Individual crypt genetic heterogeneity and the origin of metaplastic glandular epithelium in human Barrett’s oesophagus,” Gut, 2008, 57(8), 1041-1048.
Leeman K.T., et al., “Mesenchymal Stem Cells Increase Alveolar Differentiation in Lung Progenitor Organoid Cultures,” Scientific reports, Apr. 23, 2019, vol. 9(1), 10 pages.
Lehner, R. et al., “A Comparison of Plasmid DNA Delivery Efficiency and Cytotoxicity of Two Cationic Diblock Polyoxazoline Copolymers”, Nanotechnology, 28, 2017, pp. 111.
Li B., et al., “Benchmarking Spatial and Single-Cell Transcriptomics Integration Methods for Transcript Distribution Prediction and Cell Type Deconvolution,” Nature Methods, Jun. 2022, vol. 19, No. 6, pp. 662-670.
Li H., et al., “Directed Differentiation of Human Embryonic Stem Cells into Keratinocyte Progenitors In Vitro: An Attempt with Promise of Clinical Use,” In Vitro Cellular & Developmental Biology—Animal, 2016, 52(8), pp. 885-893.
Li H. et al., “Fast and accurate short read alignment with Burrows-Wheeler transform,” Bioinformatics, 2009, 25(14), 1754-1760.
Li H.J. et al., Basic helix-loop-helix transcription factors and enteroendocrine cell differentiation. Diabetes Obes Metab, 2011, 13(01), Suppl 1, 5-12, 16 pages.
Li J., et al., “An Obligatory Role for Neurotensin in High Fat Diet-Induced Obesity,” Nature, 2016, vol. 533, No. 7603, pp. 411-415.
Li, Y., et al., “The Renin-Angiotensin-Aldosterone System (RAAS) Is One of the Effectors by Which Vascular Endothelial Growth Factor (VEGF)/Anti-VEGF Controls the Endothelial Cell Barrier,” American Journal of Pathology, 2020, vol. 190, pp. 1971-1981.
Li Y., et al., “Synthesis and Characterization of an Amphiphilic Graft Polymer and its Potential as a pH-Sensitive Drug Carrier”, Polymer, vol. 58, No. 15, Jul. 2011, pp. 3304-3310.
Lin Y. C., et al., “Genetic Variants in GCKR and PNPLA3 Confer Susceptibility to Nonalcoholic Fatty Liver Disease in Obese Individuals,” American Journal of Clinical Nutrition, 2014, vol. 99, pp. 869-874.
Lindstrm N. O., et al., “Integrated-catenin, BMP, PTEN, and Notch signalling patterns the nephron.” eLife, 4, e04000. 2015, 29 pages. https://doi.org/10.7554/eLife.04000.
Lindstrm N. O., et al., “Spatial Transcriptional Mapping of the Human Nephrogenic Program.” Developmental Cell, 56(16), 2021, pp. 2381-2398.e6. https://doi.org/10.1016/j.devcel.2021.07.017.
Lindstrom N.O., et al., “Integrated Beta-Catenin, BMP, PTEN, and Notch Signalling Patterns the Nephron,” eLife, 2015, vol. 3, e04000.
Liu D., Chinese Encyclopedia of Medicine—Pathophysiology, “China Signal Pathway and Targeted Therapeutics”, edited by Yu Yuanxun, Anhui Science and Technology Press, May 2013, 1st edition.
Liu K., et al., “Sox2 Cooperates with Inflammation-Mediated Stat3 Activation in the Malignant Transformation of Foregut Basal Progenitor Cells,” Cell Stem Cell, 2013, 12(3), 304-315.
Liu T., et al., “Regulation of Cdx2 expression by promoter methylation, and effects of Cdx2 transfection on morphology and gene expression of human esophageal epithelial cells,” Carcinogenesis, 2007, 28(2), 488-496.
Lloyd D. J., et al., “Antidiabetic Effects of Glucokinase Regulatory Protein Small-Molecule Disruptors.” Nature, 504, 2013, 16 pages.
Lois C. et al., “Germline transmission and tissue-specific expression of transgenes delivered by lentiviral vectors,” Science, 2002, 295, 868-872.
Loomba, R., et al., “Combination Therapies Including Cilofexor and Firsocostat for Bridging Fibrosis and Cirrhosis Attributable to NASH.” Hepatology, vol. 73, No. 2, Feb. 2021, pp. 625-643.
Loomba R., et al., “Heritability of Hepatic Fibrosis and Steatosis Based on a Prospective Twin Study,” Gastroenterology, 2015, vol. 149, pp. 1784-1793.
Loquet PH., et al., “Influence of Raising Maternal Blood Pressure With Angiotensin II on Utero-Placental and Feto-Placental Blood Velocity Indices in the Human,” Clinical Science, 1990, vol. 78, pp. 95-100.
Low, J.H., et al., “Generation of Human PSC-Derived Kidney Organoids with Patterned Nephron Segments and a De Novo Vascular Network,” Cell Stem Cell, 2019, vol. 25, pp. 373-387 e379.
Lu T.M., et al., “Pluripotent Stem Cell-Derived Epithelium Misidentified as Brain Microvascular Endothelium Requires ETS Factors to Acquire Vascular Fate,” Proceedings of the National Academy of Sciences of the United States of America, 2021, vol. 118.
Lubinsky M. Sonic Hedgehog, VACTERL, and Fanconi anemia: Pathogenetic connections and therapeutic implications. American Journal of Medical Genetics, Part A, 2015, 167(11), 2594-2598.
Luca Selfa, I., et al., “Directed Differentiation of Human Pluripotent Stem Cells for the Generation of High-Order Kidney Organoids.” Methods in Molecular Biology, vol. 2258, 2021, pp. 171-189.
Lustig B. et al., “Negative feedback loop of Wnt signaling through upregulation of conductin/axin2 in colorectal and liver tumors,” Molecular and Cellular Biology, 2002, 22(4), 1184-93.
Luzio J.P. et al., “Lysosomes: fusion and function”, Nature reviews Molecular cell biology, 2007, vol. 8, No. 8, pp. 622-632.
Ma, R., et al., “Metabolic and non-metabolic liver zonation is established non-synchronously and requires sinusoidal Wnts,” eLife, 2020, vol. 9, e46206.
Mace O. J. et al., “Pharmacology and physiology of gastrointestinal enteroendocrine cells,” Pharmacol Res Perspect, 2015 3(4), e00155, 26 pages.
Maddaluno L., et al., “EndMT Contributes to the Onset and Progression of Cerebral Cavernous Malformations.” Nature, vol. 498, 2013, 7 pages.
Madisen L. et al., “A robust and high-throughput Cre reporting and characterization system for the whole mouse brain,” Nat Neurosci, 2020, 13, 133-140.
Madsen K., et al., “Angiotensin II Promotes Development of the Renal Microcirculation through AT1 Receptors,” Journal of the American Society of Nephrology, 2010, vol. 21, pp. 448-459.

(56) References Cited

OTHER PUBLICATIONS

Mahieu-Caputo D., et al., "Twin-to-Twin Transfusion Syndrome: Role of the Fetal Renin-Angiotensin System," American Journal of Pathology, 2000, vol. 156, pp. 629-636.
Nyeng P. et al., FGF10 signaling controls stomach morphogenesis. Developmental Biology, 2007, 303, 295-310.
Oberg, K. C., et al., "Renal Tubular Dysgenesis in Twin-Twin Transfusion Syndrome." Pediatric Developmental Pathology, vol. 2, No. 1, 1999, pp. 25-32.
Offield M.F. et al., "PDX-1 is required for pancreatic outgrowth and differentiation of the rostral duodenum," Development, 1996, 122(3), 983-995.
Ohashi T., "Enzyme replacement therapy for lysosomal storage diseases," Pediatr Endocrinol Rev. Oct. 1, 2012;10(supp 1):26 34.
Ohmori T et al. "Efficient expression of a transgene in platelets using simian immunodeficiency virus based vector harboring glycoprotein Iba promoter: in vivo model for platelet targeting gene therapy," FASEB J. (2006);20(9):1522 4.
Ohsie S. et al., "A paucity of colonic enteroendocrine and/or enterochromaffin cells characterizes a subset of patients with chronic unexplained diarrhea/malabsorption," Hum Pathol , 2009, 40(7), 1006-1014.
Ohta et al., "Hemogenic endothelium differentiation from human pluripotent stem cells in a feeder and xeno free defined condition," Journal of Visualized Experiments. Jun. 16, 2019;148:e59823 in 6 pages.
Oliverio M. I., et al., "Reduced Growth, Abnormal Kidney Structure, and Type 2 (AT2) Angiotensin Receptor-Mediated Blood Pressure Regulation in Mice Lacking Both AT1A and AT1B Receptors for Angiotensin II," Proceedings of the National Academy of Sciences USA, 1998, vol. 95, pp. 15496-15501.
Omer, D., et al., "Human Kidney Spheroids and Monolayers Provide Insights into SARS-CoV-2 Renal Interactions," Journal of the American Society of Nephrology, 2021, vol. 32, pp. 2242-2254.
Onaga T., et al., "Multiple Regulation of Peptide YY Secretion in the Digestive Tract," Peptides, 2002, vol. 23, pp. 279-290.
Onlilsoy Aksu A., et al., "Mutant Neurogenin-3 in a Turkish Boy with Congenital Malabsorptive Diarrhea," Pediatrics International, 2016, vol. 58, pp. 379-382.
Orho-Melander M., et al., "Common Missense Variant in the Glucokinase Regulatory Protein Gene Is Associated with Increased Plasma Triglyceride and C-Reactive Protein but Lower Fasting Glucose Concentrations," Diabetes, 2008, vol. 57, pp. 3112-3121.
Orskov C. et al., "GLP-2 stimulates colonic growth via KGF, released by subepithelial myofibroblasts with GLP-2 receptors," Regulatory peptides, 2005, 124, 105-112.
Ortiz-Meoz, R. F., et al., "A Small Molecule that Inhibits OGT Activity in Cells." ACS Chemical Biology, vol. 10, No. 6, Jun. 19, 2015, pp. 1392-1397.
Pan S., "Physiology," Science and Technology of China Press, Chapter 6, "Digestion within Large Intestine," 149-150, Jan. 2014.
Pankevich D.E. et al., "Improving and accelerating drug development for nervous system disorders," Neuron, 2014, 84, 546-553.
Paris, J., et al., "Liver zonation, revisited," Hepatology, 2022, vol. 76.
Park E.J. et al., "System for tamoxifen-inducible expression of Cre-recombinase from the Foxa2 locus in mice," Developmental Dynamics, 2008, 237(2), 447-453.
Patel Y. C., "Somatostatin and Its Receptor Family," Frontiers in Neuroendocrinology, 1999, 20, 157-198.
Patro R., et al., "Salmon Provides Fast and Bias-Aware Quantification of Transcript Expression using Dual-Phase Inference," Nature Methods, 2017, vol. 14, pp. 417-419.
Pedersen J. et al., "The glucagon-like peptide 2 receptor is expressed in enteric neurons and not in the epithelium of the intestine," Peptides, 2015, 67, 20-28.
Peng K., et al., "Regulation of O-Linked N-Acetyl Glucosamine Transferase (OGT) Through E6 Stimulation of the Ubiquitin Ligase Activity of E6AP." Journal of Molecular Sciences, 22, 2021, 10286. https://doi. org/10.3390/ijms221910286.
Perdomo J., et al., "Megakaryocyte differentiation and platelet formation from human cord blood derived CD34+ cells," Journal of Visualized Experiments. Dec. 27, 2017;130:e56420 in 8 pages.
Petta S., et al., "Glucokinase Regulatory Protein Gene Polymorphism Affects Liver Fibrosis in Non-Alcoholic Fatty Liver Disease," PLoS One, 2014, vol. 9, e87523.
Pham D., et al., "stLearn: Integrating Spatial Location, Tissue Morphology and Gene Expression to Find Cell Types, Cell-Cell Interactions and Spatial Trajectories Within Undissociated Tissues," bioRxiv, May 2020, doi: 10.1101/2020.05.31.125658.
Picelli S., et al., "Smart-seq2 for Sensitive Full-length Transcriptome Profiling in Single Cells," Nature Methods, Nov. 2013, vol. 10(11), pp. 1096-1098.
Pierre C., et al., "Can We Live Without a Functional Renin-Angiotensin System?" Clinical and Experimental Pharmacology and Physiology, 2008, vol. 35, pp. 431-433.
Pinney S. E. et al., "Neonatal diabetes and congenital malabsorptive diarrhea attributable to a novel mutation in the human neurogenin-3 gene coding sequence," The Journal of clinical endocrinology and metabolism, 2011, 96, 1960-1965.
Pirola, C.J., et al., "A Rare Nonsense Mutation in the Glucokinase Regulator Gene Is Associated with a Rapidly Progressive Clinical Form of Nonalcoholic Steatohepatitis," Hepatology Communications, 2018, vol. 2, pp. 1030-1036.
Pless G., "Artificial and Bioartificial Liver Support," Organogenesis, Jan. 2007, vol. 3(1), pp. 2024.
Podolsky D. K., "Healing the Epithelium: Solving the Problem from Two Sides," Journal of Gastroenterology, 1997, vol. 32, pp. 122-126. DOI: 10.1007/BF01213309.
Pollin T. I., et al., "Triglyceride Response to an Intensive Lifestyle Intervention Is Enhanced in Carriers of the GCKR Pro446Leu Polymorphism," Journal of Clinical Endocrinology Metabolism, 2011, vol. 96, pp. E1142-E1147.
Powell D. W., et al., "Myofibroblasts. II. Intestinal Subepithelial Myofibroblasts," American Journal of Physiology, 1999, vol. 277, pp. C183-C201. DOI: 10.1152/ajpcell.1999.277.2.C183.
Prakash Y., et al., "Neurotrophins in Lung Health and Disease," Expert Review of Respiratory Medicine, 2010, vol. 4, pp. 395-411.
Prakash Y. S., et al., "Brain-Derived Neurotrophic Factor in the Airways," Pharmacology Therapeutics, 2014, vol. 143, pp. 74-86.
Pupilli C., et al., "Angiotensin II Stimulates the Synthesis and Secretion of Vascular Permeability Factor/Vascular Endothelial Growth Factor in Human Mesangial Cells," Journal of the American Society of Nephrology, 1999, vol. 10, pp. 245-255.
Pyke C., et al., "GLP-1 Receptor Localization in Monkey and Human Tissue: Novel Distribution Revealed With Extensively Validated Monoclonal Antibody," Endocrinology, 2014, 155, 1280-1290.
Qian T., et al., "Directed Differentiation of Human Pluripotent Stem Cells to Blood-Brain Barrier Endothelial Cells," Science Advances, 2017, vol. 3, e1701679.
Qiu X., et al., "Single-Cell mRNA Quantification and Differential Analysis with Census," Nature Methods, 2017, vol. 14, pp. 309-315.
Qiu X., et al., "Reversed Graph Embedding Resolves Complex Single-Cell Trajectories," Nature Methods, 2017, vol. 14, pp. 979-982.
Que J. et al., "Multiple dose-dependent roles for Sox2 in the patterning and differentiation of anterior foregut endoderm," Development (Cambridge, England), 2007,134(13), 2521-31.
Que J. et al., "Multiple roles for Sox2 in the developing and adult mouse trachea," Development (Cambridge, England), 2009, 136(11), 1899-1907.
Que J., "The initial establishment and epithelial morphogenesis of the esophagus: a new model of tracheal-esophageal separation and transition of simple columnar into stratified squamous epithelium in the developing esophagus," Wiley Interdiscip. Rev. Dev. Biol., 2015, 4(4), 419-430.
Raisner, R., et al., "Enhancer Activity Requires CBP/P300 Bromodomain-Dependent Histone H3K27 Acetylation," Cell Reports, 2018, vol. 24, pp. 1722-1729.
Ramilowski J. A., et al., "A Draft Network of Ligand-Receptor-Mediated Multicellular Signalling in Human," Nature Communications, 2015, vol. 6, Article 7866, 11 pages.

(56) References Cited

OTHER PUBLICATIONS

Raredon M.S.B., et al., "Computation and Visualization of Cell-Cell Signaling Topologies in Single-Cell Systems Data Using Connectome," Scientific Reports, 2022, vol. 12, 4187. doi: 10.1038/s41598-022-07959-x.
Ren, X., et al., "Postnatal Alveologenesis Depends on FOXF1 Signaling in c-KIT+ Endothelial Progenitor Cells." American Journal of Respiratory and Critical Care Medicine, vol. 200, No. 9, 2019, pp. 1164-1176.
Revencu N. et al. "Cerebral cavernous malformation: new molecular and clinical insights," J Med Genet, 2006, 43, 716-721.
Reyes-Palomares A., et al., "Remodeling of Active Endothelial Enhancers is Associated with Aberrant Gene Regulatory Networks in Pulmonary Arterial Hypertension," Nature Communications, Apr. 2020, vol. 11, No. 1, 1673. doi: 10.1038/s41467-020-15463-x.
Reza H.A., et al., "Organoid Transplant Approaches for the Liver," Transplant International, Nov. 2021, vol. 34, No. 11, pp. 2031-2045.
Uzquiano, A. et al., "Proper acquisition of cell class identity in organoids allows definition of fate specification programs of the human cerebral cortex," Cell, 2022, 185, pp. 3770-3788.e3727.
Valdoz, J.C. et al., "Soluble extracellular matrix promotes organotypic formation in lung alveolar model," Biomaterials, 2022, 283, pp. 121464.
Van Der Meijden, P.E.J. et al., "Platelet biology and functions: new concepts and clinical perspectives," Nature Reviews Cardiology, 2018, 14, pp. 14 pages.
Vazquez-Armendariz, A.I. et al., "From Clones to Buds and Branches: The Use of Lung Organoids to Model Branching Morphogenesis Ex Vivo," Frontiers in Cell and Developmental Biology, 2021, 9, pp. 631579.
Velasco, S. et al., "Individual brain organoids reproducibly form cell diversity of the human cerebral cortex," Nature, 2019, 1317, 570, pp. 523-527.
Venema, W.T.C.U. et al., "Gut mucosa dissociation protocols influence cell type proportions and single-cell gene expression levels," Scientific Reports, 2022, 12, pp. 9897.
Wang, C. et al., "A critical role of RUNX1 in governing megakaryocyte-primed hematopoietic stem cell differentiation," Blood Advances, 2023, 7, pp. 2590-2605.
Wang, X. et al., "Genome-wide analysis of PDX1 target genes in human pancreatic progenitors," Molecular Metabolism, 2018, 9, pp. 57-68.
Watanabe, S. et al., "Transplantation of intestinal organoids into a mouse model of colitis," Nature Protocols, 2022, 17, pp. 649-671.
Weijts, B. et al., "Blood flow-induced Notch activation and endothelial migration enable vascular remodeling in zebrafish embryos," Nature Communications, 2018, 9, 5314, 11 Pages.
Wiedenmann, S. et al., "Single-cell-resolved differentiation of human induced pluripotent stem cells into pancreatic duct-like organoids on a microwell chip," Nature Biomedical Engineering, 2021, 5, pp. 897-913.
Willenbring H., et al., "Transplantable Liver Organoids Made From Only Three Ingredients," Cell Stem Cell, Aug. 1, 2013, vol. 13, No. 2, 4 pages, DOI: 10.1016/j.stem.2013.07.014.
Wong H. R., et al., "Biomarkers for Estimating Risk of Hospital Mortality and Long-Term Quality of Life Morbidity after Surviving Pediatric Septic Shock: A Secondary Analysis of the LAPSE Investigation" Pediatric Critical Care Medicine, Jan. 1, 2021, vol. 22, No. 1, pp. 8-15.
Worsdorfer, P. et al., "Generation of complex human organoid models including vascular networks by incorporation of mesodermal progenitor cells," Scientific Reports, 2019, 9, pp. 15663.
Wu, H. et al., "Progressive Pulmonary Fibrosis Is Caused by Elevated Mechanical Tension on Alveolar Stem Cells," Cell, 2020, 180, pp. 107-121.e117.
Wu, L. et al., "Filaggrin and tight junction proteins are crucial for IL-13-mediated esophageal barrier dysfunction," American Journal of Physiology—Gastrointestinal and Liver Physiology, 2018, ajpgi.00404.2017, pp. 39 pages.
Wynne, K. et al., "Diabetes of the exocrine pancreas," Journal of Gastroenterology and Hepatology, 2019, 34, pp. 346-354.
Xinaris C., et al., "In Vivo Maturation of Functional Renal Organoids Formed from Embryonic Cell Suspensions," Journal of the American Society of Nephrology, Nov. 1, 2012, vol. 23, No. 11, pp. 1857-1868.
Xu T.Y., et al., "HiFi-Slide Spatial RNA Sequencing," Protocol.io, 2023, pp. 12 pages.
Yu I., et al., "A Novel 96-Well Plate Cell Culture Assay for Lineage-Specific Hematopoietic Cell Toxicity Screening," Stemcell Technologies, Retreived from: https://www.stemcell.com/media/files/poster/SP00174-A_Novel_96-well_Plate_Cell_Culture_Assay_for_Lineage-Specific_Hematopoietic_Cell_Toxicity_Screening.pdf.
Yu, Y. et al., "Research progress of Hedgehog signaling pathway in liver fibrosis," Chinese Journal of Anatomy, 2019, 42, No. 6, pp. Machine Translated Abstract.
Zepp, J.A. et al., "Genomic, epigenomic, and biophysical cues controlling the emergence of the lung alveolus," Science, 2021, 371, pp. doi:10.1126/science.abc3172.
Zhang T., et al., "The Role of Glycosphingolipids in Immune Cell Functions," Frontiers in Immunology, Jan. 29, 2019, vol. 10, 22 pages.
Asano H., et al., "Astrocyte Differentiation of Neural Precursor Cells is Enhanced by Retinoic Acid Through a Change in Epigenetic Modification," Stem Cells, 2009, vol. 27, pp. 2744-2752, Retrieved from the Internet URL: https://academicoup.com/stmcls/article/27/11/2744/6401847.
Bakhti. M., et al., "Modelling the Endocrine Pancreas in Health and Disease," Nat Rev Endocrinol, 2019, vol. 15, pp. 155-171.
Balboa. D., et al., "Functional, Metabolic and Transcriptional Maturation of Human Pancreatic Islets Derived from Stem Cells," Nat Biotechnol, 2022, vol. 40, pp. 1042-1055.
Bar-Nur O., et al., "Small Molecules Facilitate Rapid and Synchronous iPSC Generation" Nature Methods, Nov. 2024, vol. 11, No. 11, pp. 1170-1179.
Basak O., et al., "Induced Quiescence of Lgr5+ Stem Cells in Intestinal Organoids Enables Differentiation of Hormone-Producing Enteroendocrine Cells", Cell Stem Cell, Feb. 2, 2017, vol. 20, No. 2, pp. 177-190.
Binek. A., et al., "Flow Cytometry Has a Significant Impact on the Cellular Metabolome," Journal of Proteome Research, 2019, vol. 18, pp. 169-181.
Bipat. R., et al., "Drinking Water with Consumption of a Jelly Filled Doughnut Has a Time Dependent Effect on the Postprandial Blood Glucose Level in Healthy Young Individuals," Clinical Nutrition ESPEN, 2018, vol. 27, pp. 20-23.
Box. A., et al., "Evaluating the Effects of Cell Sorting on Gene Expression," Journal of Biomolecular Techniques, 2020, vol. 31, pp. 100-111.
Breslin S., et al., "Receptor Tyrosine Kinase Targeting in Multicellular Spheroids," Methods and Protocols, Methods in Molecular Biology, Jan. 2015, vol. 1233, pp. 161-168.
Campinho. P., et al., "Blood Flow Forces in Shaping the Vascular System: A Focus on Endothelial Cell Behavior," Frontiers in Physiology, 2020, vol. 11, pp. 552.
Cervantes D. C., et al., "Peering Into Tunneling Nanotubes—The Path Forward," The EMBO Journal, 2021, vol. 40, 22 pages.
Coll. M., et al., "Generation of Hepatic Stellate Cells from Human Pluripotent Stem Cells Enables In Vitro Modeling of Liver Fibrosis," Cell Stem Cell, 2018, vol. 23, pp. 101-113.
Crouch. E.E., et al., "Ensembles of Endothelial and Mural Cells Promote Angiogenesis in Prenatal Human Brain," Cell, 2022, vol. 185, pp. 3753-3769.
Dana-Farber Cancer Institute, "Clinical Trials for Relapsed Cancer," 2025, [retrieved on Mar. 28, 2025], 4 pages, Retrieved from the Internet URL: https://www.danafarberbostonchildrens.org/our-services/innovative-approaches/clinical-trials-relapsed-cancer.
Dao. L., etal., "Modeling Blood-Brain Barrier Formation and Cerebral Cavernous Malformations in Human PSC-Derived Organoids," Cell Stem Cell, Jun. 6, 2024, vol. 31, pp. 818-833.

(56) References Cited

OTHER PUBLICATIONS

Darrigrand. J. F., et al., "Acinar-Ductal Cell Rearrangement Drives Branching Morphogenesis of the Murine Pancreas in an IGF/PI3K-Dependent Manner," Developmental Cell, 2024, vol. 59, pp. 326-338.
Duester G., "Retinoic Acid Synthesis and Signaling During Early Organogenesis," Cell, Sep. 19, 2008, vol. 134, No. 6, pp. 921-931.
Duggal G., et al., "Alternative Routes to Induce Naive Pluripotency in Human Embryonic Stem Cells," Stem Cells, 2015, vol. 33, pp. 2686-2698.
Edwards. N.A., etal., "Developmental Basis of Trachea-Esophageal Birth Defects," Developmental Biology, 2021, vol. 477, pp. 85-97.
Eicher. A.K., et al., "Engineering Functional Human Gastrointestinal Organoid Tissues Using the Three Primary Germ Layers Separately Derived from Pluripotent Stem Cells," Biorxiv, 2021, 41 pages.
Elmentaite. R., et al., "Single-Cell Sequencing of Developing Human Gut Reveals Transcriptional Links to Childhood Crohn's Disease," Developmental Cell, 2020, vol. 55, pp. 771-783.
Eubelen. M., et al., "A Molecular Mechanism for Wnt Ligand-Specific Signaling," Science, Jul. 19, 2018, vol. 361, 14 pages.
Eze. U.C., et al., "Single-cell atlas of early human brain development highlights heterogeneity of human neuroepithelial cells and early radial glia," Nature Neuroscience, 2021, vol. 24, pp. 584-594.
Fan. X., et al., "Single-Cell Transcriptome Analysis Reveals Cell Lineage Specification in Temporal-Spatial Patterns in Human Cortical Development," Science Advances, 2020, vol. 6, 15 pages.
Feng. Y., et al., "Identification of Rare Heterozygous Missense Mutations in FANCA in Esophageal Atresia Patients Using Next Generation Sequencing," Gene, 2018, vol. 661, pp. 182-188.
Gehart. H., et al., "Identification of Enteroendocrine Regulators by Real-Time Single-Cell Differentiation Mapping," Cell, 2019, vol. 176, pp. 1158-1173.
Geudens. I., et al., "Artery-Vein Specification in the Zebrafish Trunk is Pre-Patterned by Heterogeneous Notch Activity and Balanced by Flow-Mediated Fine-Tuning," Development, 2019, vol. 146, No. 16, 26 pages.
Gieseck R. L., et al., "Maturation of Induced Pluripotent Stem Cell Derived Hepatocytes by 3D-Culture," PLoS ONE, vol. 9, No. 1, Jan. 22, 2014, vol. 9, No. 1, 7 pages, DOI: 10.1371/journal.pone.0086372.
Goodwin. K., et al., "Branching Morphogenesis," Development, 2020, vol. 147, 6 Pages.
Granato A., et al., "Bilirubin Inhibits Bile Acid Induced Apoptosis in Rat Hepatocytes," Gut, Dec. 2003, vol. 52, No. 12, pp. 1774-1778, DOI: 10.1136/gut.52.12.1774.
Guo, Z., et al., "Human Vascularized Brain Organoids with Blood-Brain-Barrier Formation for Study of Brain Vascular Disorders," Center for Stem Cell & Organoid Medicine (CUSTOM), Division of Developmental Biology Cincinnati Children's Hospital Medical Center, Frontiers in Stem Cell & Organoid Medicine Symposium, Mar. 24, 2022.
Gupta A. K., et al., "An Efficient Method to Generate Kidney Organoids at the Air-Liquid Interface," Journal of Biological Methods, 2021, vol. 8, No. 2, 11 pages.
Hagey. D. W., et al., "SOX2 Regulates Common and Specific Stem Cell Features in the CNS and Endoderm-Derived Organs," PLOS Genetics, 2018, vol. 14, No. 2, 20 pages.
Han. X., et al., "Construction of a Human Cell Landscape at Single-Cell Level," Nature, 2020, vol. 581, pp. 303-309.
Hancili S., et al., "A Novel NEUROG3 Mutation in Neonatal Diabetes Associated with a Neuro-Intestinal Syndrome," Pediatric Diabetes, 2018, vol. 19, pp. 381-387.
Hao Y., et al., "Dictionary Learning for Integrative, Multimodal and Scalable Single-Cell Analysis," Nature Biotechnology, 2024, vol. 42, pp. 293-304.
Harley J. B., et al., "Transcription Factors Operate Across Disease Loci, with EBNA2 Implicated in Autoimmunity," Nature Genetics, 2018, vol. 50, No. 5, pp. 699-707.
Harrison S.P., et al., "Scalable Production of Tissue-like Vascularized Liver Organoids from Human PSCs," bioRxiv, Dec. 2, 2020, 31 pages, DOI: 10.1101/2020.12.02.406835v1.full.pdf.
Herring C. A., et al., "Human Prefrontal Cortex Gene Regulatory Dynamics from Gestation to Adulthood at SingleCell Resolution," Cell, 2020, vol. 185, pp. 4428-4447.
Honda A., et al., "Discrimination of Stem Cell Status After Subjecting Cynomolgus Monkey Pluripotent Stem Cells to Naive Conversion," Scientific Reports, Mar. 28, 2017, vol. 7, 14 pages, DOI: 10.1038/srep45285.
Huang L., et al., "Commitment and Oncogene-Induced Plasticity of Human Stem Cell-Derived Pancreatic Acinar and Ductal Organoids," Cell Stem Cell, 2021, vol. 28, pp. 1090-1104.
Huang L., et al., "Revealing the Structure and Organization of Intercellular Tunneling Nanotubes (TNTs) by STORM Imaging", Nanoscale Advances, 2022, vol. 4, pp. 4258-4262.
International Search Report and Written Opinion for Application No. PCT/US2023/067716, mailed Nov. 29, 2023, 12pages.
Jaeseo L., et al., "A 3D Alcoholic Liver Disease Model on a Chip", Integrative Biology, Jan. 1, 2016, vol. 8, No. 3, pp. 302-308.
Kamada T., et al., "Evidence-Based Clinical Practice Guidelines for Peptic Ulcer Disease 2020," Journal of Gastroenterology, 2021, vol. 56, pp. 303-322.
Kasagi Y., et al., "The Esophageal Organoid System Reveals Functional Interplay Between Notch and Cytokines in Reactive Epithelial Changes," Cellular and Molecular Gastroenterology and Hepatology, 2018, vol. 5(3), pp. 333-352.
Katsura H., et al., "Human Lung Stem Cell-Based Alveolospheres Provide Insights into SARS-CoV-2 Mediated Interferon Responses and Pneumocyte Dysfunction," Cell Stem Cell, 2020, doi:10.1016/j.stem.2020.10.005.
Kechele D.O., et al., "Recent Advances in Deriving Human Endodermal Tissues from Pluripotent Stem Cells," Current Opinion in Cell Biology, 2019, vol. 61, pp. 92-100.
Kendig K.I., et al., "Sentieon DNASeq Variant Calling Workflow Demonstrates Strong Computational Performance and Accuracy," Frontiers in Genetics, 2019, vol. 10, pp. 736.
Kishimoto K., et al., "Bidirectional Wnt Signaling Between Endoderm and Mesoderm Confers Tracheal Identity in Mouse and Human Cells," Nature Communications, 2020, vol. 11.
Kishimoto K., et al., "Directed Differentiation of Human Pluripotent Stem Cells into Diverse Organ-Specific Mesenchyme of the Digestive and Respiratory Systems," Nature Protocols, 2022, vol. 17, pp. 2699-2719.
Kishimoto. K., et al., "Mammalian tracheal development and reconstruction: insights from in vivo and in vitro studies," Development, 2021, vol. 148, No. 13, 43 pages.
Kitazawa T., et al., "Regulation of Gastrointestinal Motility by Motilin and Ghrelin in Vertebrates," Frontiers in Endocrinology (Lausanne), 2019, vol. 10, 17 Pages.
Li R., et al., "Myofibroblast Contraction is Essential for Generating and Regenerating the Gas-Exchange Surface," Journal of Clinical Investigation, 2020, vol. 130, pp. 2859-2871.
Llurfrio E.M., et al., "Sorting Cells Alters Their Redox State and Cellular Metabolome," Redox Biology, 2018, vol. 16, pp. 381-387.
Loomans N., et al., "Expansion of Adult Human Pancreatic Tissue Yields Organoids Harboring Progenitor Cells with Endocrine Differentiation Potential," Stem Cell Reports, 2018, vol. 10, pp. 712-724.
Lopez-Ramirez. M.A., et al., "Astrocytes Propel Neurovascular Dysfunction During Cerebral Cavernous Malformation Lesion Formation," Journal of Clinical Investigation, 2021, vol. 131, 15 pages.
Lyu H., et al., "The Role of Bone-Derived Exosomes in Regulating Skeletal Metabolism and Extraosseous Diseases," Frontiers in Cell and Developmental Biology, 2020, vol. 8, pp. 1-17.
Macea M.M.I., et al., "Quantitative Study of Brunner's Galnds in the Human Duodenal Submucosa," Int. J. Morphol, Jan. 1, 2006, vol. 24, No. 1, pp. 7-12, Retrieved from the Internet: URL: https://www.scielo.cl/pdf/ijmorphol/v24n1/art02.pdf.
Matthisa.L., etal., "Deficient Active Transport Activity in Healing Mucosa After Mild Gastric Epithelial Damage," Digestive Diseases and Sciences, 2020, vol. 65, No. 1, pp. 119-131.

(56) References Cited

OTHER PUBLICATIONS

Maxwell K.G., et al., "Gene-edited Human Stem Cell-Derived Cells from a Patient with Monogenic Diabetes Reverse Preexisting Diabetes in Mice," Science Translational Medicine, 2020, vol. 12, No. 540, 23 pages.
Mayran A., et al., "Pioneer Transcription Factors Shape the Epigenetic Landscape," Journal of Biological Chemistry, 2018, vol. 293, pp. 13795-13804.
Mead B.E., et al., "All Models are Wrong, but Some Organoids May be Useful," Genome Biology, 2019, vol. 20, 3 pages.
Menard D., et al., "Explant Culture of Human Fetal Small Intestine," Gastroenterology, Mar. 1985, vol. 88, No. 3, pp. 691-700.
Mitchell M.J., et al., "Engineering Precision Nanoparticles for Drug Delivery," Nature Reviews Drug Discovery, 2021, vol. 20, pp. 101-124.
Mulvihill E.E., "Regulation of Intestinal Lipid and Lipoprotein Metabolism by the Proglucagon-Derived Peptides Glucagon Like Peptide 1 and Glucagon like Peptide 2," Current Opinion in Lipidology, 2018, vol. 29, No. 2, pp. 95-103.
Munera. J.O., "Development of functional resident macrophages in human pluripotent stem cell-derived colonic organoids and human fetal colon," Cell Stem Cell, 2023, vol. 30(11), pp. 1434-1451.e9.
Neuschulz A., et al., "A Single-Cell RNA Labeling Strategy for Measuring Stress Response Upon Tissue Dissociation," Molecular Systems Biology, 2023, vol. 19, 13 pages.
Ng W.H., et al., "Recapitulate Human Cardio-pulmonary Codevelopment Using Simultaneous Multilineage Differentiation of Pluripotent Stem Cells," bioRxiv, Mar. 3, 2021., 24 pages.
Ni X., et al., "A Region-Resolved Mucosa Proteome of the Human Stomach," Nature Communications, 2019, vol. 10, pp. 1-11.
Nostro M. C., et al., Stage-Specific Signaling Through TGF Family Members and WNT Regulates patterning and Pancreatic Specification of Human Pluripotent Stem Cells, Development, Mar. 2011, vol. 138, No. 5, pp. 861-871.
Oberg H-H., et al., "Differential Expression of CD126 and CD130 Mediates Different STAT-3 Phosphorylation in CD4+ CD25− and CD25high Regulatory T Cells," International Immunology, 2006, vol. 18, No. 4, pp. 555-563.
Ouelette J., et al., "Vascular Contributions to 16p11.2 Deletion Autism Syndrome Modeled in Mice," Nature Neuroscience, 2020, vol. 23, pp. 1090-1101.
Oz-Levi D., et al., "Noncoding Deletions Reveal a Gene that is Critical for Intestinal Function," Nature, 2019, vol. 571, pp. 107-111.
Pera M. F., et al., The Exploration of Pluripotency Space: Charting Cell State Transitions in Peri-Implantation Development, Cell Stem Cell, Nov. 4, 2021, vol. 28, No. 11, pp. 1896-1906.
Pfister G., et al., "An Evaluation of Sorter Induced Cell Stress (SICS) on Peripheral Blood Mononuclear Cells (PBMCs) After Different Sort Conditions—Are your sorted cells getting SICS?" Journal of Immunological Methods, 2020, vol. 487, 7 pages.
Pode-Shakked N., et al., "RAAS-Deficient Organoids Indicate Delayed Angiogenesis as a Possible Cause for Autosomal Recessive Renal Tubular Dysgenesis," Nature Communications, 2023, vol. 14.
Pradhan. S., et al., "Tissue Responses to Shiga Toxin in Human Intestinal Organoids," Cellular and Molecular Gastroenterology Hepatology, 2020, vol. 10, pp. 171-190.
Protze. S.I., et al., "Human Pluripotent Stem Cell-Derived Cardiovascular Cells: From Developmental Biology to Therapeutic Applications," Cell Stem Cell, 2019, vol. 25, pp. 311-327.
Ramaiahgari S. C., et al., "A 3D in Vitro Model of Differentiated HepG2 Cell Spheroids with Improved Liver-Like Properties for Repeated Dose High-Throughput Toxicity Studies," Archives of Toxicology, Mar. 6, 2014, pp. 1083-1095, DOI: 10.1007/s00204-014-1215-9.
Raouf Z., et al., "Colitis-Induced Small Intestinal Hypomotility Is Dependent on Enteroendocrine Cell Loss in Mice," Cellular and Molecular Gastroenterology and Hepatology, 2024, vol. 18, No. 1, pp. 53-70, DOI: 10.1016/j.jcmgh.2024.02.017.
Ren. H., et al., "Identifying multicellular spatiotemporal organization of cells with SpaceFlow," Nature Communications, 2022, vol. 13, Article 4076, 14 pages.
Romayor I., et al., "A Comparative Study of Cell Culture Conditions During Conversion from Primed to Naive Human Pluripotent Stem Cells," Biomedicines, Jun. 9, 2022, vol. 10, 19 pages.
Rutherford. D., et al., "Therapeutic Potential of Human Intestinal Organoids in Tissue Repair Approaches in Inflammatory Bowel Diseases," Inflammatory Bowel Diseases, 2023, vol. 29, pp. 1488-1498.
Ryu. S., et al., "Enhancing the Fitness of Embryoid Bodies and Organoids by Chemical Cytoprotection," bioRxiv preprint, Mar. 23, 2022, 40 pages.
Schmidt S., et al., "A Blood Vessel Organoid Model Recapitulating Aspects of Vasculogenesis, Angiogenesis and Vessel Wall Maturation" Organoids, Apr. 28, 2022, vol. 1, No. 1, pp. 41-53, DOI: 10.3390/organoids1010005.
Selvaggi. G., et al., "Overview of intestinal and multivisceral transplantation," UpToDate, Jul. 3, 2024, https://www.uptodate.com/contents/overview-of-intestinal-and-multivisceral-transplantation/print, accessed Sep. 11, 2024, 3 pages.
Shi M., et al., "Directed differentiation of ureteric bud and collecting duct organoids from human pluripotent stem cells," Nature Protocols, 2023, vol. 18, pp. 2485-2508.
Shi. M., et al., "Human ureteric bud organoids recapitulate branching morphogenesis and differentiate into functional collecting duct cell types," Nature Biotechnology, 2023, vol. 41, pp. 252-261.
Simunovic M., et al., "Embryoids, Organoids and Gastruloids: New Approaches to Understanding Embryogenesis," Development, 2017, vol. 144, pp. 976-985, doi:10.1242/dev.143529.
Stirparo. G.G., et al., "Integrated analysis of single-cell embryo data yields a unified transcriptome signature for the human pre-implantation epiblast," Development, 2018, vol. 145(3), 26 pages.
Stresser. D., et al., "Validation of Pooled Cryopreserved Human Hepatocytes as a Model for Metabolism Studies," ResearchGate, Jan. 1, 2004, Retrieved from: https://www.researchgate.net/publication/268359224, accessed Jun. 28, 2024.
Sweeney. M., et al., "It Takes Two: Endothelial-Perivascular Cell Cross-Talk in Vascular Development and Disease," Cell Reports, 2018, vol. 24, pp. 2705-2715.
Sweeney, M.D. et al., "Blood-brain barrier breakdown in Alzheimer disease and other neurodegenerative disorders," Nature Reviews Neurology, 2018, 14, pp. 133-150.
Takahashi, Y. et al., "Organoid-derived intestinal epithelial cells are a suitable model for preclinical toxicology and pharmacokinetic studies," iScience, 2022, 25, pp. 104542.
Takebe, T. et al., "Organoids by design," Science, 2019, vol. 364, pp. 956-959.
The Tabula Muris Consortium, "Single-cell transcriptomics of 20 mouse organs creates a Tabula Muris," Nature, 2018, 562, pp. 367-372.
Trujillo, CA. et al., "Complex Oscillatory Waves Emerging from Cortical Organoids Model Early Human Brain Network Development," Cell Stem Cell, 2019, 25, pp. 558-569 e557.
Ungrin M.D., et al., "Rational Bioprocess Design for Human Pluripotent Stem Cell Expansion and Endoderm Differentiation Based on Cellular Dynamics," Biotechnology and Bioengineering, Apr. 2012, vol. 109, No. 4, pp. 853-866.
Blot F., et al., "Gut Microbiota Remodeling and Intestinal Adaptation to Lipid Malabsorption After Enteroendocrine Cell Loss in Adult Mice," Cellular and Molecular Gastroenterology and Hepatology, 2023, vol. 15, No. 6, 19 pages.
Cleveland Clinic, "Malabsorption," Apr. 6, 2022, retrieved on [May 19, 2025], 11 pages, Retrieved from Internet URL: https://my.clevelandclinicorg/health/diseases/22722-malabsorption.
Gut P., et al., "Chromogranin A—Unspecific Neuroendrocrine Marker. Clinical Utility and Potential Diagnostic Pitfalls," Archives of Medical Science, Feb. 1, 2016, vol. 12, No. 1, pp. 1-9, DOI: 10.5114/aoms.2016.57577.
Miao Y., et al., "Deciphering Endothelial and Mesenchymal organ Specification in Vascularized Lung and Intestinal Organoids," bioRxiv, Feb. 7, 2024, 65 pages, Retrieved from the Internet URL: https://doi.org/10.1101/2024.02.06.577460.

(56) References Cited

OTHER PUBLICATIONS

Posovszky C., et al., "Loss of Enteroendocrine Cells in Autoimmune-Polyendocrine-Candidiasis-Ectodermal-Dystrophy (APECED) Syndrome with Gastrointestinal Dysfunction," The Journal of Clinical Endocrinology and Metabolism, Feb. 2012, vol. 97, No. 2, pp. E292-E300, DOI: 10.1210/jc2011-2044.
Zuvarox T., et al., "Malabsorption Syndromes," A Service of the National Library of Medicine, National Institutes of Health, Jul. 4, 2023, retrieved on [Jan. 2025], 13 pages, Retrieved from the Internet URL: https://www.ncbi.nlm.nih.gov/books/NBK553106/.
Audiger C., et al., "Mis-Expression of GATA6 Re-Programs Cell Fate During Early Hematopoiesis," Cell Reports, May 28, 2024, vol. 43, No. 5, 14 pages.
Duncan S.A., "Mechanisms Controlling Early Development of the Liver," Mechanisms of Development, 2003, vol. 120, pp. 19-33.
Harrison S.P., et al., "Scalable Production of Tissue-Like Vascularized Liver Organoids from Human PSCs," Experimental and Molecular Medicine, Sep. 1, 2023, 20 pages, Retrieved from the Internet URL: https://www.nature.com/articles/s12276-023-01074-1.pdf.
Hohwieler M., et al., "Pancreatic Progenitors and Organoids as a Prerequisite to Model Pancreatic Diseases and Cancer," Stem Cell International, Feb. 25, 2019, vol. 2019, 11 pages, DOI: 10.1155/2019/9301382.
Koike H., et al., "Modelling human hepato-biliary-pancreatic organogenesis from the foregut-midgut boundary," Nature, Oct. 3, 2019, vol. 574, 19 pages.
Liu X., et al., "Comprehensive Characterization of Distinct States of Human Naive Pluripotency Generated by Reprogramming," Nature Methods, Nov. 2017, vol. 14, No. 11, pp. 1055-1061.
Mcculley D., et al., "The Pulmonary Mesenchyme Directs Lung Development", Current Opinion in Genetics & Development, Mar. 19, 2015, vol. 32, pp. 98-105, Retrieved from the Internet: URL: http://dx.doi.org/10.1016/j.gde.2015.01.011.
Nonaka S., et al., "Determination of Leftright Patterning of the Mouse Embryo by Artificial Nodal Flow," letters to nature, Jul. 4, 2002, vol. 418, pp. 96-99.
Olgasi C., et al., "iPSC-Derived Liver Organoids: A Journey from Drug Screening, to Disease Modeling, Arriving to Regenerative Medicine," International Journal of Molecular Sciences, Aug. 27, 2020, vol. 21, No. 17, 27 pages, DOI: 10.3390/ijms21176215.
Phan S.H., "Biology of Fibroblasts and Myofibroblasts," Proceedings of the American Thoracic Society, Apr. 2008, vol. 05, DOI: 10.1513/pats.200708-146DR, pp. 334-337.
Rashid S. T., et al., "Modeling Inherited Metabolic Disorders of the Liver Using Human Induced Pluripotent Stem Cells," The Journal of Clinical Investigation, Sep. 2010, vol. 120, No. 9, pp. 3127-3136, DOI: 10.1172/JCI43122.
Reza H.A., et al., "Multi-zonal zonal Organoids from Human Pluripotent Stem Cells," Nature, May 29, 2025, [retrieved on Apr. 16, 2025], vol. 641, 38 pages, DOI: 10.1038/S41586-025-08850-1.
Reza H.A., et., "Self-Assembled Generation of Multi-zonal Liver Organoids from Human Pluripotent Stem Cells," bioRxiv., Aug. 30, 2024, 39 pages, Retrieved from the Internet URL: https://www.biorxiv.org/content/10.1101/2024.08.30.610426v1.full.pdf.
Sakhneny L., et al., "Seminars in Cell & Developmental Biology," Seminars in Cell and Developmental Biology, 2019, vol. 92, pp. 89-96.
Van Der Brink G.R., "Hedgehog Signaling in Development and Homeostasis of the Gastrointestinal Tract," Physiological Reviews, Oct. 1, 2007, vol. 87, doi:10.1152/physrev.00054.2006, pp. 1343-1375.
Warburton D., et al., "The Molecular Basis of Lung Morphogenesis," Mechanisms of Development, 2000, vol. 92, pp. 55-81.
Loh K.M., et al., "Protocol for Efficient Generation of Human Artery and Vein Endothelial Cells from Pluripotent Stem Cells,". STAR Protocols, vol. 6, 103494, Mar. 1, 2025, 38 pages.
Snyder J., et al."Materials and Microenvironments for Engineering the Intestinal Epithelium", Annals of Biomedical Engineering, vol. 48, No. 7, Feb. 4, 2020, XP037195182, pp. 1916-1940.
Yan Y., et al., Improved Differentiation of Human Pluripotent Stem Cell-derived Neurons Through Reduction of Progenitor Proliferation, Thermofisher, 2016, 1 page.
Zhang Y., et al., "3D Modeling of Esophageal Development Using Human PSC-derived Basal Progenitors Reveals a Critical Role for Notch Signaling," Cell Stem Cell, 2018, vol. 23, pp. 516-529.
He S. et al., "Single-Cell Transcriptome Profiling of an Adult Human Cell Atlas of 15 Major Organs," Genome Biology, 2020, vol. 21, No. 294, 34 pages.
Sugimoto S., et al., "Hepatic organoid formation in collagen sponge of cells isolated from human liver tissues," Tissue Engineering., 2005, vol. 11, No. 3-4, pp. 626-633.
Zeng Z., et al., "Generation of Patterned Kidney Organoids That Recapitulate the Adult Kidney Collecting Duct System from Expandable Ureteric Bud Progenitors," Nature Communications, 2021, vol. 12(3641), 15 pages.
Sumi S., et al., "A Multiple-funnels Cell Culture Insert for the Scale-up Production of Uniform Cell Spheroids," Regenerative Therapy, 2017, vol. 7, pp. 52-60.
Bouffi C., et al., "In Vivo Development of Immune Tissue in Human Intestinal Organoids Transplanted Into Humanized Mice", Nature Biotechnology, Nature Portfolio, Jan. 26, 2023, vol. 41 (6), pp. 824-831.
Nozaki K., et al., "Co-culture With Intestinal Epithelial Organoids Allows Efficient Expansion and Motility Analysis of Intraepithelial Lymphocytes," Journal of Gastroenterology, Springer, Jan. 22, 2016, vol. 51 (3), pp. 206-213.
Prior., et al., "Liver Organoids: From Basic Research to Therapeutic Applications", Gut, Dec. 1, 2019, vol. 68, No. 12, BMJ Publishing Group, DOI: 10.1136/gutjnl-2019-319256, URL: https://www.ncbi.nlm.nih.gov/pmc/articles/PMC6872443/pdf/gutjnl-2019-319256.pdf, ISSN: 0017-5749, XP055861709, 10 pages.
Toth A., et al., "Alveolar Epithelial Progenitor Cells Require Nkx2-1 to Maintain Progenitor-Specific Epigenomic State During Lung Homeostasis and Regeneration," Nature Communications, Dec. 19, 2023, vol. 14, No. 1, Nature Publishing Group, p. 8452, XP093408471, ISSN: 2041-1723, DOI: 10.1038/s41467-023-44184-0.
Zacharias W., et al., "Isolation and Culture of Human Alveolar Epithelial Progenitor Cells", Protocol Exchange, Jun. 11, 2018, Nature Publishing Group, XP093408476, ISSN: 2043-0116, DOI: 10.1038/protex.2018.015.
Kumashiro N., et al., "Cellular Mechanism of Insulin Resistance in Nonalcoholic Fatty Liver Disease," Proceedings of the National Academy of Sciences, 2011, vol. 108, No. 39, pp. 16381-16385.
World Health Organization, "Polycystic Ovary Syndrome," World Health Organization, 2025, 4 pages, Retrieved from https://www.who.int/news-room/fact-sheets/detail/polycystic-ovary-syndrome.br.
Beckstead., et al., "Esophageal epithelial cell interaction with synthetic and natural scaffolds for tissue engineering," Biomaterials, 26, 2005, pp. 6217-6228.
Das A.T., et al., "Tet-On Systems for Doxycycline-inducible Gene Expression," Current Gene Therapy, 2016, vol. 16 (3), pp. 156-167.
Endo R., et al., "Niche-preserving transplantation promotes functional engraftment of intestinal organoids in rat short bowel syndrome," Cell Stem Cell, Jan. 8, 2026, vol. 33, pp. 157-165.
Flett T., et al., "Gulonolactone Addition to Human Hepatocellular Carcinoma Cells with Gene Transfer of Gulonolactone Oxidase Restores Ascorbate Biosynthesis and Reduces Hypoxia Inducible Factor 1," Biomedicines, Mar. 5, 2014, vol. 2 (1), pp. 98-109.
Furuyama K., et al., "Continuous cell supply from a Sox9-expressing progenitor zone in adult liver, exocrine pancreas and intestine," Nature Genetics, Jan. 2011, vol. 43 (1), pp. 34-41.
Gjorevski N., et al., "Designer matrices for intestinal stem cell and organoid culture," Nature, Nov. 16, 2016, vol. 539, pp. 560-564.
Haass., "Re: How to seperate spheroids from single cells after spheroid formation," Retrieved from:https://www.researchgate.net/post/How_to_seperate_spheroids_from_single_cells_after_spheroid_formation/5881c10b96b7e4cf296662a4/citation/download , 2017, 2 pages.
Hong G., et al., "Mifepristone-inducible recombinant adenovirus attenuates paraquat-induced lung injury in rats," Human and Experimental Toxicology, 2015, vol. 34 (1), pp. 32-43.

(56) References Cited

OTHER PUBLICATIONS

Li M., et al., "Multimodality reporter gene imaging: Construction strategies and application," Theranostics, Apr. 18, 2018, vol. 8 (11), pp. 2954-2973.
Li R., et al., "Glycans and the Platelet Life Cycle," Platelets [online], May 2, 2016, vol. 27 (6), pp. 505-511, Retrieved from the Internet: URL: https://www.ncbi.nlm.nih.gov/pmc/articles/PMC5396182/.
Martn-Belmonte F., et al., "Cell-Polarity Dynamics Controls the Mechanism of Lumen Formation in Epithelial Morphogenesis," Current Biology, Apr. 8, 2008, vol. 18, pp. 507-513.
Mitrofanova., et al., "Bioengineered human colon organoids with in vivo-like cellular complexity and function," Cell Stem Cell0, vol. 31, 2024, pp. 1175-1186.
Sachs N., et al., "Intestinal epithelial organoids fuse to form self-organizing tubes in floating collagen gels," Development, 2017, vol. 144, pp. 1107-1112.
Sendi., et al., "miR-122 inhibition in a human liver organoid model leads to liver inflammation, necrosis, steatofibrosis and dysregulated insulin signaling," PloS one 13.7 (2018): e0200847, 17 pages.
Silva A.C., et al., "Developmental co-emergence of cardiac and gut tissues modeled by human iPSC-derived organoids," bioRxiv [online], 2020, 65 pages.
Togawa H., et al., "Induction of Human UGT1A1 by Bilirubin Through AhR Dependent Pathway," Drug Metabolism Letters, 2008, vol. 2, pp. 231-237.
Voos K.M., et al., "Desialylation of O-glycans activates von Willebrand factor by destabilizing its autoinhibitory module," Journal of Thrombosis and Haemostasis [online], Jan. 2022, vol. 20 (1), pp. 196-207, Retrieved from the Internet: URL: https://doi.org/10.1111/jth.15528.
Watson., et al., "An in vivo model of human small intestine using pluripotent stem cells," Nature Medicine., vol. 20 (11), 2014, pp. 1310-1314.
Whitehead., et al., "A Method for the Isolation and Culture of Human Colonic Crypts in Collagen Gels," In Vitro Cellular and Developmental Biology, vol. 23(6), 1987, pp. 436-442.
Yoneyama Y., et al., "Intercellular mRNA Transfer Alters the Human Pluripotent Stem Cell State," Proceedings of the National Academy of Sciences, 2025, vol. 122, No. 4 (e2413351122), 12 pages.
Yueh M.F., et al., "Nrf2-Keap1 Signaling Pathway Regulates Human UGT1A1 Expression in Vitro and in Transgenic UGT1 Mice," Journal of Biological Chemistry, 2007, vol. 282 (12), pp. 8749-8758.
Jinlong Y., et al. "Mesenchymal drift: A convergent framework for the hallmarks of aging," Cell 189.11, 2026, pp. 3184-3213.
Kozyra M., et al., "Human Hepatic 3D Spheroids as a Model for Steatosis and Insulin Resistance", Scientific Reports, Sep. 2018, vol. 8, No. 1, Nature Publishing Group, Article 14297, 12 pages, DOI: 10.1038/s41598-018-32722-6.
Tokai HIT., "What is MiViVo," Reverted from: https://en.tokaihit-excyte.com/about-mivivo , Retrieved on Sep. 24, 2025, 5 pages.
Xing Z., et al., "Advances in research on in vitro differentiation of embryonic stem cell into liver cells and myocardial cells," Drug Evaluation Research, 2014, vol. 37, Issue. 6, 4 Pages.
Aakerlund, L., et al., "Y1 receptors for neuropeptide Y are coupled to mobilization of intracellular calcium and inhibition of adenylate cyclase," FEBS Letters, 1990, vol. 260, pp. 73-78.
Abbott N.J., "Astrocyte-Endothelial Interactions and Blood-Brain Barrier Permeability," Journal of Anatomy, 2002, vol. 200, pp. 629-638.
Adams S. H. et al., "Effects of peptide YY [3-36] on short-term food intake in mice are not affected by prevailing plasma ghrelin levels," Endocrinology, 2004, 145, 4967-4975.
Aday S., et al., "Stem Cell-Based Human Blood-Brain Barrier Models for Drug Discovery and Delivery," Trends in Biotechnology, 2016, vol. 34, pp. 382-393.
Afgan E., et al., "The Galaxy Platform for Accessible, Reproducible and Collaborative Biomedical Analyses: 2016 Update," Nucleic Acids Research, 2016, vol. 44, pp. W3-W10.
Ager E. I., et al., "The Renin-Angiotensin System and Malignancy," Carcinogenesis, 2008, vol. 29, pp. 1675-1684.
Aird W.C. et al., "Endothelial cell heterogeneity," Cold Spring Harb Perspect Med, 2012, 2, a006429, 14 pages.
Aizarani N., et al., "A Human Liver Cell Atlas Reveals Heterogeneity and Epithelial Progenitors," Nature, Aug. 2019, vol. 572, No. 7770, pp. 199-204.
Akbari S., et al., "Next-Generation Liver Medicine Using Organoid Models", Frontiers in Cell and Developmental Biology, vol. 7, Dec. 20, 2019, 15 pages.
Akers A., et al., "Synopsis of Guidelines for the Clinical Management of Cerebral Cavernous Malformations: Consensus Recommendations Based on Systematic Literature Review by the Angioma Alliance Scientific Advisory Board Clinical Experts Panel," Neurosurgery, 2017, vol. 80, pp. 665-680.
Al Alam D., et al., "Contrasting expression of canonical Wnt signaling reporters TOPGAL, BATGAL and Axin2(LacZ) during murine lung development and repair," PLoS One, 2011, 6, 8, e23139, 11 pages.
Alber A.B., et al., "Directed Differentiation of Mouse Pluripotent Stem Cells into Functional Lung-Specific Mesenchyme," bioRxiv, Aug. 2022, doi: 10.1101/2022.08.12.502651.
Alber A.B., et al., "Directed Differentiation of Mouse Pluripotent Stem Cells into Functional Lung-specific Mesenchyme," Nature Communications, Jun. 13, 2023 , vol. 14:3488. 18 pages.
Allanson J.E., et al., "Possible New Autosomal Recessive Syndrome With Unusual Renal Histopathological Changes," American Journal of Medical Genetics, 1983, vol. 16, pp. 57-60.
Almeida, L. F., et al., "Role of the Renin-Angiotensin System in Kidney Development and Programming of Adult Blood Pressure." Clinical Science, vol. 134, No. 6, Mar. 27, 2020, pp. 641-656.
Alvira C. M., "Aberrant Pulmonary Vascular Growth and Remodeling in Bronchopulmonary Dysplasia," Frontiers in Medicine (Lausanne), 2016, vol. 3, p. 21.
Alvira C. M., "Nuclear Factor-Kappa-B Signaling in Lung Development and Disease: One Pathway, Numerous Functions," Birth Defects Research Part A: Clinical and Molecular Teratology, 2014, vol. 100, pp. 202-216.
Amir et al., "Comparing the Cellular Phenotype of Nave and Primed Human Embryonic Stem Cells," Fertility and Sterility, Sep. 1, 201810(4):e36 Abstract.
Amir M., et al., "Hepatic Autonomic Nervous System and Neurotrophic Factors Regulate the Pathogenesis and Progression of Non-Alcoholic Fatty Liver Disease," Frontiers in Medicine (Lausanne), 2020, vol. 7, Article 62. doi: 10.3389/fmed.2020.00062.
Amireddy N., et al., "The Unintended Mitochondrial Uncoupling Effects of the FDA-Approved Anti-Helminth Drug Nitazoxanide Mitigates Experimental Parkinsonism in Mice," Journal of Biological Chemistry, 2017, vol. 292, pp. 15731-15743.
Andl C.D. et al., "Epidermal growth factor receptor mediates increased cell proliferation, migration, and aggregation in esophageal keratinocytes in vitro and in vivo," Journal of Biological Chemistry, 2003, 278(3), 1824-1830.
Andrews T.S., et al., "Single-Cell, Single-Nucleus, and Spatial RNA Sequencing of the Human Liver Identifies Cholangiocyte and Mesenchymal Heterogeneity," Hepatology Communications, Nov. 2022, vol. 6, No. 11, pp. 821-840.
Anstee, Q.M., et al., "Genome-wide association study of non-alcoholic fatty liver and steatohepatitis in a histologically characterised cohort," Journal of Hepatology, 2020, vol. 73, pp. 505-515.
Appuhn S.V., et al., "Capillary Changes Precede Disordered Alveolarization in a Mouse Model of Bronchopulmonary Dysplasia," American Journal of Respiratory Cell and Molecular Biology, Mar. 2021, vol. 65, No. 1, pp. 81-91. doi: 10.1165/rcmb.2021-0004OC.
Arnold K. et al., "Sox2+ Adult Stem and Progenitor Cells Are Important for Tissue Regeneration and Survival of Mice," Cell Stem Cell, 2011, 9(4), 317-329.

(56) References Cited

OTHER PUBLICATIONS

Artegiani B., et al., "Fast and Efficient Generation of Knock-in Human Organoids Using Homology-independent CRISPRCas9 Precision Genome Editing", Nature Cell Biology, 2020, vol. 22, No. 3, pp. 321-331.
Auerbach A. D., "Fanconi anemia and its diagnosis," Mutation Research—Fundamental and Molecular Mechanisms of Mutagenesis, 2009, 668(1-2), 4-10.
Aven L., et al., "An NT4/TrkB Dependent Increase in Innervation Links Early-Life Allergen Exposure to Persistent Airway Hyperreactivity," FASEB Journal, 2014, vol. 28, pp. 897-907.
Bagnat M. et al., "Genetic control of single lumen formation in the zebrafish gut," Nat Cell Biol, 2007, 9, 954-960.
Bakker S. T. et al., "Learning from a paradox: recent insights into Fanconi anaemia through studying mouse models," Disease Models Mechanisms, 2013, 6(1), 40-47.
Baldelli, S., et al., "Glutathione and Nitric Oxide: Key Team Players in Use and Disuse of Skeletal Muscle," Nutrients, 2019, vol. 11.
Ballermann B. J., "Dependence of Renal Microvessel Density on Angiotensin II: Only in the Fetus?" Journal of the American Society of Nephrology, 2010, vol. 21, pp. 386-388.
Bamberger C. et al., "Retinoic acid inhibits downregulation of DeltaNp63alpha expression during terminal differentiation of human primary keratinocytes," The Journal of Investigative Dermatology, 2002, 118(1), 133-8.
Bandara, N., et al., "Molecular Control of Nitric Oxide Synthesis through eNOS and Caveolin-1 Interaction Regulates Osteogenic Differentiation of Adipose-Derived Stem Cells by Modulation of Wnt/-Catenin Signaling," Stem Cell Research Therapy, 2016, vol. 7, No. 182, pp. 1-15.
Barbera M. et al., "The human squamous oesophagus has widespread capacity for clonal expansion from cells at diverse stages of differentiation," Gut, 2015, 64, 11-19.
Bartl, M., et al., "Optimality in the Zonation of Ammonia Detoxification in Rodent Liver." Archives of Toxicology, vol. 89, 2015, pp. 2069-2078.
Basu-Roy U. et al., "Sox2 maintains self renewal of tumor-initiating cells in osteosarcomas," Oncogene, 2012, 31(18), 2270-2282.
Batra S., et al., "Cavernous Malformations: Natural History, Diagnosis and Treatment." Nature Reviews Neurology, 2009, vol. 5, pp. 659-670.
Beer N. L., et al., "The P446L Variant in GCKR Associated with Fasting Plasma Glucose and Triglyceride Levels Exerts Its Effect through Increased Glucokinase Activity in Liver," Human Molecular Genetics, 2009, vol. 18, pp. 4081-4088.
Belalcazar L. M., et al., "Lifestyle Intervention for Weight Loss and Cardiometabolic Changes in the Setting of Glucokinase Regulatory Protein Inhibition: Glucokinase Regulatory Protein-Leu446Pro Variant in Look AHEAD," Circulation: Cardiovascular Genetics, 2016, vol. 9, pp. 71-78.
Bellentani, S., et al., "Epidemiology of Non-Alcoholic Fatty Liver Disease." Digestive Diseases, vol. 28, 2010, pp. 155-161.
Bergers G. et al., "The role of pericytes in blood-vessel formation and maintenance," Neuro Oncol, 2005, 7, 452-464.
Besserer-Offroy, E., et al., "The signaling signature of the neurotensin type 1 receptor with endogenous ligands," Eur J Pharmacol, 2017, vol. 805, pp. 1-13.
Beucher A., et al., "The homeodomain-containing transcription factors Arx and Pax4 control enteroendocrine subtype specification in mice," PLoS One, 2012, 7(5), e36449, 11 pages.
Bhatt A. J., et al., "Disrupted Pulmonary Vasculature and Decreased Vascular Endothelial Growth Factor, Flt-1, and TIE-2 in Human Infants Dying with Bronchopulmonary Dysplasia," American Journal of Respiratory and Critical Care Medicine, 2001, vol. 164, pp. 1971-1980.
Biancalani T., et al., "Deep Learning and Alignment of Spatially Resolved Single-Cell Transcriptomes with Tangram," Nature Methods, Nov. 2021, vol. 18, No. 11, pp. 1352-1362.
Bilchik A. J., et al., "Peptide YY Augments Postprandial Small Intestinal Absorption in the Conscious Dog," The American Journal of Surgery, 1994, vol. 167, pp. 570-574.
Biology Stack Exchange., "Are there situations where in vivo results work better than in vitro results would have shown?", Forum post , reply on Sep. 28, 2018; Retrieved Jul. 25, 2024 from https://biology.stackexchange.com/questions/77736/are-there-situations-where-in-vivo-results-work-better-th (Year: 2018).
Blair T.A., et al., "Mass cytometry reveals distinct platelet subtypes in healthy subjects and novel alterations in surface glycoproteins in Glanzmann thrombasthenia," Scientific Reports. Jul. 9, 2018; 8(1):10300 in 13 pages.
Blakenberg D. et al., "Manipulation of FASTQ data with Galaxy," Bioinformatics, 2010, 26(14), 1783-1785.
Jarmas, A.E., et al., "Progenitor translatome changes coordinated by Tsc1 increase perception of Wnt signals to end nephrogenesis," Nature Communications, 2021, vol. 12.
Jason R. S., et al., "Directed Differentiation of Human Pluripotent Stem Cells into Intestinal Tissue in Vitro," Nature, Feb. 3, 2011, vol. 470, No. 7332, pp. 105-109, DOI: 10.1038/NATURE09691.
Jennings R. E., et al., "Development of the Human Pancreas from Foregut to Endocrine Commitment," Diabetes, 2013, vol. 62, pp. 3514-3522.
Jennings R. E., et al., "Human Pancreas Development," Development, 2015, vol. 142, pp. 3126-3137.
Jensen E. A., et al., "Epidemiology of Bronchopulmonary Dysplasia," Birth Defects Research Part A: Clinical and Molecular Teratology, 2014, vol. 100, pp. 145-157.
Jensen K. J., et al., "Hepatic Nervous System and Neurobiology of the Liver," Comprehensive Physiology, 2013, vol. 3, pp. 655-665.
Jeong, Y., et al., "Identification and genetic manipulation of human and mouse oesophageal stem cells," Gut, 2015, pp. 1-10.
Jho E. et al., "Wnt/beta-catenin/Tcf signaling induces the transcription of Axin2, a negative regulator of the signaling pathway," Molecular and Cellular Biology, 2002, 22(4), 1172-83.
Jiang C., et al., "Comparative Transcriptomics Analyses in Livers of Mice, Humans, and Humanized Mice Define Human-Specific Gene Networks," Cells, Nov. 2020, vol. 9, No. 2566.
Jiang H., et al., "Tyrosine Kinase Receptor B Protects Against Coronary Artery Disease and Promotes Adult Vasculature Integrity by Regulating Ets1-Mediated VE-Cadherin Expression," Arteriosclerosis, Thrombosis, and Vascular Biology, 2015, vol. 35, pp. 580-588.
Jiang M. et al., "BMP-driven NRF2 activation in esophageal basal cell differentiation and eosinophilic esophagitis," The Journal of Clinical Investigation, 2015, 125(14), 1-12.
Jiang M., et al., "Transitional Basal Cells at the Squamous-Columnar Junction Generate Barrett's Oesophagus," Nature, 2017, 550(7677), pp. 529-533.
Jin W., et al., "Regulation of BDNF-TrkB Signaling and Potential Therapeutic Strategies for Parkinson's Disease," Journal of Clinical Medicine, Jan. 2020, vol. 9, No. 1, doi: 10.3390/jcm9010257.
Jonatan D., et al., "Sox17 regulates insulin secretion in the normal and pathologic mouse beta cell," PloS one, 2014, 9, e104675, 16 pages.
Kaczmarek J. C., et al., "Polymer-Lipid Nanoparticles for Systemic Delivery of mRNA to the Lungs," Angewandte Chemie International Edition, 2016, vol. 55, pp. 13808-13812.
Kaczmarek J.C., et al., "Optimization of a Degradable Polymer-Lipid Nanoparticle for Potent Systemic Delivery of mRNA to the Lung Endothelium and Immune Cells," Nano Letters, 2018, vol. 18, No. 10, 6449-6454. doi: 10.1021/acs.nanolett.8b02917.
Kaiser J., Virus used in gene therapies may pose cancer risk, dog study hints, Science—Jan. 6, 2020 doi:10.1126/science.aba7696 in 3 pages.
Kajiwara, K., et al., "Molecular Mechanisms Underlying Twin-to-Twin Transfusion Syndrome," Cells, 2022, vol. 11, 18 pages.
Kalabis J. et al., "A subpopulation of mouse esophageal basal cells has properties of stem cells with the capacity for self-renewal and lineage specification," Journal of Clinical Investigation, 2008, (118), 3860-3869.

(56) References Cited

OTHER PUBLICATIONS

Kalabis J. et al., "Isolation and characterization of mouse and human esophageal epithelial cells in 3D organotypic culture," Nature Protocols, 2012, 7(2), 235-246.
Kang, J., et al., "Simultaneous deletion of the methylcytosine oxidases Tet1 and Tet3 increases transcriptome variability in early embryogenesis," Proceedings of the National Academy of Sciences, 2015, vol. 112, pp. E4236-E4245.
Kang, S. D., et al., "Effect of Productive Human Papillomavirus 16 Infection on Global Gene Expression in Cervical Epithelium." Journal of Virology, vol. 92, No. 20, Oct. 15, 2018, e01261-18.
Kapadia, B., et al., "PIMT regulates Hepatic Gluconeogenesis in Mice," iScience, 2023, 106120.
Kawaguchi T., et al., "Genetic Polymorphisms of the Human PNPLA3 Gene Are Strongly Associated with Severity of Non-Alcoholic Fatty Liver Disease in Japanese," PLoS One, 2012, vol. 7, e38322.
Kazumori H. et al., "Bile acids directly augment caudal related homeobox gene Cdx2 expression in oesophageal keratinocytes in Barrett's epithelium," Gut, 2006, 55(1), 16-25.
Kazumori H. et al., "Roles of caudal-related homeobox gene Cdx1 in oesophageal epithelial cells in Barrett's epithelium development," Gut, 2009, 58(5), 620-628.
KC K. et al., "In vitro model for studying esophageal epithelial differentiation and allergic inflammatory responses identifies keratin involvement in eosinophilic esophagitis," PloS One, 2015, 10(6), e0127755.
Kearns N. A. et al, "Generation of organized anterior foregut epithelia from pluripotent stem cells using small molecules," Stem Cell Res., 2013, 11, 1003-1012.
Kebschull et al., "High-throughput mapping of single-neuron projections by sequencing of barcoded RNA", Neuron, 2016, vol. 91(5), pp. 975-987.
Keebler M. E., et al., "Fine-Mapping in African Americans of 8 Recently Discovered Genetic Loci for Plasma Lipids: The Jackson Heart Study," Circulation: Cardiovascular Genetics, 2010, vol. 3, pp. 358-364.
Keeley, T.P., et al., "Defining Physiological Normoxia for Improved Translation of Cell Physiology to Animal Models and Humans," Physiological Reviews, 2019, vol. 99, pp. 161-234.
Kennedy D., et al., "Optimal Absorptive Transport of the Dipeptide Glycylsarcosine Is Dependent on Functional Na?/H? Exchange Activity," Pflugers Archiv, 2002, vol. 445, pp. 139-146.
Kermani P., et al., "Neurotrophins Promote Revascularization by Local Recruitment of TrkB+ Endothelial Cells and Systemic Mobilization of Hematopoietic Progenitors," Journal of Clinical Investigation, 2005, vol. 115, pp. 653-663.
Kietzmann, T., et al., "Metabolic zonation of the liver: The oxygen gradient revisited," Redox Biol, 2017, vol. 11, pp. 622-630.
Kim et al., "Recent progress in development of siRNA delivery vehicles for cancer therapy", Advanced Drug Delivery Reviews, 2016, vol. 104, pp. 61-77.
Kim M., et al., "O-Linked N-Acetylglucosamine Transferase Promotes Cervical Cancer Tumorigenesis through Human Papillomavirus E6 and E7 Oncogenes." Oncotarget, 7(28), 2016, 44596-44607.
Kim, S. G., et al., "Bilirubin Activates Transcription of HIF-1a in Human Proximal Tubular Cells Cultured in the Physiologic Oxygen Content," J Korean Med Sci, 2014, vol. 29, pp. S146-S154.
Kim Y. K., et al., "Gene-Edited Human Kidney Organoids Reveal Mechanisms of Disease in Podocyte Development," Stem Cells, 2017, vol. 35, pp. 2366-2378.
Kimura M., et al., "En Masse Organoid Phenotyping Informs Metabolic-Associated Genetic Susceptibility to NASH," Cell, Jun. 2022, vol. 185, No. 12, pp. 4216-4232.e4216.
Kitamoto A., et al., "Association of Polymorphisms in GCKR and TRIB1 with Nonalcoholic Fatty Liver Disease and Metabolic Syndrome Traits," Endocrine Journal, 2014, vol. 61, pp. 683-689.
Kleshchevnikov V., et al., "Comprehensive Mapping of Tissue Cell Architecture via Integrated Single Cell and Spatial Transcriptomics," bioRxiv, Nov. 2020, doi: 10.1101/2020.11.15.378125.
Kligerman S. J., et al., "From the Radiologic Pathology Archives: Organization and Fibrosis as a Response to Lung Injury in Diffuse Alveolar Damage, Organizing Pneumonia, and Acute Fibrinous and Organizing Pneumonia," Radiographics, 2013, 33, doi:10.1148/rg.337130057. PMID—24224590.
Kolbe E., et al., "Mutual Zonated Interactions of Wnt and Hh Signaling Are Orchestrating the Metabolism of the Adult Liver in Mice and Human," Cell Reports, Nov. 2019, vol. 29, No. 11, pp. 4553-4567.e4557.
Kong J. et al., "Ectopic Cdx2 expression in murine esophagus models an intermediate stage in the emergence of Barrett's esophagus," PLoS ONE, 2011, 6(4), 1-12.
Kong J. et al., "Induction of intestinalization in human esophageal keratinocytes is a multistep process," Carcinogenesis, 2009, 30(1), 122-130.
Kormish J.D. et al., "Interactions between SOX factors and Wnt/beta-catenin signaling in development and disease," Developmental Dynamics: An Official Publication of the American Association of Anatomists, 2010, 239, 56-68.
Koui Y., et al., "An In Vitro Human Liver Model by iPSC-Derived Parenchymal and Non-Parenchymal Cells," Stem Cell Reports, 2017, 9, pp. 490-498.
Kouznetsova I. et al., Self-renewal of the human gastric epithelium: new insights from expression profiling using laser microdissection. Mol Biosyst, 2011, 7, 1105-1112.
Kowalski P.S., et al., "Delivering the messenger: Advances in Technologies for Therapeutic mRNA delivery," Molecular Therapy . Apr. 10, 2019;27(4):710-728.
Kozyra M., et al., "Human Hepatic D Spheroids as a Model for Steatosis and Insulin Resistance", Scientific Reports, vol. 8, No. 1, Sep. 24, 2018, 12 pages, Retrieved from the Internet: URL: https://www.nature.com/articles/ s41598-018-32722-6.
Reza, H.A., et al., "Synthetic augmentation of bilirubin metabolism in human pluripotent stem cell-derived liver organoids," Stem Cell Reports, 2023.
Rhoads, K., et al., "A Role for Hox A5 in Regulating Angiogenesis and Vascular Patterning." Lymphatic Research and Biology, vol. 3, No. 4, 2005, pp. 240-252.
Rich, N.E., et al., "Racial and Ethnic Disparities in Nonalcoholic Fatty Liver Disease Prevalence, Severity, and Outcomes in the United States: A Systematic Review and Meta-Analysis," Clinical Gastroenterology and Hepatology, 2018, vol. 16, pp. 198-210 e192.
Robbins D. J. et al., "The Hedgehog Signal Transduction Network," Science Signaling 2012, 5(246), re6-re6, 28 pages.
Robinson B.D., et al., "Measurement of Microvascular Endothelial Barrier Dysfunction and Hyperpermeability In Vitro," Methods in Molecular Biology, Feb. 2018, vol. 1717, pp. 237-242.
Rochman M., et al., "Profound Loss of Esophageal Tissue Differentiation in Patients with Eosinophilic Esophagitis," Journal of Allergy and Clinical Immunology, 2017, 140(3), pp. 738-749.e3.
Roitbak T., et al., "Neural Stem/Progenitor Cells Promote Endothelial Cell Morphogenesis and Protect Endothelial Cells against Ischemia via HIF-1a-Regulated VEGF Signaling," Journal of Cerebral Blood Flow Metabolism, 2008, vol. 28, pp. 1530-1542.
Rosekrans S. L. et al., "Esophageal development and epithelial homeostasis," American Journal of Physiology—Gastrointestinal and Liver Physiology, 2015, 309(4), G216-228.
Ross M.G. et al., "Development of ingestive behavior.," Am J Physiol, 1998, 274, R879-893.
Rossi J.M. et al., "Distinct mesodermal signals, including BMPs from the septum transversum mesenchyme, arc required in combination for hepatogenesis from the endoderm," Genes Dev, 2001, 15, 1998-2009.
Rubio-Cabezas O., et al., "Permanent Neonatal Diabetes and Enteric Anendocrinosis Associated with Biallelic Mutations in NEUROG3," Diabetes, 2011, vol. 60, pp. 1349-1353.
Sahdeo S., et al., "High-Throughput Screening of FDA-Approved Drugs Using Oxygen Biosensor Plates Reveals Secondary Mitofunctional Effects," Mitochondrion, 2014, vol. 17, pp. 116-125.

(56) References Cited

OTHER PUBLICATIONS

Saili K. S., et al., "Blood-Brain Barrier Development: Systems Modeling and Predictive Toxicology," Birth Defects Research, 2017, vol. 109, pp. 1680-1710.
Sajiki T., et al., "Transmission Electron Microscopic Study of Hepatocytes in Bioartificial Liver," Tissue Engineering, 2000, vol. 6, No. 6, pp. 627-640.
Samson A. et al., "Effect of somatostatin on electrogenic ion transport in the duodenum and colon of the mouse, *Mus domesticus*," Comparative Biochemistry and Physiology Part A: Molecular Integrative Physiology, 2000, 125, 459-468.
Samuel, V.T., et al., "Nonalcoholic Fatty Liver Disease, Insulin Resistance, and Ceramides," New England Journal of Medicine, 2019, vol. 381, pp. 1866-1869.
Sankoda N., et al., "Epithelial Expression of Gata4 and Sox2 Regulates Specification of the Squamous-columnar Junction via MAPK/ERK Signaling in Mice," Nature Communications, 2021, vol. 12, pp. 1-15.
Santoro N., et al., "Variant in the Glucokinase Regulatory Protein (GCKR) Gene Is Associated with Fatty Liver in Obese Children and Adolescents," Hepatology, 2012, vol. 55, pp. 781-789.
Sarkar A., et al., "Sox2 Suppresses Gastric Tumorigenesis in Mice," Cell Reports, 2016, 16(7), pp. 1929-1941.
Sato T., et al., "Growing Self-Organizing Mini-Guts from a Single Intestinal Stem Cell: Mechanism and Applications," Science, 2013, vol. 340, pp. 1190-1194. DOI: 10.1126/science.1234852.
Saunders N. R., et al., "Barrier Mechanisms in the Developing Brain," Frontiers in Pharmacology, 2012, vol. 3, Article 46, 18 pages.
Sayar E., et al., "Chromogranin-A Staining Reveals Enteric Anendocrinosis in Unexplained Congenital Diarrhea," Journal of Pediatric Gastroenterology and Nutrition, 2013, vol. 57, No. 4, pp. e21.
Sayar E., et al., "Extremely Rare Cause of Congenital Diarrhea: Enteric Anendocrinosis," Pediatrics International, 2013, vol. 55, pp. 661-663.
Scheidecker, B., et al., "Induction of in vitro Metabolic Zonation in Primary Hepatocytes Requires Both Near-Physiological Oxygen Concentration and Flux," Frontiers in Bioengineering and Biotechnology, 2020, vol. 8.
Schreiber R., et al., "Inherited Renal Tubular Dysgenesis May Not Be Universally Fatal," Pediatric Nephrology, 2010, vol. 25, pp. 2531-2534.
Schreiber R., et al., "Renal Tubular Dysgenesis Secondary to Mutations in Genes Encoding the Renin-Angiotensin System," Harefuah, 2021, vol. 160, pp. 822-826.
Schuldiner et al. "Induced Neuronal Differentiation of Human Embryonic Stem Cells," Brain Research 2001, Sep. 21, 2001, vol. 913(2):201-205.
Schupp J.C., et al., "Integrated Single-Cell Atlas of Endothelial Cells of the Human Lung," Circulation, May 2021, vol. 144, No. 4, 286-302. doi: 10.1161/CIRCULATIONAHA.120.052318.
Sebrell T.A., et al., "Live Imaging Analysis of Human Gastric Epithelial Spheroids Reveals Spontaneous Rupture, Rotation and Fusion Events,". Cell and Tissue Research, 2018, vol. 371, pp. 293-307.
Sekar R. and Chow B. K. C., "Secrelin Receptor-Knockout Mice Are Resistant to High-Fat Diet-Induced Obesity and Exhibit Impaired Intestinal Lipid Absorption," The FASEB Journal, 2014, vol. 28, pp. 3494-3505.
Self M. et al, "Six2 activity is required for the formation of the mammalian pyloric sphincter," Dev Biol, 2009, 334, 409-417.
Shafa M., et al., "Expansion and Long-Term Maintenance of Induced Pluripotent Stem Cells in Stirred Suspension Bioreactors", Journal of Tissue Engineering and Regenerative Medicine, Jun. 1, 2012, vol. 6, No. 6, pp. 462-472, DOI: 10.1002/term.450.
Shaham O. et al., "Pax6 is essential for lens fiber cell differentiation," Development (Cambridge, England), 2009, 136(15), 2567-2578.
Shankar A.S., et al., "Human Kidney Organoids Produce Functional Renin," Kidney International, 2021, vol. 99, pp. 134-147.
Shao Z. et al., "MAnorm: a robust model for quantitative comparison of ChIP-Seq data sets," Genome Biol, 2012, 13, R16, 17 pages.
Shapiro E., et al., "Single-cell Sequencing-based Technologies will Revolutionize Whole Organism Science," Nature Reviews Genetics, 2013, vol. 14(9), pp. 618-630.
Shen H., et al., "Glucokinase Regulatory Protein Gene Polymorphism Affects Postprandial Lipemic Response in a Dietary Intervention Study," Human Genetics, 2009, vol. 126, pp. 567-574.
Shoyaib A.A., et al., "Intraperitoneal Route of Drug Administration: Should it Be Used in Experimental Animal Studies?," Pharm Res, Dec. 23, 2019, vol. 37(1):12.
Simon, M., et al., "Expression of Vascular Endothelial Growth Factor and Its Receptors in Human Renal Ontogenesis and in Adult Kidney." American Journal of Physiology, vol. 268, No. 2, Feb. 1995, pp. F240-F250.
Simon T.G., et al., "Mortality in Biopsy-Confirmed Nonalcoholic Fatty Liver Disease: Results from a Nationwide Cohort," Gut, 2021, vol. 70, pp. 1375-1382. doi: 10.1136/gutjnl-2020-322786.
Sinagoga K. L., et al., "Distinct Roles for the mTOR Pathway in Postnatal Morphogenesis, Maturation and Function of Pancreatic Islets," Development, 2017, vol. 144, pp. 2402-2414.
Sinagoga K.L., et al., "Deriving Functional Human Enteroendocrine Cells from Pluripotent Stem Cells," Development, 2018, vol. 145.
Singh A., et al., "Transplanted Human Intestinal Organoids: A Resource for Modeling Human Intestinal Development," Development, 2023, vol. 150, dev201416. doi: 10.1242/dev.201416.
Singh S. K., et al., "Glucose-Dependent Insulinotropic Polypeptide (GIP) Stimulates Transepithelial Glucose Transport," Obesity, 2008, vol. 16, pp. 2412-2416.
Sinner D. et al. "Sox17 and Sox4 differentially regulate beta-catenin/T-cell factor activity and proliferation of colon carcinoma cells," Molecular and Cellular Biology, 27(22), 2007, 7802-7815.
Sloan S. A., et al., "Human Astrocyte Maturation Captured in 3D Cerebral Cortical Spheroids Derived from Pluripotent Stem Cells," Neuron, 2017, vol. 95, pp. 779-790.e1-e6.
Sloth B. et al., "Effect of subcutaneous injections of PYY1-36 and PYY3-36 on appetite, ad libitum energy intake, and plasma free fatty acid concentration in obese males," American Journal of Physiology Endocrinology and Metabolism, 2007, 293, E604-E609.
Sluch V.M., et al., "Highly Efficient Scarless Knock-in of Reporter Genes into Human and Mouse Pluripotent Stem Cells via Transient Antibiotic Selection", PLOS ONE, vol. 13, No. 11, Nov. 29, 2018. 18 pages, Retrieved from the Internet: URL :https://www.ncbi.nlm.nih.gov/pmc/articles/PMC6264506/pdf/ pone.0201683.pdf.
Smith, S.M., et al., "Obeticholic Acid: A Farnesoid X Receptor Agonist for Primary Biliary Cholangitis," Journal of Pharmacy Technology, 2017, vol. 33 (2), pp. 66-71.
Snellings D.A., et al., "Cerebral Cavernous Malformation: From Mechanism to Therapy," Circulation Research, 2021, vol. 129, pp. 195-215. doi: 10.1161/CIRCRESAHA.121.318174.

* cited by examiner

| | | | | |
|---|---|---|---|---|
| Drug | BOSENTAN | | IRINOTECAN | |
| Gene | CYP2C9*2 | | UGT1A1*6 | |
| rs ID | rs96702047 | | rs4148323 | |
| Clone name | C/C | C/T | G/G | G/A |
| TkDA | 1 | 1 | 1 | 0 |
| H | 1 | 0 | 1 | 0 |
| 1 | 1 | 0 | 1 | 0 |
| F | 1 | 0 | 1 | 0 |

| Class | Compound | Mechanism of toxicity |
|---|---|---|
| Control | DMSO | |
| Negative control | Streptomycin | |
| Class A | Diclofenac | Reactive metabolite; oxidative stress; mitochondrial toxicity; inflammatory-immune reactions |
| | Tolcapone | Mitochondrial toxicity |
| Class B | Cyclosporin A | Cholestasis (inhibition of bile acid transport; BSEP inhibition); oxidative stress;<br>Mitochondrial toxicity |
| | Troglitazone | Cholestasis (inhibition of bile acid transport; BSEP inhibition); mitochondrial toxicity;<br>Reactive metabolite; oxidative stress |
| | Nefazodone | Reactive metabolite; mitochondrial toxicity; cholestasis (inhibition of bile acid transport; BSEP inhibition) |
| | Bosentan | Cholestasis: BSEP inhibition |
| Class C | Entacapone | (Unknown)/not applicable |
| | Pioglitazone | (Unknown)/not applicable |

FIG. 5C

Total number of organoidat D20 were 305. Organoidwith lumen: 216, Organoidswithout lumen: 89.

| | |
|---|---|
| **Correction formula** | Y = 0.1043x |

LIVER ORGANOID COMPOSITIONS AND METHODS OF MAKING AND USING SAME

CROSS REFERENCE TO RELATED APPLICATIONS

This application claims priority to and benefit of International Patent Application PCT/US18/18585, entitled "Liver Organoid Compositions and Methods of Making and Using Same," filed Feb. 19, 2018, which claims priority to and benefit of U.S. Provisional Patent Application 62/517,414, filed Jun. 9, 2017, the contents of each are incorporated by reference in their entirety for all purposes.

BACKGROUND

The liver is a vital organ that provides many essential metabolic functions for life such as the detoxification of exogenous compounds and coagulation as well as producing lipids, proteins, ammonium, and bile. In vitro reconstitution of a patient's liver may provide applications including regenerative therapy, drug discovery and drug toxicity studies. Existing methodology using liver cells exhibit extremely poor functionality, largely due to a lack of essential anatomical structures, which limits their practical use for the pharmaceutical industry.

Billions of dollars are lost annually from drug development in the pharmaceutical industry due to the failures of drug candidates identified in initial screens, and nearly a third of drugs are withdrawn from the market due to such failures (Takebe and Taniguchi, 2014). A failure of drug candidates results in a tremendous loss of a patient's treatment opportunity. Preclinical studies generally consist of an in vitro evaluation as a primary efficacy screen to identify a "hit" compound, followed by safety studies in vitro and in vivo to assess the mechanisms of metabolism and toxicology. This inefficiency can be explained by the substantial lack of physiologically relevant preclinical models with high throughput in evaluating drug induced liver injury (DILI) in humans and thus, an urgent need to develop an in vitro humanistic screen model for the evaluation of the vast amounts of continuously growing compound libraries.

Primary hepatocytes are a highly polarized metabolic cell type, and form a bile canaliculi structure with microvilli-lined channels, separating peripheral circulation from the bile acid secretion pathway. The most upstream aspects of DILI include drug (or their reactive metabolites) detoxification by hepatocytes and excretion into bile canaliculi through transporters such as multi-drug resistance-associated protein (MRP) transporters. This suggests the need to reconstruct these uniquely organized structures as a crucial property of hepatocytes in vivo for predicting DILI pathology. However, there are considerable differences in drug toxicity profiles between the current simplified culture model with the use of isolated primary human hepatocytes or hepatic cell lines, and in vivo physiology, resulting in failed translation of drugs or drug discontinuation, as in the case of Troglitazone, Nefazodone and Tolcapone (https://livertox.nlm.nih.gov/index.html). The determination of toxicological properties thus mainly relies on animals as an essential step for drug development, however, due to the pronounced differences in physiology between humans and animals, there is a significant lack of fidelity to human outcomes (Leslie et al., 2007; Yang et al., 2014). In addition, the onset of idiosyncratic DILI (IDILI), which is very rare but nonetheless responsible for about 10-15% of acute liver failures in the USA (Reuben et al., 2010), is almost impossible to predict (Kullak-Ublick et al., 2017). Collectively, effective human cell models are needed to screen for compounds that test the detoxification and excretion of proposed drugs.

Despite the progressive advancement of human hepatocyte differentiation methods from pluripotent stem cell (PSC), clinical trials in a dish using human stem cells remain 'hype'. [Besides drug screens for efficacy and/or toxicity, there is a need for liver cell models for use in bio-artificial liver devices as a bridge for transplant, for example, and for precision (personalized medicine). The instant disclosure seeks to address one or more of the aforementioned needs in the art.

BRIEF SUMMARY

Disclosed are methods of inducing formation of a liver organoid from precursor cells, such as iPSC cells. The disclosed liver organoids may be used for screening for a serious adverse event (SAE), such as liver failure and/or drug induced liver injury (DILI), and/or drug toxicity. The disclosed liver organoids may also be used to treat an individual having liver damage, or for identifying a preferred therapeutic agent.

BRIEF DESCRIPTION OF THE DRAWINGS

Those of skill in the art will understand that the drawings, described below, are for illustrative purposes only. The drawings are not intended to limit the scope of the present teachings in any way.

DETAILED DESCRIPTION OF THE INVENTION

Figure 1A:
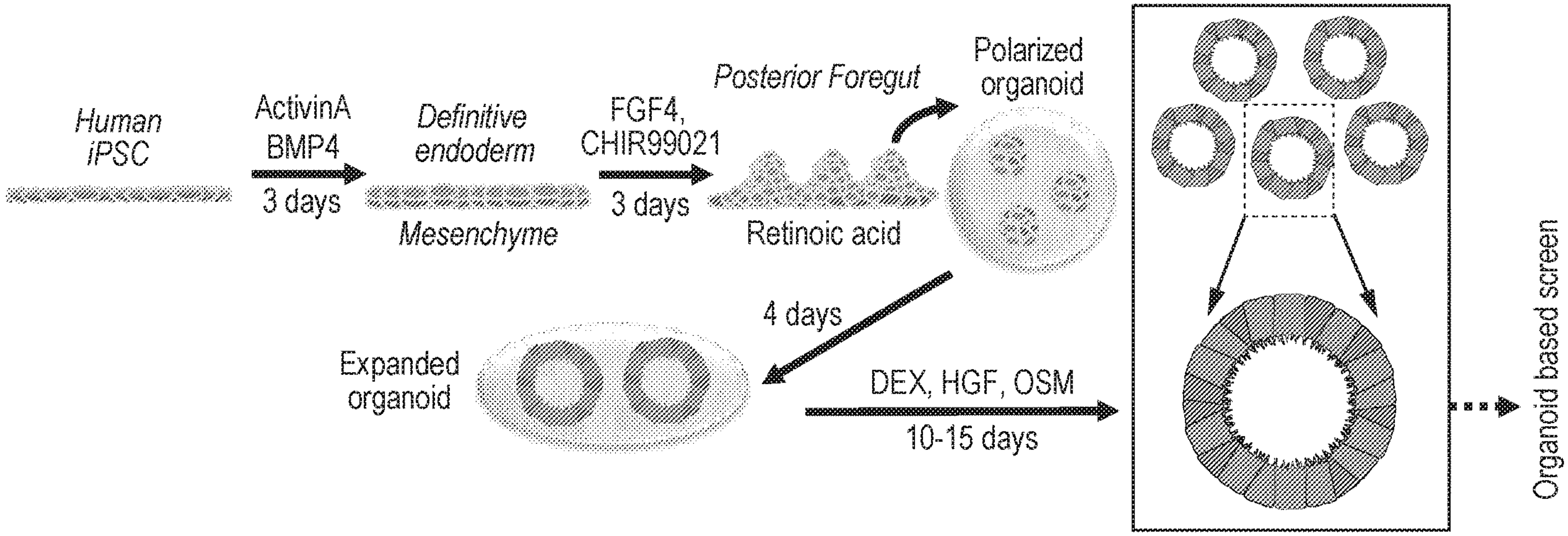
FIG. 1. Generation of human liver organoid from iPSC with luminal structure. A. Overview of the differentiation method for liver organoid. B. Phase contrast image of human liver organoids C Immunostaining for Albumin (ALB), Type IV collagen (Collagen IV) and ZO-1 in organoids. Nuclei were stained with Haematoxylin (blue). Bars, 50 μm. D. Quantitative RT-PCR of Alpha-fetoprotein (AFP), Albumin (ALB), Retinol-Binding Protein 4 (RBP4), Cytokeratin 19 (CK19), Hepatocyte nuclear factor 6 (HNF6) and Cytochrome P450 3A4 (CYP3A4) in undifferentiated iPS cells, organoids at Day 7, 11, 20 and 30 of differentiation and Primary hepatocytes (PH). Relative expression values were compared with undifferentiated iPSCs (AFP, ALB, RBP4 and CK19) or Day 7 organoids (HNF6) or Day 11 organoids (CYP3A4). Bars represent the mean±SD, n=3. E. Principal component analysis based on RNA sequence data in undifferentiated iPS cells (iPSC), Definitive endoderm (DE), Hepatic Specified cells (HS), Hepatic Progenitor (HP), iPSC-Derived Cholangiocytes (iDC), Normal Human Cholangiocyte (NHC), iPSC-derived Posterior foregut (pFG), iPSC-derived human liver organoid, Primary hepatocytes, Fetal liver tissue, Liver tissue and Right lobe of human Liver. F. Albumin (ALB, n=10) and Fibrinogen (FBG, n=4) secretion levels from organoids at Day 25-30. Bars represent the mean±SEM. G. Complement factors secretion level from organoids at Day 25-30. FH: Factor H, FB: Factor B. Bars represent the mean±SEM, n=5.
Figure 1B:
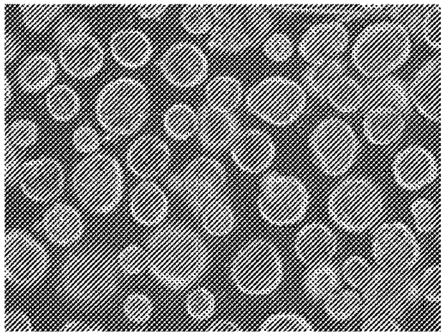
Figure 1C:
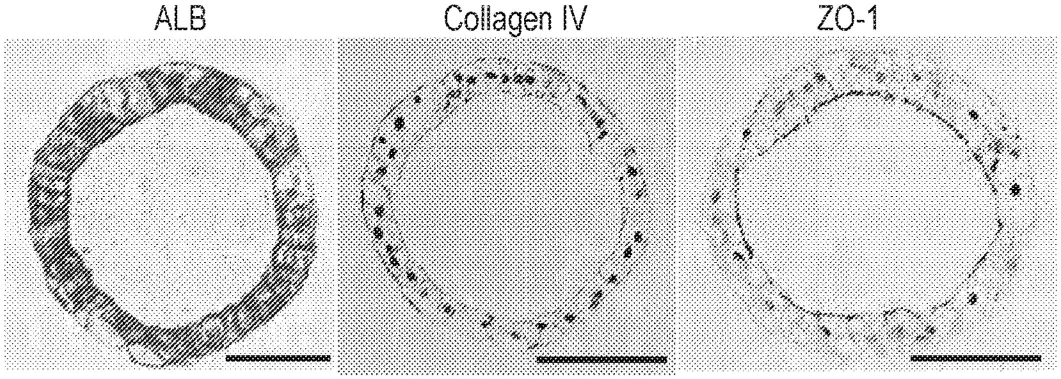
Figure 1D:
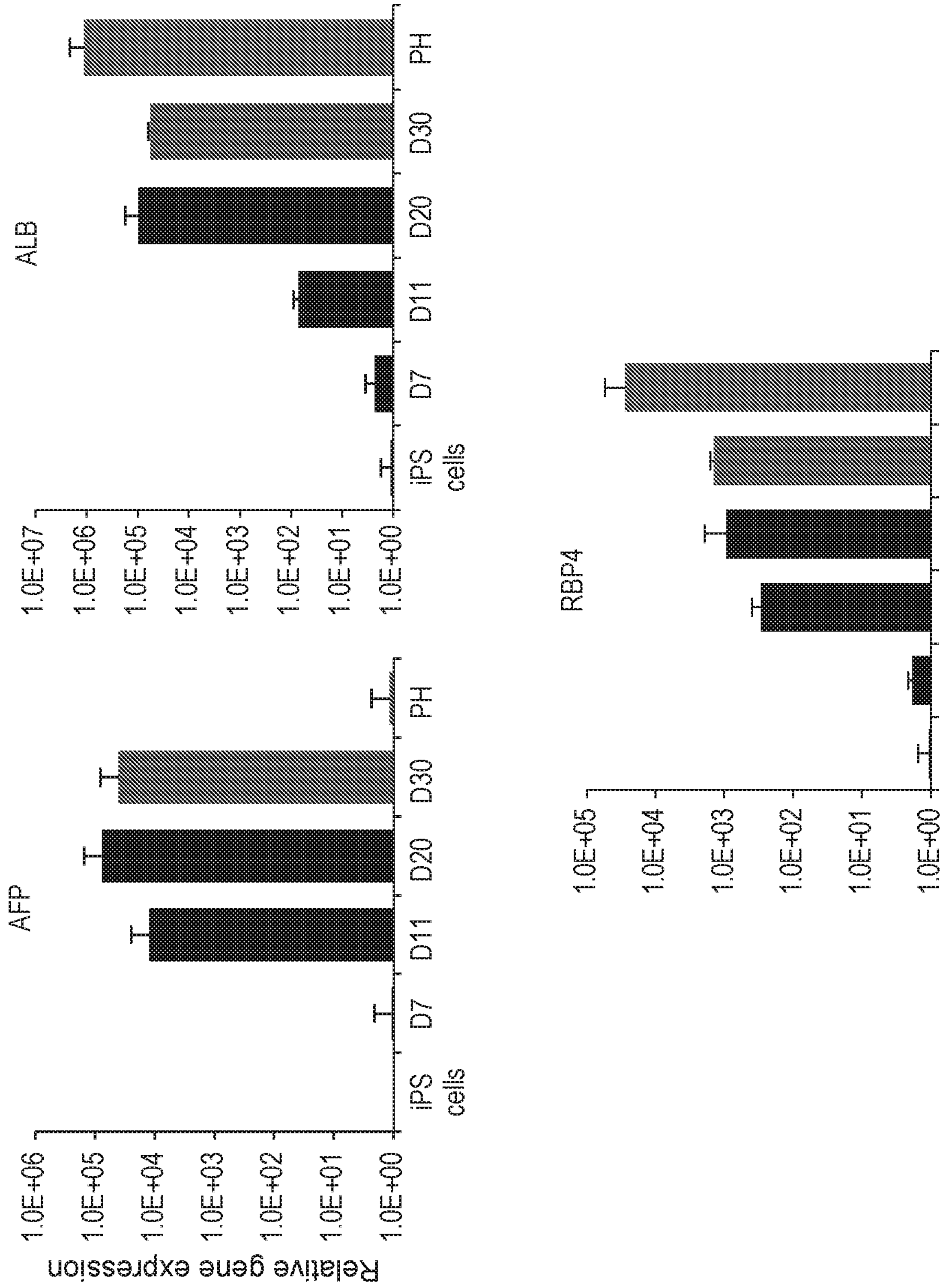
Figure 1E:
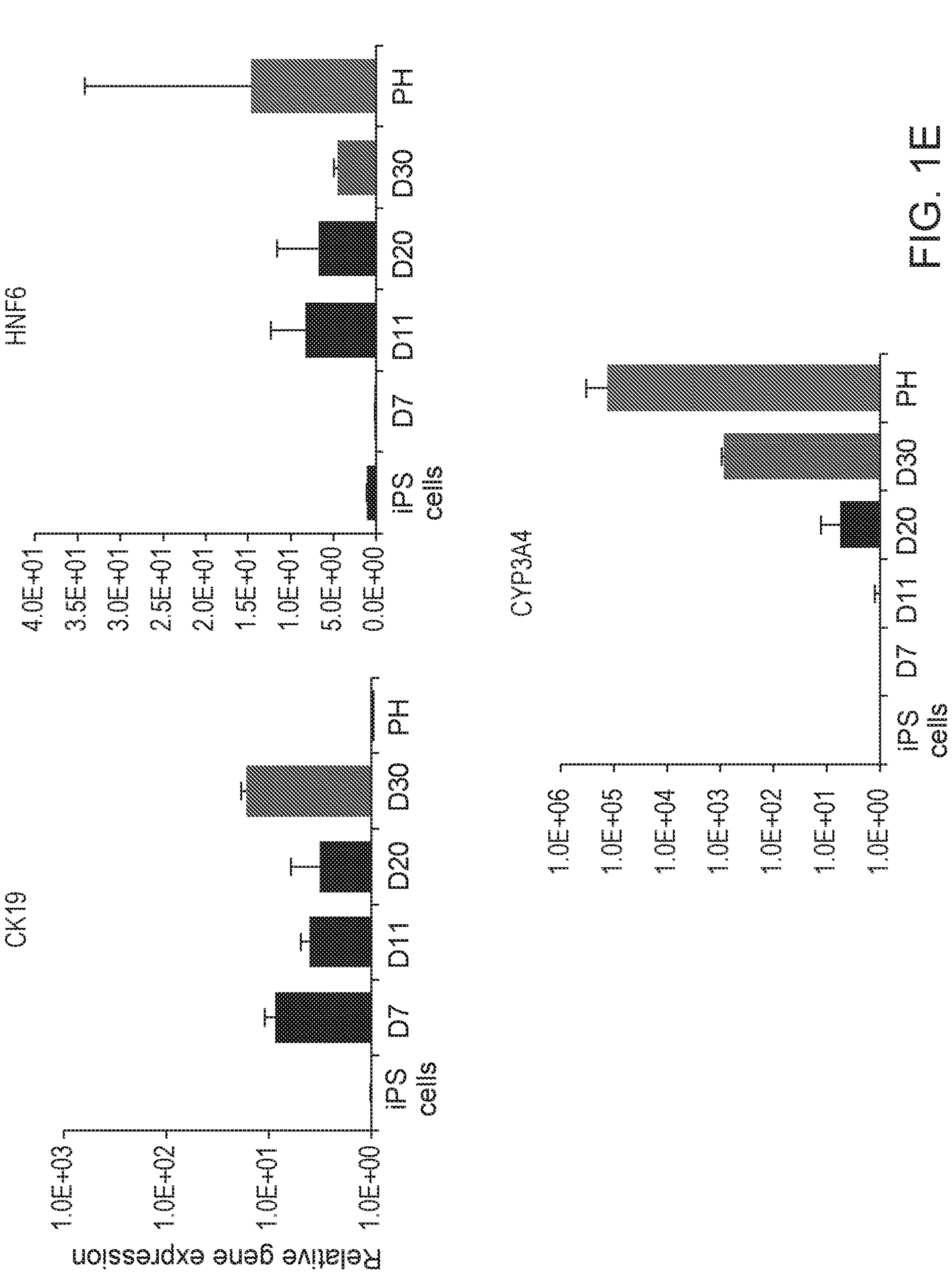
Figure 1F:
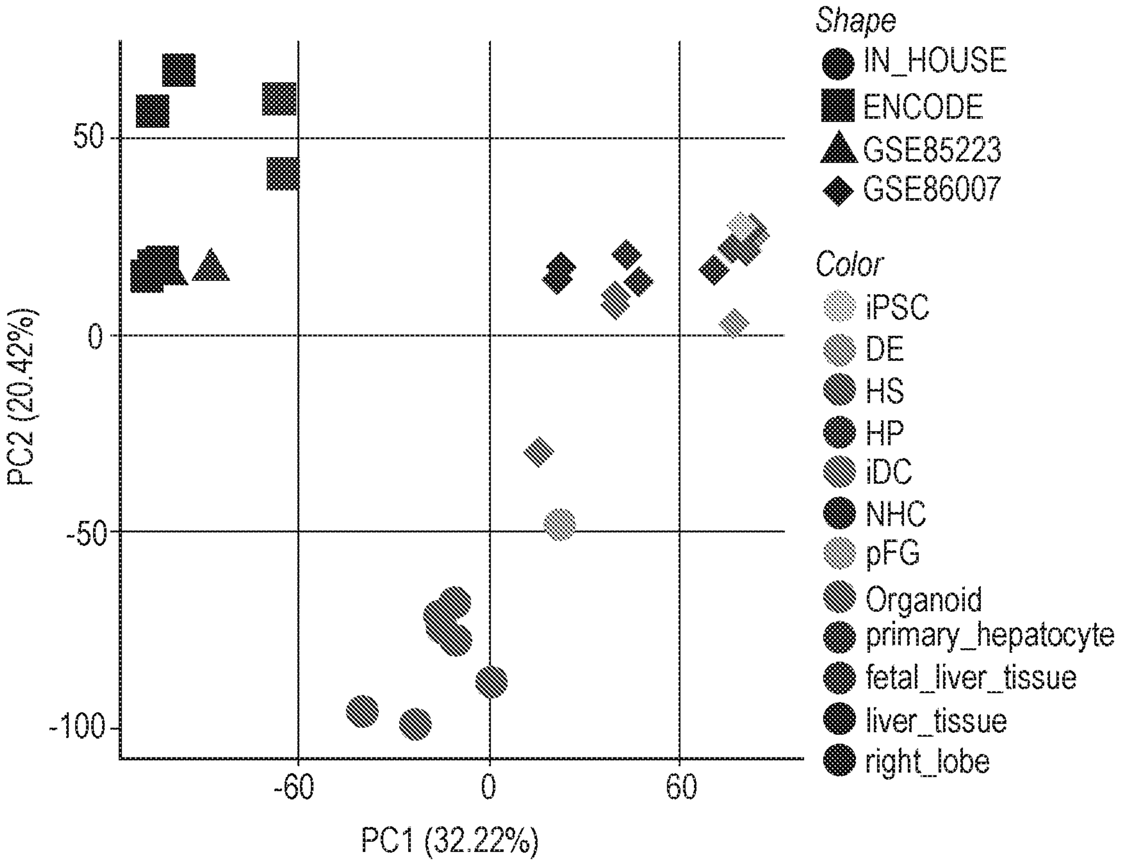
Figure 1G:
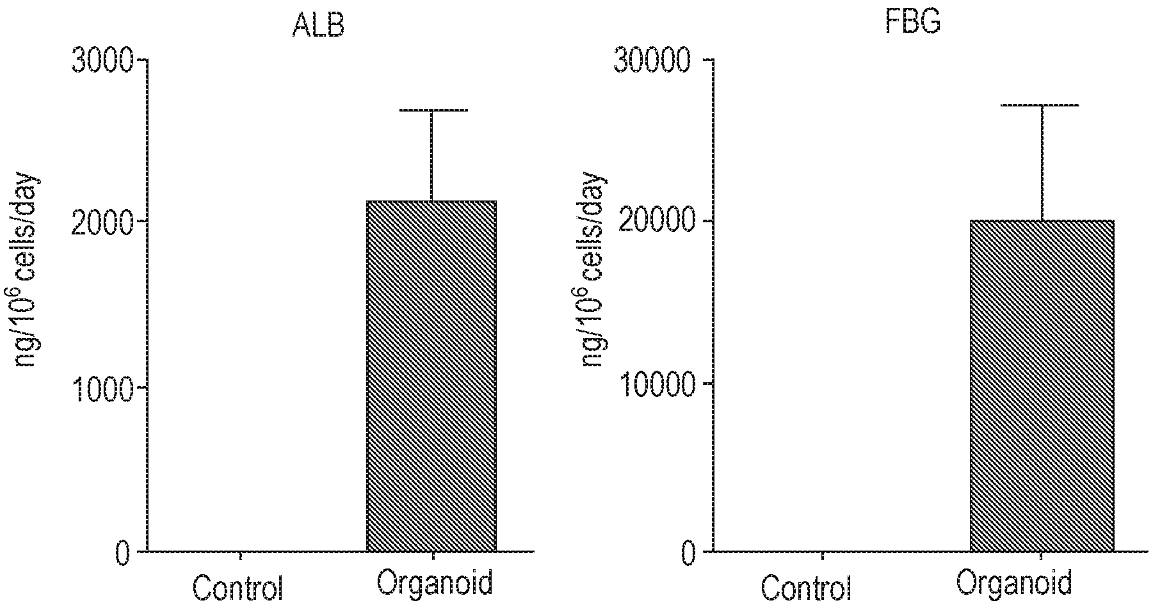
Figure 1H:
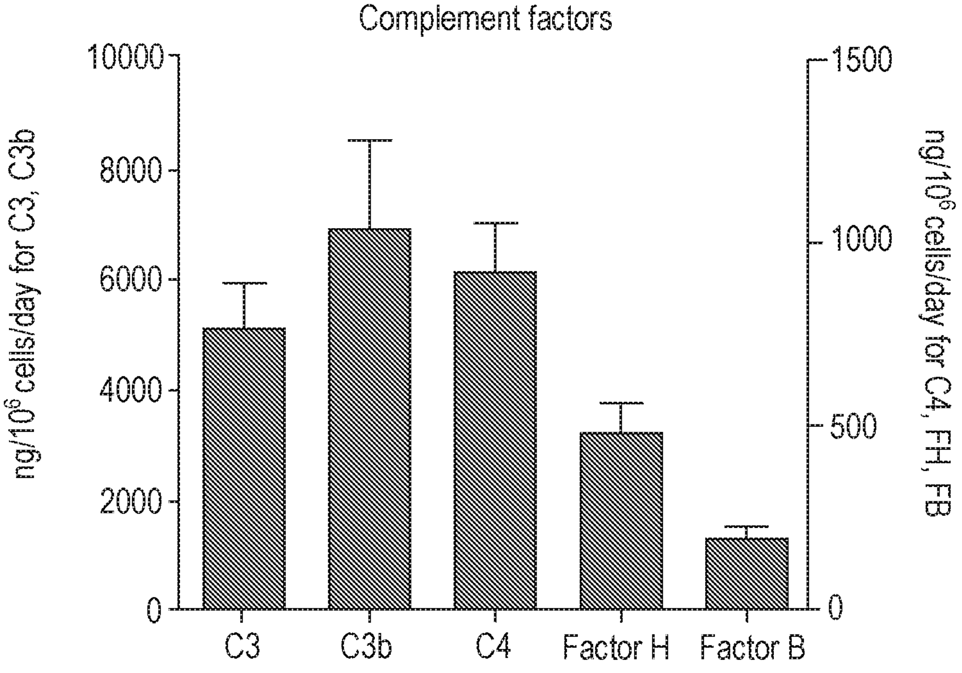
Figure 2A:
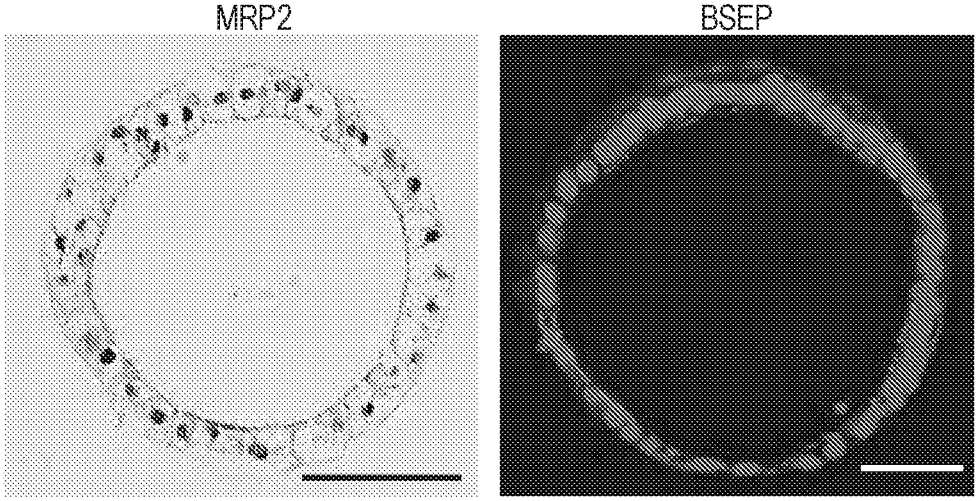
FIG. 2. Bile acid synthesis, uptake and excretion in human iPSC liver organoid. A Immunostaining for Multidrug resistance-associated protein 2 (MRP2) and Bile salt export pump (BSEP) in a single organoid. Bars, 50 μm. B. Transmission electron micrograph of organoid showing microvilli (V) intra-luminal surface; N: nuclei. Bars, 10 μm. C. Quantitative RT-PCR of ATP-binding cassette, sub-family B member 11 (ABCB11) and Sodium taurocholate co-transporting polypeptide (NTCP) in undifferentiated iPSCs, organoids at Day 20 (NTCP) and 30 (ABCB11) of differentiation and Primary hepatocytes (PH). Relative expression value was compared with undifferentiated iPS cells (ABCB11) or Day 11 organoids (NTCP). Bars represent the mean±SD, n=3. D. Total bile acid secretion level inside organoids at day 27. Bars represent the mean±SEM, n=4. E. Bile acid uptake by organoid after 30 min of culture in the presence of fluorescent bile acid (CGamF). F. CLF transport activity on organoids derived from 4 iPSC lines. T, W, 1 and F indicate clone name of iPS cell lines. Green: CLF.
Figure 2B:
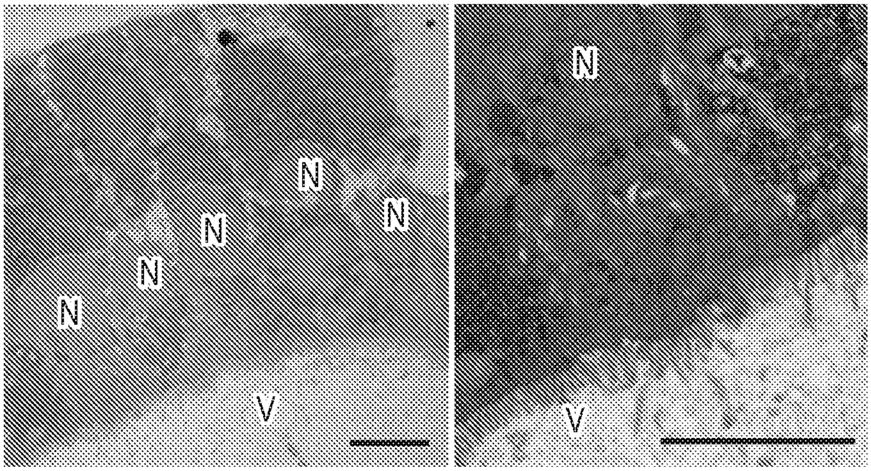
Figure 2C:
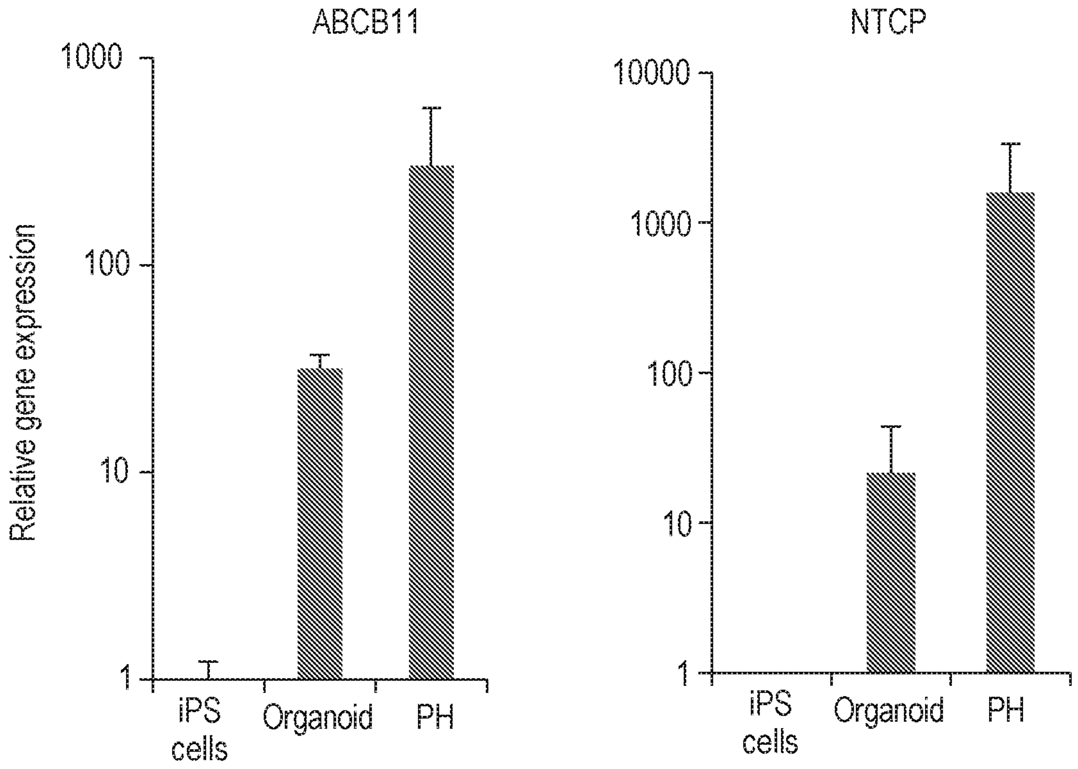
Figure 2D:
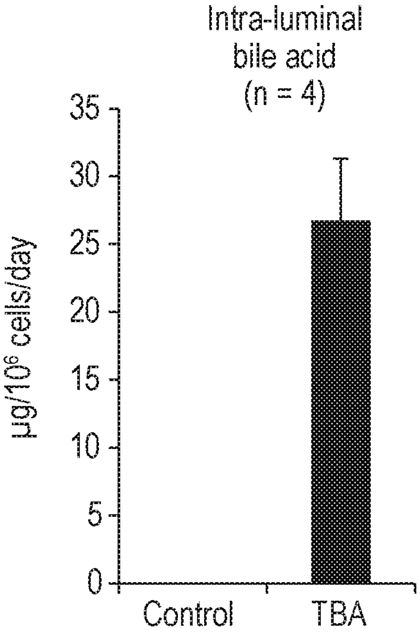
Figure 2E:
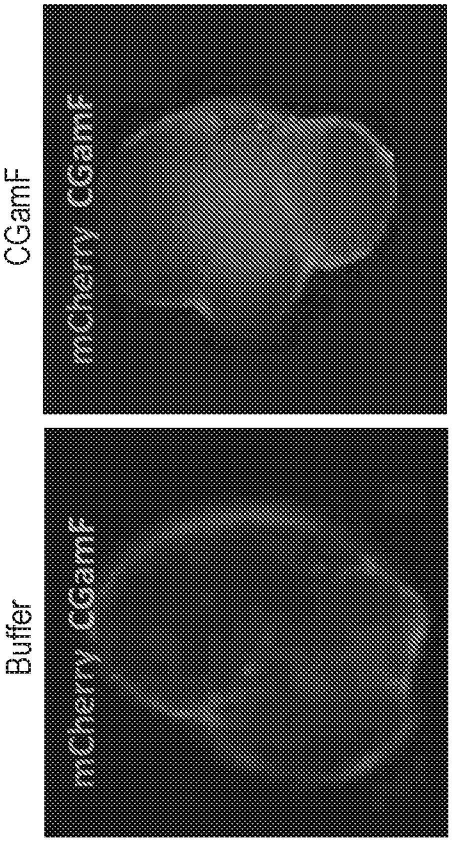
Figure 2F:
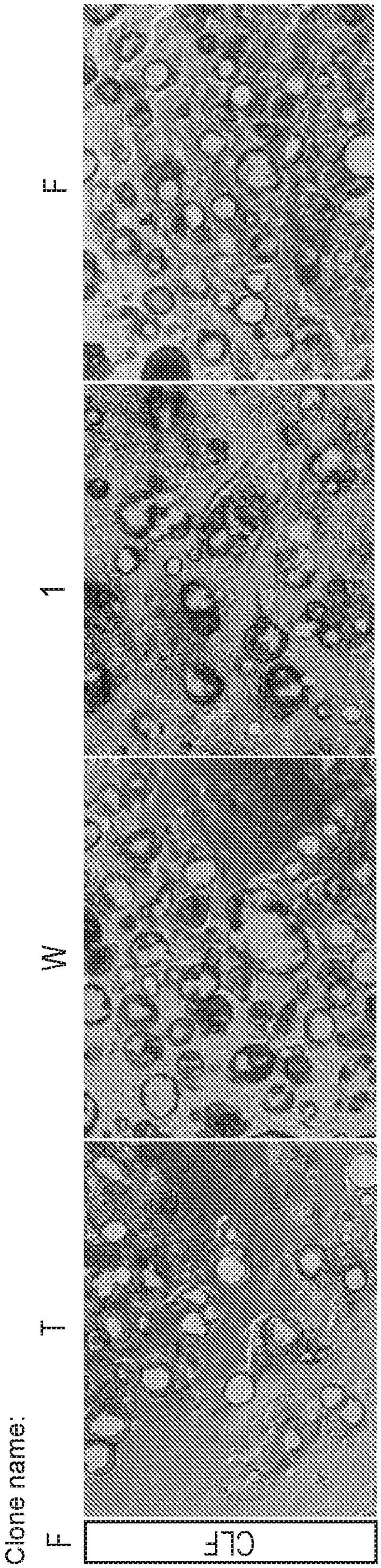
Figure 3A:
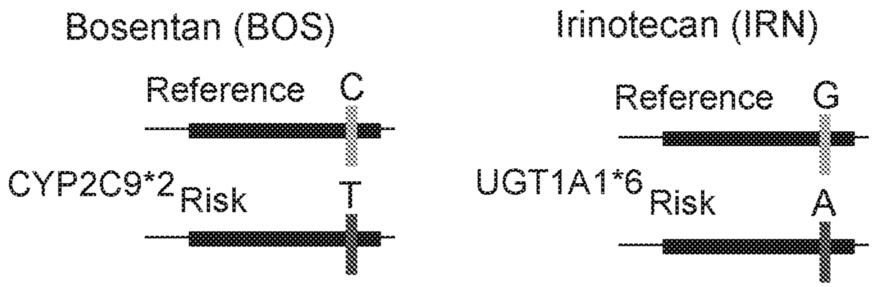
FIG. 3. Bosetan induced cholestasis is specific to CYP2C9*2 iPSC-liver organoids. A. Representative allele images of rs1799853 in CYP2C9*2 and rs4148323 in UGT1A1*6 show risk SNPs for DILI by Bosentan and Irinotecan, respectively. The table indicates the possession of risk alleles in each iPS cell line. B. Images of CLF transport activity and inhibition by Bosentan. C. CLF intensity levels in individual organoids derived from different 4 iPS cell lines. *: p<0.01, : p<1E-4, **: p<1E-8, Wilcoxon-Mann-Whitney Test. NS: not significant. In the box plots, the top and bottom of the box represent the 75th and 25th percentiles, the center line represents the median. Dot indicates the data from each organoid.
Figure 3B:
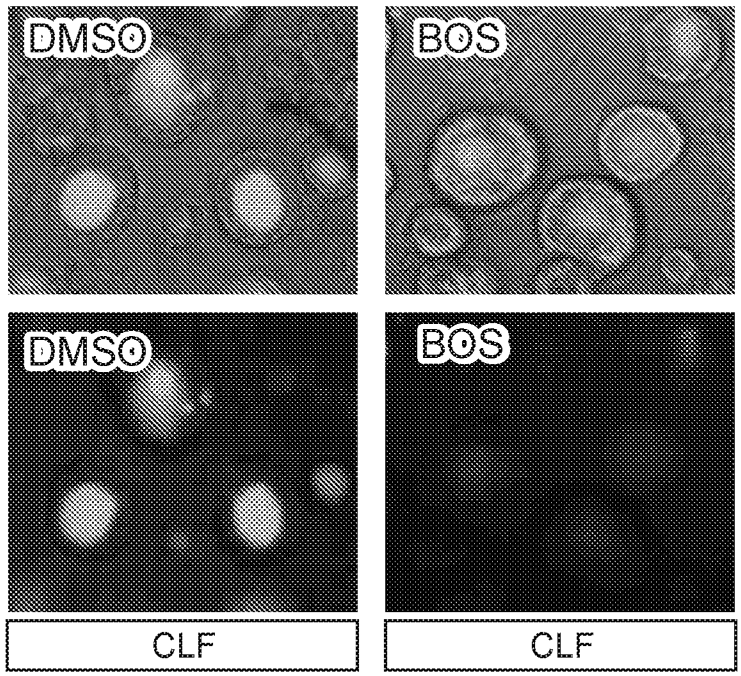
Figure 3C:
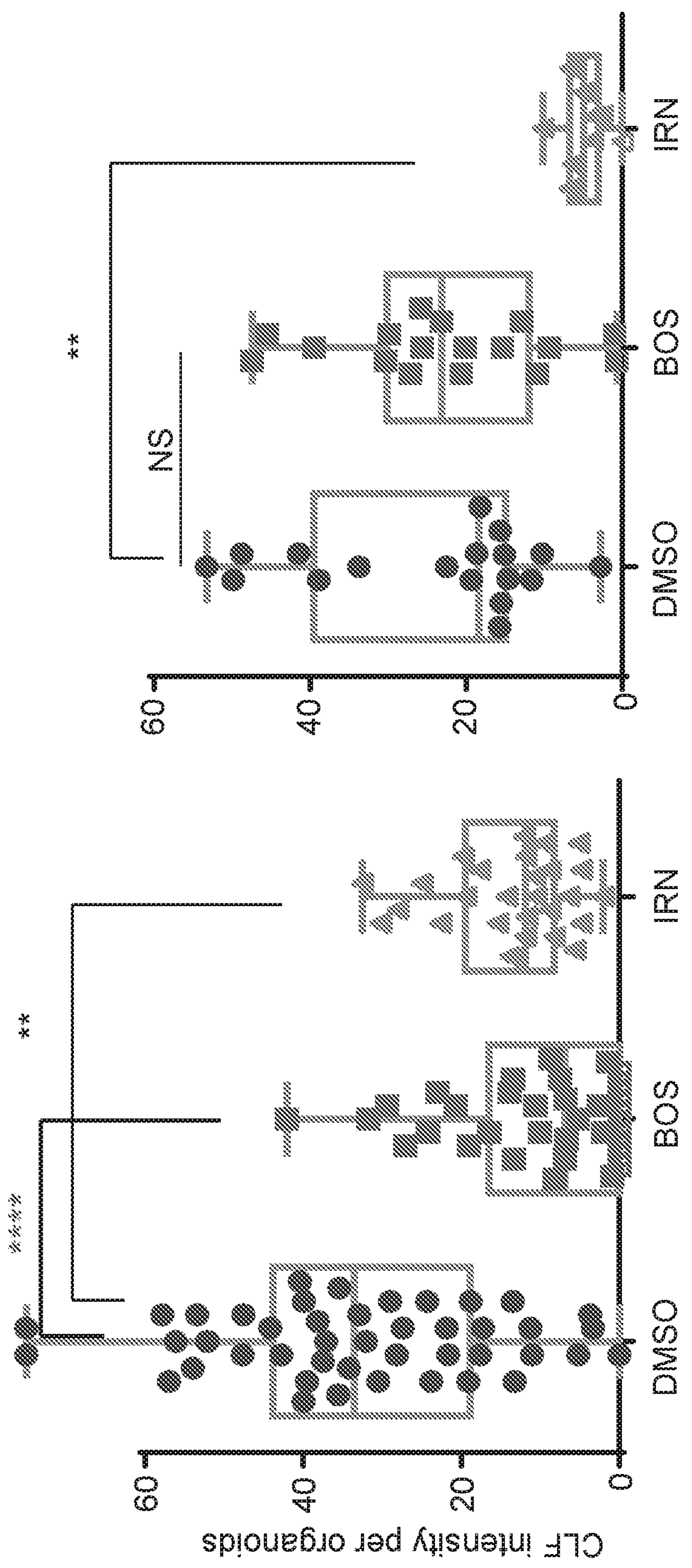
Figure 3D:
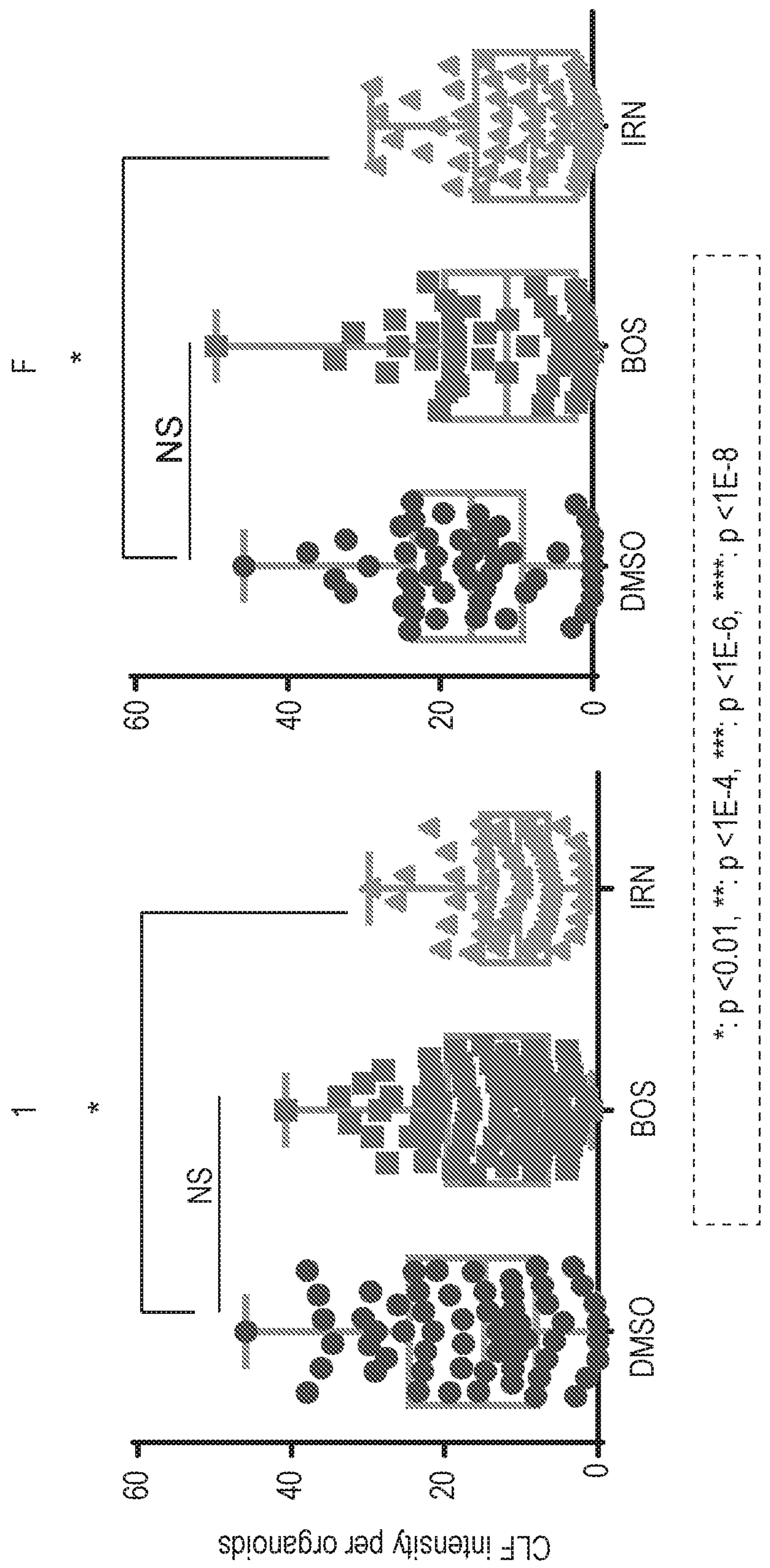
Figure 4A:
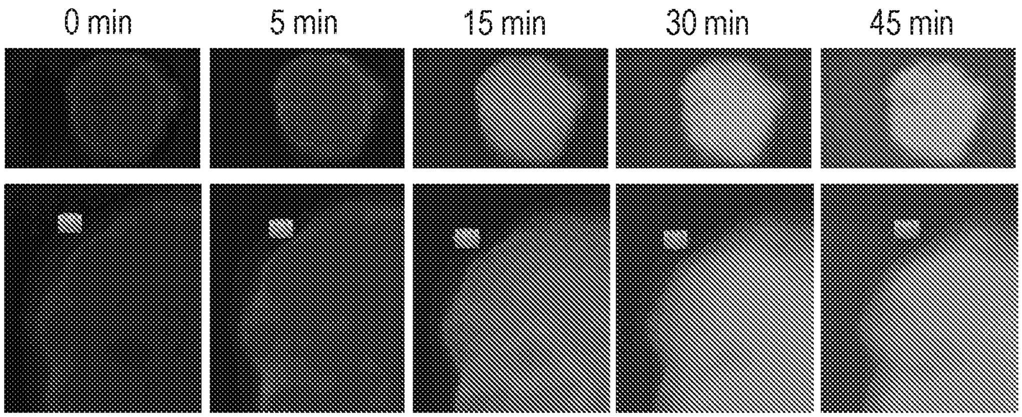
FIG. 4. High fidelity drug induced cholestasis model using organoids. A. Sequential images for efflux of fluorescein diacetate from outside to inside of the organoids. B. Comparison of fluorescein diacetate efflux transport. C. Quantification of fluorescein diacetate efflux transport into organoid. Example left image was quantified ratio of fluorescein intensity between inside and outside the organoid. Right graph indicates the result of validation study using control (DMSO), Cyclosporin A (CSA) and Streptomycin (STP) as negative control. Bars represent the mean±SD, **: p<0.01, n=4. D. Image of fluorescein diacetate transport inhibition after treatment of 9 training compounds for 24 h. E. Quantification of transport inhibition after treatment of training compounds, Bars represent the mean±SD, *: p<0.05, **: p<0.01, n=4-6. Quantification of MMP change after treatment of training compounds, Bars represent the mean±SD, *: p<0.05, **: p<0.01, n=4-5. CON: Control sample, STP: Streptomycin, TOL: Tolcapone, DICLO: Diclofenac, BOS: Bosentan, CSA: Cyclosporin A.
Figure 4B:
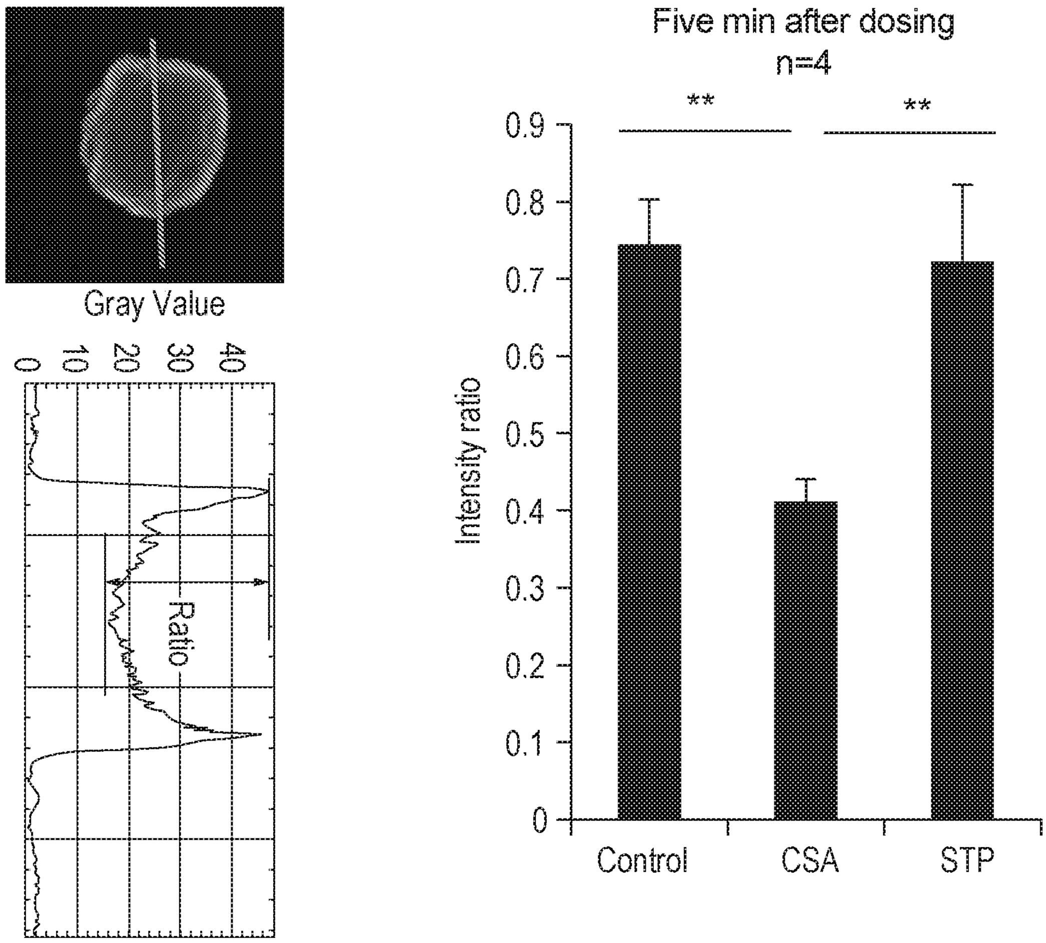
Figure 4C:
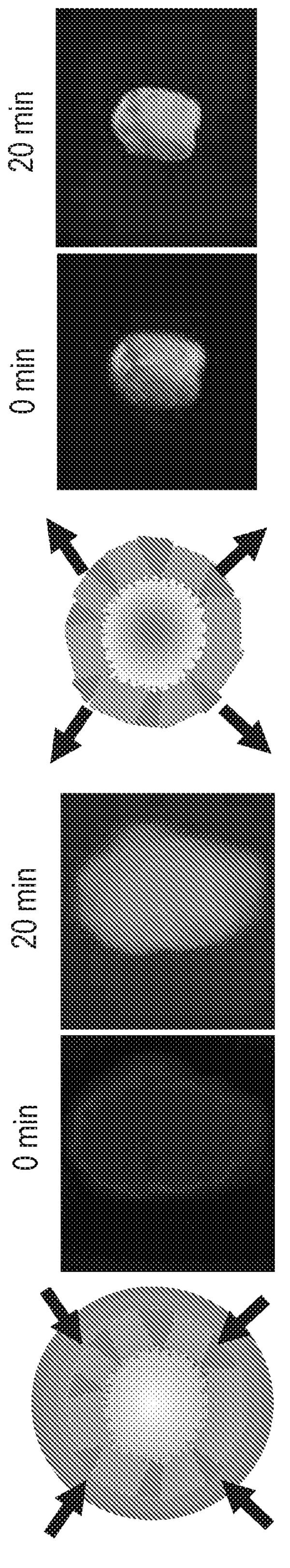
Figure 4D:
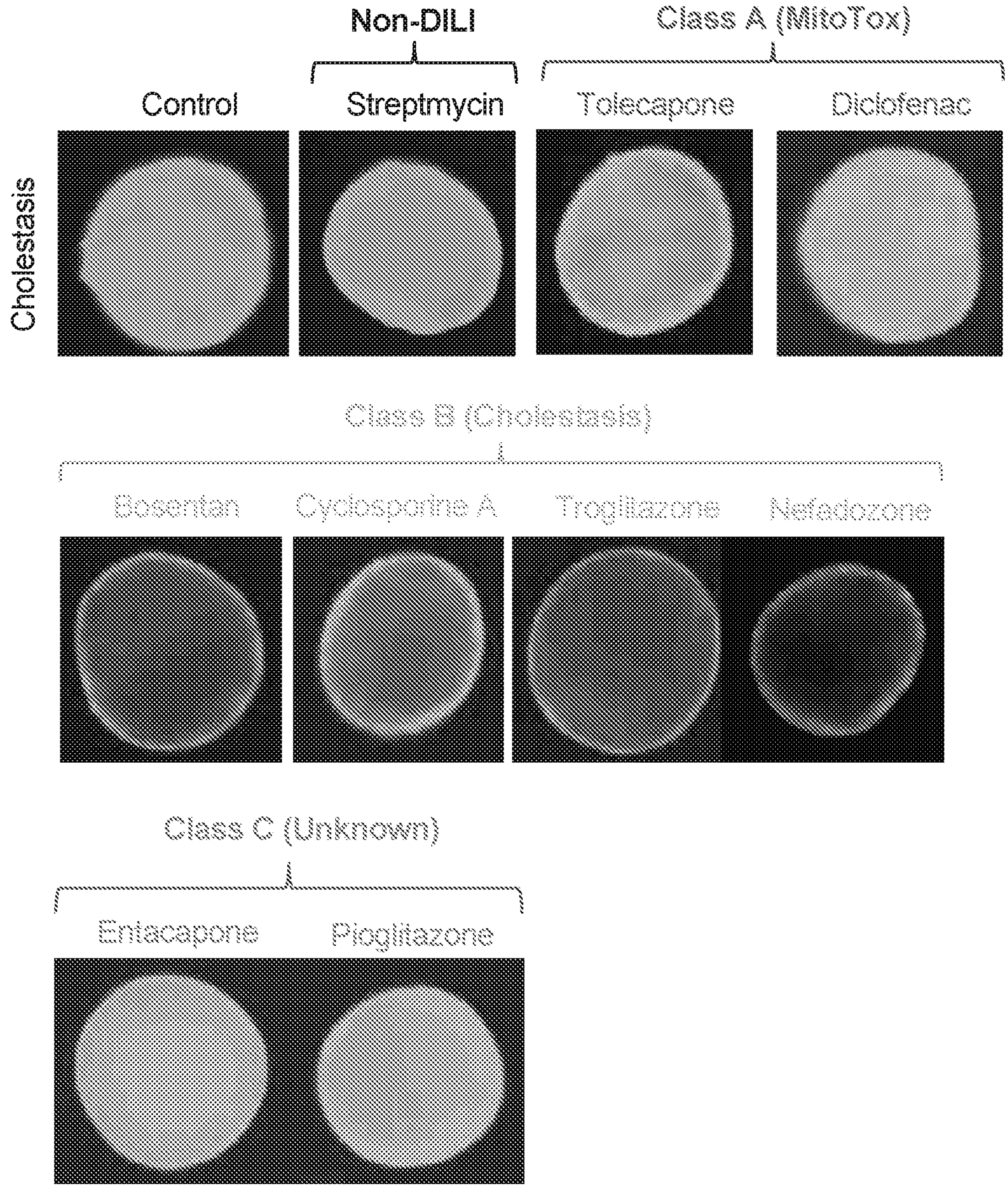
Figure 4E:
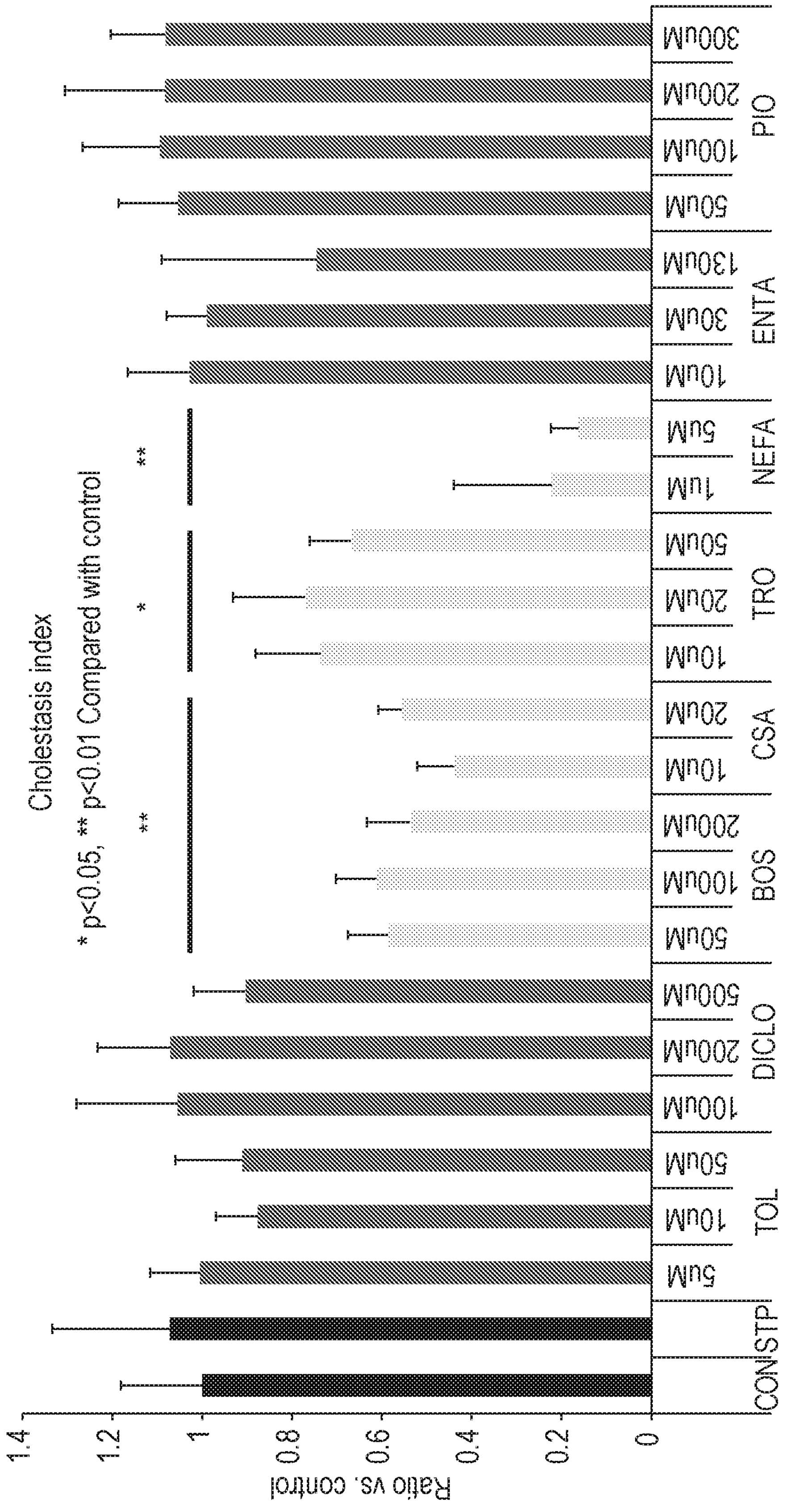

Unless otherwise noted, terms are to be understood according to conventional usage by those of ordinary skill in the relevant art.

The term “about” or “approximately” means within an acceptable error range for the particular value as determined by one of ordinary skill in the art, which will depend in part on how the value is measured or determined, e.g., the limitations of the measurement system. For example, “about” can mean within 1 or more than 1 standard deviation, per the practice in the art. Alternatively, “about” can mean a range of up to 20%, or up to 10%, or up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

As used herein, the term "totipotent stem cells" (also known as omnipotent stem cells) are stem cells that can differentiate into embryonic and extra-embryonic cell types. Such cells can construct a complete, viable organism. These cells are produced from the fusion of an egg and sperm cell. Cells produced by the first few divisions of the fertilized egg are also totipotent.

As used herein, the term "pluripotent stem cells (PSCs)" encompasses any cells that can differentiate into nearly all cell types of the body, i.e., cells derived from any of the three germ layers (germinal epithelium), including endoderm (interior stomach lining, gastrointestinal tract, the lungs), mesoderm (muscle, bone, blood, urogenital), and ectoderm (epidermal tissues and nervous system). PSCs can be the descendants of inner cell mass cells of the preimplantation blastocyst or obtained through induction of a non-pluripotent cell, such as an adult somatic cell, by forcing the expression of certain genes. Pluripotent stem cells can be derived from any suitable source. Examples of sources of pluripotent stem cells include mammalian sources, including human, rodent, porcine, and bovine.

As used herein, the term "induced pluripotent stem cells (iPSCs)," also commonly abbreviated as iPS cells, refers to a type of pluripotent stem cells artificially derived from a normally non-pluripotent cell, such as an adult somatic cell, by inducing a "forced" expression of certain genes. hiPSC refers to human iPSCs.

As used herein, the term "embryonic stem cells (ESCs)," also commonly abbreviated as ES cells, refers to cells that are pluripotent and derived from the inner cell mass of the blastocyst, an early-stage embryo. For purpose of the present invention, the term "ESCs" is used broadly sometimes to encompass the embryonic germ cells as well.

As used herein, the term "precursor cell" encompasses any cells that can be used in methods described herein, through which one or more precursor cells acquire the ability to renew itself or differentiate into one or more specialized cell types. In some embodiments, a precursor cell is pluripotent or has the capacity to becoming pluripotent. In some embodiments, the precursor cells are subjected to the treatment of external factors (e.g., growth factors) to acquire pluripotency. In some embodiments, a precursor cell can be a totipotent (or omnipotent) stem cell; a pluripotent stem cell (induced or non-induced); a multipotent stem cell; an oligopotent stem cells and a unipotent stem cell. In some embodiments, a precursor cell can be from an embryo, an infant, a child, or an adult. In some embodiments, a precursor cell can be a somatic cell subject to treatment such that pluripotency is conferred via genetic manipulation or protein/peptide treatment.

In developmental biology, cellular differentiation is the process by which a less specialized cell becomes a more specialized cell type. As used herein, the term "directed differentiation" describes a process through which a less specialized cell becomes a particular specialized target cell type. The particularity of the specialized target cell type can be determined by any applicable methods that can be used to define or alter the destiny of the initial cell. Exemplary methods include but are not limited to genetic manipulation, chemical treatment, protein treatment, and nucleic acid treatment.

Pluripotent Stem Cells Derived from Embryonic Cells

In some embodiments, one step is to obtain stem cells that are pluripotent or can be induced to become pluripotent. In some embodiments, pluripotent stem cells are derived from embryonic stem cells, which are in turn derived from totipotent cells of the early mammalian embryo and are capable of unlimited, undifferentiated proliferation in vitro. Embryonic stem cells are pluripotent stem cells derived from the inner cell mass of the blastocyst, an early-stage embryo. Methods for deriving embryonic stem cells from blastocytes are well known in the art. Human embryonic stem cells H9 (H9-hESCs) are used in the exemplary embodiments described in the present application, but it would be understood by one of skill in the art that the methods and systems described herein are applicable to any stem cells.

Additional stem cells that can be used in embodiments in accordance with the present invention include but are not limited to those provided by or described in the database hosted by the National Stem Cell Bank (NSCB), Human Embryonic Stem Cell Research Center at the University of California, San Francisco (UCSF); WISC cell Bank at the Wi Cell Research Institute; the University of Wisconsin Stem Cell and Regenerative Medicine Center (UW-SCRMC); Novocell, Inc. (San Diego, Calif.); Cellartis AB (Goteborg, Sweden); ES Cell International Pte Ltd (Singapore); Technion at the Israel Institute of Technology (Haifa, Israel); and the Stem Cell Database hosted by Princeton University and the University of Pennsylvania. Exemplary embryonic stem cells that can be used in embodiments in accordance with the present invention include but are not limited to SA01 (SA001); SA02 (SA002); ES01 (HES-1); ES02 (HES-2); ES03 (HES-3); ES04 (HES-4); ES05 (HES-5); ES06 (HES-6); BG01 (BGN-01); BG02 (BGN-02); BG03 (BGN-03); TE03 (13); TE04 (14); TE06 (16); UC01 (HSF1); UC06 (HSF6); WA01 (H1); WA07 (H7); WA09 (H9); WA13 (H13); WA14 (H14).

More details on embryonic stem cells can be found in, for example, Thomson et al., 1998, "Embryonic Stem Cell Lines Derived from Human Blastocysts," Science 282 (5391):1145-1147; Andrews et al., 2005, "Embryonic stem (ES) cells and embryonal carcinoma (EC) cells: opposite sides of the same coin," Biochem Soc Trans 33:1526-1530; Martin 1980, "Teratocarcinomas and mammalian embryogenesis,". Science 209 (4458):768-776; Evans and Kaufman, 1981, "Establishment in culture of pluripotent cells from mouse embryos," Nature 292(5819): 154-156; Klimanskaya et al., 2005, "Human embryonic stem cells derived without feeder cells," Lancet 365 (9471): 1636-1641; each of which is hereby incorporated herein in its entirety.

Induced Pluripotent Stem Cells (iPSCs)

In some embodiments, iPSCs are derived by transfection of certain stem cell-associated genes into non-pluripotent cells, such as adult fibroblasts. Transfection is typically achieved through viral vectors, such as retroviruses. Transfected genes include the master transcriptional regulators Oct-3/4 (Pouf51) and Sox2, although it is suggested that other genes enhance the efficiency of induction. After 3-4 weeks, small numbers of transfected cells begin to become morphologically and biochemically similar to pluripotent stem cells, and are typically isolated through morphological selection, doubling time, or through a reporter gene and antibiotic selection. As used herein, iPSCs include but are not limited to first generation iPSCs, second generation iPSCs in mice, and human induced pluripotent stem cells. In some embodiments, a retroviral system is used to transform human fibroblasts intopluripotent stem cells using four pivotal genes: Oct3/4, Sox2, Klf4, and c-Myc. In alternative embodiments, a lentiviral system is used to transform somatic cells with OCT4, SOX2, NANOG, and LIN28. Genes whose expression are induced in iPSCs include but are not limited to Oct-3/4 (e.g., Pou5fl); certain members of the Sox gene family (e.g., Sox1, Sox2, Sox3, and Sox15); certain members of the Klf family (e.g., Klf1, Klf2, Klf4, and Klf5), certain members of the Myc family (e.g., C-myc, L-myc, and N-myc), Nanog, and LIN28.

In some embodiments, non-viral based technologies are employed to generate iPSCs. In some embodiments, an adenovirus can be used to transport the requisite four genes into the DNA of skin and liver cells of mice, resulting in cells identical to embryonic stem cells. Since the adenovirus does not combine any of its own genes with the targeted host, the danger of creating tumors is eliminated. In some embodiments, reprogramming can be accomplished via plasmid without any virus transfection system at all, although at very low efficiencies. In other embodiments, direct delivery of proteins is used to generate iPSCs, thus eliminating the need for viruses or genetic modification. In some embodiment, generation of mouse iPSCs is possible using a similar methodology: a repeated treatment of the cells with certain proteins channeled into the cells via poly-arginine anchors was sufficient to induce pluripotency. In some embodiments, the expression of pluripotency induction genes can also be increased by treating somatic cells with FGF2 under low oxygen conditions.

More details on embryonic stem cells can be found in, for example, Kaji et al., 2009, "Virus free induction of pluripotency and subsequent excision of reprogramming factors," Nature 458:771-775; Woltjen et al., 2009, "piggyBac transposition reprograms fibroblasts to induced pluripotent stem cells," Nature 458:766-770; Okita et al., 2008, "Generation of Mouse Induced Pluripotent Stem Cells Without Viral Vectors," Science 322(5903):949-953; Stadtfeld et al., 2008, "Induced Pluripotent Stem Cells Generated without Viral Integration," Science 322(5903):945-949; and Zhou et al., 2009, "Generation of Induced Pluripotent Stem Cells Using Recombinant Proteins," Cell Stem Cell 4(5):381-384; each of which is hereby incorporated herein in its entirety.

In some embodiments, exemplary iPS cell lines include but not limited to iPS-DF19-9; iPS-DF19-9; iPS-DF4-3; iPS-DF6-9; iPS(Foreskin); iPS(IMR90); and iPS(IMR90).

More details on the functions of signaling pathways relating to DE development can be found in, for example, Zorn and Wells, 2009, "Vertebrate endoderm development and organ formation," Annu Rev Cell Dev Biol 25:221-251; Dessimoz et al., 2006, "FGF signaling is necessary for establishing gut tube domains along the anterior-posterior axis in vivo," Mech Dev 123:42-55; McLin et al., 2007, "Repression of Wnt/β-catenin signaling in the anterior endoderm is essential for liver and pancreas development. Development," 134:2207-2217; Wells and Melton, 2000, Development 127:1563-1572; de Santa Barbara et al., 2003, "Development and differentiation of the intestinal epithelium," Cell Mol Life Sci 60(7): 1322-1332; each of which is hereby incorporated herein in its entirety.

Any methods for producing definitive endoderm from pluripotent cells (e.g., iPSCs or ESCs) are applicable to the methods described herein. Any method for producing definitive endoderm from pluripotent cells (e.g., iPSCs or ESCs) are applicable to the methods described herein. Exemplary methods are disclosed in, for example, "Methods and systems for converting precursor cells into intestinal tissues through directed differentiation," U.S. Pat. No. 9,719,068B2 to Wells et al., and "Methods and systems for converting precursor cells into gastric tissues through directed differentiation," US20170240866A1, to Wells et al. In some embodiments, pluripotent cells are derived from a morula. In some embodiments, pluripotent stem cells are stem cells. Stem cells used in these methods can include, but are not limited to, embryonic stem cells. Embryonic stem cells can be derived from the embryonic inner cell mass or from the embryonic gonadal ridges. Embryonic stem cells or germ cells can originate from a variety of animal species including, but not limited to, various mammalian species including humans. In some embodiments, human embryonic stem cells are used to produce definitive endoderm. In some embodiments, human embryonic germ cells are used to produce definitive endoderm. In some embodiments, iPSCs are used to produce definitive endoderm. Additional methods for obtaining or creating DE cells that can be used in the present invention include but are not limited to those described in U.S. Pat. No. 7,510,876 to D'Amour et al.; U.S. Pat. No. 7,326,572 to Fisk et al.; Kubol et al., 2004, "Development of definitive endoderm from embryonic stem cells in culture," Development 131:1651-1662; D'Amour et al., 2005, "Efficient differentiation of human embryonic stem cells to definitive endoderm," Nature Biotechnology 23:1534-1541; and Ang et al., 1993, "The formation and maintenance of the definitive endoderm lineage in the mouse: involvement of HNF3/forkhead proteins," Development 119:1301-1315.

Applicant has discovered methods for producing 3D liver structures using human iPSCs. The structures comprise micro-liver architectures, including polarized hepatic epithelium, stellate cells, and canalicula structures. The disclosed compositions display improvements in hepatic functions, bile transport activity, and durability compared to existing models. The 3D structures model may be used as a new and robust model for drug screening tests and/or drug toxicity screening, transplantation, production of serum protein products, and development of personalized therapy. In one particular application, the compositions and methods may be used to screen drug compounds for liver toxicity.

While 3D aggregated liver cells have been reported, the disclosed compositions have very high functional activity such as albumin production (up to a 10-fold increase compared with conventional highest standard models using iPSC-derived hepatocytes), and allow for improved oxygen and/or nutrition supply due to the internal luminal structure, which allows for much longer culture (at least over 60 days) and a long-term testing platform useful for drug testing. The disclosed compositions may also be useful for production of plasma products like albumin, coagulation factor products for treatment of hypoalbuminemia, and for therapeutic transplantation, in which the human iPSC-derived miniature livers can be transplanted to treat disorders in vivo. Lastly, the disclosed compositions may be used for personalized medicine (therapy personalization).

In one aspect, a method of inducing formation of a liver organoid from iPSC cells is disclosed. The method may comprise the steps of a) contacting definitive endoderm (DE) derived from iPSC cells with a FGF pathway activator and an activator of the Wnt signaling pathway (which may be activated by a GSK3 inhibitor), for a period of time sufficient to form posterior foregut spheroids, preferably for a period of time of from about 1 day to about 3 days and b) incubating the resulting posterior foregut spheroids of step a in the presence of retinoic acid (RA) for a period of time sufficient to form a liver organoid, preferably for a period of time of from about 1 to about 5 days, preferably about 4 days.

Fibroblast growth factors (FGFs) are a family of growth factors involved in angiogenesis, wound healing, and embryonic development. The FGFs are heparin-binding proteins and interactions with cell-surface associated heparan sulfate proteoglycans have been shown to be essential for FGF signal transduction. Suitable FGF pathway activators will be readily understood by one of ordinary skill in the art. Exemplary FGF pathway activators include, but are not limited to: one or more molecules selected from the group consisting of FGF1, FGF2, FGF3, FGF4, FGF8, FGF9, FGF10, FGF11, FGF12, FGF13, FGF14, FGF15, FGF16, FGF17, FGF18, FGF19, FGF20, FGF21, FGF22, and FGF23. In some embodiments, siRNA and/or shRNA targeting cellular constituents associated with the FGF signaling pathway may be used to activate these pathways.

In some embodiments, DE culture is treated with the one or more molecules of the FGF signaling pathway described herein at a concentration of 10 ng/ml or higher; 20 ng/ml or higher; 50 ng/ml or higher; 75 ng/ml or higher; 100 ng/ml or higher; 120 ng/ml or higher; 150 ng/ml or higher; 200 ng/ml or higher; 500 ng/ml or higher; 1,000 ng/ml or higher; 1,200 ng/ml or higher; 1,500 ng/ml or higher; 2,000 ng/ml or higher; 5,000 ng/ml or higher; 7,000 ng/ml or higher; 10,000 ng/ml or higher; or 15,000 ng/ml or higher. In some embodiments, concentration of signaling molecule is maintained at a constant throughout the treatment. In other embodiments, concentration of the molecules of a signaling pathway is varied during the course of the treatment. In some embodiments, a signaling molecule in accordance with the present invention is suspended in media comprising DMEM and fetal bovine serine (FBS). The FBS can be at a concentration of 2% and more; 5% and more; 10% or more; 15% or more; 20% or more; 30% or more; or 50% or more. One of skill in the art would understand that the regiment described herein is applicable to any known molecules of the signaling pathways described herein, alone or in combination, including but not limited to any molecules in the FGF signaling pathway.

Suitable FGF signaling pathway activators will be readily appreciated by one of skill in the art. In one aspect, the FGF signaling pathway activator may be selected from a small molecule or protein FGF signaling pathway activator, FGF1, FGF2, FGF3, FGF4, FGF8, FGF9, FGF10, FGF11, FGF12, FGF13, FGF14, FGF15, FGF16, FGF17, FGF18, FGF19, FGF20, FGF21, FGF22, FGF23, or combinations thereof. The WNT signaling pathway activator may be selected from a small molecule or protein Wnt signaling pathway activator such as Lithium Chloride; 2-amino-4,6-disubstituted pyrimidine (hetero) arylpyrimidines; IQ1; QS11; NSC668036; DCA beta-catenin; 2-amino-4-[3,4-(methylenedioxy)-benzyl-amino]-6-(3-methoxyphenyl) pyrimidine, Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11, Wnt16, a GSK3 inhibitor, preferably CHIRON, R-spondin, or combinations thereof. In one aspect, the BMP activator may be selected from BMP2, BMP4, BMP7, BMP9, small molecules that activates the BMP pathway, proteins that activate the BMP pathway, and may include the following: Noggin, Dorsomorphin, LDN189, DMH-1, ventromophins, and combinations thereof. Suitable GSK3 inhibitors will be readily understood by one of ordinary skill in the art. Exemplary GSK3 inhibitors include, but are not limited to: Chiron/CHIR99021, for example, which inhibits GSK3β. One of ordinary skill in the art will recognize GSK3 inhibitors suitable for carrying out the disclosed methods. The GSK3 inhibitor may be administered in an amount of from about 1 uM to about 100 uM, or from about 2 uM to about 50 uM, or from about 3 uM to about 25 uM. One of ordinary skill in the art will readily appreciate the appropriate amount and duration. In some aspects, siRNA and/or shRNA targeting cellular constituents associated with the Wnt and/or FGF signaling pathways may be used to activate these pathways.

In one aspect, the stem cells may be mammalian, or human, iPSCs.

In one aspect, the foregut spheroids may be embedded in a basement membrane matrix, such as, for example, the commercially available basement membrane matrix sold under the tradename Matrigel.

In one aspect, the liver organoids may be characterized in that the liver organoids may express alpha-fetoprotein (AFP), albumin (ALB), retinol binding protein (RBP4), cytokeratin 19 (CK19), hepatocyte nuclear factor 6 (HNF6), and cytochrome P450 3A4 (CYP3A4), HNF4a, E-cadherin, DAPI, and Epcam. Such expression may occur, for example, at day 40 to day 50. The expression level may be similar to that observed in human liver cells, for example, that of an adult liver cell.

In one aspect, the liver organoid may be characterized in that the liver organoid has bile transport activity.

In one aspect, the liver organoid may be derived from a stem cell and may comprise a luminal structure further containing internalized microvilli and mesenchymal cells. The luminal structure may be surrounded by polarized hepatocytes and a basement membrane. The liver organoid may comprise functional stellate cells and functional Kupffer cells.

The liver organoid may, in certain aspects, be characterized by having one or more of the following: bile production capacity, bile transport activity, Complement factor H expression of at least 50 ng/mL/1xe$^6$ cells/24 hr, Complement factor B of at least 40 ng/mL/1xe$^6$ cells/24 hr, C3 expression of at least 1000 ng/mL/1xe$^6$ cells/24 hr; C4 expression of at least 1000 ng/mL/1xe$^6$ cells/24 hr, fibrinogen production of at least 1,000 ng/mL/1xe$^6$ cells/24 hr and albumin production of at least 1,000 ng/mL/1xe$^6$ cells/24 hr. In one aspect, the liver organoid may be characterized by having total hepatic protein expression of at least 10,000 ng/mL 1xe$^6$ cells/24 hours. The liver organoid may be characterized in that it may express one or more genes selected from PROX1, RBP4, CYP2C9, CYP3A4, ABCC11, CFH, C3, C5, ALB, FBG, MRP2, ALCAM, CD68, CD34, CD31. In one aspect, the liver organoid may comprise cells comprising a drug metabolism cytochrome variant, such as, for example, a CY2C9*2 variant. The liver organoid may comprise a vasculature, such as that described in US 20160177270.

In one aspect, the liver organoid may be characterized in that the liver organoid does not comprise inflammatory cells, for example T-cells or other inflammatory secreted proteins.

In one aspect, a method of screening for a serious adverse event (SAE) is disclosed. The SAE may be liver failure and/or drug induced liver injury (DILI). The method may include the step of contacting a drug of interest, of which toxicity is of interest, with a liver organoid as described herein. In one aspect, the method may comprise the step of measuring intake and/or efflux of fluorescein diacetate (FD), wherein impaired efflux indicates that said drug is likely to induce a serious adverse event. The toxicity of a drug of interest may be determined by measurement of a parameter selected from mitochondria membrane potential, measurement of ROS, swelling of liver mitochondria, and combinations thereof, wherein injury to said mitochondria indicates that said drug is likely to induce a serious adverse event. In one aspect, the method comprises the step of assaying organoid viability, wherein impaired or decreased organoid viability indicates that said a drug of interest is likely to induce a serious adverse event.

In one aspect, a method of treating an individual having liver damage is disclosed, wherein the method may comprise the step implanting a liver organoid as described herein into an individual in need thereof. The liver damage may include, for example, metabolic liver disease, end stage liver disease, or a combination thereof.

In one aspect, methods for identifying a preferred therapeutic agent for an individual are disclosed. In this aspect, the method may include the step of contacting a liver organoid derived from an iPSC of interest with a candidate compound, such as wherein the iPSC of interest comprises one or more mutations found in said individual, or such as wherein said iPSC of interest is derived from the same ethic background of said individual, or further, wherein said iPSC of interest is derived from said individual.

EXAMPLES

In the present study, Applicant tested bile transport activity using Fluorescein Diacetate, which was excreted by MRP2 across the canalicular membrane into the bile canalicular networks (Tian et al., 2004). It has previously been reported that Troglitazone and Cyclosporin inhibit the MRP2 (Chang et al., 2013; Lechner et al., 2010). In addition, the efflux transporter MRP2 mediates export of Bosentan (Fahrmayr et al., 2013). Although the inhibition of MRP2 by Nefazodone was not reported, mitochondria stress by Nefazodone may be related to a decrease of the bile transport activity, efflux of Fluorescein Diacetate, because MRP2 is an ATP-dependent bile salt transporter for canalicular excretion of bile acids in hepatocytes.

Preclinical detection of risk compounds for drug induced liver injury (DILI) remains a significant challenge in drug development, highlighting a need for a predictive human system. Here, Applicant developed a human liver organoid (HLO) model for analyzing clinical DILI pathology at organoid resolution. Differentiated HLO from human iPSC contain polarized hepatocytes with an internal lumen lined by bile canaliculi-like architecture, establishing the unidirectional bile acid transport pathway. Applicant has leveraged the organoid's structural features by modeling DILI using live organoid imaging, called LoT (Liver organoid-based Toxicity screen). LoT is functionally validated with 10 marketed drugs and 5 different donors based on cholestatic and/or mitochondrial toxicity. Bosentan-induced cholestasis is specific to CYP2C9 poor metabolizer donor-derived HLO. Interestingly, steatotic organoids were vulnerable to Rosiglitazone toxicity as suggested in clinics, followed by chemical rescue from massive organoid death. Thus, LoT is a high-fidelity organoid model that can be used to analyze drug safety, and is further a cost-effective platform, facilitates compound optimization, provides mechanistic studies, and produces personalized medicine as well as anti-DILI therapy screening applications.

Billions of dollars are lost annually from drug development in the pharmaceutical industry due to the failures of drug candidates identified in initial screens, and nearly (a third or one-third) of drugs are withdrawn from the market (Takebe and Taniguchi, 2014). Despite the promising efficacy, a failure of drug candidates results in a tremendous loss of a patient's treatment opportunity. Preclinical studies generally consist of an in vitro evaluation as a primary efficacy screen to identify a "hit" compound, followed by safety studies in vitro and in vivo to assess the mechanisms of metabolism and toxicology. This inefficiency can be explained by the substantial lack of physiologically relevant preclinical models in evaluating drug induced liver injury (DILI) in humans and thus, an urgent need to develop an in vitro humanistic screen model for the evaluation of the vast amounts of continuously growing compound libraries.

Primary hepatocytes are a highly polarized metabolic cell type, and form a bile canaliculi structure with microvilli-lined channels, separating peripheral circulation from the bile acid secretion pathway. The most upstream aspects of DILI include drug (or their reactive metabolites) detoxification by hepatocytes and excretion into bile canaliculi through transporters such as multi-drug resistance-associated protein (MRP) transporters. This suggests the need to reconstruct these uniquely organized structures as a crucial property of hepatocytes in vivo for predicting DILI pathology. However, there are considerable differences in drug toxicity profiles between the current simplified culture model with the use of isolated primary human hepatocytes or hepatic cell lines, and in vivo physiology, resulting in failed translation of drugs or drug discontinuation, as in the case of Troglitazone, Nefazodone and Tolcapone (https://livertox.nlm.nih.gov/index.html). The determination of toxicological properties thus mainly relies on animals as an essential step for drug development, however, due to the pronounced differences in physiology between humans and animals, there is a significant lack of fidelity to human outcomes (Leslie et al., 2007; Yang et al., 2014). In addition, the onset of idiosyncratic DILI (IDILI), which is very rare but nonetheless responsible for about 10-15% of acute liver failures in the USA (Reuben et al., 2010), is almost impossible to predict (Kullak-Ublick et al., 2017). Collectively, effective human cell models are eagerly anticipated to screen for compounds that test the detoxification and excretion of proposed drugs.

Despite the progressive advance of human hepatocyte differentiation methods from pluripotent stem cell (PSC), clinical trials in a dish using human stem cells remains 'hype'. To a certain degree, this can be explained by challenges in previous cell-based approaches including: (1) overcoming lot-differences, (2) minimization of experimental batch-differences, (3) enhancement of assay throughput and (4) improvement in relevance to clinical trial data. Applicant addresses these issues by developing a relatively simple and robust organoid based testing platform using stably expandable human stem cells, i.e. iPSC. Applicant first directed the human PSCs into posterior foregut organoids, followed by progressive hepatocyte differentiation through a polarization culture with defined factors and matrix. Generated human liver organoids possessed intraluminal structure surrounded by polarized hepatocytes, and have shown to be capable of performing critical human hepatocyte functions including protein and bile acid production and transport functions. Interestingly, Applicant found that live image based dynamic detection of fluorescent diacetate uptake and excretion precisely models cholestasis induced by arrays of DILI drugs characterized as inhibitors for bile excretion with a high level of reproducibility. Separately, mitochondrial membrane potential assessment enabled an independent risk assessment for each of the compound, reflecting a conventional classification of DILI drugs established by clinical trials. Furthermore, Applicant extended the approach to model conditions induced by lipotoxic stress and confirmed enhanced DILI potential through reactive oxygen species (ROS) production. Organoid-based viability assessment confirmed the reversal of DILI by N-acetylcysteine, highlighting the potential of Applicant's approach for anti-DILI drug screening. Taken together, this robust assay, named Liver Organoid based Toxicity screen (LoT), is believed to be the first functional readout developed in human liver organoids, and will facilitate diagnosis, functional studies, drug development and personalized medicine.

Results

Figure 8A:
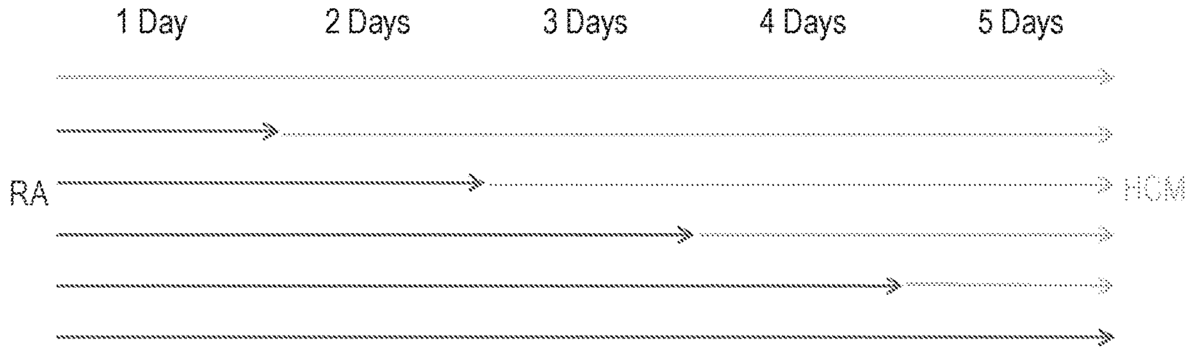
FIG. 8. Optimization of retinoic acid treatment protocols A. Scheme for timing and duration of retinoic acid treatment. RA: retinoic acid, HCM: hepatocyte culture medium. B. Albumin secretion level in organoids at day 25 in different duration of RA treatment.
Figure 8B:
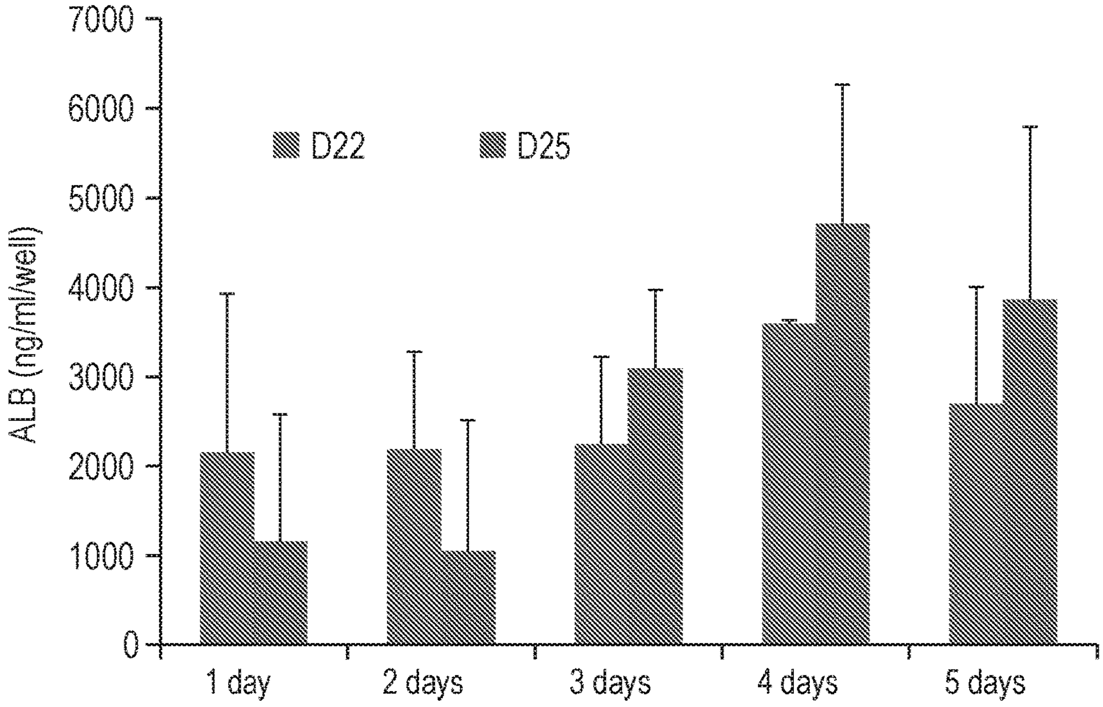
Figure 9:
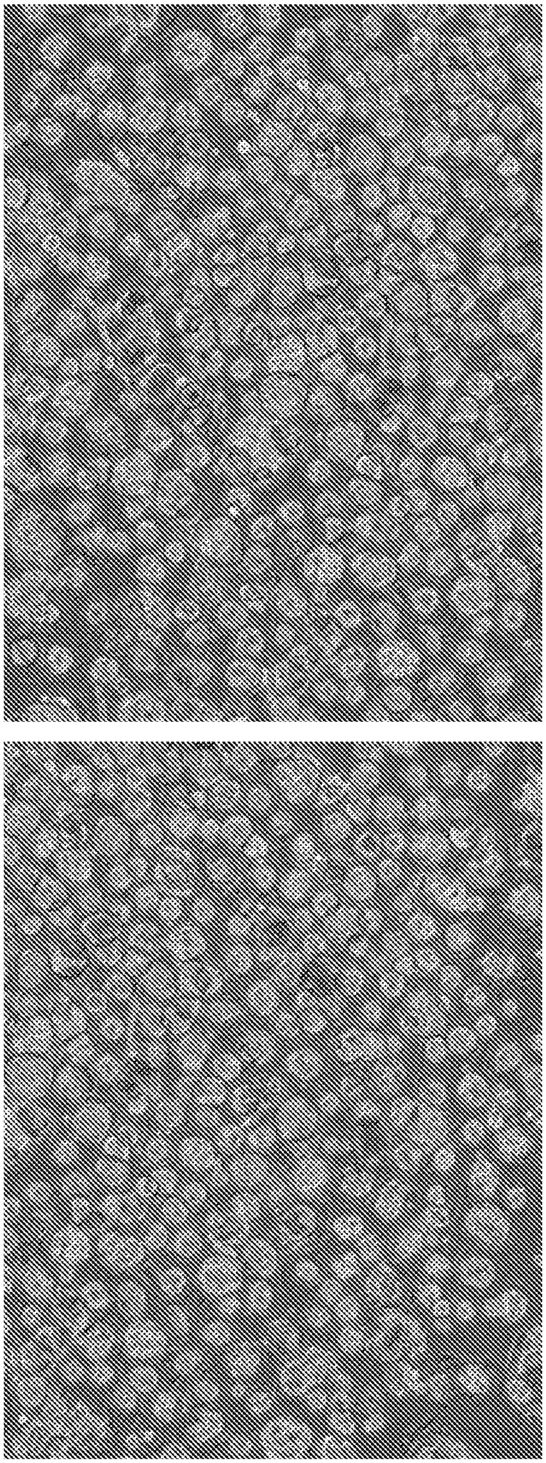
FIG. 9. The morphology of organoids at D20 Total number of organoid at D20 were 305. Organoid with lumen: 216, Organoids without lumen: 89.

Generation and Characterization of Polarized Liver Organoids from Multiple Human iPSC Applicant first established a new liver organoid differentiation method by using human iPSC-derived foregut spheroids (Spence et al., 2011) (FIG. 1A). As a first step, Applicant used BMP and Activin A to promote differentiation into definitive endoderm as previously described (D'Amour et al., 2005). In addition, FGF4, and a GSK3 inhibitor (CHIR99021) were used to induce foregut spheroids and budded spheroids were observed. Organoids were embedded in Matrigel after delamination with mesenchymal cells plated on the dish by gentle pipetting. It has been reported that retinoic acid (RA) enhances cell polarity as indicated by increased size and complexity of the bile canaliculi and the pericanalicular sheaths (Falasca et al., 1998). To generate polarized organoids suited for bile transport modeling, organoids were treated with RA. To optimize the organoid generation method, Applicant first varied the duration of RA treatment. The albumin secretion levels of organoids were 1160, 1054, 3092, 4709 and 3865 ng/mL at D25, for 1, 2, 3, 4 and 5 days of RA treatment, respectively, and the 4 day-RA treatment protocol tended to reach the highest level (FIG. 8). Thus, duration of RA was set for 4 days based on the level of albumin secretion. Morphologically, around 10 days after RA treatment, over 300 organoids covered with epithelial cells were successfully generated, and the ratio of organoids with lumenized structure was 71% (216/305) (FIG. 1, panel B and FIG. 9). Immunohistochemistry analysis revealed that albumin was positive in epithelial cells of organoids, and interestingly, Type IV collagen was localized to the outer surface and ZO-1 (zonula occludens) stained the intraluminal lining, suggesting that these organoids have polarized characteristics (FIG. 1, panel C).

Figure 10A:
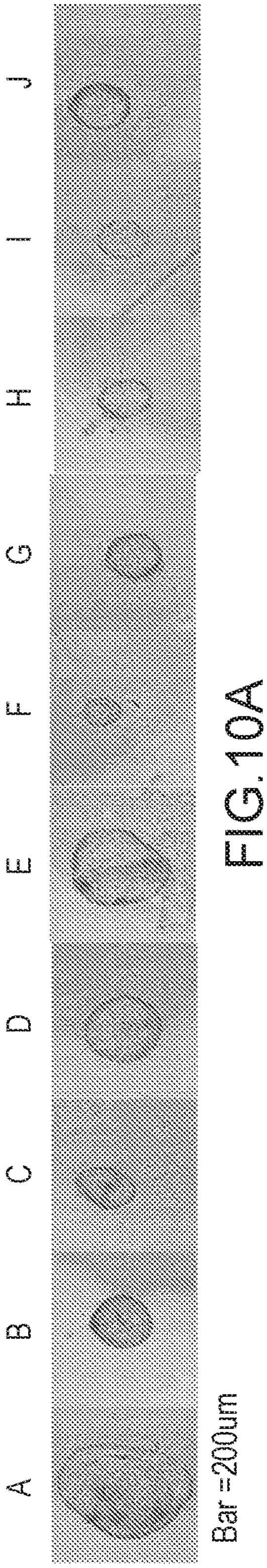
FIG. 10. Conversion formula to determine the number of cells in organoids A. Phase contrast image of single organoids. B. The diameter and cell number of each single organoid. C. Correlation between diameter and cell number in single organoid.
Figure 10B:
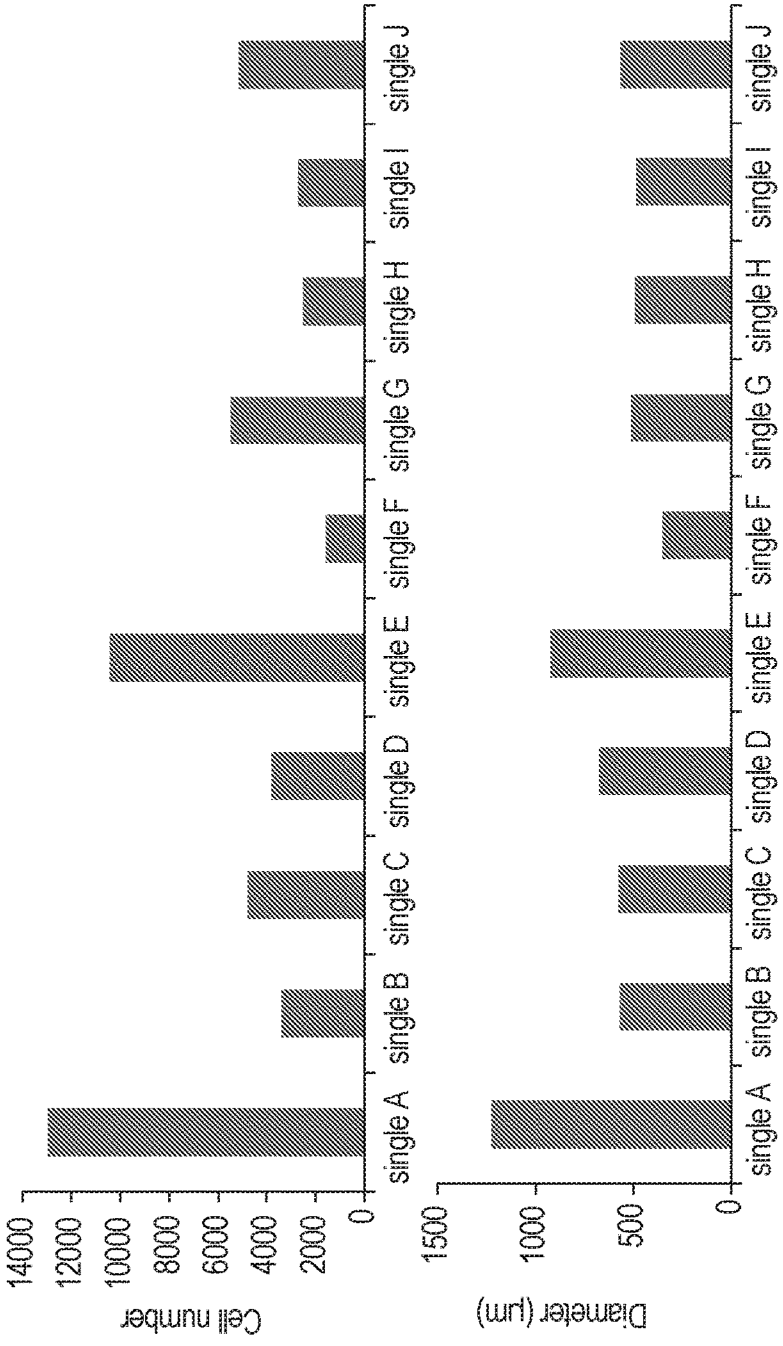
Figure 10C:
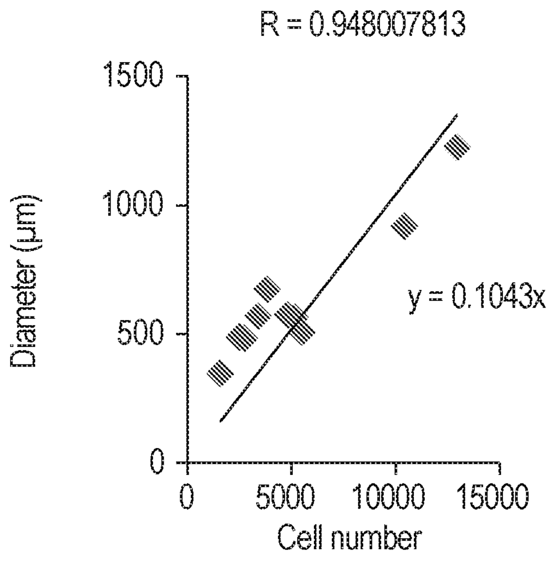
Figure 11:
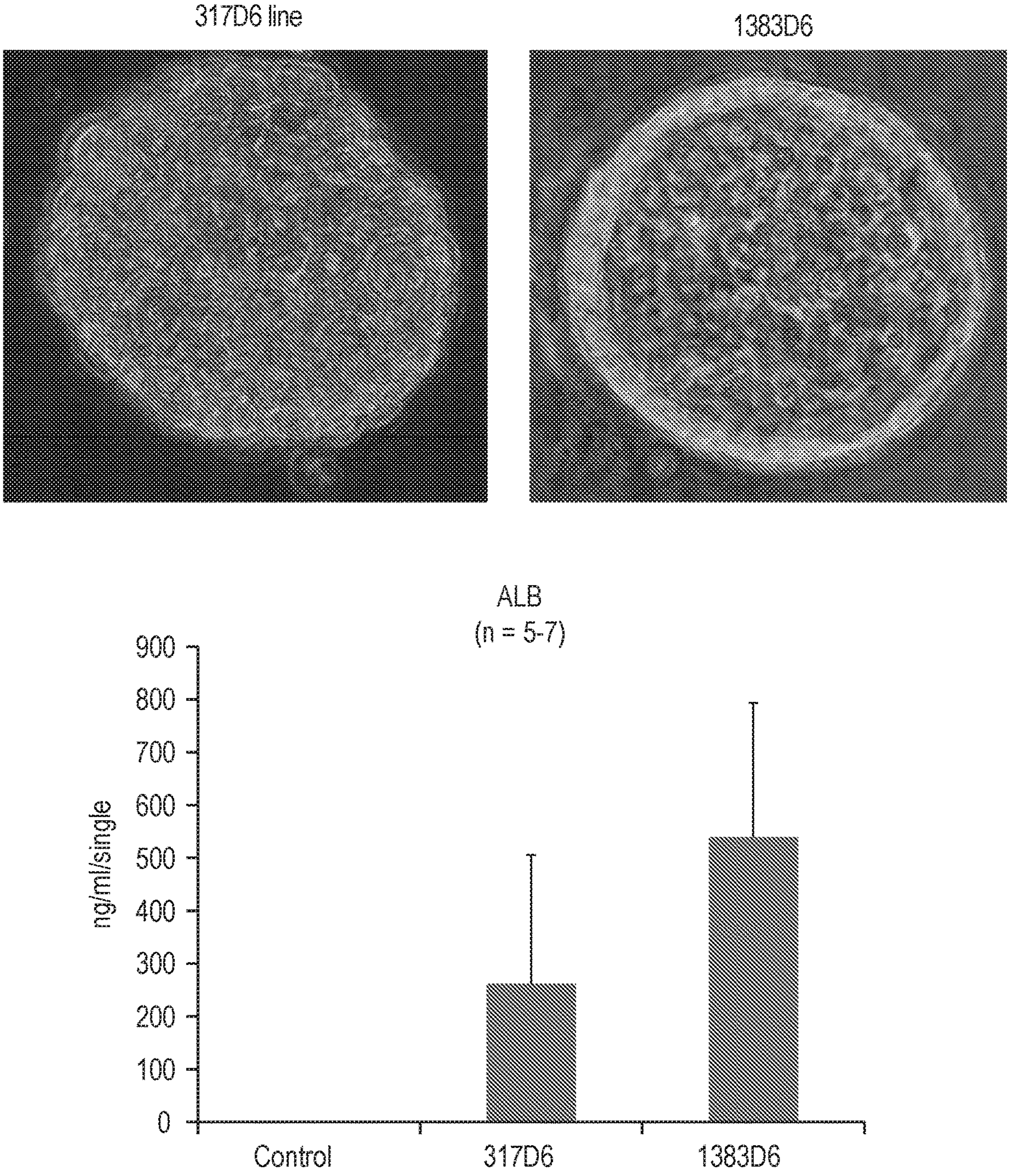
FIG. 11—Supplementary FIG. 4 The generation of organoids from multiple PSC lines. Phase contrast image and albumin secretion level of different iPS cell line (317D6 and 1383D6)-derived organoid.

Quantitative polymerase chain reaction (qPCR) analysis revealed that cells in organoids had a significant increase in expression of hepatic marker genes such as alpha-fetoprotein (AFP), albumin (ALB), retinol binding protein 4 (RBP4), Cytokeratin 19 (CK19), hepatocyte nuclear factor 6 (HNF6) which controls cholangiocyte differentiation, and Cytochrome P450 3A4 (CYP3A4) during differentiation (FIG. 1, panel D). However, the expression level of the most hepatic genes extracted from bulk organoid-derived RNA was lower in organoids than in primary hepatocytes. Without intending to be limited by theory, it is believed that these distinct mRNA profiles are partly due to the presence of stromal lineages as approximately 30% of cells are non-parenchymal cells which were identified by stromal cell markers (Unpublished observation), making the organoids more similar to in vivo liver tissue than primary hepatocytes. Applicant further profiled the organoids by a comprehensive gene expression analysis using RNA-sequence (RNA-seq). Principal component analysis demonstrated that gene expression in organoids was not similar to iPSC-derived cholangiocytes and normal human cholangiocyte (FIG. 1, panel E). Additionally, hepatocyte specific proteins such as ALB, fibrinogen (Fbg) and complement factors were confirmed in culture supernatant by ELISA (FIG. 1, panels F-G). To quantitate the hepatic functionality of the organoids, Applicant investigated the albumin secretion level normalized by cell number (FIG. 10). The albumin secretion level was 2133 ng/day/$10^6$ cells (FIG. 1, panel F) and higher than other experiments in 2D and 3D differentiation of hPSCs into HLC (150-1000 ng/day/$10^6$ cell) relative to published iPSC-derived hepatocytes (Miki et al., 2011; Song et al., 2015; Song et al., 2009; Vosough et al., 2013), while primary hepatocytes produce 30-40 μg/day/$10^6$ cell in 3D scaffolds (Davidson et al., 2016; Dvir-Ginzberg et al., 2003). These results indicated that liver organoids contained hepatocytes with reasonable albumin secretion activity compared to stem cell-derived hepatocytes in the published literature. Importantly, this organoid generation method is reproducible and therefore, applicable to other PSC lines, as intraluminal organoids were generated from both 317D6 and 1383D6 iPS cell lines with albumin secretion capacity (FIG. 11). Overall, Applicant established a protocol for generating a large number of polarized liver organoids with hepatocyte characteristics.

Micro-Anatomical Characterization of Bile Acid Producing Human iPSC-Liver Organoids Next, to test if liver organoids have bile transport activity, Applicant first characterized organoids by staining key proteins involved in bile synthesis and excretion function Immunofluorescence staining of BSEP and MRP2 demonstrated that these proteins preferentially localized in the intraluminal region (FIG. 2, panel A). The bile canaliculus is the smallest intrahepatic secretory channel and the canalicular lumen consists of a space formed by a modified apical region of the opposing plasma membranes of contiguous hepatocytes (Cutrin et al., 1996; Tsukada et al., 1995). In addition, it is delimited by tight junction complexes and the microvilli are located on the inside of the canalicular lumen (Tsukada et al., 1995). ZO-1 staining is known to stain canalicular region in liver, and FIG. 1, panel C suggested that tight junctions were located inside of liver organoids. Transmission electron microscopy revealed organoids contained microvilli directed towards the lumen (FIG. 2, panel B). Consistent with these anatomical features, qRT-PCR analysis revealed that organoids had gene expression of ABCB11 and Na+-taurocholate co-transporting polypeptide (NTCP), yet the levels were lower in organoids than primary hepatocytes (FIG. 2, panel C). Therefore, the organoid contained polarized human hepatocytes separated from internal lumen by tight junctions, which reflects a unique micro-anatomical architecture resembling in vivo hepatic canaliculi.

Next, in order to determine bile acid (BA) production capacity, Applicant conducted ELISAs on intra-luminal fluid collected from organoid culture. The level of total BA pool of intra-luminal fluid was 26.7 μg/day/$10^6$ cells (approximately 125 μmol/L in an organoid with a 200 μm diameter) (FIG. 2, panel D) and, surprisingly, the BA concentration was comparable to that in primary hepatocytes derived from sandwich culture (approximately 40 μg/day/$10^6$ cells, 10 μmol/L in culture supernatant) in previous reports (Ni et al., 2016). Thus, organoids do not merely have the canaliculi-like morphology but possess bile acid production and secretion activity, suggesting that the bile acids transport pathway is correctly constructed.

Dynamic Visualization of Bile Acid Intake and Excretion in Human Liver Organoids Bile acid excretion is the major determinant of bile flow, therefore, defects in this system may result in impaired bile secretion (cholestasis) associated with various liver disease pathologies (Nishida et al., 1991). Efflux transport proteins located in the apical (canaliculi) membranes of hepatocytes play an important role in the hepatic elimination of many endogenous and exogenous compounds, including drugs and metabolites (Kock and Brouwer, 2012). BSEP and MRP2 mediate canaliculi bile salt transport in humans. After demonstrating the positive expression of key proteins for bile transport, the applicant next wondered if the organoids can actively transport bile acid into its lumen. First, to check the intake of bile acids into the organoid, applicant challenged the organoids with cholylglycylamido-fluorescein (CGamF), which is a bile salt analog (Mork et al., 2012). After treatment of CGamF from outside, the accumulation of CGamF into the intra-lumen of organoids was successfully confirmed (FIG. 2, panel E). Similarly, the fluorescent bile acid cholyl-lysyl-fluorescein (CLF) was found to be reproducibly excreted and accumulated into organoids from multiple human iPSC lines (FIG. 2, panel F). To determine the specificity of this assay, Applicant has developed an iPSC line carrying a BSEP defunctionalized allele using the CRISPR-Cas9 based gene editing approach. BSEP is responsible for bile transport, and consistent with this, BSEP-KO iPSC-organoids failed to accumulate fluorescent bile acid compared with parental control organoids. Taken together, these data suggest that organoids have the ability to uptake bile acid from the outside and efflux them inside the organoids.

Bosentan Induced Cholestasis Specific to CYP2C9*2 iPSC-Liver Organoids

To test the clinical relevance of organoid based cholestatic phenotyping method, Applicant employed pharmacogenomics insights into Applicant's system to address the fidelity question. Specifically, multiple iPSC lines have been collected, which carry a well-known susceptibility gene variant (i.e. CYP2C9*2 for Bosentan, described in, for example, Clin Pharmacol Ther. 2013 December; 94(6):678-86. doi: 10.1038/clpt.2013.143. Epub 2013 Jul. 17. Association of CYP2C9*2 with bosentan-induced liver injury.) (FIG. 3, panel A), and compared their cholestatic potential in the presence of Bosentan (FIG. 3, panel B). Interestingly, CLF excretion into organoids was severely impaired in CY2C9*2 carrier organoids but not in non-carrier organoids. This matches the clinical tendency to cholestasis induced by Bosentan, shown in three-different iPSC derived organoids in the absence of CYP2C9*2 as shown in FIG. 3, panel C. In contrast, irinotecan based cholestasis was not specific to CYP2C9*2 iPSC lines. These results indicated the organoid based cholestasis assay predicts some aspects of human variation.

High-Throughput Drug Induced Cholestasis Evaluation in Organoids

Considering the significant role of cholestasis in DILI induced by drugs, the applicant next wondered if this organoid model reflects the pathology of DILI in the presence of particular compounds. Before testing a number of compounds, the applicant first sought to develop a high-throughput fluorescence based assay because both CLF and CGamF are not applicable for high-speed imaging due to several issues: 1. background is strong, necessitating a manual washing process; 2. signal intensity is weak, requiring a careful acquisition setting. Alternatively, the use of fluorescein diacetate (FD), a reportedly useful marker of efflux transport in hepatocytes (Barth and Schwarz, 1982; Bravo et al., 1998) is proposed. The polar fluorescent metabolite fluorescein, is trapped in the cells until it is actively transported from the cells into the canaliculi space (Malinen et al., 2014). To determine if FD can be used for live assessment of transport capacity without exchanging the medium and adjusting exposure, chronological hepatobiliary transport activity was further investigated with time-lapse imaging. Organoids were incubated with fluorescein diacetate for 45 minutes and intraluminal accumulation was observed inside of organoids at 20 minutes after treatment (FIG. 4, panels A, B). The opposite directionality of this transport flow was determined by the micro-injection of FD into organoids. After micro-injection of diacetate into the lumen, fluorescein remained inside, and was never observed outside the organoids (FIG. 4, panel C). In summary, this FD based evaluation model has high-throughput potential to assess unidirectional efflux bile transport in liver organoids by a simple fluorescent live imaging analysis.

Figure 12:
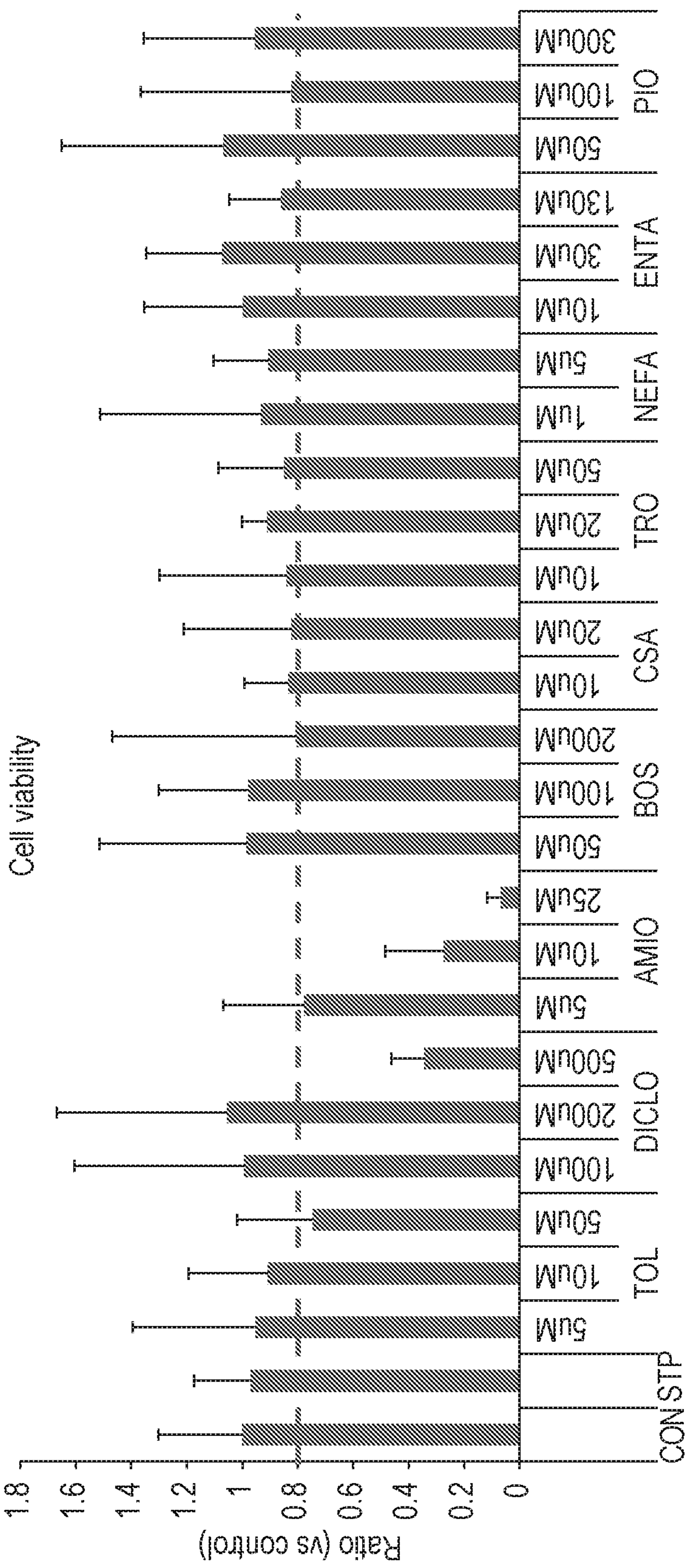
FIG. 12. The cell viability at 24 h after treatment of 10 compounds. Viability assessment on lipid accumulation-induced vulnerable organoid model. CON: Control sample, STP: Streptomycin, TOL: Tolcapone, DICLO: Diclofenac, AMIO: Amiodarone, BOS: Bosentan, CSA: Cyclosporin A, TRO: Troglitazone, NEFA: Nefazodone, ENTA: Entacapone, PIO: Pioglitazone. Bars represent the mean±SD, n=4-6.

Next, applicant validated the fidelity of a FD-based assay by evaluating the viable dosing of 10 FDA approved drugs and measured any secondary disturbance by cell damage. Applicant successfully found an optimal dose for nine compounds with acceptable viability. In contrast, amiodarone (AMIO) was significantly toxic to organoids within the tested range, therefore AMIO was excluded in further potential DILI assessment studies (FIG. 12). Applicant investigated cholestasis potential in organoids using FD with nine training compounds (TCs) which were classified as one of three types based on DILI mechanism; DILI compounds without cholestasis (Class A), DILI compounds with cholestasis (Class B) and compounds not reported as DILI compounds (Class C) (FIG. 4, panel D) (Oorts et al., 2016). To quantify the inhibitory potential for FD excretion, Applicant developed a simple but robust quantification method by determining the fluorescent intensity ratio between outside and inside the organoid by image J (FIG. 4, panel B). As a validation study, Applicant first confirmed the ability to assess the inhibition ratio using Cyclosporin A (CSA). At five minutes after treatment of FD, a significant decrease (0.4 compared to control) was observed in the group treated with CSA for 24 h, compared to control (DMSO) (FIG. 4, panel B). Applicant then screened nine TCs at multiple concentrations to assess the fidelity of this approach. Interestingly, in this screening system, at 24 hr after treatment of TCs, the efflux of FD was significantly decreased ($p<0.01$ or 0.05) in Class B compounds) Bosentan, CSA, Troglitazone and Nefazodone), similar to clinical observations, while this inhibitory effect was not observed in Class A and Class C compounds (FIG. 4, panel D upper images and FIG. 4, panel E). These results suggested that the liver organoid model is useful for classifying the bile transport inhibition potency for candidate compounds in drug development with a high relevance to human phenotypes.

Evaluating Mitochondrial Overload in Organoids

Further, Applicant investigated the mitochondria health assessment because mitochondrial toxicity plays a central role in DILI in multiple mechanisms associated with the onset of DILI (Pessayre et al., 2012). In this study, to investigate mitochondrial health in organoids, an index of mitochondrial membrane potential (MMP) was used to monitor MMP of intact cells as a direct readout of mitochondrial health (Li et al., 2014). After treatment of TCs for 24 h, dose-dependent increases of MMP were observed with treatment of Tolcapone (2-8-fold change, $p<0.01$), Diclofenac (7-13 Fold change, $p<0.05$ or 0.01), CSA (3-7-fold change, $p<0.01$) and Nefazodone (4-42 fold change, p<0.01) (FIG. 5, panel A lower images and graph). In addition, Troglitazone also increased MMP in organoids (3-5-fold change, p<0.05), although dose-dependence was not observed. On the other hand, after treatment of Bosentan, Entacapone and Pioglitazone, increases of MMP were not clearly observed even in multiple doses. These results demonstrated that this live image based assay, named Liver organoid-based Toxicity screen (LoT), discriminated between compounds with and without mitochondrial toxicity.

Revisiting Mechanistic Classification of DILI Compounds by LoT System

Severe manifestations of human DILI are multifactorial, highly associated with combinations of drug potency specifically related to known mechanisms of DILI such as mitochondrial and BSEP inhibition (Aleo et al., 2014). However, current in vitro functional models are difficult to assess such multi-factorial contributions. Given the advantage of multiplexed and live functional readouts in LoT system, Applicant attempted to analyze the relationship among survival, cholestasis and mitochondrial stress. Of note, drugs with dual action at 24 hours (cholestasis and mitochondrial stress) such as CSA, TRO and NEFA significantly lowered cell viability at 72 hours relative to TOL, DICLO and BOS. These data are comparable to clinical data that shows that dual toxicities were highly associated with the severity of DILI consistent previous reports (Aleo et al., 2014) (FIG. 5, panels B, C). Additionally, Applicant also noted that Entacapone treatment at 130 μM decreased organoid viability (From 85% at 24 h to 64% at 72 h). Entacapone requires extensive binding to plasma proteins, mainly to albumin, to induce DILI (Fisher et al., 2002). However, based on available methods, it remains elusive how Entacapone is toxic to the liver (Oorts et al., 2016). Taken together, the LoT system is an advantageous human model system for the major mechanistic classification of DILI, and a useful testing platform for further delineating unknown complex mechanisms.

Assessing Vulnerability for DILI in Human Liver Organoids

Figure 13A:
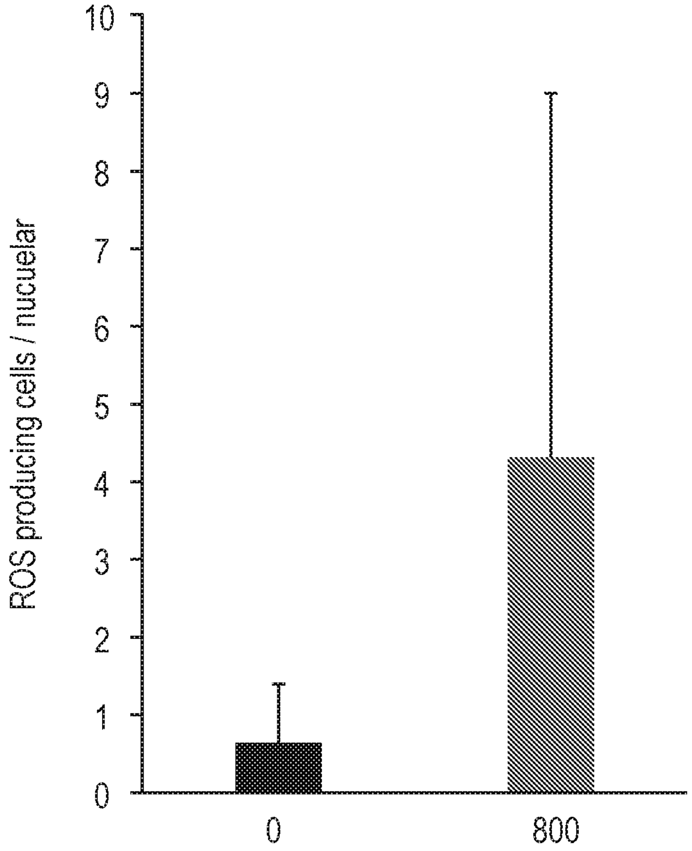
FIG. 13. ROS production and the morphological change of mitochondria in lipotoxic liver organoid. A. The ratio of cell number producing ROS in total cells on lipid accumulation-induced vulnerable organoid model by treatment of 800 μM oleic acid (OA). B. Image of mitochondria in organoid on vulnerable organoid model. Red: mitochondria, Purple: F-actin, Blue: Nucleus. C. The number and size of mitochondria on vulnerable organoid model. Bars represent the mean±SD, *: p<0.05, n=5-6.
Figure 13B:
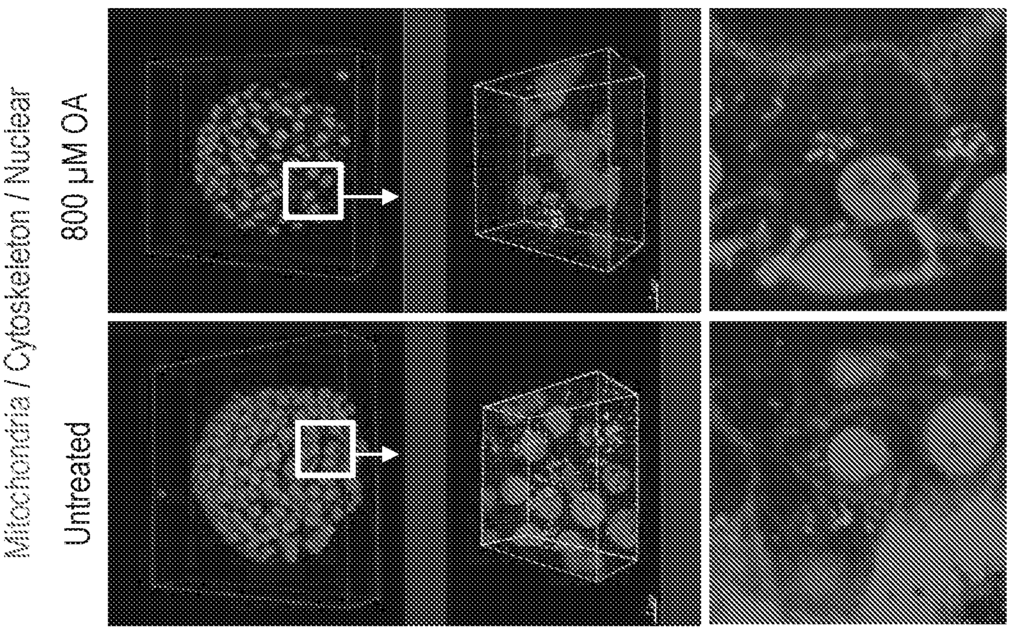
Figure 13C:
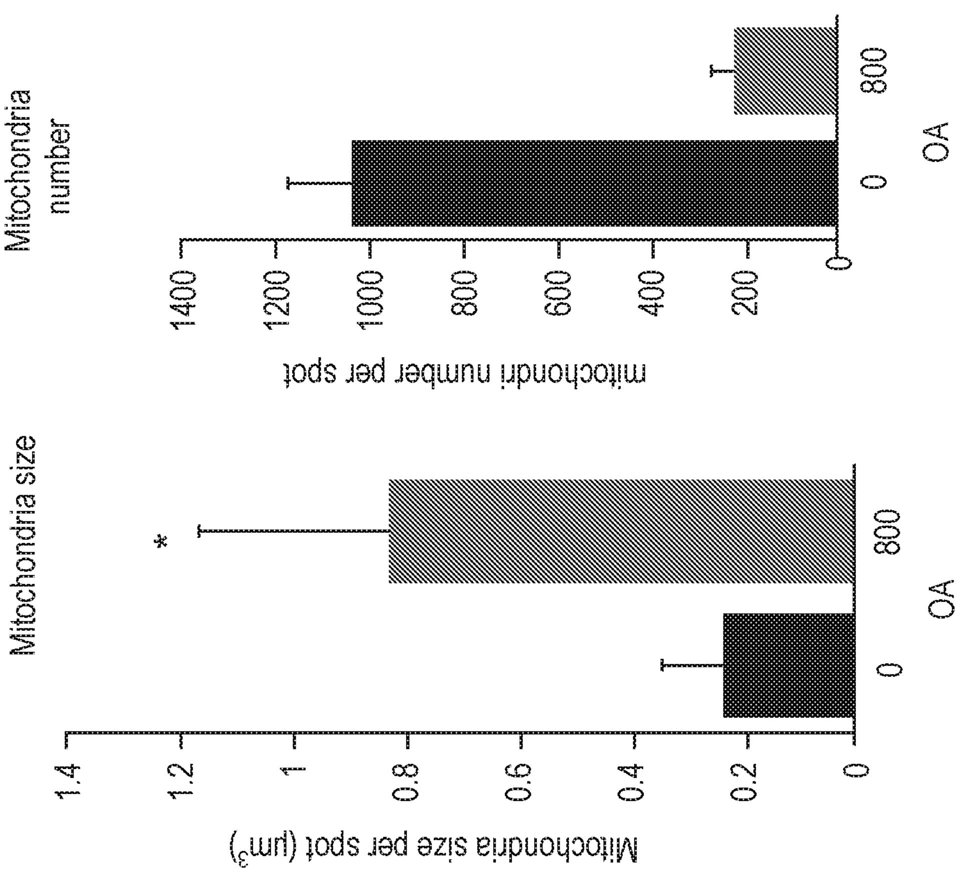
Figure 14:
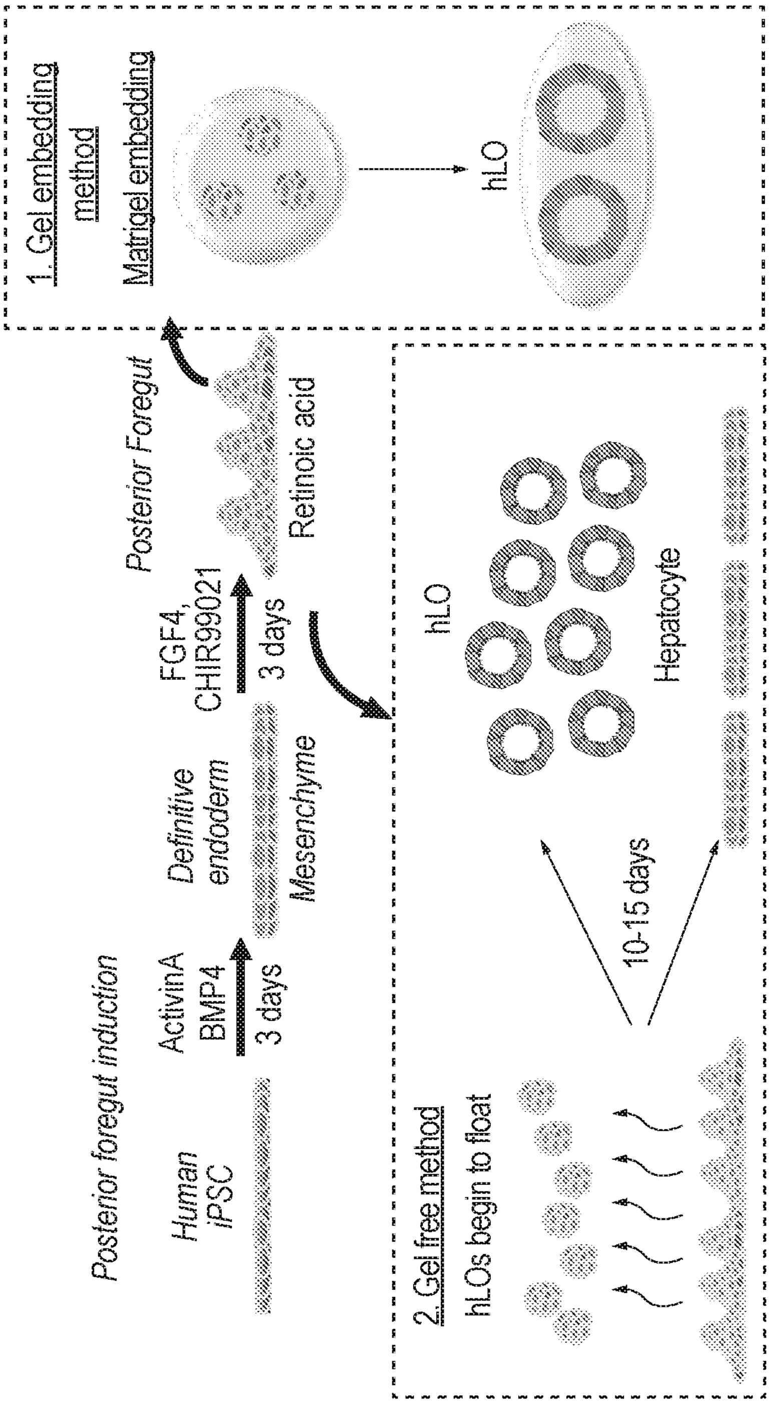
FIG. 14. Schematic of Cell Matrigel-Free Method. Shown is a schematic for a liver organoid generation method that does not use matrigel for generating organoids.

DILI incidence is known to be often confounded by a number of host factors. Indeed, there is growing evidence that the risk of hepatotoxicity from some drugs such as acetaminophen is greatly increased due to obesity and NAFLD, both in rodents and humans (APAP) (Fromenty, 2013; Michaut et al., 2016). Therefore, it is important to predict DILI potential in such a "vulnerable" condition with a patient even in the subclinical phase. In the present study, Applicant established a lipotoxic organoid model by co-exposure to an unsaturated fatty acid, oleic acid (FIG. 6, panel A). At 3 days after oleic acid treatment to organoids, lipid accumulation in organoids was intense (FIG. 6, panel B). The oxidation of fatty acids is an important source of reactive oxygen species (ROS), which leads to depletion of ATP and nicotinamide dinucleotide, and induces DNA damage in fatty livers (Browning and Horton, 2004). Consistent with this, ROS production was observed in lipid treated organoids (FIG. 6, panel C and FIG. 13, panel A). Additionally, fatty acids induced massive swelling of liver mitochondria (FIG. 6, panel D and FIG. 13, panel B) similar to published phenotypes (Zborowski and Wojtczak, 1963). As hepatic mitochondrial dysfunction precedes the development of NAFLD in a rat model (Rector et al., 2010), these results indicate that the lipotoxic organoids model to some degree in vivo fatty liver model.

Recognizing this lipotoxic organoid model as a vulnerable condition with enhanced ROS production, Troglitazone (0-50 μM) was treated for 24 h and cell viability in organoids was assessed. By treatment of Troglitazone alone at 50 μM, cell viability was 85% at 24 hours while it was decreased to 67% at 72 h. However, after treatment of Troglitazone on lipotoxic condition, massive fragmentation of organoids was observed due to an organoid death. Subsequent cell viability analysis confirmed this result (−40% compared to control, p<0.05) (FIG. 6, panel E and 6, panel F).

Next, Applicant investigated whether organoids can be recovered from a DILI-like condition by a potential therapeutic compound. The applicant used N-acetylcysteine (NAC), an antioxidant, to inhibit ROS production because intravenous NAC improves survival in patients with non-acetaminophen-related acute liver failure (Lee et al., 2009) and diminished the Troglitazone-induced cytotoxicity (Rachek et al., 2009). As expected, cell viability was significantly improved by NAC, suggesting that NAC rescued cell death in organoids even in vulnerable conditions (FIG. 6, panel E and 6, panel F). In most DILI cases, the only intervention is the removal of the causative drug if identified (Polson and Lee, 2005) (Bohan et al., 2001; Navarro and Senior, 2006). This LoT system may be a useful tool for identifying causal drugs linked to multi-drug regimens as well as drug discovery for treating DILI.

Serious adverse events (SAE) including liver failure are a major cause of drug attrition during clinical development or withdrawal of marketed pharmaceuticals. In particular, DILI is a critical challenge in drug development, in which drug induced cholestasis induced by inhibitions of transporter activity is one major cause. Sandwich culture using human primary hepatocytes is the current best choice in pharmaceuticals. Although recent reports showed the promise of hepatocyte based cholestasis model using transdifferentiated cells from human fibroblasts (Ni et al., 2016), these assay platforms still have reproducibility challenges as well as throughput problems because of variable and limited human hepatocyte sources and the need for complex quantitation algorithms. In addition, HepaRG cells, a human hepatoma cell line, is also useful to evaluate cholestatic features, but their low BSEP (Bile Salt Export Pump, or ABCB11, important transporter for bile acid excretion, as well as major target for cholestatic agents) activity and time-consuming differentiation procedure, limit their use (Le Vee et al., 2013). More importantly, a lack of essential anatomical structures limits their practical use for the pharmaceutical industry. Alternatively, the described methods allow for a simple, robust and high-throughput system to measure bile transport activity by live fluorescent imaging in the presence of testing compounds. The major advantages of the LoT assay include: 1. the cost effectiveness ($12.35 per 50 organoids; $94.85 per 384 well), 2. the assay throughput (measurable at single organoid) and 3. the multiplexed readouts for analyzing interplay between other factors such as mitochondrial stress. Especially, as mentioned above, retrospective studies revealed that multiple cell stress potentials were associated with the incidence of DILI (Aleo et al., 2014) and the LoT assay showed the comparable results with that study, since cell viability was decreased dependent on dual readouts; mitochondrial and cholestatic stress. Oxidative stress plays an important role in cell death and has been linked to the development of cholestatic liver injury (Serviddio et al., 2004). Hydrophobic bile acids accumulate intracellularly during cholestasis and interfere with normal mitochondrial electron transport, inhibiting the activity of respiratory complexes I and III and consequently reducing adenosine triphosphate synthesis (Krahenbuhl et al., 1994), resulting in mitochondrial dysfunction-induced apoptosis (Bernardi, 1996). In line with these findings, Applicant's correlational analysis of these dual readouts indicated cholestatic stress was a more dominating factor for liver injury compared with mitochondria stress as was seen in FIG. 5. Thus, the LoT system may be used as a model system for investigating DILI mechanisms.

Figure 7:
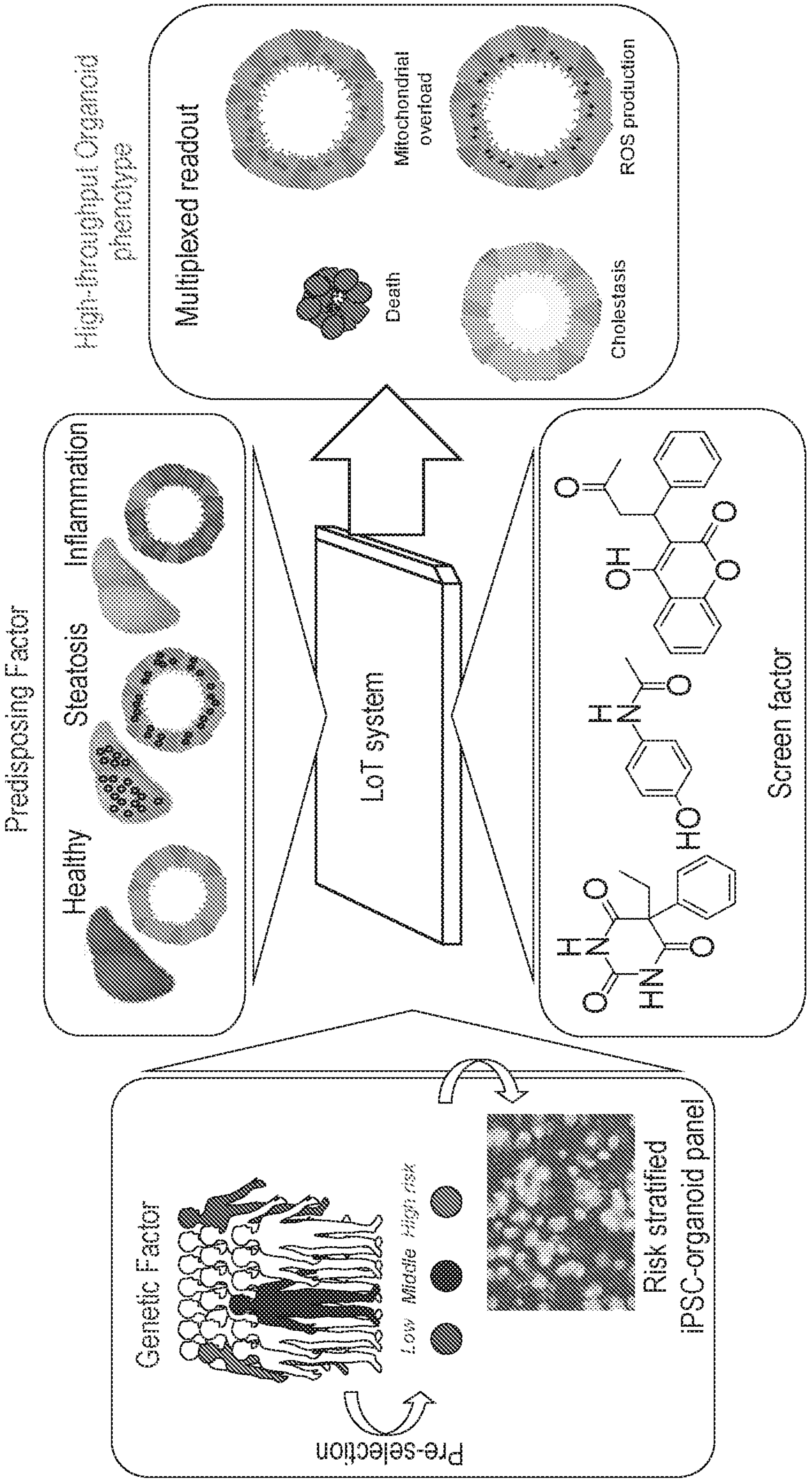
FIG. 7. Multiplexed liver organoid based screening for predicting toxicity

In addition, given the recent establishment of population of iPSC panels, potential assessment for different susceptibility in individuals is also promising (Inoue et al., 2014). Predicting SAE in conventional in vitro assay system does not generally focus on individual differences, however, SAE often occur in a small SAE-prone patient subgroup (Stevens and Baker, 2009). Applying the LoT system to diverse population iPSC panels will provide previously inaccessible about different susceptibilities to SAE. In light of the extremely rare nature of DILI, the use of patients' cells with specific genomic or ethnic factors will aid in elucidating the currently unknown idiosyncratic mechanism of DILI. Thus, LoT might serve as a game changing strategy for pharmaceutical industries by providing essential insight for minimizing DILI potential (FIG. 7).

One limitation in this organoid model is the lack of immunological reactions. The immunological effect resulting from a hypersensitivity reaction is one possible mechanism for idiosyncratic DILI. There are limited in vitro models to assess the hypersensitivity by drugs, although the sensitivity by Troglitazone-induced cytotoxicity was increased using in vitro co-culture model using hepatic cell line, Huh7 and THP-1 cells (Edling et al., 2009). Thus, advancing the LoT platform by focusing on immune lineages will be of interest to assess hepatocellular inflammation. Nevertheless, the LoT testing platform seems superior in generating reproducible and large data sets from an individual organoid as the inhibition of bile efflux function by multiple FDA approved drugs is reproducibly observed in this assay. Considering cholestasis is induced by a broad spectrum of liver diseases including drug-induced, lipotoxic, infectious, and congenital conditions (Chatterjee et al., 2014), the organoid based LoT assay is useful for analyzing intra-hepatic cholestasis in a variety of contexts with the potential for mechanistic studies as well as drug screening applications beyond DILI.

Studying Vulnerable Human Liver Condition with LoT Assay

Host factors such as obesity are known to significantly influence the onset of DILI (Heidari et al., 2014), yet they are often understudied in the clinical setting due to its complex nature. The presence of obesity or fatty liver might make patients vulnerable to hepatic injury induced by xenobiotics and non-toxic chemicals (e.g., drugs) and these might become hepatotoxic in lower doses in the presence of risk factors (Fromenty, 2013). Despite this, the current clinical trial system is not designed for stratifying volunteers under vulnerable liver conditions with handful of biomarker (ALT, AST) levels. Since number of patients with steatosis are subclinical with no detectable biomarkers before dosing, it is critical to foresee the outcomes in this vulnerable condition before entering the clinical phase.

With an effort to advance the LoT system to assess the toxicity in these vulnerable conditions on early drug screening stage such as lead compound generation/optimization, Applicant applied lipotoxic stress to liver organoids and demonstrated the exaggerated synergistic effect of Troglitazone, an antidiabetic drug, on DILI. Indeed, the organoid system successfully reflects this feature by showing massive hepatocyte death, promoted by triglyceride accumulation into hepatocytes in an organoid. One of the mechanisms of DILI in obesity could explain reduced levels of glutathione (GSH) (Michaut et al., 2016). Drug-induced oxidative stress could have several origins, in particular, through GSH depletion and inhibition of the mitochondrial respiratory chain (Begriche et al., 2011; Pessayre et al., 2010). The vulnerable model might reflect the decrease in intracellular GSH levels and worsened Troglitazone induced oxidative stress through mitochondrial dysfunction, ameliorated by providing NAC. Considering the dramatic rise in non-alcoholic steatohepatitis (NASH) prevalence, it is noteworthy that there is still a minimal list of drugs for either aggravating pre-existing NAFLD or inducing more frequently an acute hepatitis. Additionally, an in vitro reductionist system provides a previously unforeseen window to study previously untested host factors as the isolated host factor can effectively deployed into organoids.

LoT Based Precision Medicine

The selection of optimal drug therapy using LoT will be of major interest in clinics from a personalized medicine perspective. For instance, the strategy considered in the choice of antipsychotic agent must take into account the hepatic tolerance according to the non-negligible incidence of liver disorders among psychiatric population; 16% of possible DILI agents are neuropsychiatric drugs (Dumortier et al., 2002). Given that NASH is often accompanied by psychological disorders such as depression, safer combinatorial selection of anti-depressive drugs (tricyclic agents or SSRI), mood stabilizing agents and neuroleptic drugs is needed (Dumortier et al., 2002). Also, due to an age-associated increase in chronic conditions, multiple medication use (i.e., polypharmacy) is a common consequence of providing health care to older adults (Marcum and Gellad, 2012), making it extremely difficult to identify causative drugs when DILI is suspected. As patient derived iPSC-organoids provide an unlimited and reproducible source, LoT may serve as a panel to stratify the potential of DILI in patients and provide information to choose safer medication from a personalization perspective.

LoT Based New Drug Discovery to DILI

Equally important is the potential use for anti-DILI therapeutic compound screen using LoT system. A large number of drugs have deleterious effects on liver and DILI and it is a major clinical problem. Actually, acetaminophen accounts for approximately half of cases of DILI in the United States (Russo et al., 2004). In other regions of the world, for instance in developing countries, other drugs such as anti-tuberculosis medications might be the leading cause of DILI (Bell and Chalasani, 2009). However, there are only several symptomatic therapies available. Here, as a proof-of-concept experiment, Applicant established an organoid survival experiment to assess the therapeutic effect of a compound to resist a toxic mechanism of DILI as evidenced by Troglitazone. While NAC is the major treatment choice for paracetamol overdose (Makin et al., 1995; Verma and Kaplowitz, 2009), recently, the research focus has shifted to investigating the use of NAC in non-paracetamol DILI (Chughlay et al., 2016). LoT system is useful to assess the efficacy of NAC to DILI by non-paracetamol drugs. Beyond, this higher throughput approach will serve as a powerful tool for screening larger scale compound libraries that restore DILI-like symptoms in vitro. Combined, methods described here can be used to identify and study cell-intrinsic and extrinsic factors associated with clinical DILI phenotypes, and would facilitate lead compound optimization, mechanistic study, and precision medicine, as well as anti-DILI therapy screening applications.

Methods

Maintenance of PSCs

TkDA3 with CYP2C9*2 variant human iPSC clone used in this study was kindly provided by K. Eto and H. Nakauchi. Other suitable lines include human iPSC lines gifted from Kyoto University and those purchased from Coriell Biorepository. were maintained as described previously (Takahashi et al., 2007). Undifferentiated hiPSCs were maintained on feeder-free conditions in mTeSR1 medium (StemCell technologies, Vancouver, Canada). Other suitable media include E8 from Lonza, or StemFit from Aijinomoto Co. Plates are coated with Matrigel (Corning Inc., New York, N.Y., USA) of 1/30 dilution at 37 °C in an incubator with 5% $CO_2$/95% air. hPSCs Maintenance. In place of Matrigel, Laminin511, Laminin411 from Mippi Co or Biolamina Co can be used.

Production of Liver Organoids (HLO)

Differentiation of hiPSCs into definitive endoderm was induced using previously described methods with several modifications (Spence et al., 2011). In brief, colonies of hiPSCs were isolated in Accutase (Thermo Fisher Scientific Inc., Waltham, MA, USA) and 150000-300000 cells were plated on Matrigel or laminin coated tissue culture 24 well plate (VWR Scientific Products, West Chester, PA). When the cells become a high-density (over 90% of the cells covering the well), medium was changed to RPMI 1640 medium (Life Technologies, Carlsbad, CA) containing 100 ng/mL Activin A (R&D Systems, Minneapolis, MN) and 50 ng/mL bone morphogenetic protein 4 (BMP4; R&D Systems) at Day 1, 100 ng/mL Activin A and 0.2% fetal calf serum (FCS; Thermo Fisher Scientific Inc.) at Day 2 and 100 ng/mL Activin A and 2% FCS at Day 3. For Day 4-6, cells were cultured in Advanced DMEM/F12 (Thermo Fisher Scientific Inc.) with B27 (Life Technologies) and N2 (Gibco, Rockville, MD) containing 500 ng/ml fibroblast growth factor (FGF4; R&D Systems) and 3 μM CHIR99021 (Stemgent, Cambridge, MA, USA). Cultures for cell differentiation were maintained at 37 °C in an atmosphere of 5% $CO_2$/95% air and the medium was replaced every day. Differentiated definitive endoderm showed budding on the plate at Day 7. If the spheroids were not enough to be embedded into Matrigel, Day 4-6 media is added again and incubated with at 37 °C overnight.

Differentiation into Liver Organoids.

Three methods may be used to differentiate the DE into liver organoids: The "Matrigel Drop Method," the "Matrigel Sandwich Method," and the Matrigel-Free Method," each of which is described below.

Matrigel Drop Method:

On Day 7-8, definitive endoderm organoids with plated cells were gently pipetted to delaminate from dishes. Isolated spheroids were centrifuged at 800 rpm for 3 minutes and, after removing supernatant, embedded in 100% matrigel drop on the dishes. The plates were placed at 37 °C in an atmosphere of 5% $CO_2$/95% air for 5-15 min. After the Matrigel was solidified, Advanced DMEM/F12 was added with B27, N2 and Retinoic acid (RA; Sigma, St. Louis, MO) 2 μM for 1-5 days. The media was replaced every other day. After RA treatment, organoids embedded in Matrigel drop were cultured in Hepatocyte culture medium (HCM Lonza, Walkersville, MD) with 10 ng/mL hepatocyte growth factor (HGF; PeproTech, Rocky Hill, NJ), 0.1 μM Dexamethasone (Dex; Sigma) and 20 ng/mL Oncostatin M (OSM; R&D Systems). Cultures for cell differentiation were maintained at 37 °C in an atmosphere of 5% $CO_2$/95% air and the medium was replaced every 3 days. Around Day 20-30, organoids embedded in Matrigel drop were isolated by scratching and gentle pipetting for any analyses.

Matrigel Sandwich Method:

On Day 7-8, definitive endoderm organoids with plated cells were gently pipetted to delaminate from dishes. Isolated spheroids were centrifuged at 800 rpm for 3 minutes, and after removing supernatant, they were mixed with 100% Matrigel. At the same time, hepatocyte culture medium with all supplements was mixed with the same volume of 100% Matrigel. HCM and Matrigel mix was plated to the bottom of dish to make a thick coating on the plate (0.3-0.5 cm), and placed at 37 °C in an atmosphere of 5% $CO_2$/95% air for 15-30 min. After the Matrigel was solidified, spheroids mixed with Matrigel was seeded on Matrigel thick coated plated. The plate was placed at 37 °C in an atmosphere of 5% $CO_2$/95% air for 5 min. Advanced DMEM/F12 was added with B27, N2 and Retinoic acid (RA; Sigma, St. Louis, MO) 2 μM for 1-5 days. The media was replaced every other day. After RA treatment, organoids embedded in Matrigel drop were cultured in Hepatocyte culture medium (HCM Lonza, Walkersville, MD) with 10 ng/mL hepatocyte growth factor (HGF; PeproTech, Rocky Hill, NJ), 0.1 μM Dexamethasone (Dex; Sigma) and 20 ng/mL Oncostatin M (OSM; R&D Systems). Cultures for cell differentiation were maintained at 37 °C in an atmosphere of 5% $CO_2$/95% air and the medium was replaced every 3 days. Around Day 20-30, organoids embedded in Matrigel drop were isolated by scratching and gentle pipetting for any analyses.

Matrigel-Free Method:

On Day 7-8, definitive endoderm organoids with plated cells were continued planar culture in Advanced DMEM/F12 (Thermo Fisher Scientific Inc.) with B27 (Life Technologies) and N2 (Gibco, Rockville, MD) Retinoic acid (RA; Sigma, St. Louis, MO) 2 μM for 4 days. The media was replaced every other day. After the 4 days planar culture, the organoids begin to bud, whereas 2D cells differentiate into hepatocytes. Both organoids and hepatocytes can be maintained for over 60 days under Hepatocyte culture medium (HCM Lonza, Walkersville, MD) with 10 ng/mL hepatocyte growth factor (HGF; PeproTech, Rocky Hill, NJ), 0.1 μM Dexamethasone (Dex; Sigma) and 20 ng/mL Oncostatin M (OSM; R&D Systems) for 10 days. For organoid assays, floating organoids can be collected in Ultra-Low attachment multiwell plates 6 well plate and used for subsequent assays whenever appropriate. Cultures for cell differentiation were maintained at 37 °C in an atmosphere of 5% $CO_2$/95% air and the medium was replaced every 3 days.

H&E Staining and Immunohistochemistry

Liver organoids were collected from Matrigel, fixed in 4% paraformaldehyde and embedded in paraffin. Sections were subjected to H&E and immunohistochemical staining. The following primary antibodies were used: anti-human albumin antibody (1:200 dilution abcam, Cambridge, UK), anti-type IV collagen antibody (1:200 dilution eBioscience, San Diego, CA, USA), anti-ZO-1 antibody (1:200 dilution BD Transduction Laboratories (San Jose, CA, USA) and anti-MRP2 antibody (1:200 dilution Novus Biologicals, Littleton, CO). Dye-conjugated secondary antibodies, Alexa Fluor 568-conjugated donkey anti-rabbit immunoglobulin (IgG; 1:1000; Invitrogen, A10042) was applied to the organoids at room temperature for 2 h. Nuclei were stained with 10 μg/mL Hoechst 33342 (Sigma) at room temperature for 10 min, after which organoids were washed again three times with washing buffer. The specimens were observed under a Fluorescent microscope or bright-field. For whole mount immunohistochemical staining, after liver organoids were fixed in 4% paraformaldehyde for 30 min and permeabilized with 2.5% Tween 20 (Sigma) at room temperature, organoids were incubated overnight at 4 °C with the following primary antibodies diluted in PBS: polyclonal anti-B SEP antibody (1:200 Sigma). Fluorescent dye-conjugated secondary antibodies, Alexa Fluor 568-conjugated donkey anti-rabbit immunoglobulin (IgG; 1:500; Invitrogen, A10042) were applied to the organoids at room temperature for 2 h. After the reaction, the cells were washed three times with washing buffer (PBS containing 0.5% Triton-X 100 [Sigma] and 0.5% bovine serum albumin [BSA; Sigma]). Nuclei were stained with 10 μg/mL Hoechst 33342 (Sigma) at room temperature for 10 min, after which organoids were washed again three times with washing buffer. The specimens were observed under a confocal imaging performed on a Nikon A1Rsi inverted confocal microscope.

RNA Isolation, RT-qPCR

RNA was isolated using the RNeasy mini kit (Qiagen, Hilden, Germany). Reverse transcription was carried out using the SuperScriptIII First-Strand Synthesis System for RT-PCR (Invitrogen, CA, USA) according to manufacturer's protocol. qPCR was carried out using TaqMan gene expression master mix (Applied Biosystmes) on a QuantStudio 3 Real-Time PCR System (Thermo). All primers and probes information for each target gene were obtained from the Universal ProbeLibrary Assay Design Center (https://qper.probefinder.com/organism.jsp).

Principal Component Analysis of RNA-Seq Data

RNA isolation, cDNA synthesis, sequencing on Illumina HiSeq 2500 are described previously (Asai et al., 2017). The RNA-Seq reads were aligned to the human genome (GRCh37/hg19) using TopHat (version 2.0.13). The alignment data from Tophat were fed to an assembler, Cufflinks (version 2.2.1), to assemble aligned RNA-Seq reads into transcripts. Annotated transcripts were obtained from the UCSC genome browser (http://genome.ucsc.edu) and the Ensembl database. Transcript abundances were measured in Fragments Per Kilobase of exon per Million fragments mapped (FPKM).

To compare the lineage of pHLO, Applicant combined in-house RNA-seq data (pFG and organoids) with preprocessed public data as follows: Transcript abundances of iPSC, DE, HS, HP, iDH and NHC were obtained from GSE86007 (Jalan-Sakrikar et al., 2016); ones of child liver tissue, adult liver tissue, adult right lobe tissue, fetal liver tissue and primary hepatocyte were obtained from ENCODE (ENCFF418BVF, ENCFF804QWF, ENCFF965IQH, ENCFF918SJO, ENCFF367FJJ, ENCFF029IUF, ENCFF280YNO, ENCFF347TXW, ENCFF724CQI, ENCFF624LQL, ENCFF962SOD, ENCFF170AEC) (Consortium, 2012; Sloan et al., 2016) and GSE85223 (Asai et al., 2017). Genes were used if all dataset have identical gene symbol after possible data preprocessing. Applicant performed quantile-normalization of FPKM+1 and RPKM+1 data in log2 space followed by selected genes within the top 10000 of median expression levels. Principal component analysis was performed by using the scaled gene expression levels by using R package FactoMineR (version 1.35) (Sébastien Lê, 2008).

Protein Secretion Analysis

For measuring albumin, fibrinogen and complement factors secreted level of organoids, 200 μL of culture supernatant of organoids on Ultra-Low attachment 96 well plates (Corning) were collected. The culture supernatants were collected and stored at −80 °C until use. The supernatant was assayed with Human Albumin ELISA Quantitation Set (Bethyl Laboratories, Inc., TX, USA) and fibrinogen (Thermo Fisher Scientific) according to the manufacturer's instructions. For analyzing complement factors, supernatants were measured with Luminex System (Luminex Corporation, Austin, TX) according to the manufacturer's instructions. To calculate albumin production per the number of cells, the linear regression equation of cell numbers by diameter of an organoid was used. For measuring total bile acid secreted level intra-luminal organoids, fluid inside organoids was absorbed using microinjection Nanoject II (Drummond Scientific, Broomall, PA, USA). Fluid absorbed was dilute in PBS and assayed with Total Bile Acid ELISA Kit (Antibodies-online, Inc., GA, USA). To calculate the volume of total bile acid, the number of cells in organoid was calculated using the linear regression equation in the same manner for albumin production and the molecular weight of cholic acid was used for calculation and comparing with volume in previous report.

Transmission Electron Microscopy

For transmission electron microscopy, briefly, organoids were fixed in 3% glutaraldehyde for overnight at 4 °C, washed in 0.1 M sodium cacodylate buffer, and incubated for 1 h in 4% osmium tetroxide. They were subsequently washed then dehydrated in ethanol series, and finally embedded in propylene oxide/LX112. Tissue was then sectioned and stained with 2% uranyl acetate followed by lead citrate. Images were visualized on Hitachi transmission electron microscope.

CGamF Assay

Briefly, organoids were pre-incubated with a transport buffer (118 mM NaCl, 23.8 mM NaHCO3, 4.83 mM KCl, 0.96 mM KH2PO4, 1.20 mM MgSO4, 12.5 mM HEPES, 5 mM glucose, 1.53 mM CaCl2, adjusted to pH 7.4) for 30 min. Next, organoids were treated by 10 μM fluorescently labeled bile acid (CGamF; a kind gift from Dr Hofmann) for 1 h, after then, organoids were washed three times with PBS. Images were captured on fluorescent microscopy BZ-X710 (Keyence, Osaka, Japan).

Evaluation of Bile Transport Inhibition

Fluorescein diacetate was used for evaluating bile transport activity in organoids. Around Day 25, the organoids were rinsed with PBS, and, fluorescein diacetate was treated to organoids in medium. In addition, to investigate the direction of transport, fluorescein diacetate was injected to organoids using by Nanoject III (Drummond Scientific). After treatment or injection of fluorescein diacetate, images were captured on fluorescent microscopy BZ-X710 (Keyence). Next, to check the feasibility of test system, 10 mg/mL fluorescein diacetate (Sigma) in HCM was added with 20 μM Cyclosporin A (CSA; Sigma) for 45 minutes and images were captured sequentially using fluorescent microscopy BZ-9000 (Keyence). For evaluation of bile transport inhibition, 10 mg/mL fluorescein diacetate in HCM was added after treatment of dimethyl sulfoxide (DMSO; Sigma), Streptomycin (STP; Sigma) as a negative control, Tolcapone (Tol; Sigma), Diclofenac (Diclo; Sigma), Bosentan (BOS; Sigma), CSA, Troglitazone (Tro; Sigma), Nefadozone (Nefa; Sigma), Entacapone (Enta; Sigma) and Pioglitazone (PIO, Sigma). After 5 minutes incubation, the organoids were rinsed three times with PBS and images were captured sequentially using fluorescent microscopy BZ-X710. Analysis was performed by calculating ratio between the intensities outside and inside organoids using Imagej 1.48 k software (Wayne Rasband, NIHR, USA, http://imagej.nih.gov/ij). Changes in brightness or contrast during processing were applied equally across the entire image.

Mitochondria Toxicity Potential Evaluation

After being cultured in on Ultra-Low attachment multiwell plates 6 well plate in each culture condition, organoids were picked up and seeded in Microslide 8 Well Glass Bottom (Ibidi, WI, USA). For evaluation of mitochondria membrane potential (MMP), 250 nM Tetramethylrhodamine, Methyl Ester, Perchlorate (TMRM; Thermo Fisher Scientific) was added after treatment of dimethyl sulfoxide (DMSO; Sigma), Streptomycin (STP; Sigma) as a negative control, Tolcapone (Tol; Sigma), Diclofenac (Diclo; Sigma), Bosentan (BOS; Sigma), Cyclosporin A (CSA; Sigma), Troglitazone (Tro; Sigma), Nefadozone (Nefa; Sigma), Entacapone (Enta; Sigma) and Pioglitazone (PIO, Sigma) for 24 h. After 30 minutes incubation, the organoids were rinsed three times with PBS and images were scanned on a Nikon A1 Inverted Confocal Microscope (Japan) using 60× water immersion objectives. Arias and intensity of TMRM were calculated as MMP by IMARIS8 (Bitplane AG, Switzerland). For assessment of cholestatic and mitochondrial stress, cell viability was measured by using the CellTiter-Glo® luminescent cell viability assay (Promega, Mannheim, Germany) per organoid at 24 h after treatment of drugs and confirmed not to decrease the viability in each dose for avoiding secondary change due to cell damage toward death.

Analysis of Relationship of Cell Viability in Organoids with Mitochondria and Cholestatic Stress To demonstrate the relationship of cell viability with mitochondrial and cholestatic stress, first, indexes were setup using following formula; "Index=−(Sample value−Control value)×100" based on the value provided from mitochondrial and cholestatic stress assays. For analyzing cell damage associated with mitochondrial and cholestatic stress, at 72 h after treatment of drugs, the ATP content per organoid was determined using the CellTiter-Glo® luminescent cell viability assay (Promega). These data were shown as FIG. 4, panel B using Infogr.am (http://infogr.am): a free, web-based tool.

Evaluation of Viability in Organoids on Vulnerable Condition

Figure 5A:
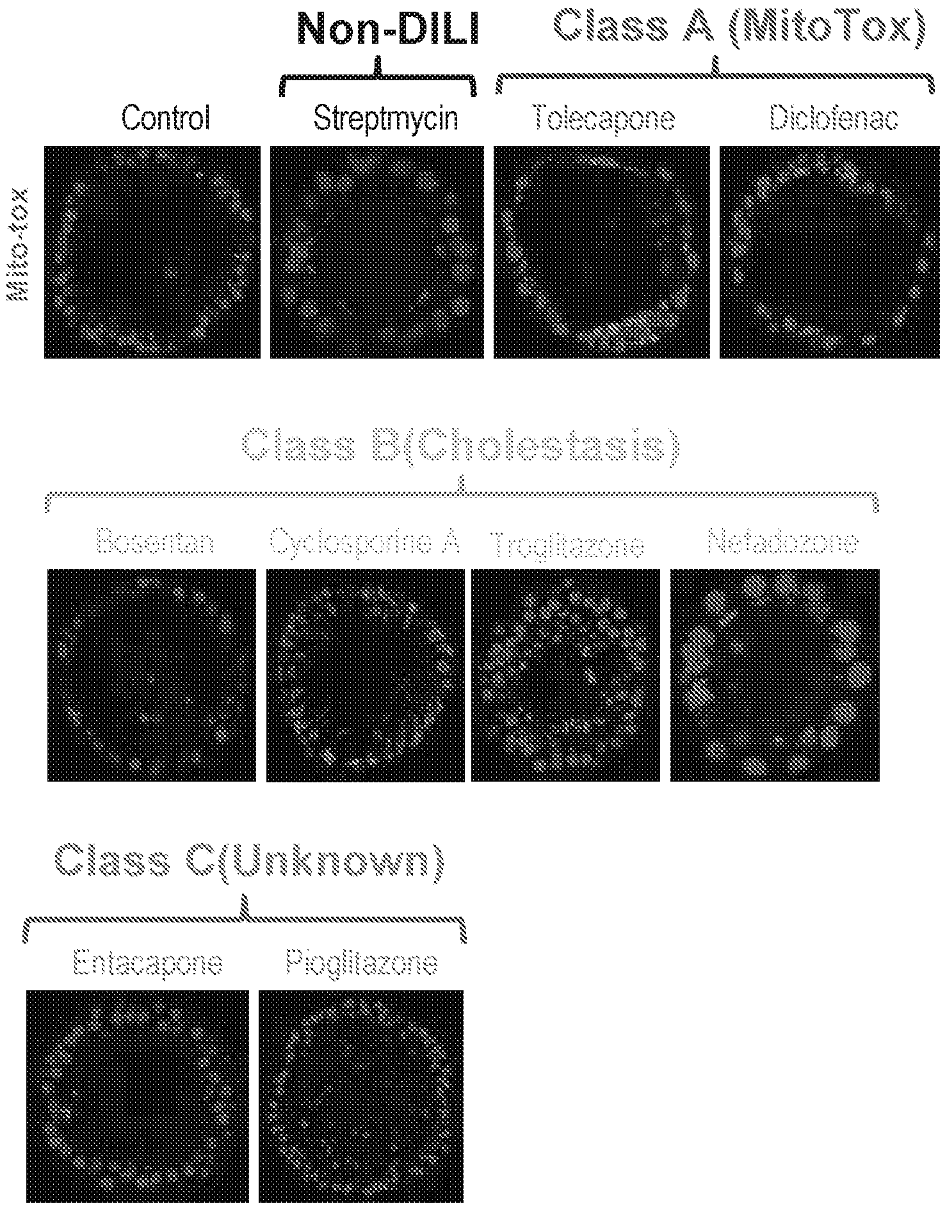
FIG. 5. High-fidelity drug induced mitochondria-toxicity screen using organoids. A. Image of mitochondria membrane potential (MMP) on TMRM after treatment of 9 training compounds. Lower: Quantification of transport inhibition after treatment of training compounds, Bars represent the mean±SD, *: p<0.05, **: p<0.01, n=4-6. C. Quantification of MMP change after treatment of training compounds, Bars represent the mean±SD, *: p<0.05, : p<0.01, n=4-5. CON: Control sample, STP: Streptomycin, TOL: Tolcapone, DICLO: Diclofenac, BOS: Bosentan, CSA: Cyclosporin A, TRO: Troglitazone, NEFA: Nefazodone, ENTA: Entacapone, PIO: Pioglitazone. B. Classification of the set of 9 training compounds (TC) referred to Oorts., et al 2016 (Oorts et al., 2016). Class A represents TCs with known reports on DILI in vivo, while those in Class B are TCs with reports on drug-induced cholestasis in vivo. The mechanism of toxicity based on literature data is also provided. Class C compounds are generally considered safe regarding DILI. C. Analysis between viability for 72 h after treatment of drugs and dual risk parameters, drug-induced cholestasis potential and mitochondria toxicity potential. Cholestasis and Mitochondria toxicity (Mito-tox) indexes were derived from data in FIG. 3**. The size of circles indicated the magnitude of viability decreases.
Figure 5B:
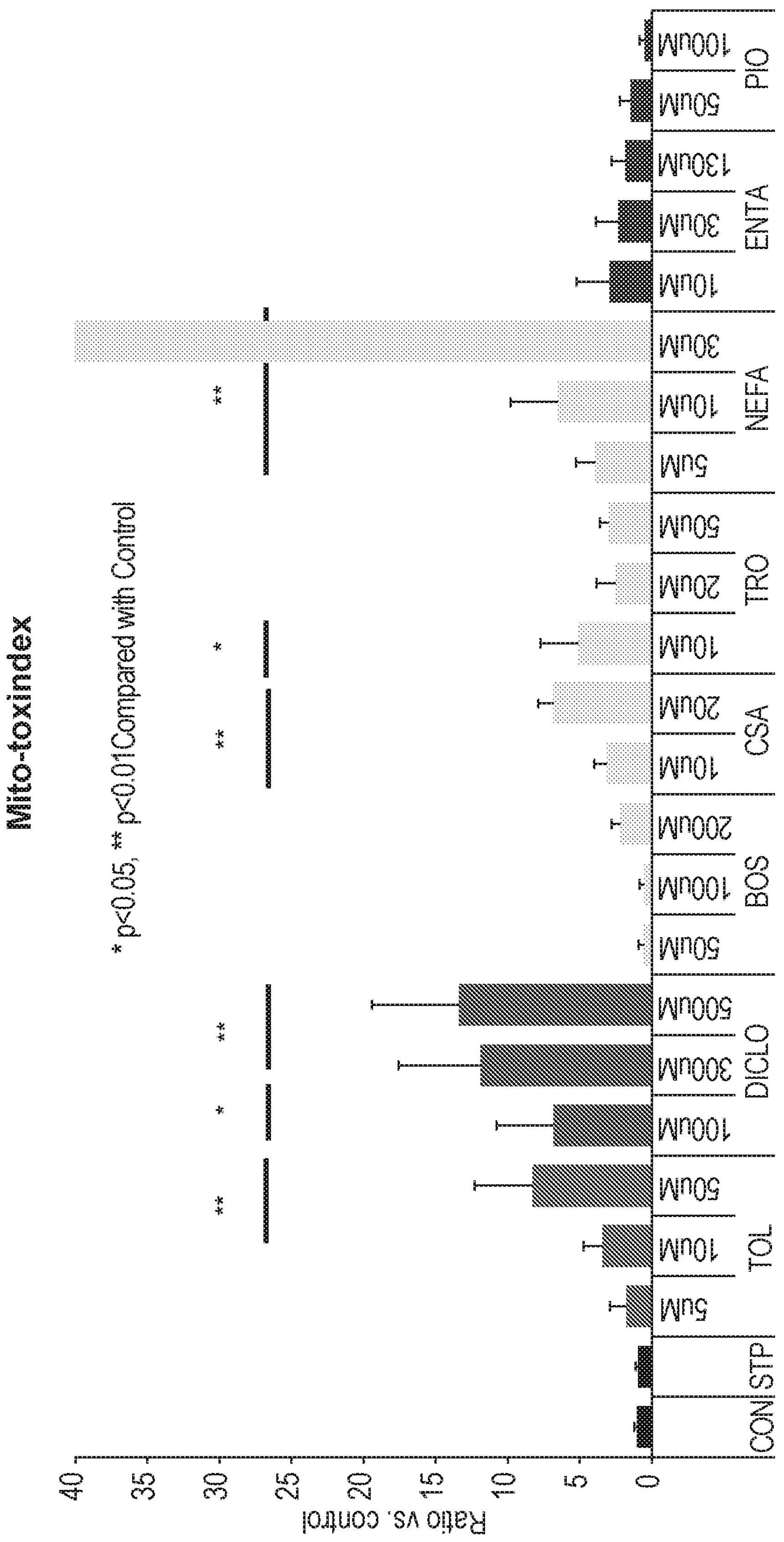
Figure 5D:
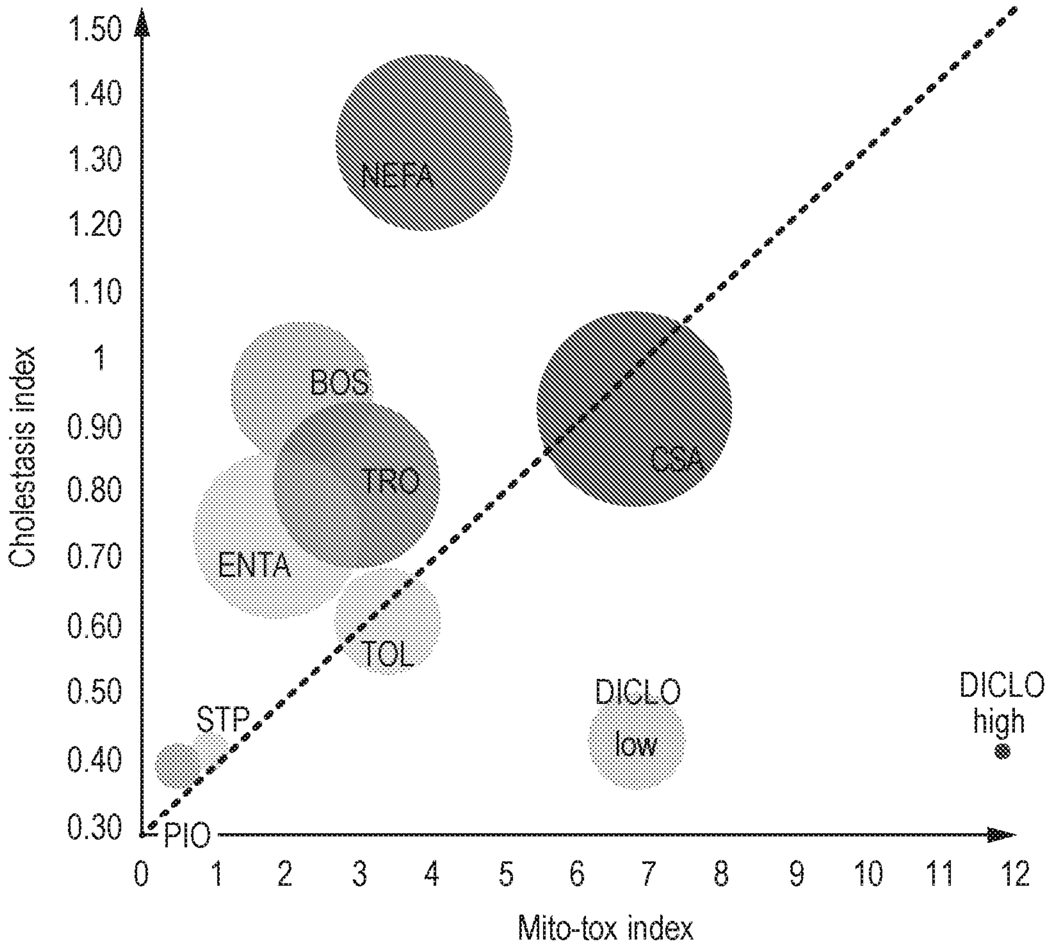
Figure 6A:
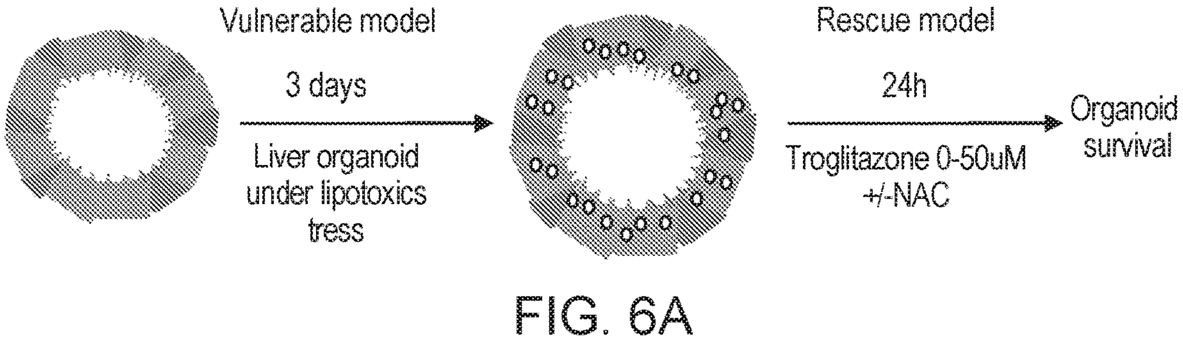
FIG. 6. Modeling drug-induced liver injury in vulnerable conditions rescued by NAC exposure. A. Overview of evaluation of drug-induced cytotoxicity on vulnerable organoid model. B. Profiling of vulnerable model on lipid accumulation (Blue: nuclei, Green: Lipid, Red: F-actin). C ROS production (Blue: nuclei, Green: ROS) and D. mitochondria health (Blue: nuclei, Red: Mitochondria). E. Image of organoids at 24 h after drugs treatment. F. Viability assessment on lipid accumulation-induced vulnerable organoid model. Bars represent the mean±SD, *: p<0.05, n=5-6. CON: control, STP: Streptomycin, TRO: Troglitazone, NAC: N-acetylcysteine.
Figure 6B:
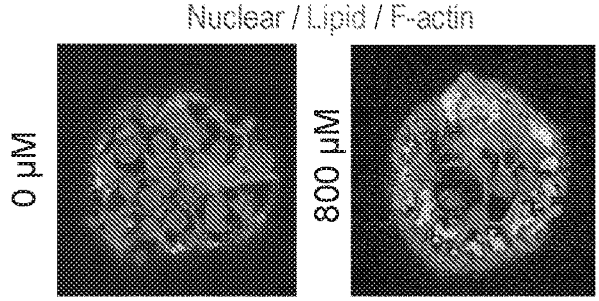
Figure 6C:
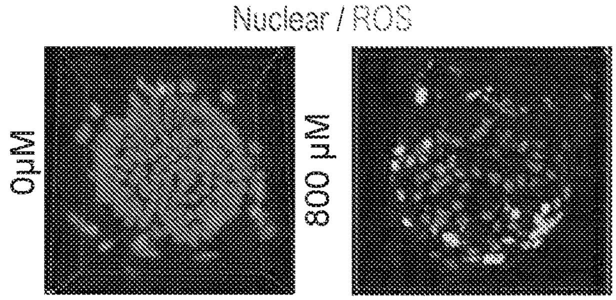
Figure 6D:
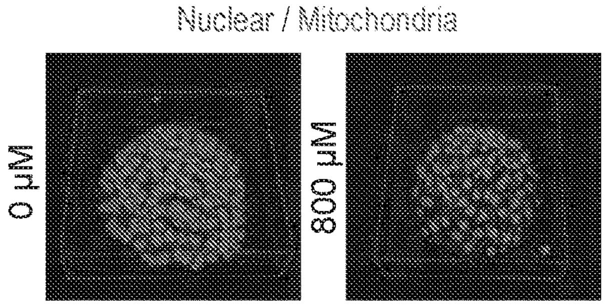
Figure 6E:
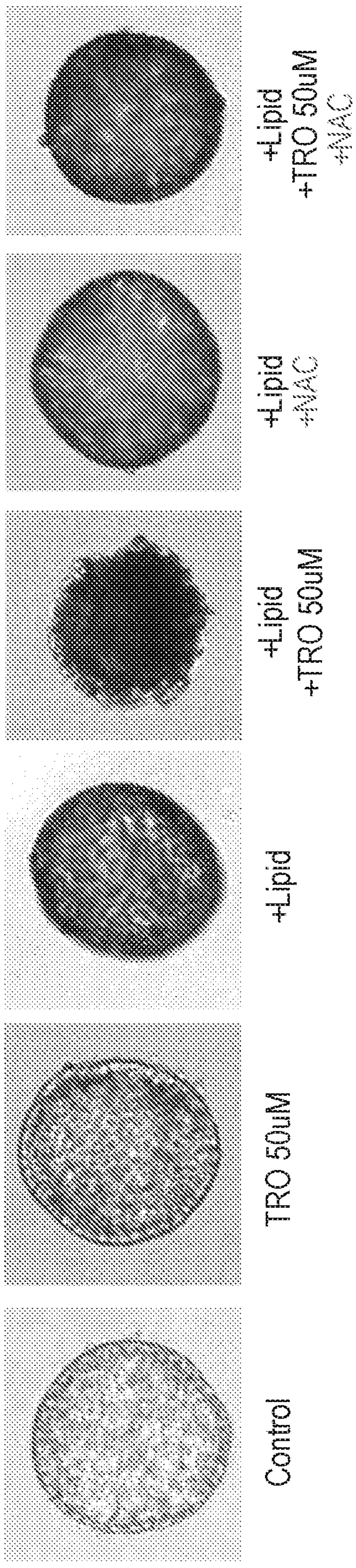
Figure 6F:
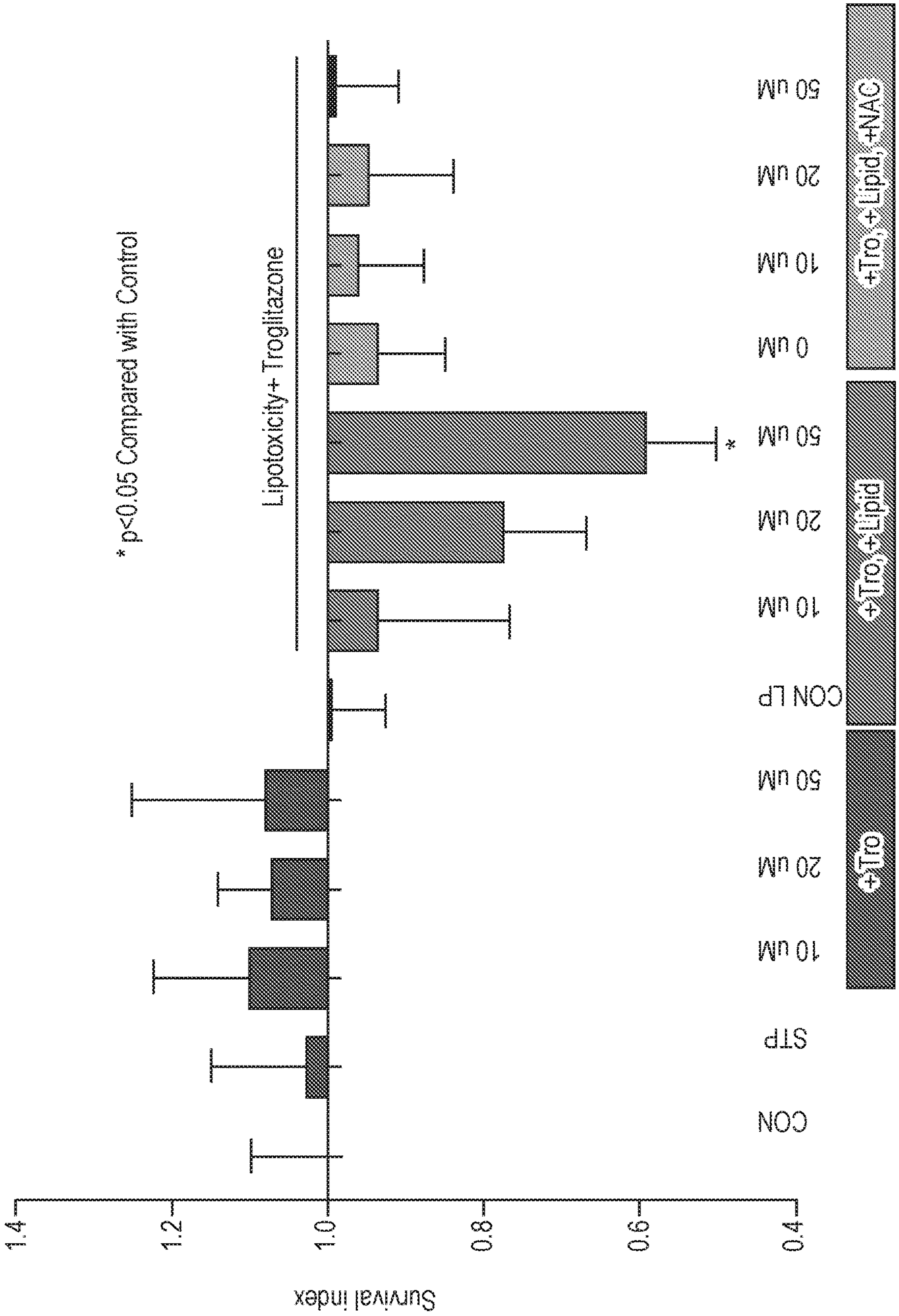

The experiment was performed as shown in FIG. 5A. After being excluded from Matrigel and washed, organoids were treated 800 μM oleic acid on Ultra-Low attachment multiwell plates 6 well plate (Corning) for 3 days. Next, 50 μM of Troglitazone was treated with or without 50 μM NAC for 24 h. Cell viability was performed by using the CellTiter-Glo® luminescent cell viability assay (Promega). Images were captured sequentially using fluorescent microscopy BZ-9000.

Lipid Induced Mitochondria Stress Evaluation

After being cultured in on Ultra-Low attachment multiwell plates 6 well plate in each culture condition, twenty organoids were picked up and seeded in Microslide 8 Well Glass Bottom (Ibidi, WI, USA) and subjected to live-cell staining. The following regents or kits were used: BODIPY® 493/503 for lipids (Thermo Fisher Scientific), and SiR Actin Kit for cytoskeleton (USA Scientific, FL, USA), CellROX® Green Reagent for ROS (Fisher Scientific), TMRM (Thermo Fisher Scientific) for mitochondria. Organoids were visualized and scanned on a Nikon A1 Inverted Confocal Microscope (Japan) using 60× water immersion objectives. ROS production, mitochondria size and number were analyzed by IMARIS8.

Statistics

Statistical significance was determined using unpaired Student's t-test or one-way ANOVA with Dunnett's multiple comparison post-hoc test. $P<0.05$ was considered significant.

REFERENCES

Aleo, M. D., Luo, Y., Swiss, R., Bonin, P. D., Potter, D. M., and Will, Y. (2014). Human drug-induced liver injury severity is highly associated with dual inhibition of liver mitochondrial function and bile salt export pump. Hepatology 60, 1015-1022.

Asai, A., Aihara, E., Watson, C., Mourya, R., Mizuochi, T., Shivakumar, P., Phelan, K., Mayhew, C., Helmrath, M., Takebe, T., et al. (2017). Paracrine signals regulate human liver organoid maturation from induced pluripotent stem cells. Development 144, 1056-1064.

Barth, C. A., and Schwarz, L. R. (1982). Transcellular transport of fluorescein in hepatocyte monolayers: evidence for functional polarity of cells in culture. Proc Natl Acad Sci USA 79, 4985-4987.

Begriche, K., Massart, J., Robin, M. A., Borgne-Sanchez, A., and Fromenty, B. (2011). Drug-induced toxicity on mitochondria and lipid metabolism: mechanistic diversity and deleterious consequences for the liver. J Hepatol 54, 773-794.

Bell, L. N., and Chalasani, N. (2009). Epidemiology of idiosyncratic drug-induced liver injury. Semin Liver Dis 29, 337-347.

Bernardi, P. (1996). The permeability transition pore. Control points of a cyclosporin A-sensitive mitochondrial channel involved in cell death. Biochim Biophys Acta 1275, 5-9.

Bohan, T. P., Helton, E., McDonald, I., Konig, S., Gazitt, S., Sugimoto, T., Scheffner, D., Cusmano, L., Li, S., and Koch, G. (2001). Effect of L-carnitine treatment for valproate-induced hepatotoxicity. Neurology 56, 1405-1409.

Bravo, P., Bender, V., and Cassio, D. (1998). Efficient in vitro vectorial transport of a fluorescent conjugated bile acid analogue by polarized hepatic hybrid WIF-B and WIF-B9 cells. Hepatology 27, 576-583.

Browning, J. D., and Horton, J. D. (2004). Molecular mediators of hepatic steatosis and liver injury. J Clin Invest 114, 147-152.

Chang, J. H., Plise, E., Cheong, J., Ho, Q., and Lin, M. (2013). Evaluating the in vitro inhibition of UGT1A1, OATP1B1, OATP1B3, MRP2, and BSEP in predicting drug-induced hyperbilirubinemia. Mol Pharm 10, 3067-3075.

Chatterjee, S., Richert, L., Augustijns, P., and Annaert, P. (2014). Hepatocyte-based in vitro model for assessment of drug-induced cholestasis. Toxicol Appl Pharmacol 274, 124-136.

Chughlay, M. F., Kramer, N., Spearman, C. W., Werfalli, M., and Cohen, K. (2016). N-acetylcysteine for non-paracetamol drug-induced liver injury: a systematic review. Br J Clin Pharmacol 81, 1021-1029.

Consortium, E. P. (2012). An integrated encyclopedia of DNA elements in the human genome. Nature 489, 57-74.

Cutrin, J. C., Cantino, D., Biasi, F., Chiarpotto, E., Salizzoni, M., Andorno, E., Massano, G., Lanfranco, G., Rizzetto, M., Boveris, A., et al. (1996). Reperfusion damage to the bile canaliculi in transplanted human liver. Hepatology 24, 1053-1057.

D'Amour, K. A., Agulnick, A. D., Eliazer, S., Kelly, O. G., Kroon, E., and Baetge, E. E. (2005). Efficient differentiation of human embryonic stem cells to definitive endoderm. Nat Biotechnol 23, 1534-1541.

Davidson, M. D., Ballinger, K. R., and Khetani, S. R. (2016). Long-term exposure to abnormal glucose levels alters drug metabolism pathways and insulin sensitivity in primary human hepatocytes. Sci Rep 6, 28178.

Dumortier, G., Cabaret, W., Stamatiadis, L., Saba, G., Benadhira, R., Rocamora, J. F., Aubriot-Delmas, B., Glikman, J., and Januel, D. (2002). [Hepatic tolerance of atypical antipsychotic drugs]. Encephale 28, 542-551.

Dvir-Ginzberg, M., Gamlieli-Bonshtein, I., Agbaria, R., and Cohen, S. (2003). Liver tissue engineering within alginate scaffolds: effects of cell-seeding density on hepatocyte viability, morphology, and function. Tissue Eng 9, 757-766.

Edling, Y., Sivertsson, L. K., Butura, A., Ingelman-Sundberg, M., and Ek, M. (2009). Increased sensitivity for troglitazone-induced cytotoxicity using a human in vitro co-culture model. Toxicol In Vitro 23, 1387-1395.

Fahrmayr, C., Konig, J., Auge, D., Mieth, M., Munch, K., Segrestaa, J., Pfeifer, T., Treiber, A., and Fromm, M. (2013). Phase I and II metabolism and MRP2-mediated export of bosentan in a MDCKII-OATP1B1-CYP3A4-UGT1A1-MRP2 quadruple-transfected cell line. Br J Pharmacol 169, 21-33.

Falasca, L., Favale, A., Serafino, A., Ara, C., and Conti Devirgiliis, L. (1998). The effect of retinoic acid on the re-establishment of differentiated hepatocyte phenotype in primary culture. Cell Tissue Res 293, 337-347.

Fisher, A., Croft-Baker, J., Davis, M., Purcell, P., and McLean, A. J. (2002). Entacapone-induced hepatotoxicity and hepatic dysfunction. Mov Disord 17, 1362-1365; discussion 1397-1400.

Fromenty, B. (2013). Drug-induced liver injury in obesity. J Hepatol 58, 824-826.

Heidari, R., Niknahad, H., Jamshidzadeh, A., and Abdoli, N. (2014). Factors affecting drug-induced liver injury: antithyroid drugs as instances. Clin Mol Hepatol 20, 237-248.

Inoue, H., Nagata, N., Kurokawa, H., and Yamanaka, S. (2014). iPS cells: a game changer for future medicine. EMBO J 33, 409-417.

Jalan-Sakrikar, N., De Assuncao, T. M., Lu, J., Almada, L. L., Lomberk, G., Fernandez-Zapico, M. E., Urrutia, R., and Huebert, R. C. (2016). Hedgehog Signaling Overcomes an EZH2-Dependent Epigenetic Barrier to Promote Cholangiocyte Expansion. PLoS One 11, e0168266.

Kock, K., and Brouwer, K. L. (2012). A perspective on efflux transport proteins in the liver. Clin Pharmacol Ther 92, 599-612.

Krahenbuhl, S., Talos, C., Fischer, S., and Reichen, J. (1994). Toxicity of bile acids on the electron transport chain of isolated rat liver mitochondria. Hepatology 19, 471-479.

Le Vee, M., Noel, G., Jouan, E., Stieger, B., and Fardel, 0. (2013). Polarized expression of drug transporters in differentiated human hepatoma HepaRG cells. Toxicol In Vitro 27, 1979-1986.

Lechner, C., Reichel, V., Moenning, U., Reichel, A., and Fricker, G. (2010). Development of a fluorescence-based assay for drug interactions with human Multidrug Resistance Related Protein (MRP2; ABCC2) in MDCKII-MRP2 membrane vesicles. Eur J Pharm Biopharm 75, 284-290.

Lee, W. M., Hynan, L. S., Rossaro, L., Fontana, R. J., Stravitz, R. T., Larson, A. M., Davern, T. J., 2nd, Murray, N. G., McCashland, T., Reisch, J. S., et al. (2009). Intravenous N-acetylcysteine improves transplant-free survival in early stage non-acetaminophen acute liver failure. Gastroenterology 137, 856-864, 864 e851.

Leslie, E. M., Watkins, P. B., Kim, R. B., and Brouwer, K. L. (2007). Differential inhibition of rat and human Na+-dependent taurocholate cotransporting polypeptide (NTCP/SLC10A1) by bosentan: a mechanism for species differences in hepatotoxicity. J Pharmacol Exp Ther 321, 1170-1178.

Li, N., Oquendo, E., Capaldi, R. A., Robinson, J. P., He, Y. D., Hamadeh, H. K., Afshari, C. A., Lightfoot-Dunn, R., and Narayanan, P. K. (2014). A systematic assessment of mitochondrial function identified novel signatures for drug-induced mitochondrial disruption in cells. Toxicol Sci 142, 261-273.

Makin, A. J., Wendon, J., and Williams, R. (1995). A 7-year experience of severe acetaminophen-induced hepatotoxicity (1987-1993). Gastroenterology 109, 1907-1916.

Malinen, M. M., Kanninen, L. K., Corlu, A., Isoniemi, H. M., Lou, Y. R., Yliperttula, M. L., and Urtti, A. O. (2014). Differentiation of liver progenitor cell line to functional organotypic cultures in 3D nanofibrillar cellulose and hyaluronan-gelatin hydrogels. Biomaterials 35, 5110-5121.

Marcum, Z. A., and Gellad, W. F. (2012). Medication adherence to multidrug regimens. Clin Geriatr Med 28, 287-300.

Michaut, A., Le Guillou, D., Moreau, C., Bucher, S., McGill, M. R., Martinais, S., Gicquel, T., Morel, I., Robin, M. A., Jaeschke, H., et al. (2016). A cellular model to study drug-induced liver injury in nonalcoholic fatty liver disease: Application to acetaminophen. Toxicol Appl Pharmacol 292, 40-55.

Miki, T., Ring, A., and Gerlach, J. (2011). Hepatic differentiation of human embryonic stem cells is promoted by three-dimensional dynamic perfusion culture conditions. Tissue Eng Part C Methods 17, 557-568.

Mork, L. M., Isaksson, B., Boran, N., Ericzon, B. G., Strom, S., Fischler, B., and Ellis, E. (2012). Comparison of culture media for bile Acid transport studies in primary human hepatocytes. J Clin Exp Hepatol 2, 315-322.

Navarro, V. J., and Senior, J. R. (2006). Drug-related hepatotoxicity. N Engl J Med 354, 731-739.

Ni, X., Gao, Y., Wu, Z., Ma, L., Chen, C., Wang, L., Lin, Y., Hui, L., and Pan, G. (2016). Functional human induced hepatocytes (hiHeps) with bile acid synthesis and transport capacities: A novel in vitro cholestatic model. Sci Rep 6, 38694.

Nishida, T., Gatmaitan, Z., Che, M., and Arias, I. M. (1991). Rat liver canalicular membrane vesicles contain an ATP-dependent bile acid transport system. Proc Natl Acad Sci USA 88, 6590-6594.

Oorts, M., Baze, A., Bachellier, P., Heyd, B., Zacharias, T., Annaert, P., and Richert, L. (2016). Drug-induced cholestasis risk assessment in sandwich-cultured human hepatocytes. Toxicol In Vitro 34, 179-186.

Pessayre, D., Fromenty, B., Berson, A., Robin, M. A., Letteron, P., Moreau, R., and Mansouri, A. (2012). Central role of mitochondria in drug-induced liver injury. Drug Metab Rev 44, 34-87.

Pessayre, D., Mansouri, A., Berson, A., and Fromenty, B. (2010). Mitochondrial involvement in drug-induced liver injury. Handb Exp Pharmacol, 311-365.

Polson, J., and Lee, W. M. (2005). AASLD position paper: the management of acute liver failure. Hepatology 41, 1179-1197.

Rachek, L. I., Yuzefovych, L. V., Ledoux, S. P., Julie, N. L., and Wilson, G. L. (2009). Troglitazone, but not rosiglitazone, damages mitochondrial DNA and induces mitochondrial dysfunction and cell death in human hepatocytes. Toxicol Appl Pharmacol 240, 348-354.

Rector, R. S., Thyfault, J. P., Uptergrove, G. M., Morris, E. M., Naples, S. P., Borengasser, S. J., Mikus, C. R., Laye, M. J., Laughlin, M. H., Booth, F. W., et al. (2010). Mitochondrial dysfunction precedes insulin resistance and hepatic steatosis and contributes to the natural history of non-alcoholic fatty liver disease in an obese rodent model. J Hepatol 52, 727-736.

Russo, M. W., Galanko, J. A., Shrestha, R., Fried, M. W., and Watkins, P. (2004). Liver transplantation for acute liver failure from drug induced liver injury in the United States. Liver Transpl 10, 1018-1023.

Sébastien Lê, J. J., François Husson (2008). FactoMineR: An R Package for Multivariate Analysis. Journal of Statistical Software 25.

Serviddio, G., Pereda, J., Pallardo, F. V., Carretero, J., Borras, C., Cutrin, J., Vendemiale, G., Poli, G., Vina, J., and Sastre, J. (2004). Ursodeoxycholic acid protects against secondary biliary cirrhosis in rats by preventing mitochondrial oxidative stress. Hepatology 39, 711-720.

Sloan, C. A., Chan, E. T., Davidson, J. M., Malladi, V. S., Strattan, J. S., Hitz, B. C., Gabdank, I., Narayanan, A. K., Ho, M., Lee, B. T., et al. (2016). ENCODE data at the ENCODE portal. Nucleic Acids Res 44, D726-732.

Song, W., Lu, Y. C., Frankel, A. S., An, D., Schwartz, R. E., and Ma, M. (2015). Engraftment of human induced pluripotent stem cell-derived hepatocytes in immunocompetent mice via 3D co-aggregation and encapsulation. Sci Rep 5, 16884.

Song, Z., Cai, J., Liu, Y., Zhao, D., Yong, J., Duo, S., Song, X., Guo, Y., Zhao, Y., Qin, H., et al. (2009). Efficient generation of hepatocyte-like cells from human induced pluripotent stem cells. Cell Res 19, 1233-1242.

Spence, J. R., Mayhew, C. N., Rankin, S. A., Kuhar, M. F., Vallance, J. E., Tolle, K., Hoskins, E. E., Kalinichenko, V. V., Wells, S. I., Zorn, A. M., et al. (2011). Directed differentiation of human pluripotent stem cells into intestinal tissue in vitro. Nature 470, 105-109.

Stevens, J. L., and Baker, T. K. (2009). The future of drug safety testing: expanding the view and narrowing the focus. Drug Discov Today 14, 162-167.

Takahashi, K., Tanabe, K., Ohnuki, M., Narita, M., Ichisaka, T., Tomoda, K., and Yamanaka, S. (2007). Induction of pluripotent stem cells from adult human fibroblasts by defined factors. Cell 131, 861-872.

Takebe, T., and Taniguchi, H. (2014). Human iPSC-derived miniature organs: a tool for drug studies. Clin Pharmacol Ther 96, 310-313.

Tian, X., Zamek-Gliszczynski, M. J., Zhang, P., and Brouwer, K. L. (2004). Modulation of multidrug resistance-associated protein 2 (Mrp2) and Mrp3 expression and function with small interfering RNA in sandwich-cultured rat hepatocytes. Mol Pharmacol 66, 1004-1010.

Tsukada, N., Ackerley, C. A., and Phillips, M. J. (1995). The structure and organization of the bile canalicular cytoskeleton with special reference to actin and actin-binding proteins. Hepatology 21, 1106-1113.

Verma, S., and Kaplowitz, N. (2009). Diagnosis, management and prevention of drug-induced liver injury. Gut 58, 1555-1564.

Vosough, M., Omidinia, E., Kadivar, M., Shokrgozar, M. A., Pournasr, B., Aghdami, N., and Baharvand, H. (2013). Generation of functional hepatocyte-like cells from human pluripotent stem cells in a scalable suspension culture. Stem Cells Dev 22, 2693-2705.

Yang, K., Woodhead, J. L., Watkins, P. B., Howell, B. A., and Brouwer, K. L. (2014). Systems pharmacology modeling predicts delayed presentation and species differences in bile acid-mediated troglitazone hepatotoxicity. Clin Pharmacol Ther 96, 589-598.

Zborowski, J., and Wojtczak, L. (1963). Induction of Swelling of Liver Mitochondria by Fatty Acids of Various Chain Length. Biochim Biophys Acta 70, 596-598.

All percentages and ratios are calculated by weight unless otherwise indicated.

All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "20 mm" is intended to mean "about 20 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of inducing formation of a liver organoid from pluripotent stem cells (PSCs), comprising the steps of:

a) contacting definitive endoderm (DE) derived from said PSCs with an FGF pathway activator and a Wnt signaling pathway activator for a first period of time until posterior foregut spheroids are obtained;

b) incubating said posterior foregut spheroids of step a in the presence of retinoic acid (RA) for a second period of time until said liver organoid is obtained, wherein the liver organoid has bile transport activity, bile production capacity and comprises polarized hepatocytes exhibiting localized expression of BSEP and MRP2 in an intraluminal region.

2. The method of claim 1, wherein said stem cells are human PSCs.

3. The method of claim 1, wherein said posterior foregut spheroids are embedded in a basement membrane matrix.

4. The method of claim 1, wherein said liver organoid expresses alpha-fetoprotein (AFP), albumin (ALB), retinol binding protein (RBP4), cytokeratin 19 (CK19), hepatocyte nuclear factor 6 (HNF6), cytochrome P450 3A4 (CYP3A4), HNF4a, E-cadherin, DAPI, and Epcam.

5. The method of claim 1 wherein said FGF pathway activator is selected from a small molecule or protein FGF signaling pathway activator, FGF1, FGF2, FGF3, FGF4, FGF8, FGF9, FGF10, FGF11, FGF12, FGF13, FGF14, FGF15, FGF16, FGF17, FGF18, FGF19, FGF20, FGF21, FGF22, FGF23, or combinations thereof.

6. The method of claim 1, wherein said Wnt signaling pathway activator is selected from a small molecule or protein Wnt signaling pathway activator.

7. The method of claim 1, wherein said PSCs are human induced pluripotent stem cells (iPSCs) or human embryonic stem cells (ESCs).

8. The method of claim 1, wherein the liver organoid comprises a luminal structure comprising internalized microvilli comprising mesenchymal cells; and wherein said luminal structure is surrounded by polarized hepatocytes.

9. The method of claim 1, wherein the first period of time is about 1 day to about 3 days.

10. The method of claim 1, wherein the second period of time is about 1 day to about 5 days.

11. The method of claim 1, wherein the Wnt signaling pathway activator is selected from Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11, Wnt16, Lithium Chloride; 2-amino-4,6-disubstituted pyrimidine(hetero)arylpyrimidines; IQ1; QS11; NSC668036; and 2-amino-4-[3,4-(methylenedioxy)-benzyl-amino]-6-(3methoxyphenyl) pyrimidine, a GSK3 inhibitor, CHIR99021, or combinations thereof.

12. The method of claim 1, wherein the Wnt signaling pathway activator is not a GSK3 inhibitor.

13. The method of claim 1, wherein the FGF pathway activator is FGF4, and the Wnt signaling pathway activator is CHIR99021.

14. The method of claim 13, wherein the FGF4 is provided at a concentration of about 200 ng/mL to about 1000 ng/mL, and the CHIR99021 is provided at a concentration of about 1 μM to about 100 μM.

15. The method of claim 13, wherein the FGF4 is provided at a concentration of about 500 ng/ml, the CHIR99021 is provided at a concentration of about 3 μM, and the RA is provided at a concentration of about 2 μM.

16. The method of claim 1, wherein the method further comprises incubating said liver organoid of step b) with hepatocyte growth factor, dexamethasone, and Oncostatin M for a third period of time that is at least 10 days.

17. The method of claim 1, wherein the liver organoid comprises stellate cells and Kupffer cells.

18. The method of claim 1, wherein the liver organoid is characterized by having one or more of the following: Complement factor H expression, Complement factor B, C3 expression, C4 expression, fibrinogen production and albumin production.

19. The method of claim 1, wherein the liver organoid expresses one or more genes selected from PROX1, RBP4, CYP2C9, CYP3A4, ABCC11, CFH, C3, CS, ALB, FBG, MRP2, ALCAM, CD68, CD34, CD31.

20. The method of claim 1, wherein the liver organoid comprises a drug metabolism cytochrome variant.

21. The method of claim 1, wherein the liver organoid does not comprise inflammatory cells.

* * * * *